(12) United States Patent
Blackburn et al.

(10) Patent No.: US 6,921,821 B2
(45) Date of Patent: Jul. 26, 2005

(54) ANTAGONISTS OF MELANIN CONCENTRATING HORMONE RECEPTOR

(75) Inventors: Christopher Blackburn, Natick, MA (US); Su-Jen Lai, Somerville, MA (US); Jennifer L. Che, Cambridge, MA (US); Martin P. Maguire, Woburn, MA (US); Michael A. Patane, Andover, MA (US); Matthew J. LaMarche, Reading, MA (US); Courtney A. Cullis, Belmont, MA (US); James Brown, Framingham, MA (US); Anil Vasudevan, Gurnee, IL (US); Jennifer C. Freeman, Grayslake, IL (US); Mathew M. Mulhern, Hainesville, IL (US); John K. Lynch, Kenosha, WI (US); Ju Gao, Gurnee, IL (US); Dariusz Wodka, Waukegan, IL (US); Andrew J. Souers, Evanston, IL (US); Rajesh Iyengar, Lindenhurst, IL (US); Mary Katherin Verzal, Burlington, WI (US); Philip R. Kym, Grayslake, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 10/459,682

(22) Filed: Jun. 11, 2003

(65) Prior Publication Data

US 2004/0106645 A1 Jun. 3, 2004

Related U.S. Application Data

(60) Provisional application No. 60/388,037, filed on Jun. 12, 2002.

(51) Int. Cl.$^7$ .................. C07D 205/08; C07D 401/00; C07D 239/02
(52) U.S. Cl. .................. 540/364; 540/601; 544/284; 544/324; 546/157; 514/312
(58) Field of Search .................. 514/312; 546/157; 540/364, 601; 544/284, 324

(56) References Cited

FOREIGN PATENT DOCUMENTS

| DE | 2331438 | * | 1/1974 |
|----|---------|---|--------|
| DE | 2403786 | * | 10/1974 |
| EP | 0848060 | | 6/1998 |
| WO | 0039279 | | 7/2000 |
| WO | WO02022598 | * | 3/2004 |

OTHER PUBLICATIONS

Bahjaoui–Bouhaddi, M., et al., "Insulin Treatment Stimulates the Rat Melanin–concentrating Hormone–producing Neurons", *Neuropeptides*, 27:251–258 (1994).

Hervé, C. & Fellmann, D., "Changes in rat melanin–concentrating hormone and dynorphin messenger ribonucleic acids induced by food deprivation", *Neuropeptides*, 31(3):237–242 (1997).

Marsh, D. J., et al., "Melanin–concentrating hormone 1 receptor–deficient mice are lean, hyperactive, and hyperphagic and have altered metabolism", *PNAS*, 99(5):3240–3245 (2002).

Qu, D., et al., "A role for melanin–concentrating hormone in the central regulation of feeding behaviour", *Nature*, 380:243–247 (1996).

Rossi, M., et al., "Melanin–Concentrating Hormone Acutely Stimulates Feeding, But Chronic Administration Has No Effect on Body Weight", *Endocrinology*, 138(1):351–355 (1997).

Sahu, A., "Leptin Decreases Food Intake Induced by Melanin–Concentrating Hormone (MCH), Galanin (GAL) and Neuropeptide Y (NPY) in the Rat", *Endocrinology*, 139(11):4739–4742.

Wolf, A. M. & Colditz, G. A., "Current Estimates of the Economic Cost of Obesity in the United States", *Obesity Research*, 6(2):97–106 (1998).

* cited by examiner

*Primary Examiner*—D. Margaret Seaman
(74) *Attorney, Agent, or Firm*—Johanna M. Corbin; Cheryl L. Becker

(57) ABSTRACT

This invention provides compounds that are antagonists of melanin concentrating hormone receptor-1 (MCH-R1). The compounds are represented by formula I:

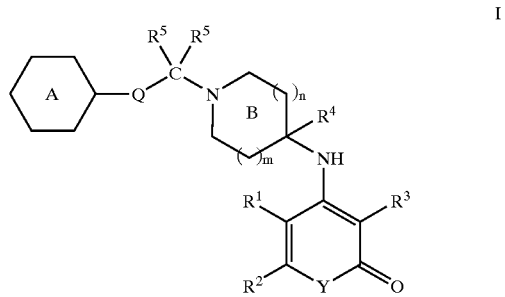

I where m is zero or one, n is zero to two, Y is oxygen or —N(R$^9$)—, R$^1$, R$^2$, R$^3$, R$^4$, R$^5$, R$^9$ and Ring A are defined in the specification. Coumarin and quinolone compounds where R$^1$ and R$^2$ together form a fused benzo ring are preferred. The invention also provides compounds of formula VI where the coumarin moiety is replaced by a quinazolinone ring. The compounds are useful for treating MCH-R1-related disorders, particularly overweight conditions including obesity.

23 Claims, No Drawings

ANTAGONISTS OF MELANIN CONCENTRATING HORMONE RECEPTOR

RELATED APPLICATIONS

This application claims the benefit of U.S. Provisional Patent Application Ser. No. 60/388,037, filed Jun. 12, 2002.

TECHNICAL FIELD

This invention relates to compounds that are antagonists of melanin concentrating hormone receptor, MCH-R1. The invention also provides pharmaceutical compositions comprising the compounds and methods of utilizing those compositions in the treatment and prevention of various disorders, particularly obesity.

BACKGROUND OF THE INVENTION

The National Institute of Diabetes and Digestive and Kidney Diseases (NIDDK) has reported that about one quarter of the US adult population suffers from obesity and over half of the population is overweight (see, e.g., www.niddk.nih.gov/health/nutrit/pubs/statobes). Furthermore, the yearly statistics show that the prevalence of obese and overweight people is trending upward. This has resulted in an increase in health-related costs due to the greater incidence of such related diseases as heart disease and diabetes. In 1998, it was reported that the direct economic cost of obesity in the US was $56 billion, a number comparable to the health cost of cigarette smoking. Wolf and Colditz, Obes. Res. 1998; 6(2):97–106. For health reasons and overall well-being, a safe and effective treatment for overweight conditions would be highly desirable. Accordingly, there has long been scientific interest in understanding biochemical mechanisms that might provide insight into this problem.

The MCH receptor (melanin concentrating hormone receptor, MCH1 MCH-R, or MCH-R1) is a receptor that has been implicated in the regulation of body weight. It is a 353 amino acid protein that is a member of the Class 1 rhodopsin-like G-protein coupled receptor (GPCR) subfamily. The receptor is found throughout the central nervous system and is predominantly expressed in the hypothalamus and zona incerta. To a lesser extent, the receptor is also found in various peripheral tissues such as in the skeletal muscle, eye, tongue, pituitary, testes, stomach and intestines. Mice deficient in MCH-R1 are lean, hyperactive, have altered metabolism and neuroendocrine profiles, and are less susceptible to diet induced obesity (Marsh, D J, et al., Proc. Natl. Acad. Sci., 99: 3240–3245 [2002]).

An endogenous ligand of MCH-R1 is MCH. Mammalian MCH is a highly conserved 19 amino acid cyclic peptide which is reportedly involved in processes related to feeding, water balance, energy metabolism, general arousal and attention state, memory and cognitive functions, and psychiatric disorders (see e.g., International publication no. WO 00/39279 and references cited therein).

A role for MCH in the central control of feeding and the regulation of body weight has been suggested by the observations that fasting increased MCH mRNA in both obese and normal mice. MCH also stimulated feeding in normal rats when injected into the lateral ventricles, and MCH is overexpressed in the hypothalamus of ob/ob mice compared with ob/+ mice (Herve and Fellman, 1997; Rossi et al., 1997; Qu et al., Nature, 380:243–247 [1996]). Furthermore, following insulin injection, a significant increase in the abundance and staining intensity of MCH immunoreactive perikarya and fibres were observed concurrent with a significant increase in the level of MCH mRNA. Treatment of rats with leptin resulted in decreased MCH mRNA levels in the hypothalamus along with decreased food intake and body weight gains (Bahjaoui-Bouhaddi et al., 1994; Sahu, 1998).

The MCH-R1 receptor is also reported to play a role in the regulation of sexual activity, stress-related disorders, Parkinson's disease, Huntington's Chorea, neurodegenerative disorders, mental illness such as schizophrenia, depression, epilepsy and memory retention.

Together the above-described data show a role for endogenous MCH and its cognate receptor MCH-R1 in the regulation of energy balance and response to stress. Accordingly, there is a strong rationale to develop new compounds that modulate MCH-R1 activity. It would be useful to provide small molecules that are effective as antagonists of MCH-R1 in order to treat metabolic disorders such as obesity, stress-related disorders, and the aforementioned diseases associated with MCH-R1 activity.

DESCRIPTION OF THE INVENTION

This invention provides a method of treating obesity and other disorders associated with the regulation of the MCH-R1 receptor. The method comprises administering to a patient a therapeutically effective amount of a compound of formula I:

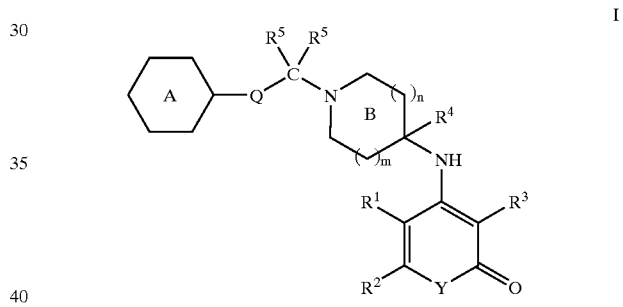

or a pharmaceutically-acceptable salt or prodrug thereof, wherein:

m is zero or one;

n is zero, one or two;

Ring A is selected from the group consisting of phenyl, $C_{3-8}$ carbocyclyl, 5–6 membered heteroaryl and 5–6 membered heterocyclyl, wherein said Ring A is optionally fused to a 5–7 membered saturated, unsaturated or partially unsaturated ring having 0–2 heteroatoms selected from N, O, or S, and wherein the Ring A system is substituted or unsubstituted;

Y is oxygen or —N($R^9$)—;

Q is absent or is a $C_{3-6}$ cycloalk-1,2-diyl, —CHN($R^8$)$_2$—, or a saturated or unsaturated carbon chain having 1–5 chain atoms, wherein each hydrogen-bearing carbon of said chain is optionally and independently substituted by a $C_{1-6}$ aliphatic group, and one saturated carbon of said chain along with the hydrogen atoms attached thereto is optionally replaced by —C($R^7$)$_2$—, —O—, —S—, —S(O)—, —S(O)$_2$—, or —N($R^8$)—;

$R^1$ is selected from R, —CN, $CO_2R$, —C(O)R, or —CON($R^8$)$_2$;

R is hydrogen, $C_{1-10}$ aliphatic, aryl, aralkyl, heteroaryl, heteroaralkyl, heterocyclyl or heterocyclylalkyl;

$R^2$ is selected from hydrogen, $C_{1-10}$ aliphatic, aryl, aralkyl, heteroaryl, heteroaralkyl, heterocyclyl, or heterocyclylalkyl, or $R^1$ and $R^2$ taken together with their intervening atoms form a fused, unsaturated or partially unsaturated, substituted or unsubstituted, 5–7 membered ring having 0–2 heteroatoms selected from O, N or S;

$R^3$ is selected from R, —CN, $CO_2R$, —C(O)R, —$CH_2N(R^8)_2$, or —C(O)N$(R^8)_2$;

$R^4$ is selected from hydrogen, $C_{1-10}$ aliphatic, —CN, —$CO_2R$, —C(O)R, or —C(O)N$(R^8)_2$;

each $R^5$ is independently selected from the group consisting of hydrogen, $C_{1-6}$ aliphatic, —CN, —$CO_2R$, —C(O)R, and —CON$(R^8)_2$, or two $R^5$ groups taken together with their intervening carbon form an optionally substituted 3–6 membered ring having 0–2 heteroatoms selected from O, N, or S;

Ring B is optionally substituted by one or more $R^6$;

each $R^6$ is independently selected from one or more $C_{1-6}$ aliphatic, hydroxyl, alkoxy, oxo, halo, —SR, —CN, —N$(R^8)_2$, —NHC(O)R, —N$(R^8)$CON$(R^8)_2$, —N$(R^8)$COR, —NHCO$_2(C_{1-8}$ aliphatic), —$CO_2R$, —C(O)R, —CON$(R^8)_2$, —S(O)$_2$R, —S(O)R, —SO$_2$N$(R^8)_2$, or —N$(R^8)$S(O)$_2$R, or two $R^6$ taken together with their intervening atoms form a 5–7 membered ring having 0–2 heteroatoms selected from N, O, or S;

each $R^7$ is independently selected from hydrogen, $C_{1-10}$ aliphatic, halo, —OR, —SR, —CN, —N$(R^8)_2$, —NHC(O)R, —N$(R^8)$CON$(R^8)_2$, —N$(R^8)$COR, —NHCO$_2$R—, —$CO_2R$, —C(O)R, —CON$(R^8)_2$, —S(O)$_2$R, —S(O)R, —SO$_2$N$(R^8)_2$, or —N$(R^8)$S(O)$_2$R, or two $R^7$ groups taken together form =O, =N—OR, =N—N$(R^8)_2$, =N—NHC(O)R, =N—NHCO$_2$R, or two $R^7$ groups taken together with their intervening carbon form an optionally substituted 3–6 membered ring having 0–2 heteroatoms selected O, N, or S;

each $R^8$ is independently selected from R, —$CO_2R$, —C(O)R, —C(O)N$(C_{1-6}$ aliphatic)$_2$, —C(O)NH$(C_{1-6}$ aliphatic), —S(O)$_2$R, —S(O)R, or —SO$_2$N$(C_{1-6}$ aliphatic)$_2$, —SO$_2$NH$(C_{1-6}$ aliphatic), or two $R^8$ groups on the same nitrogen taken together with the nitrogen form a 5–7 membered heterocyclyl ring; and $R^9$ is hydrogen, $C_{1-10}$ aliphatic, aralkyl, heteroaralkyl, or heterocyclylalkyl.

The term "aliphatic" as used herein means straight-chain, branched or cyclic $C_1$–$C_{12}$ hydrocarbons which are completely saturated or which contain one or more units of unsaturation but which are not aromatic. For example, suitable aliphatic groups include substituted or unsubstituted linear, branched or cyclic alkyl, alkenyl, alkynyl groups and hybrids thereof such as (cycloalkyl)alkyl, (cycloalkenyl) alkyl or (cycloalkyl)alkenyl. The terms "alkyl", "alkoxy", "hydroxyalkyl", "alkoxyalkyl", and "alkoxycarbonyl", used alone or as part of a larger moiety include both straight and branched chains containing one to twelve carbon atoms. The terms "alkenyl" and "alkynyl" used alone or as part of a larger moiety include both straight and branched chains containing two to twelve carbon atoms. The term "cycloalkyl" used alone or as part of a larger moiety include cyclic $C_3$–$C_{12}$ hydrocarbons which are completely saturated or which contain one or more units of unsaturation, but which are not aromatic. The term "alkoxy" refers to an —O-alkyl radical.

The terms "haloalkyl", "haloalkenyl" and "haloalkoxy" mean alkyl, alkenyl or alkoxy, as the case may be, substituted with one or more halogen atoms. The term "halogen" means F, Cl, Br, or I.

The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0–3 heteroatoms selected from oxygen, sulfur or nitrogen, the nitrogen may be N (as in 3,4-dihydro-2H-pyrrolyl), NH (as in pyrrolidinyl) or NR+ (as in N-substituted pyrrolidinyl).

The term "carbocycle", "carbocyclyl", "carbocyclo", or "carbocyclic" as used herein means an aliphatic ring system having three to fourteen members. The term "carbocycle", "carbocyclyl", "carbocyclo", or "carbocyclic" whether saturated or partially saturated, also refers to rings that are optionally substituted. The term "carbocycle", "carbocyclyl", "carbocyclo", or "carbocyclic" also includes aliphatic rings that are fused to one or more aromatic or nonaromatic rings, such as in a decahydronaphthyl or tetrahydronaphthyl, where the radical or point of attachment is on the aliphatic ring.

The term "aryl" used alone or as part of a larger moiety as in "aralkyl", "aralkoxy", or "aryloxyalkyl", refers to mono-, bi-, or tricyclic aromatic hydrocarbon ring systems having five to fourteen members, such as phenyl, benzyl, phenethyl, 1-naphthyl, 2-naphthyl, 1-anthracyl and 2-anthracyl. The term "aryl" also refers to rings that are optionally substituted. The term "aryl" may be used interchangeably with the term "aryl ring". "Aryl" also includes fused polycyclic aromatic ring systems in which an aromatic ring is fused to one or more rings. Examples include 1-naphthyl, 2-naphthyl, 1-anthracyl and 2-anthracyl. Also included within the scope of the term "aryl", as it is used herein, is a group in which an aromatic ring is fused to one or more non-aromatic rings, such as in an indanyl, phenanthridinyl, or tetrahydronaphthyl, where the radical or point of attachment is on the aromatic ring. The term "aralkyl" refers to an alkyl group substituted by an aryl. Examples of aralkyl groups include, but are not limited to, benzyl and phenethyl.

The term "heterocycle", "heterocyclyl", or "heterocyclic" unless otherwise indicated includes non-aromatic ring systems having five to fourteen members, preferably five to ten, in which one or more ring carbons, preferably one to four, are each replaced by a heteroatom such as N, O, or S. Examples of heterocyclic rings include 3–1H-benzimidazol-2-one, (1-substituted)-2-oxo-benzimidazol-3-yl, 2-tetrahydrofuranyl, 3-tetrahydrofuranyl, 2-tetrahydropyranyl, 3-tetrahydropyranyl, 4-tetrahydropyranyl, [1,3]-dioxalanyl, [1,3]-dithiolanyl, [1,3]-dioxanyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxanyl, benzopyrrolidinyl, benzopiperidinyl, benzoxolanyl, benzothiolanyl, and benzothianyl. Also included within the scope of the term "heterocyclyl" or "heterocyclic", as it is used herein, is a group in which a non-aromatic heteroatom-containing ring is fused to one or more aromatic or non-aromatic rings, such as in an indolinyl, chromanyl, phenanthridinyl, or tetrahydroquinolinyl, where the radical or point of attachment is on the non-aromatic heteroatom-containing ring. The term "heterocycle", "heterocyclyl", or "heterocyclic" whether saturated or partially unsaturated, also refers to rings that are optionally substituted. The term "heterocyclylalkyl" refers to an alkyl group substituted by a heterocyclyl.

The term "heteroaryl", used alone or as part of a larger moiety as in "heteroaralkyl" or "heteroarylalkoxy", refers to heteroaromatic ring groups having five to fourteen members, preferably five to ten, in which one or more ring carbons, preferably one to four, are each replaced by a heteroatom such as N, O, or S. Examples of heteroaryl rings include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 1-pyrazolyl, 3-pyrazolyl, 4-pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indazolyl, isoindolyl, acridinyl, or benzoisoxazolyl. Also included within the scope of the term "heteroaryl", as it is used herein, is a group in which a heteroaromatic ring is fused to one or more aromatic or nonaromatic rings where the radical or point of attachment is on the heteroaromatic ring. Examples include tetrahydroquinolinyl, tetrahydroisoquinolinyl, and pyrido[3,4-d]pyrimidinyl. The term "heteroaryl" also refers to rings that are optionally substituted. The term "heteroaryl" may be used interchangeably with the term "heteroaryl ring" or the term "heteroaromatic". The term "heteroaralkyl" refers to an alkyl group substituted by a heteroaryl.

The term "linker group" or "linker" means an organic moiety that connects two parts of a compound. Linkers are typically comprised of an atom such as oxygen or sulfur, a unit such as —NH—, —CH$_2$—, —C(O)—, —C(O)NH—, or a chain of atoms, such as an alkylidene chain. The molecular mass of a linker is typically in the range of about 14 to 200, preferably in the range of 14 to 96 with a length of up to about six atoms. Examples of linkers include a saturated or unsaturated C$_{1-6}$ alkylidene chain which is optionally substituted, and wherein one or two saturated carbons of the chain are optionally replaced by —C(O)—, —C(O)C(O)—, —CONH—, —CONHNH—, —CO$_2$—, —OC(O)—, —NHCO$_2$—, —O—, —NHCONH—, —OC(O)NH—, —NHNH—, —NHCO—, —S—, —SO—, —SO$_2$—, —NH—, —SO$_2$NH—, or —NHSO$_2$—.

The term "alkylidene chain" refers to an optionally substituted, straight or branched carbon chain that may be fully saturated or have one or more units of unsaturation. The optional substituents are as described above for an aliphatic group.

An aryl (including the aryl moiety in aralkyl, aralkoxy, aryloxyalkyl and the like) or heteroaryl (including the heteroaryl moiety in heteroaralkyl and heteroarylalkoxy and the like) group may contain one or more substituents. Examples of suitable substituents on the unsaturated carbon atom of an aryl or heteroaryl group include a halogen, —R*, —OR*, —SR*, 1,2-methylene-dioxy, 1,2-ethylenedioxy, protected OH (such as acyloxy), phenyl (Ph), substituted Ph, —O(Ph), substituted —O(Ph), —CH$_2$(Ph), substituted —CH$_2$(Ph), —CH$_2$CH$_2$(Ph), substituted —CH$_2$CH$_2$(Ph), —NO2, —CN, —N(R*)$_2$, —NR*C(O)R*, —NR*C(O)N(R*)$_2$, —NR*CO$_2$R*, —NR*NR*C(O)R*, —NR*NR*C(O)N(R*)$_2$, —NR*NR*CO$_2$R*, —C(O)C(O)R*, —C(O)CH$_2$C(O)R*, —CO$_2$R*, —C(O)R*, —C(O)N(R*)$_2$, —OC(O)N(R*)$_2$, —S(O)$_2$R*, —SO$_2$N(R*)$_2$, —S(O)R*, —NR*SO$_2$N(R*)$_2$, —NR*SO$_2$R*, —C(=S)N(R*)$_2$, —C(=NH)—N(R*)$_2$, —(CH$_2$)$_y$NHC(O)R*, —(CH$_2$)$_y$NHC(O)CH(Y—R*)(R*); wherein R* is hydrogen, a substituted or unsubstituted aliphatic group, an unsubstituted heteroaryl or heterocyclic ring, phenyl (Ph), substituted Ph, —O(Ph), substituted —O(Ph), —CH$_2$(Ph), or substituted —CH$_2$(Ph); y is 0–6; and Y is a linker group. Examples of substituents on the aliphatic group or the phenyl ring of R* include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

An aliphatic group or a non-aromatic heterocyclic ring may contain one or more substituents. Examples of suitable substituents on the saturated carbon of an aliphatic group or of a non-aromatic heterocyclic ring include those listed above for the unsaturated carbon of an aryl or heteroaryl group and the following: =O, =S, =NNHR*, =NN(R*)$_2$, =N—, =NNHC(O)R*, =NNHCO$_2$(alkyl), =NNHSO$_2$(alkyl), or =NR*, where each R* is independently selected from hydrogen, an unsubstituted aliphatic group or a substituted aliphatic group. Examples of substituents on the aliphatic group include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

Suitable substituents on the nitrogen of a non-aromatic heterocyclic ring include —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, and —NR$^+$SO$_2$R$^+$; wherein R$^+$ is hydrogen, an unsubstituted aliphatic group, a substituted aliphatic group, phenyl (Ph), substituted Ph, —O(Ph), substituted —O(Ph), CH$_2$(Ph), substituted CH$_2$(Ph), or an unsubstituted heteroaryl or heterocyclic ring. Examples of substituents on the aliphatic group or the phenyl ring include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

It will be apparent to one skilled in the art that certain compounds of this invention may exist in tautomeric forms, all such tautomeric forms of the compounds being within the scope of the invention. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structure except for the replacement of a hydrogen by a deuterium or tritium, or the replacement of a carbon by a $^{13}$C- or $^{14}$C-enriched carbon are within the scope of this invention.

The term "Ring A system" means Ring A alone or a polycyclic ring system containing Ring A that is formed when Ring A is fused to a 5–7 membered saturated, unsaturated or partially unsaturated ring having 0–2 heteroatoms selected from N, O, or S. Representative examples of the Ring A polycyclic ring system include, but not limited to, the following: 3-quinolyl, 3-isoquinolyl, 3-quinolin-2(1H)-one-yl, 2H-chromen-2-one-3-yl, 2H-chromene-3-yl, 1H-indole-2-yl, 1-benzothiophene-2-yl, 1-benzofuran-2-yl, 1H-benzimidazole-2-yl, 1,3-benzothiazole-2-yl, 1,3-benzoxazole-2-yl, naphthalen-2-yl, 1,2,3,4-tetrahydronaphthalen-2-yl, 2,3-dihydro-1,4-benzodioxin-6- yl, 1,3-benzodioxol-5-yl, quinolin-4-yl, isoquinoline-4-yl, quinolin-2(1H)-one-4-yl, 2H-chromen-2-one-4-yl, chromane-4-yl, 1H-indol-3yl, benzothiophene-3-yl, benzofuran-3-yl, 1H-benzimidazole-1-yl, naphthyl-1-yl, 1,3-benzodioxol-4-yl, 2,3-dihydro-1,4-benzodioxin-5-yl, benzofuran-5-yl, and benzofuran-6-yl.

Preferred examples of the Ring A system as a bicyclic ring system are shown in Table 1 below. It would be apparent to one skilled in the art that the points of attachment on each of these ring systems may be moved to other positions in order to provide further examples of the present compounds. As an illustration, moving the point of attachment in the quinolinyl systems A-1 and A-16 provides the following other moieties: quinolin-2-yl, quinolin-5-yl, quinolin-6-yl, quinolin-7-yl and quinolin-8-yl. When Ring A is monocyclic, a preferred Ring A is phenyl.

TABLE 1

Examples of the Bicyclic Ring A System

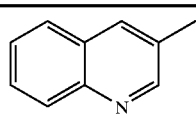

A-1

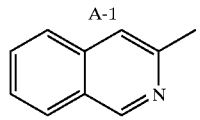

A-2

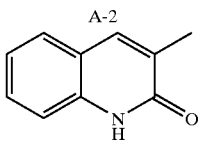

A-3

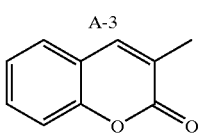

A-4

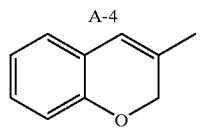

A-5

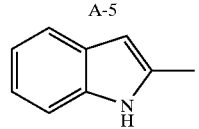

A-6

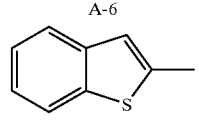

A-7

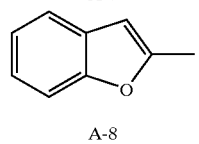

A-8

TABLE 1-continued

Examples of the Bicyclic Ring A System

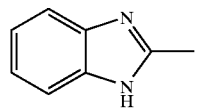

A-9

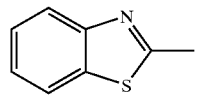

A-10

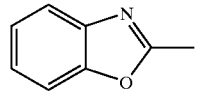

A-11

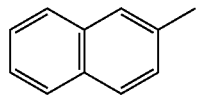

A-12

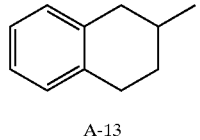

A-13

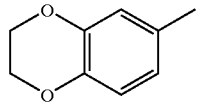

A-14

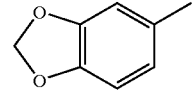

A-15

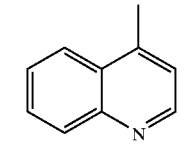

A-16

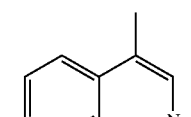

A-17

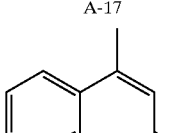

A-18

TABLE 1-continued

Examples of the Bicyclic Ring A System

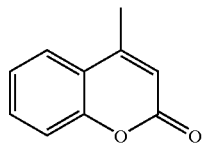

A-19

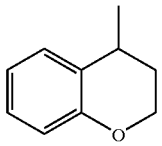

A-20

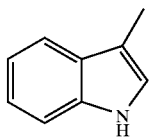

A-21

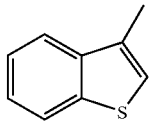

A-22

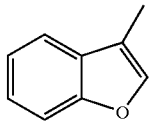

A-23

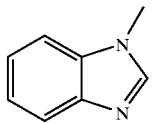

A-24

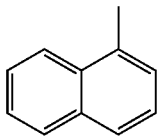

A-25

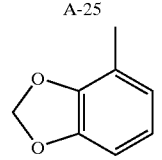

A-26

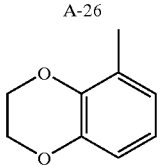

A-27

TABLE 1-continued

Examples of the Bicyclic Ring A System

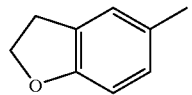

A-28

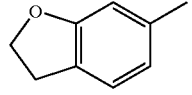

A-29

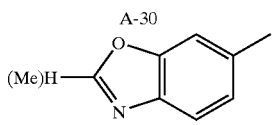

A-30

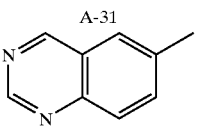

A-31

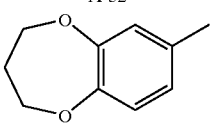

A-32

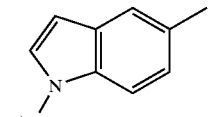

A-33

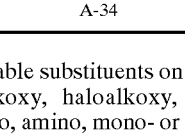

A-34

Examples of suitable substituents on Ring A include halo, $C_{1-6}$ aliphatic, alkoxy, haloalkoxy, $C_{1-6}$ haloaliphatic, alkylcarbonyl, cyano, amino, mono- or dialkylamino, mono- or dialkylaminocarbonyl, aminocarbonyl, alkoxycarbonyl, alkoxycarbonylamino, mono- or dialkylaminosulfonyl, aminosulfonyl, alkylsulfonyl, carboxy, carboxyalkyl, phenyl, phenalkyl, 5–8 membered heteroaryl or heteroaralkyl, 3–8 membered heterocyclyl or heterocyclylalkyl, cyanoalkyl, aminoalkyl, mono- or dialkylaminoalkyl, alkoxycarbonylalkyl, thioalkyl, and alkoxysulfonyl. It is preferred that the alkyl moieties of the Ring A substituents have 1–6 carbons. The alkyl moieties may be interrupted by a heteroatom selected from NH, N(alkyl), O, S, $SO_2$, or a carbonyl. When Ring A is a phenyl ring, examples of particular substituted phenyl groups include 4-chlorophenyl, 3-acetylphenyl, 4-acetylphenyl and 4-fluoro-3-methoxyphenyl.

For compounds of formula I, a preferred Y is oxygen or —N($R^9$)— where $R^9$ is hydrogen, $C_{1-6}$ alkyl, 2,2,2-trifluoroethyl, benzyl, $CH_2$-imidazolyl, $CH_2$-thiazolyl, $CH_2$-thienyl and $CH_2$-pyridyl.

In one embodiment, $R^1$ and $R^2$ are each, independently, hydrogen or $C_{1-10}$ aliphatic. In a preferred embodiment $R^1$ and $R^2$ are taken together with their intervening atoms to form a fused benzo ring. The benzo ring so formed may be substituted or unsubstituted. Examples of preferred substituents on the benzo ring, when present, include halo, alkoxy, aliphatic, haloalkoxy, haloaliphatic, aryl, aralkyl, 5–6 membered heteroaryl, alkylcarbonyl, alkylcarboxy, amino, mono- or dialkylamino, alkoxycarbonyl, cyano, aminocarbonyl, mono- or dialkylaminocarbonyl, alkylsulfonyl, alkoxycarbonylamino, and mono- or dialkylaminosulfonyl. When $R^1$ and $R^2$ form a benzo ring, the 6-position is a preferred position of substitution on either the resulting coumarin ring (where Y is oxygen,) or quinolinone ring (where Y is nitrogen).

$R^3$ is preferably hydrogen, halo, $C_{1-10}$ aliphatic, —CN, —$CO_2R$, —C(O)R, or —CON($R^8$)$_2$ or heterocyclyl.

$R^4$ is preferably hydrogen, $C_{1-6}$ aliphatic, —CN, —$CO_2R$, —C(O)R, or —CON($R^8$)$_2$. More preferably $R^4$ is hydrogen or $C_{1-3}$ aliphatic, and most preferably $R^4$ is hydrogen.

Ring B is optionally substituted by one or more $R^6$. The $R^6$ substituent may be independently selected from one or more $C_{1-6}$ aliphatic, hydroxyl, alkoxy, =O, halo, —SR, —CN, —N($R^8$)$_2$, —NHC(O)R, —N($R^8$)CON($R^8$)$_2$, —N($R^8$)COR, —NHCO$_2$R, —CO$_2$R, —C(O)R, —CON($R^8$)$_2$, —S(O)$_2$R, —S(O)R, —SO$_2$N($R^8$)$_2$, or —N($R^8$)S(O)$_2$R, or two $R^6$ taken together with their intervening atoms form a 5–7 membered ring having 0–2 heteroatoms selected from N, O, or S. Ring B is preferably a piperidine ring (where m is one and n is one). The piperidine ring is preferably unsubstituted or substituted with one or more $C_{1-6}$ aliphatic groups, or two $R^6$ groups are taken together to form a ring. An 8-aza-bicyclo[3.2.1]octane is an example of a Ring B piperidine where two $R^6$ groups are taken together. The aza-bicyclooctane may be exo or endo, with the exo configuration preferred.

It is preferred that each $R^5$ is independently selected from hydrogen or $C_{1-6}$ aliphatic, particularly methyl.

Q is preferably absent or —CH=CH— wherein the vinylic hydrogen closest to Ring B is optionally replaced by an alkyl or halo group. More preferably Q is absent or —CH=CH—.

Preferred examples of the Ring A system wherein Ring A is a monocyclic ring include substituted or unsubstituted phenyl or a 5–6 membered heteroaryl or heterocyclyl ring, such as pyridyl, furanyl, thienyl, or pyrrolyl, that is optionally fused to a 5–6 membered aromatic ring having 0–2 heteroatoms. More preferred Ring A monocyclic rings are phenyl and furanyl.

One embodiment of the invention relates to a method of treating an MCH-R1-mediated disease comprising administering to a subject a compound of formula I having one or more features selected from the group consisting of: (a) m is one and n is one; (b) Ring A is a phenyl or a 5–6 membered heteroaryl or heterocyclyl ring that is optionally fused to a 5–6 membered aromatic ring having 0–2 heteroatoms; (c) Q is absent or —CH=CH—; (d) $R^1$ and $R^2$ are taken together with their intervening atoms to form a fused benzo ring; (e) Y is oxygen, —NH—, —N(CH$_3$)—, —N(CH$_2$CF$_3$)—, or —N(CH$_2$-pyridyl)-; (f) $R^3$ is hydrogen, cyano, fluoro, $CO_2R$, or C(O)N($R^8$)$_2$; (g) $R^4$ is hydrogen; and (h) each $R^5$ is independently selected from hydrogen or CH$_3$. A more preferred method of this invention relates to the use of compounds of formula I having all of these features.

One embodiment of this invention relates to compounds of formula I wherein Q is absent providing compounds of formula II:

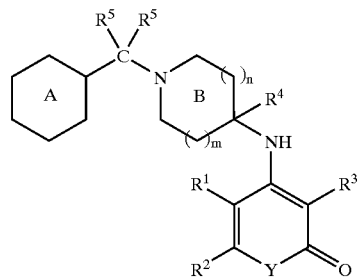

wherein $R^1$, $R^2$, $R^3$, $R^4$, $R^5$, Y, m, n, Ring A and Ring B are as described above.

Representative examples of compounds of formula II where Y is oxygen are shown in Table 2.

TABLE 2

Examples of Compounds of Formula II (Y is oxygen)

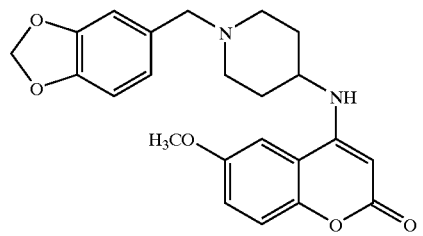

II-1

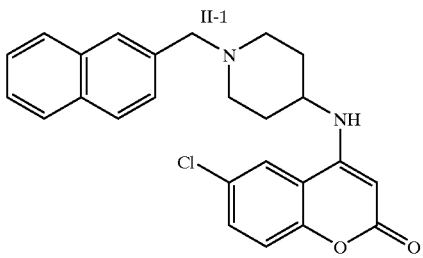

II-2

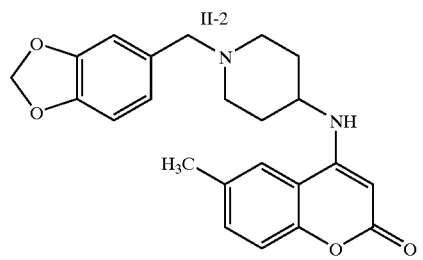

II-3

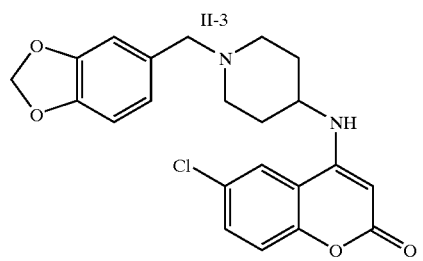

II-4

TABLE 2-continued
Examples of Compounds of Formula II (Y is oxygen)
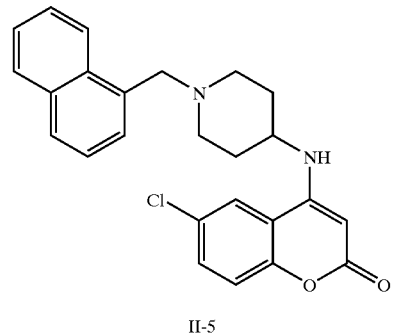
II-5
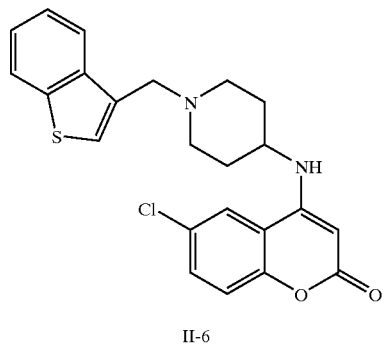
II-6
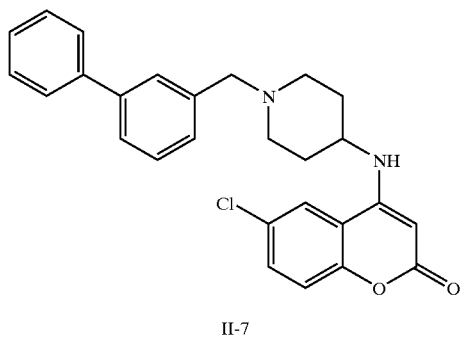
II-7
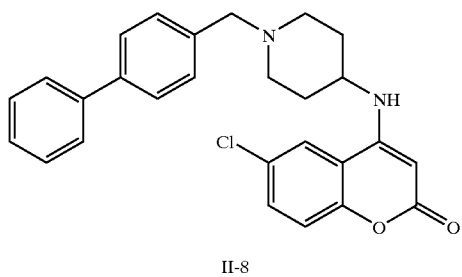
II-8
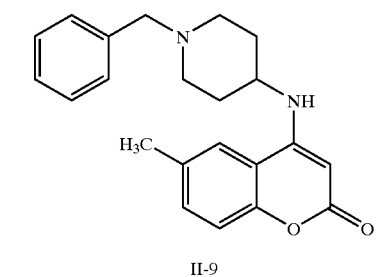
II-9
TABLE 2-continued
Examples of Compounds of Formula II (Y is oxygen)
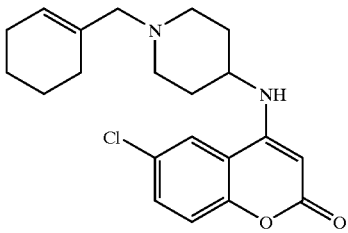
II-10
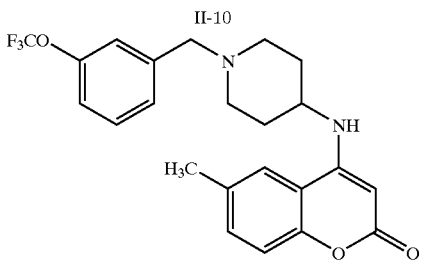
II-11
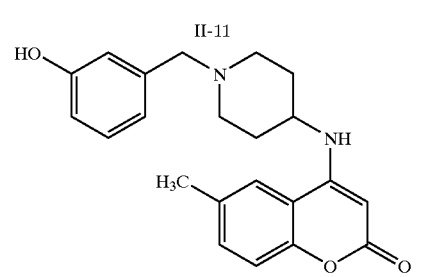
II-12
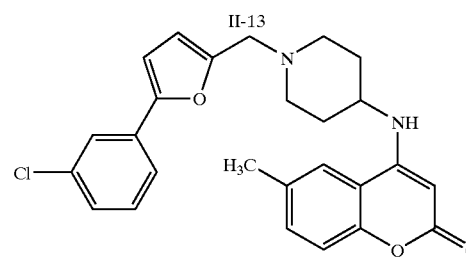
II-13
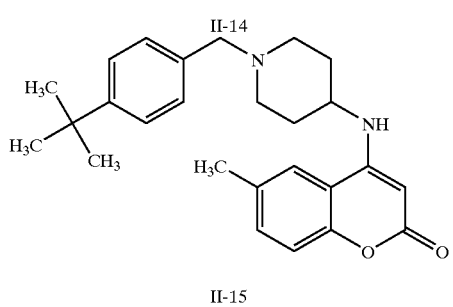
II-14
II-15

TABLE 2-continued
Examples of Compounds of Formula II (Y is oxygen)
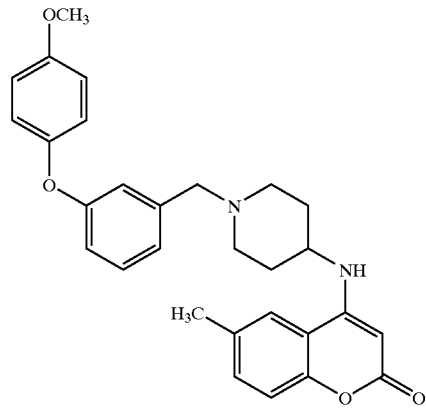
II-16
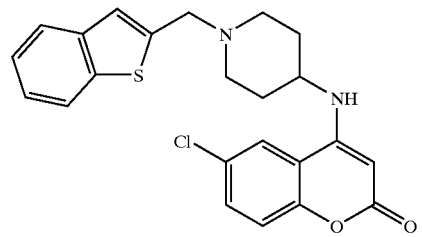
II-17
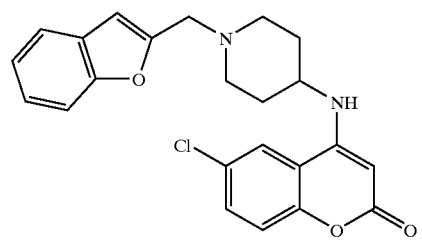
II-18
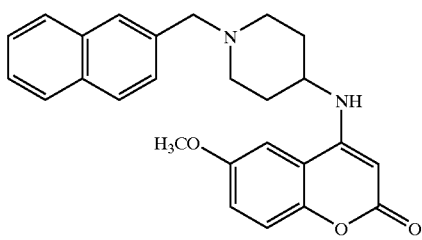
II-19
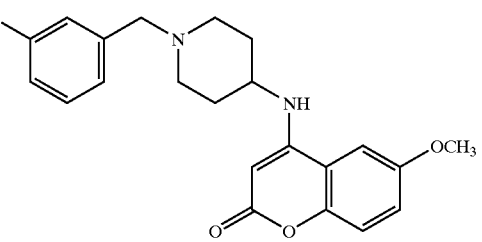
II-20
TABLE 2-continued
Examples of Compounds of Formula II (Y is oxygen)
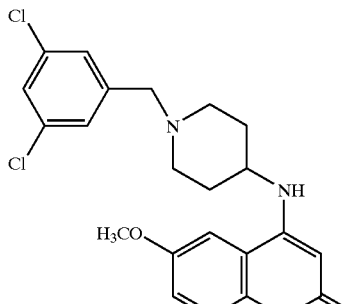
II-21
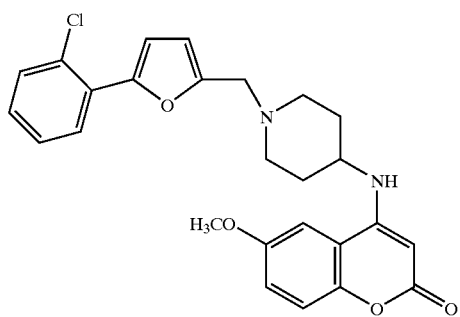
II-22
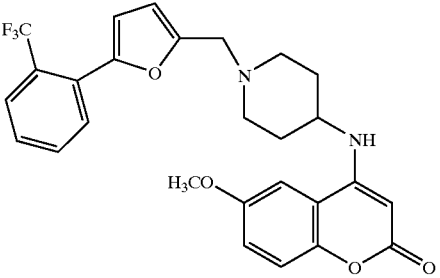
II-23
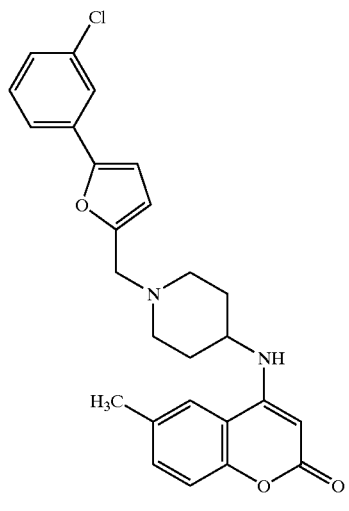
II-24

TABLE 2-continued
Examples of Compounds of Formula II (Y is oxygen)
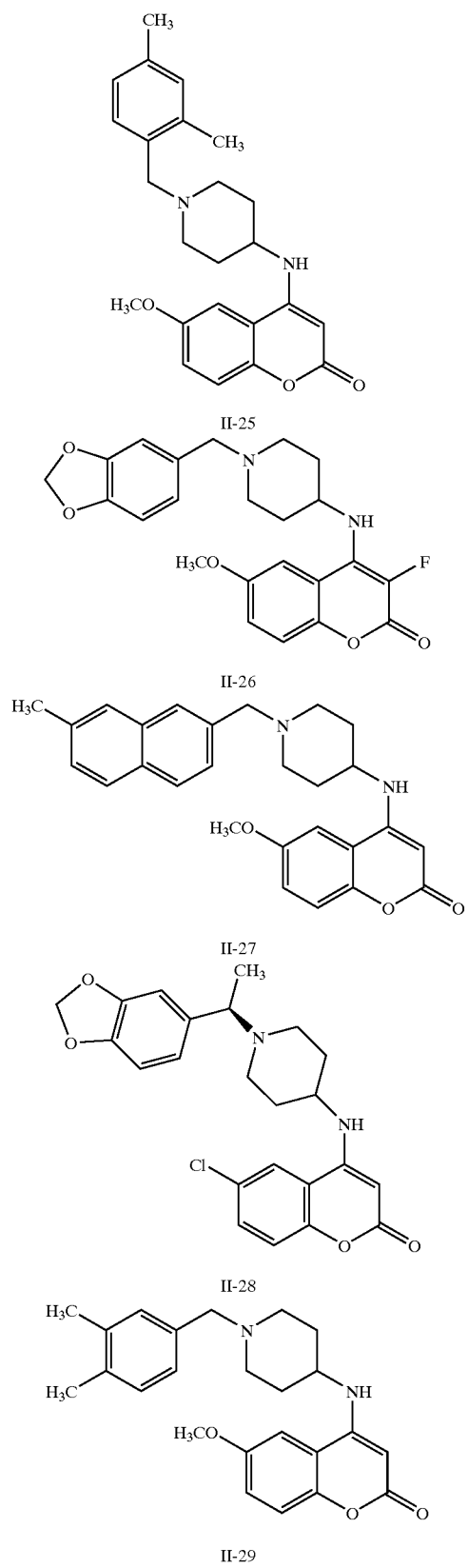
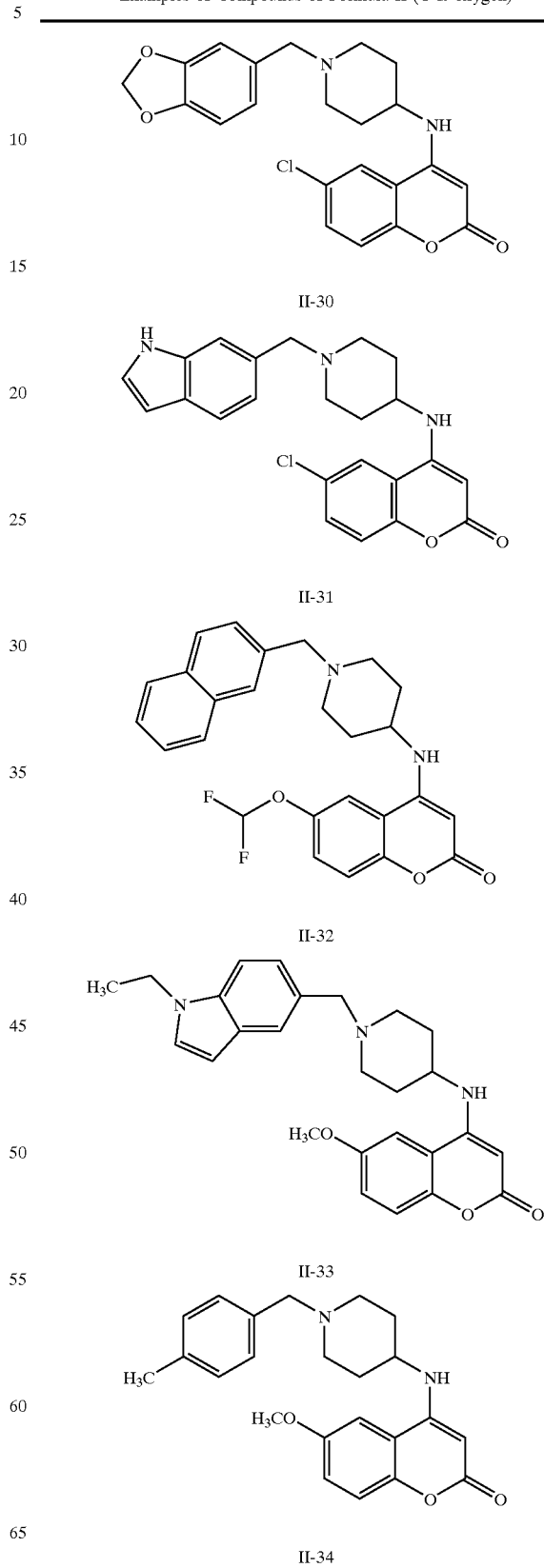

TABLE 2-continued
Examples of Compounds of Formula II (Y is oxygen)
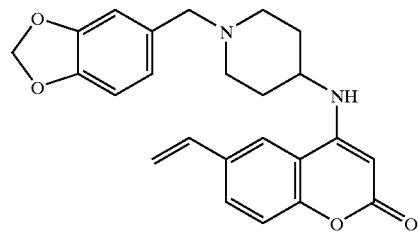
II-35
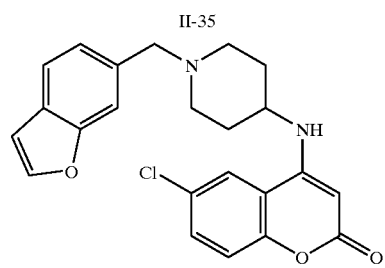
II-36
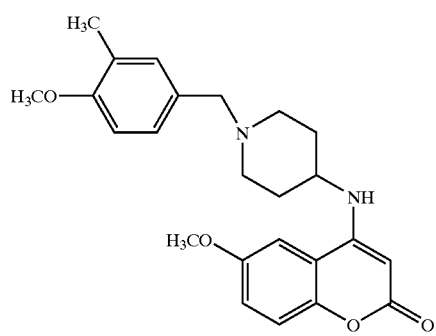
II-37
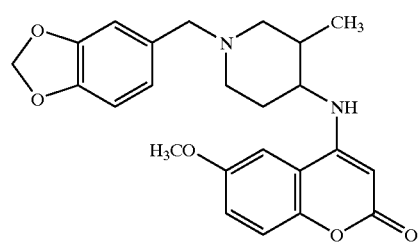
II-38
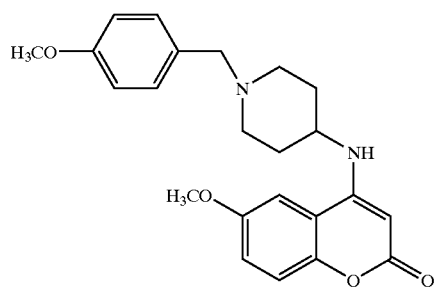
II-39
TABLE 2-continued
Examples of Compounds of Formula II (Y is oxygen)
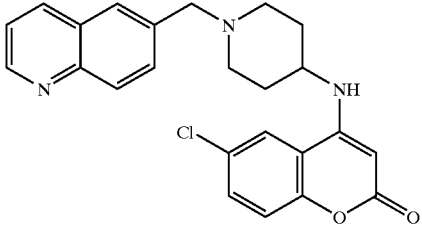
II-40
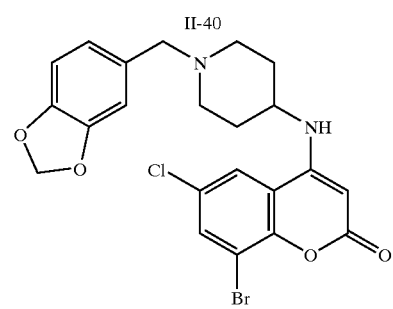
II-41
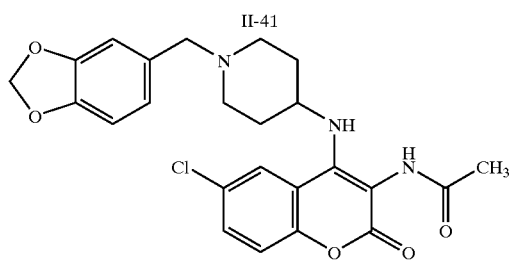
II-42
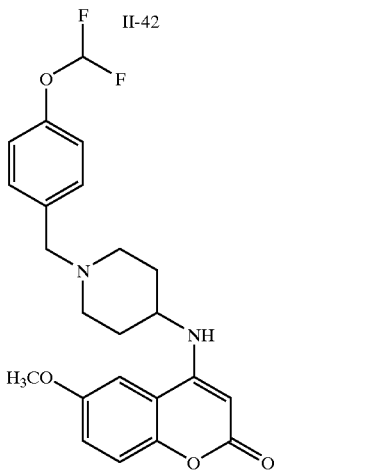
II-43
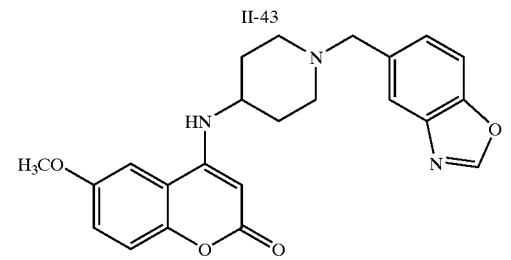
II-44

TABLE 2-continued
Examples of Compounds of Formula II (Y is oxygen)
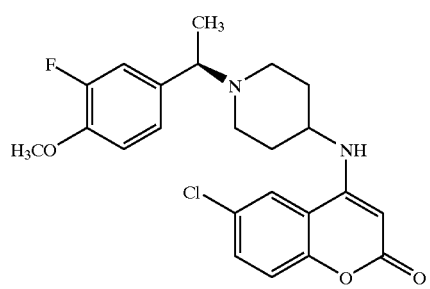
II-45
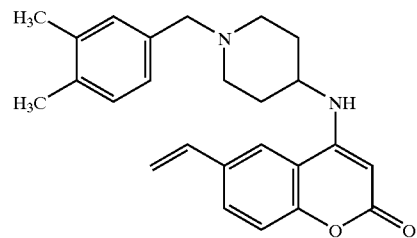
II-46
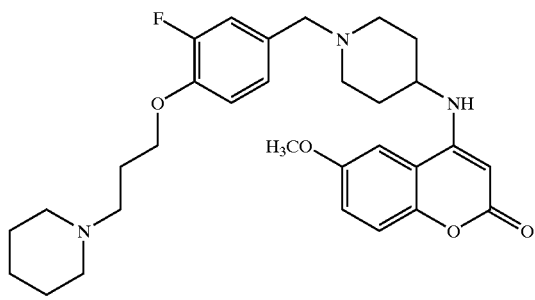
II-47
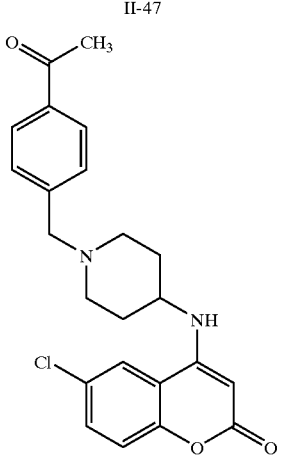
II-48
TABLE 2-continued
Examples of Compounds of Formula II (Y is oxygen)
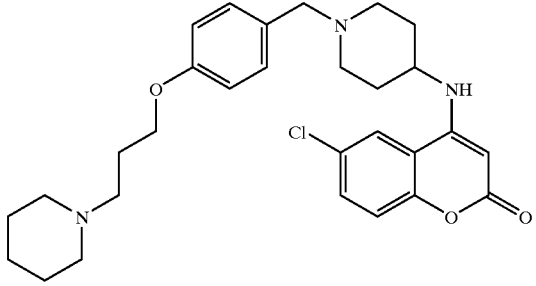
II-49
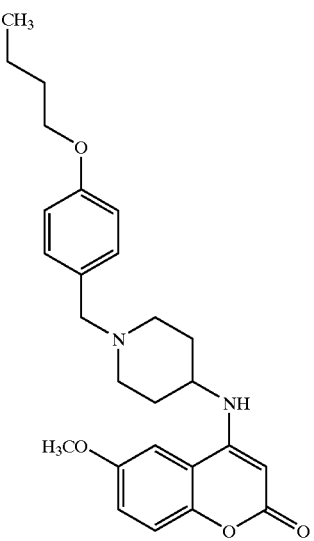
II-50
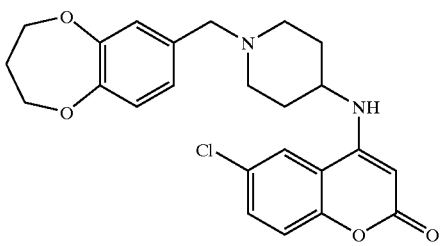
II-51
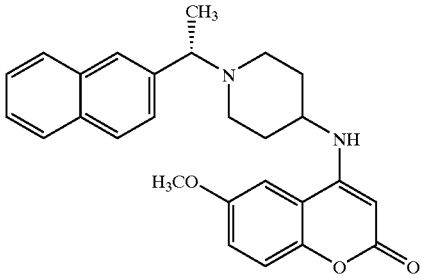
II-52

TABLE 2-continued
Examples of Compounds of Formula II (Y is oxygen)
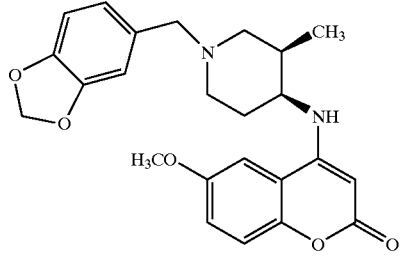
II-53
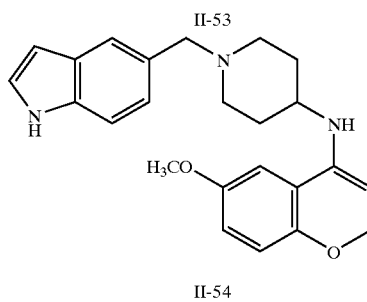
II-54
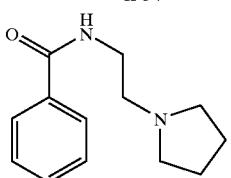
II-55
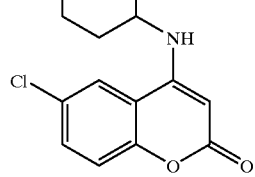
II-56
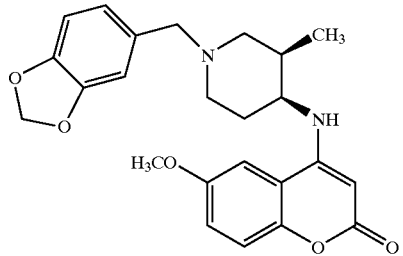
II-57
TABLE 2-continued
Examples of Compounds of Formula II (Y is oxygen)
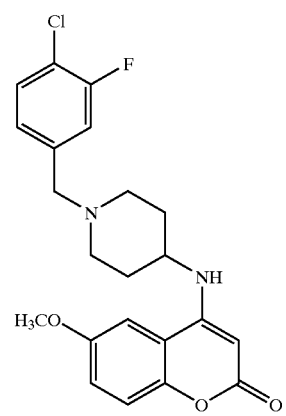
II-58
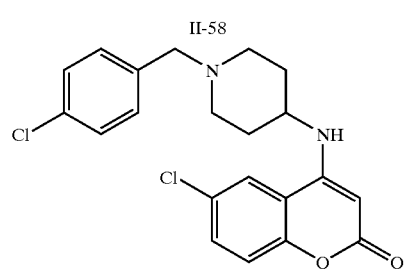
II-59
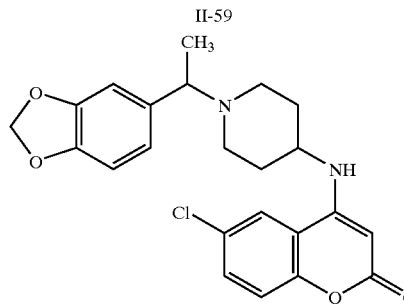
II-60
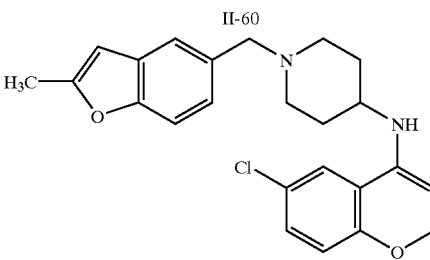
II-61
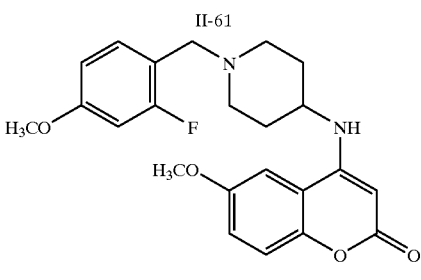
II-62

TABLE 2-continued
Examples of Compounds of Formula II (Y is oxygen)
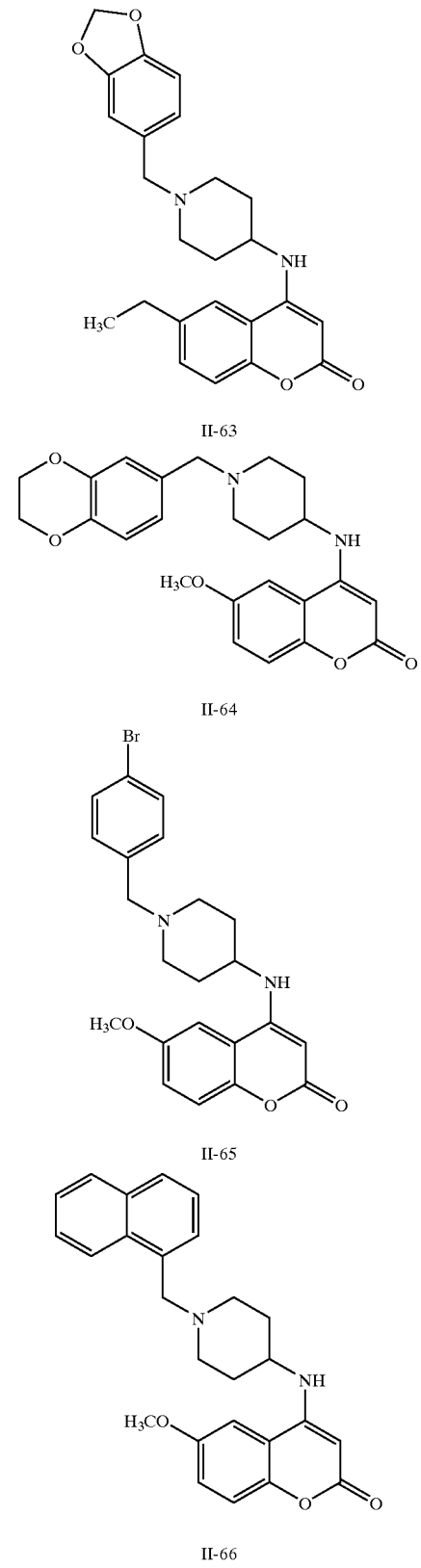
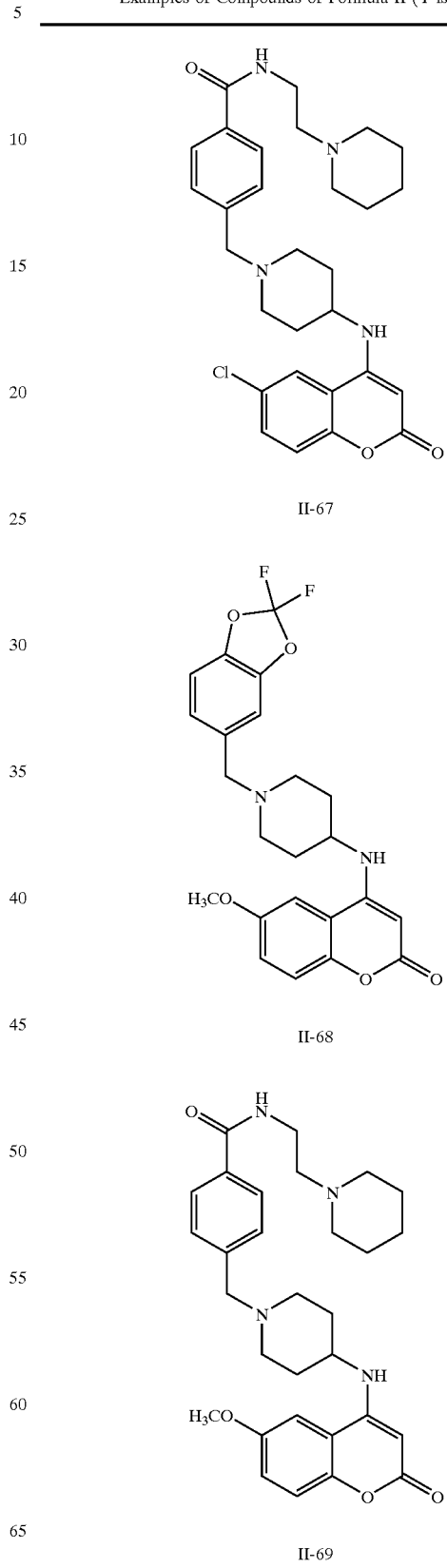

TABLE 2-continued
Examples of Compounds of Formula II (Y is oxygen)
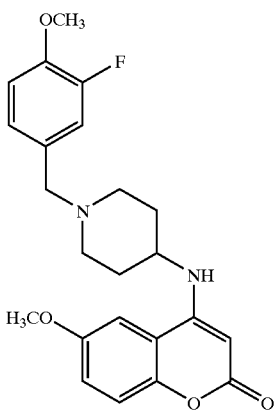
II-70
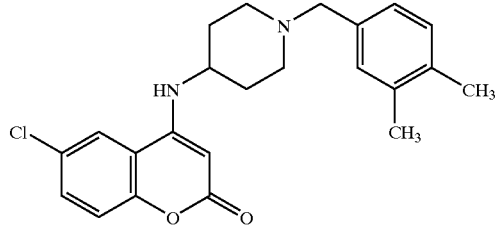
II-71
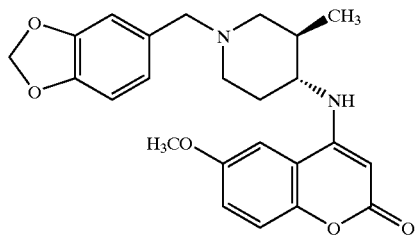
II-72
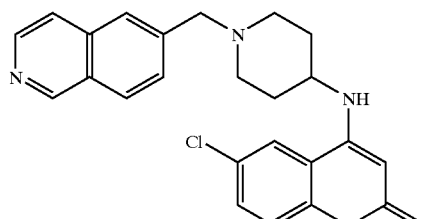
II-73
TABLE 2-continued
Examples of Compounds of Formula II (Y is oxygen)
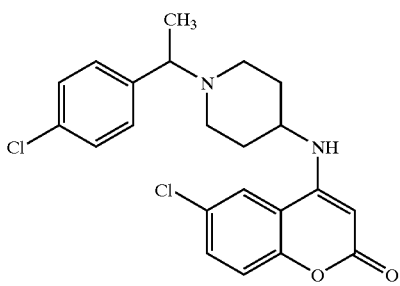
II-74
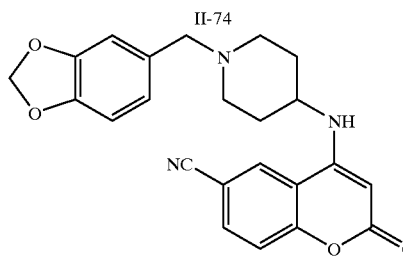
II-75
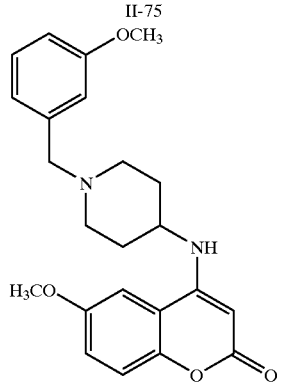
II-76
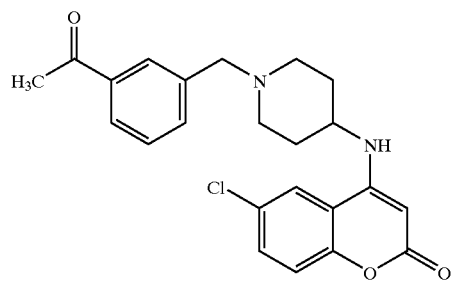
II-77
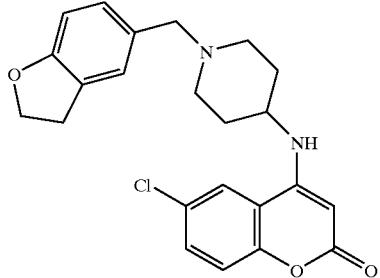
II-78

TABLE 2-continued
Examples of Compounds of Formula II (Y is oxygen)
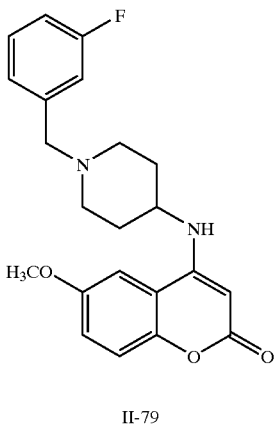
II-79
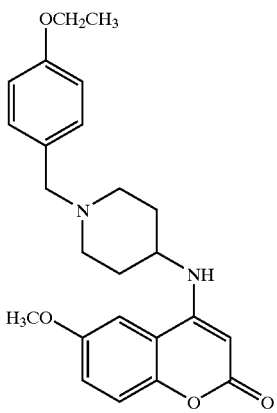
II-80
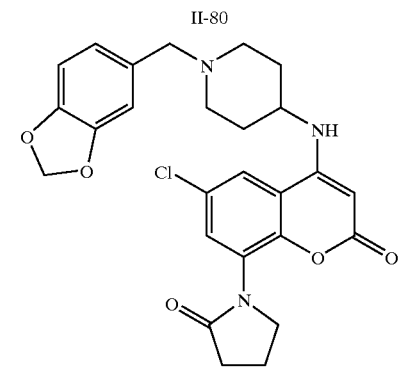
II-81
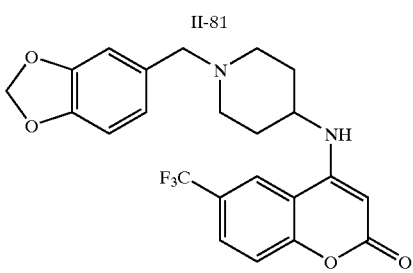
II-82
TABLE 2-continued
Examples of Compounds of Formula II (Y is oxygen)
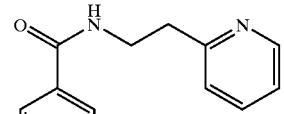
II-83
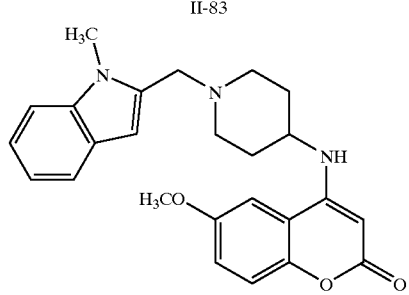
II-84
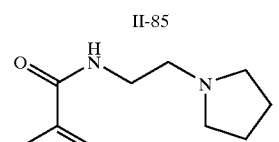
II-85
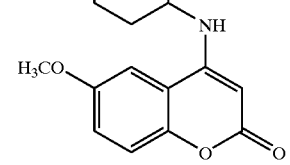
II-86

TABLE 2-continued
Examples of Compounds of Formula II (Y is oxygen)
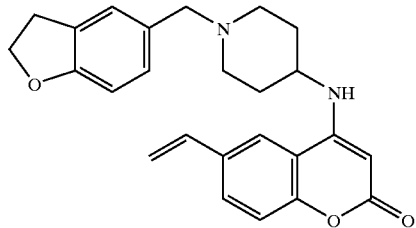
II-87
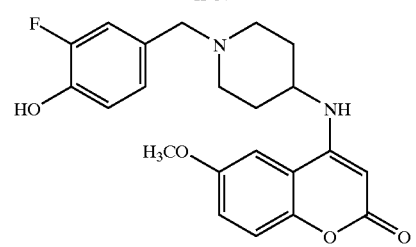
II-88
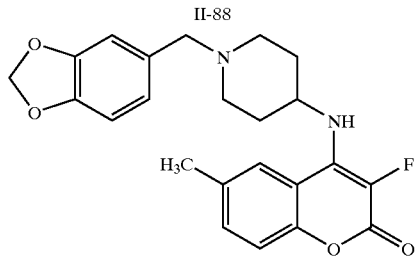
II-89
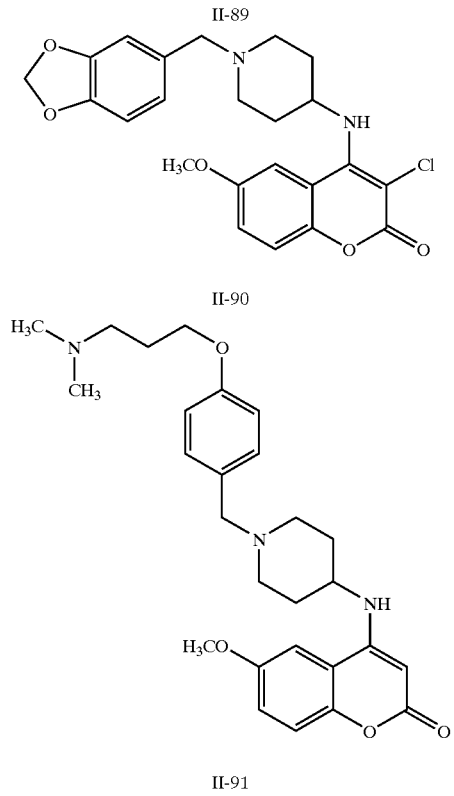
II-90
II-91
TABLE 2-continued
Examples of Compounds of Formula II (Y is oxygen)
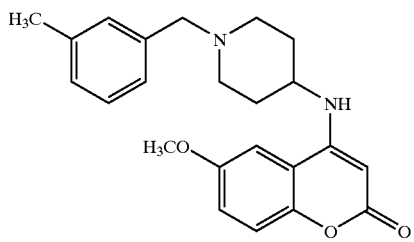
II-92
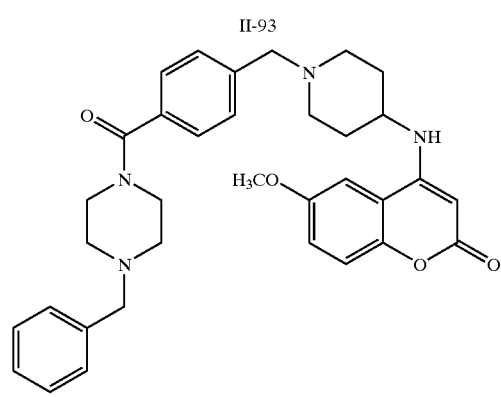
II-93
II-94
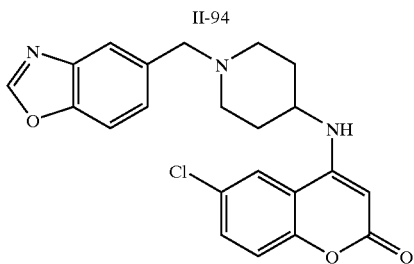
II-95
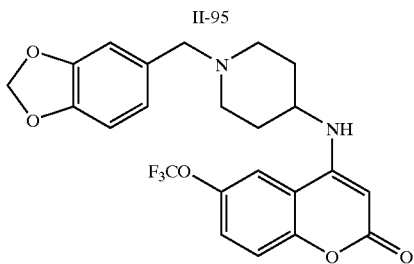
II-96

TABLE 2-continued
Examples of Compounds of Formula II (Y is oxygen)
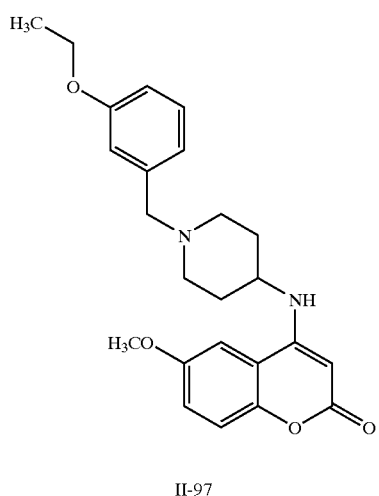
II-97
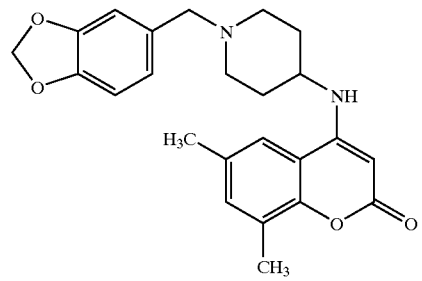
II-98
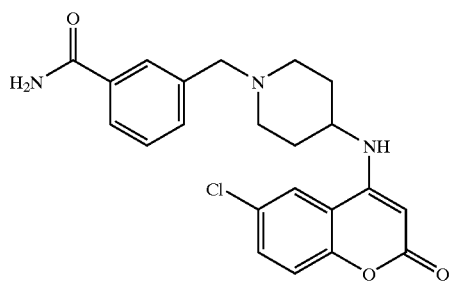
II-99
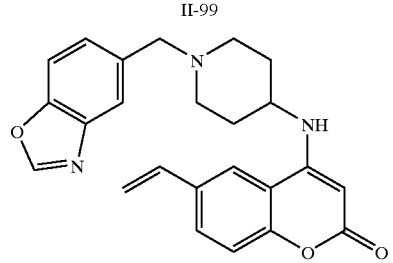
II-100
TABLE 2-continued
Examples of Compounds of Formula II (Y is oxygen)
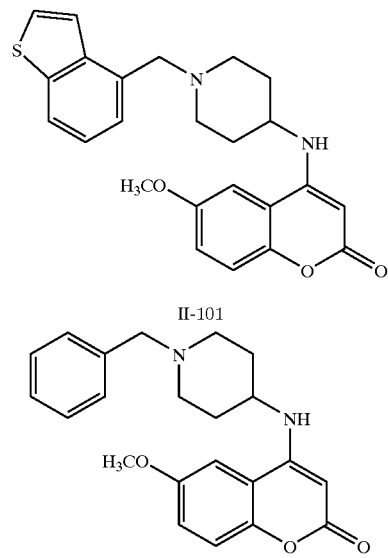
II-101
II-102
II-103
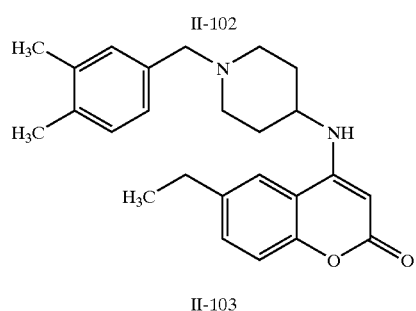
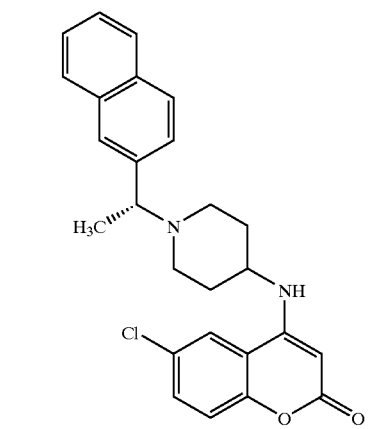
II-104
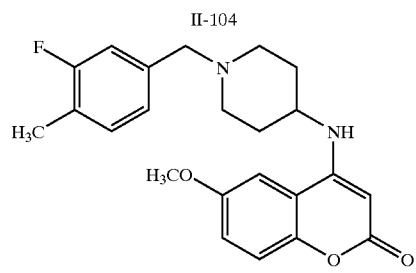
II-105

TABLE 2-continued
Examples of Compounds of Formula II (Y is oxygen)
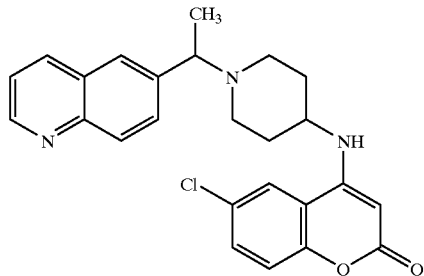
II-106
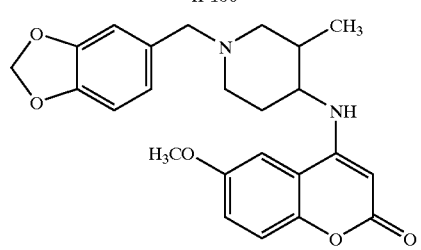
II-107
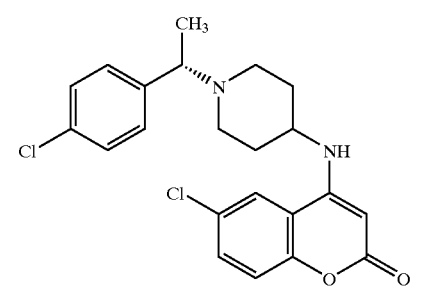
II-108
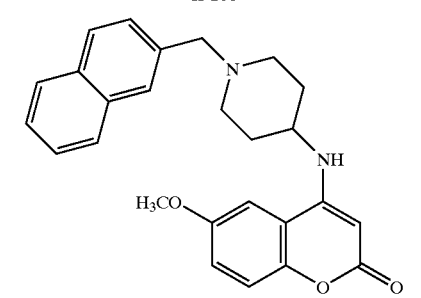
II-109
TABLE 2-continued
Examples of Compounds of Formula II (Y is oxygen)
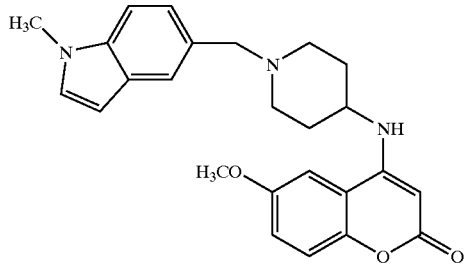
II-111
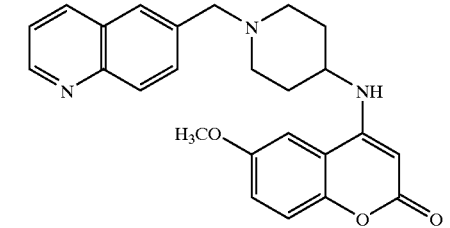
II-112
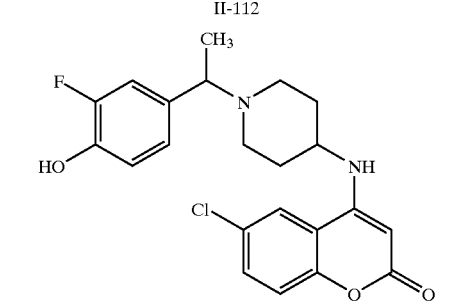
II-113
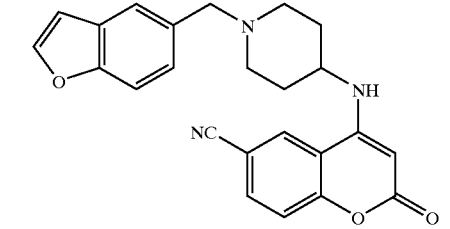
II-114
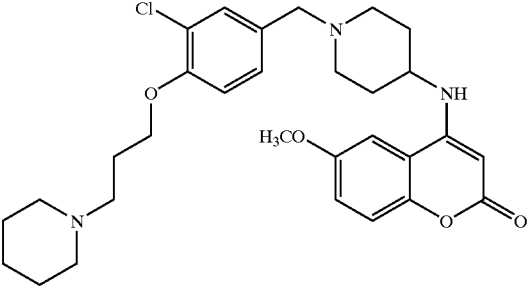
II-115

TABLE 2-continued
Examples of Compounds of Formula II (Y is oxygen)
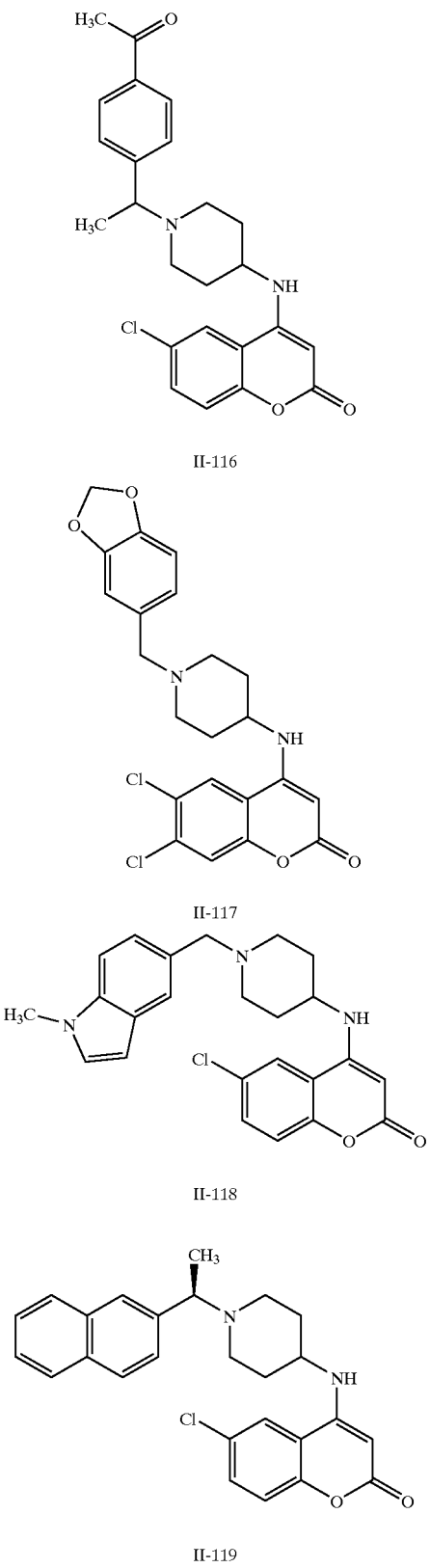
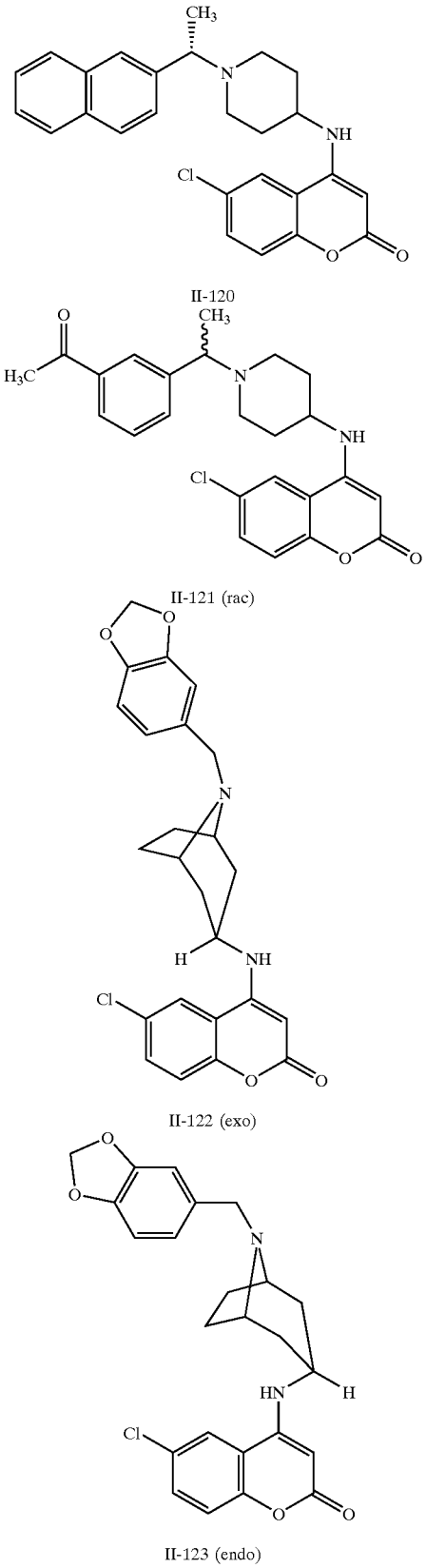

TABLE 2-continued

Examples of Compounds of Formula II (Y is oxygen)

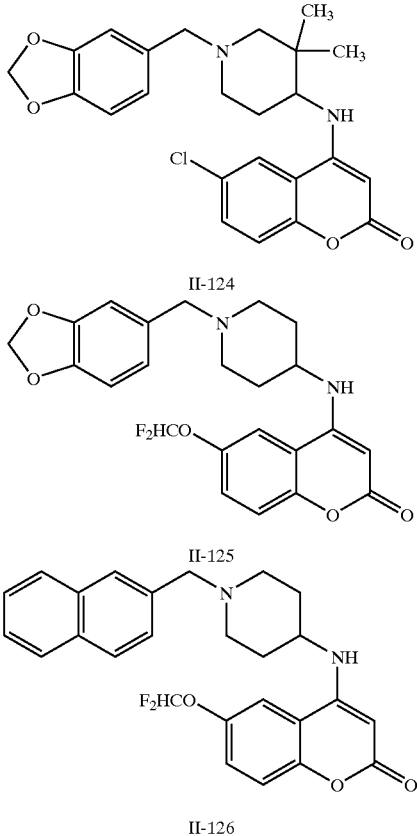

II-124

II-125

II-126

The compounds in Table 2 above may also be identified by the following chemical names:

II-1: 4-(1-Benzo[1,3]dioxol-5-ylmethyl-piperidin-4-ylamino)-6-methoxy-chromen-2-one;

II-2: 6—Chloro-4-(1-naphthalen-2-ylmethyl-piperidin-4-ylamino)-chromen-2-one;

II-3: 4-(1-Benzo[1,3]dioxol-5-ylmethyl-piperidin-4-ylamino)-6-methyl-chromen-2-one;

II-4: 4-(1-Benzo[1,3]dioxol-5-ylmethyl-piperidin-4-ylamino)-6-chloro-chromen-2-one;

II-5: 6-Chloro-4-(1-naphthalen-1-ylmethyl-piperidin-4-ylamino)-chromen-2-one;

II-6: 4-(1-Benzo[b]thiophen-3-ylmethyl-piperidin-4-ylamino)-6-chloro-chromen-2-one;

II-7: 4-(1-Biphenyl-3-ylmethyl-piperidin-4-ylamino)-6-chloro-chromen-2-one;

II-8: 4-(1-Biphenyl-4-ylmethyl-piperidin-4-ylamino)-6-chloro-chromen-2-one;

II-9: 4-(1-Benzyl-piperidin-4-ylamino)-6-methyl-chromen-2-one;

II-10: 6-Chloro-4-(1-cyclohex-1-enylmethyl-piperidin-4-ylamino)-chromen-2-one;

II-11: 6-Methyl-4-[1-(3-trifluoromethoxy-benzyl)-piperidin-4-ylamino]-chromen-2-one;

II-12: 4-[1-(3-Hydroxy-benzyl)-piperidin-4-ylamino]-6-methyl-chromen-2-one;

II-13: 6-Methyl-4-[1-(4-phenoxy-benzyl)-piperidin-4-ylamino]-chromen-2-one;

II-14: 4-{1-[5-(3-Chloro-phenyl)-furan-2-ylmethyl]-piperidin-4-ylamino}-6-methyl-chromen-2-one;

II-15: 4-[1-(4-tert-Butyl-benzyl)-piperidin-4-ylamino]-6-methyl-chromen-2-one;

II-16: 4{-1-[3-(4-Methoxy-phenoxy)-benzyl]-piperidin-4-ylamino}-6-methyl-chromen-2-one;

II-17: 4-(1-Benzo[b]thiophen-2-ylmethyl-piperidin-4-ylamino)-6-chloro-chromen-2-one;

II-18: 4-(1-Benzofuran-2-ylmethyl-piperidin-4-ylamino)-6-chloro-chromen-2-one;

II-19: 6-Methoxy-4-(1-naphthalen-2-ylmethyl-piperidin-4-ylamino)-chromen-2-one;

II-20: 6-Methoxy-4-[1-(3-trifluoromethoxy-benzyl)-piperidin-4-ylamino]-chromen-2-one;

II-21: 4-[1-(3,5-Dichloro-benzyl)-piperidin-4-ylamino]-6-methoxy-chromen-2-one;

II-22: 4{-1-[5-(2-Chloro-phenyl)-furan-2-ylmethyl]-piperidin-4-ylamino}-6-methoxy-chromen-2-one;

II-23: 6-Methoxy-4-{1-[5-(2-trifluoromethyl-phenyl)-furan-2-ylmethyl]-piperidin-4-ylamino}-chromen-2-one;

II-24: 4-{1-[5-(3-Chloro-phenyl)-furan-2-ylmethyl]-piperidin-4-ylamino}-6-methyl-chromen-2-one;

II-25: 4-[1-(2,4-Dimethyl-benzyl)-piperidin-4-ylamino]-6-methoxy-chromen-2-one;

II-26: 4-(1-Benzo[1,3]dioxol-5-ylmethyl-piperidin-4-ylamino)-3-fluoro-6-methoxy-chromen-2-one;

II-27: 6-Methoxy-4-[1-(7-methyl-naphthalen-2-ylmethyl)-piperidin-4-ylamino]-chromen-2-one;

II-28: 4-[1-(1-Benzo[1,3]dioxol-5-yl-ethyl)-piperidin-4-ylamino]-6-chloro-chromen-2-one;

II-29: 4-[1-(3,4-Dimethyl-benzyl)-piperidin-4-ylamino]-6-methoxy-chromen-2-one;

II-30: 4-(1-Benzo[1,3]dioxol-5-ylmethyl-piperidin-4-ylamino)-6-chloro-chromen-2-one;

II-31: 6-Chloro-4-[1-(1H-indol-6-ylmethyl)-piperidin-4-ylamino]-chromen-2-one;

II-32: 6-Difluoromethoxy-4-(1-naphthalen-2-ylmethyl-piperidin-4-ylamino)-chromen-2-one;

II-33: 4-[1-(1-Ethyl-1H-indol-5-ylmethyl)-piperidin-4-ylamino]-6-methoxy-chromen-2-one;

II-34: 6-Methoxy-4-[1-(4-methyl-benzyl)-piperidin-4-ylamino]-chromen-2-one;

II-35: 4-(1-Benzo[1,3]dioxol-5-ylmethyl-piperidin-4-ylamino)-6-vinyl-chromen-2-one;

II-36: 4-(1-Benzofuran-6-ylmethyl-piperidin-4-ylamino)-6-chloro-chromen-2-one;

II-37: 6-Methoxy-4-[1-(4-methoxy-3-methyl-benzyl)-piperidin-4-ylamino]-chromen-2-one;

II-38: 4-(1-Benzo[1,3]dioxol-5-ylmethyl-3-methyl-piperidin-4-ylamino)-6-methoxy-chromen-2-one;

II-39: 6-Methoxy-4-[1-(4-methoxy-benzyl)-piperidin-4-ylamino]-chromen-2-one;

II-40: 6-Chloro-4-(1-quinolin-6-ylmethyl-piperidin-4-ylamino)-chromen-2-one;

II-41: 4-(1-Benzo[1,3]dioxol-5-ylmethyl-piperidin-4-ylamino)-8-bromo-6-chloro-chromen-2-one;

II-42: N-[4-(1-Benzo[1,3]dioxol-5-ylmethyl-piperidin-4-ylamino)-6-chloro-2-oxo-2H-chromen-3-yl]-acetamide;

II-43: 4-[1-(4-Difluoromethoxy-benzyl)-piperidin-4-ylamino]-6-methoxy-chromen-2-one;

II-44: 4-(1-Benzooxazol-5-ylmethyl-piperidin-4-ylamino)-6-methoxy-chromen-2-one;

II-45: 6-Chloro-4-{1-[1-(3-fluoro-4-methoxy-phenyl)-ethyl]-piperidin-4-ylamino}-chromen-2-one;

II-46: 4-[1-(3,4-Dimethyl-benzyl)-piperidin-4-ylamino]-6-vinyl-chromen-2-one;

II-47: 4-{1-[3-Fluoro-4-(3-piperidin-1-yl-propoxy)-benzyl]-piperidin-4-ylamino}-6-methoxy-chromen-2-one;

II-48: 4-[1-(4-Acetyl-benzyl)-piperidin-4-ylamino]-6-chloro-chromen-2-one;

II-49: 6-Chloro-4-{1-[4-(3-piperidin-1-yl-propoxy)-benzyl]-piperidin-4-ylamino}-chromen-2-one;

II-50: 4-[1-(4-Butoxy-benzyl)-piperidin-4-ylamino]-6-methoxy-chromen-2-one;

II-51: 6-Chloro-4-[1-(3,4-dihydro-2H-benzo[b][1,4]dioxepin-7-ylmethyl)-piperidin-4-ylamino]-chromen-2-one;

II-52: 6-Methoxy-4-[1-(1-naphthalen-2-yl-ethyl)-piperidin-4-ylamino]-chromen-2-one;

II-53: 4-(1-Benzo[1,3]dioxol-5-ylmethyl-3-methyl-piperidin-4-ylamino)-6-methoxy-chromen-2-one;

II-54: 4-[1-(1H-Indol-5-ylmethyl)-piperidin-4-ylamino]-6-methoxy-chromen-2-one;

II-55: 4-[4-(6-Chloro-2-oxo-2H-chromen-4-ylamino)-piperidin-1-ylmethyl]-N-(2-pyrrolidin-1-yl-ethyl)-benzamide;

II-56: 4-(1-Benzo[1,3]dioxol-5-ylmethyl-3-methyl-piperidin-4-ylamino)-6-methoxy-chromen-2-one;

II-57: 4-[1-(2,3-Dihydro-benzo[1,4]dioxin-6-ylmethyl)-piperidin-4-ylamino]-6-vinyl-chromen-2-one;

II-58: 4-[1-(4-Chloro-3-fluoro-benzyl)-piperidin-4-ylamino]-6-methoxy-chromen-2-one;

II-59: 6-Chloro-4-[1-(4-chloro-benzyl)-piperidin-4-ylamino]-chromen-2-one;

II-60: 4-[1-(1-Benzo[1,3]dioxol-5-yl-ethyl)-piperidin-4-ylamino]-6-chloro-chromen-2-one;

II-61: 6-Chloro-4-[1-(2-methyl-benzofuran-5-ylmethyl)-piperidin-4-ylamino]-chromen-2-one;

II-62: 4-[1-(2-Fluoro-4-methoxy-benzyl)-piperidin-4-ylamino]-6-methoxy-chromen-2-one;

II-63: 4-(1-Benzo[1,3]dioxol-5-ylmethyl-piperidin-4-ylamino)-6-ethyl-chromen-2-one;

II-64: 4-[1-(2,3-Dihydro-benzo[1,4]dioxin-6-ylmethyl)-piperidin-4-ylamino]-6-methoxy-chromen-2-one;

II-65: 4-[1-(4-Bromo-benzyl)-piperidin-4-ylamino]-6-methoxy-chromen-2-one;

II-66: 6-Methoxy-4-(1-naphthalen-1-ylmethyl-piperidin-4-ylamino)-chromen-2-one;

II-67: 4-[4-(6-Chloro-2-oxo-2H-chromen-4-ylamino)-piperidin-1-ylmethyl]-N-(2-piperidin-1-yl-ethyl)-benzamide;

II-68: 4-[1-(2,2-Difluoro-benzo[1,3]dioxol-5-ylmethyl)-piperidin-4-ylamino]-6-methoxy-chromen-2-one;

II-69: 4-[4-(6-Methoxy-2-oxo-2H-chromen-4-ylamino)-piperidin-1-ylmethyl]-N-(2-piperidin-1-yl-ethyl)-benzamide;

II-70: 4-[1-(3-Fluoro-4-methoxy-benzyl)-piperidin-4-ylamino]-6-methoxy-chromen-2-one;

II-71: 6-Chloro-4-[1-(3,4-dimethyl-benzyl)-piperidin-4-ylamino]-chromen-2-one;

II-72: 4-(1-Benzo[1,3]dioxol-5-ylmethyl-3-methyl-piperidin-4-ylamino)-6-methoxy-chromen-2-one;

II-73: 6-Chloro-4-(1-isoquinolin-6-ylmethyl-piperidin-4-ylamino)-chromen-2-one;

II-74: 6-Chloro-4-{1-[1-(4-chloro-phenyl)-ethyl]-piperidin-4-ylamino}-chromen-2-one;

II-75: 4-(1-Benzo[1,3]dioxol-5-ylmethyl-piperidin-4-ylamino)-2-oxo-2H-chromene-6-carbonitrile;

II-76: 6-Methoxy-4-[1-(3-methoxy-benzyl)-piperidin-4-ylamino]-chromen-2-one;

II-77: 4-[1-(3-Acetyl-benzyl)-piperidin-4-ylamino]-6-chloro-chromen-2-one;

II-78: 6-Chloro-4-[1-(2,3-dihydro-benzofuran-5-ylmethyl)-piperidin-4-ylamino]-chromen-2-one;

II-79: 4-[1-(3-Fluoro-benzyl)-piperidin-4-ylamino]-6-methoxy-chromen-2-one;

II-80: 4-[1-(4-Ethoxy-benzyl)-piperidin-4-ylamino]-6-methoxy-chromen-2-one;

II-81: 1-[4-(1-Benzo[1,3]dioxol-5-ylmethyl-piperidin-4-ylamino)-6-chloro-2-oxo-2H-chromen-8-yl]-pyrrolidin-2-one;

II-82: 4-(1-Benzo[1,3]dioxol-5-ylmethyl-piperidin-4-ylamino)-6-trifluoromethyl-chromen-2-one;

II-83: 4-[4-(6-Methoxy-2-oxo-2H-chromen-4-ylamino)-piperidin-1-ylmethyl]-N-(2-pyridin-2-yl-ethyl)-benzamide;

II-84: 6-Methoxy-4-[1-(1-methyl-1H-indol-2-ylmethyl)-piperidin-4-ylamino]-chromen-2-one;

II-85: 6,8-Difluoro-4-(1-naphthalen-2-ylmethyl-piperidin-4-ylamino)-chromen-2-one;

II-86: 4-[4-(6-Methoxy-2-oxo-2H-chromen-4-ylamino)-piperidin-1-ylmethyl]-N-(2-pyrrolidin-1-yl-ethyl)-benzamide;

II-87: 4-[1-(2,3-Dihydro-benzofuran-5-ylmethyl)-piperidin-4-ylamino]-6-vinyl-chromen-2-one;

II-88: 4-[1-(3-Fluoro-4-hydroxy-benzyl)-piperidin-4-ylamino]-6-methoxy-chromen-2-one;

II-89: 4-(1-Benzo[1,3]dioxol-5-ylmethyl-piperidin-4-ylamino)-3-fluoro-6-methyl-chromen-2-one;

II-90: 4-(1-Benzo[1,3]dioxol-5-ylmethyl-piperidin-4-ylamino)-3-chloro-6-methoxy-chromen-2-one;

II-91: 4-{1-[4-(3-Dimethylamino-propoxy)-benzyl]-piperidin-4-ylamino}-6-methoxy-chromen-2-one;

II-92: 6-Methoxy-4-[1-(3-methyl-benzyl)-piperidin-4-ylamino]-chromen-2-one;

II-93: 6-Chloro-4-[1-(7-chloro-benzofuran-5-ylmethyl)-piperidin-4-ylamino]-chromen-2-one;

II-94: 4-{1-[4-(4-Benzyl-piperazine-1-carbonyl)-benzyl]-piperidin-4-ylamino}-6-methoxy-chromen-2-one;

II-95: 4-(1-Benzooxazol-5-ylmethyl-piperidin-4-ylamino)-6-chloro-chromen-2-one;

II-96: 4-(1-Benzo[1,3]dioxol-5-ylmethyl-piperidin-4-ylamino)-6-trifluoromethoxy-chromen-2-one;

II-97: 4-[1-(3-Ethoxy-benzyl)-piperidin-4-ylamino]-6-methoxy-chromen-2-one;

II-98: 4-(1-Benzo[1,3]dioxol-5-ylmethyl-piperidin-4-ylamino)-6,8-dimethyl-chromen-2-one;

II-99: 3-[4-(6-Chloro-2-oxo-2H-chromen-4-ylamino)-piperidin-1-ylmethyl]-benzamide;

II-100: 4-(1-Benzooxazol-5-ylmethyl-piperidin-4-ylamino)-6-vinyl-chromen-2-one;

II-101: 4-(1-Benzo[b]thiophen-4-ylmethyl-piperidin-4-ylamino)-6-methoxy-chromen-2-one;

II-102: 4-(1-Benzyl-piperidin-4-ylamino)-6-methoxy-chromen-2-one;

II-103: 4-[1-(3,4-Dimethyl-benzyl)-piperidin-4-ylamino]-6-ethyl-chromen-2-one;

II-104: 6-Chloro-4-[1-(1-naphthalen-2-yl-ethyl)-piperidin-4-ylamino]-chromen-2-one;

II-105: 4-[1-(3-Fluoro-4-methyl-benzyl)-piperidin-4-ylamino]-6-methoxy-chromen-2-one;

II-106: 6-Chloro-4-[1-(1-quinolin-6-yl-ethyl)-piperidin-4-ylamino]-chromen-2-one;

II-107: 4-(1-Benzo[1,3]dioxol-5-ylmethyl-3-methyl-piperidin-4-ylamino)-6-methoxy-chromen-2-one;

II-108: 6-Chloro-4-{1-[1-(4-chloro-phenyl)-ethyl]-piperidin-4-ylamino}-chromen-2-one;

II-109: 6-Methoxy-4-(1-naphthalen-2-ylmethyl-piperidin-4-ylamino)-chromen-2-one;

II-110: 4-[1-(4-Chloro-benzyl)-piperidin-4-ylamino]-6-methoxy-chromen-2-one;

II-111: 6-Methoxy-4-[1-(1-methyl-1H-indol-5-ylmethyl)-piperidin-4-ylamino]-chromen-2-one;

II-112: 6-Methoxy-4-(1-quinolin-6-ylmethyl-piperidin-4-ylamino)-chromen-2-one;

II-113: 6-Chloro-4-{1-[1-(3-fluoro-4-hydroxy-phenyl)-ethyl]-piperidin-4-ylamino}-chromen-2-one;

II-114: 4-(1-Benzofuran-5-ylmethyl-piperidin-4-ylamino)-2-oxo-2H-chromene-6-carbonitrile;

II-115: 4-{1-[3-Chloro-4-(3-piperidin-1-yl-propoxy)-benzyl]-piperidin-4-ylamino}-6-methoxy-chromen-2-one;

II-116: 4-{1-[1-(4-Acetyl-phenyl)-ethyl]-piperidin-4-ylamino}-6-chloro-chromen-2-one;

II-117: 4-(1-Benzo[1,3]dioxol-5-ylmethyl-piperidin-4-ylamino)-6,7-dichloro-chromen-2-one;

II-118: 6-Chloro-4-[1-(1-methyl-1H-indol-5-ylmethyl)-piperidin-4-ylamino]-chromen-2-one;

II-119: (R)-6-Chloro-4-[1-(1-naphthalen-2-yl-ethyl)-piperidin-4-ylamino]-chromen-2-one;

II-120: (S)-6-Chloro-4-[1-(1-naphthalen-2-yl-ethyl)-piperidin-4-ylamino]-chromen-2-one;

II-121: (rac)-4-{1-[1-(3-Acetyl-phenyl)-ethyl]-piperidin-4-ylamino}-6-chloro-chromen-2-one;

II-122: (exo)-4-(8-Benzo[1,3]dioxol-5-ylmethyl-8-aza-bicyclo[3.2.1]oct-3-ylamino)-6-chloro-chromen-2-one;

II-123: (endo)-4-(8-Benzo[1,3]dioxol-5-ylmethyl-8-aza-bicyclo[3.2.1]oct-3-ylamino)-6-chloro-chromen-2-one;

II-124: 4-(1-Benzo[1,3]dioxol-5-ylmethyl-3,3-dimethyl-piperidin-4-ylamino)-6-chloro-chromen-2-one; and II-125: 4-(1-Benzo[1,3]dioxol-5-ylmethyl-piperidin-4-ylamino)-6-difluoromethoxy-chromen-2-one.

It has been found that the MCH-R1 antagonist activity of the present compounds is sensitive to certain stereochemical effects. For example, II-119, which has the R-configuration at the benzylic position attached to the piperidine ring, is more active than II-120 having the opposite S-configuration. Also, the exo isomer II-122 is more active than the endo isomer II-123.

Another embodiment of this invention relates to compounds of formula I wherein Q is a saturated or unsaturated $C_{1-4}$ alkylidene chain providing compounds of formula III. Preferably, the alkylidene chain is CH=CH providing compounds of formula III-A:

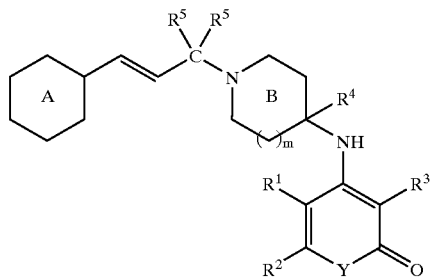

III-A wherein $R^1$, $R^2$, $R^3$, $R^4$, $R^5$, Y, m, Ring A and Ring B are as described above.

Examples of compounds of formula III are shown in Table 3 below.

TABLE 3

Examples of Compounds of Formula III

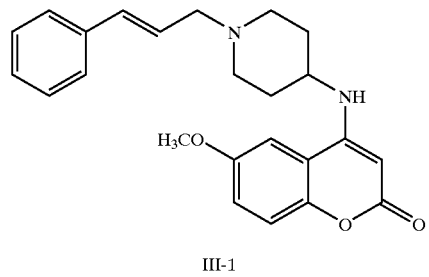

III-1

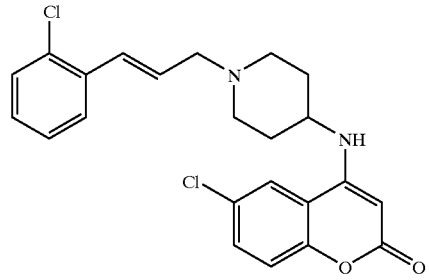

III-2

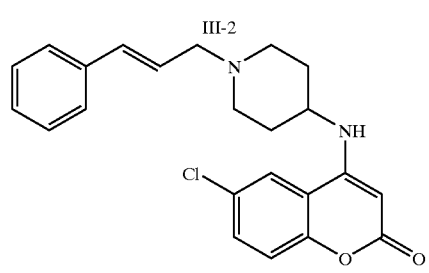

III-3

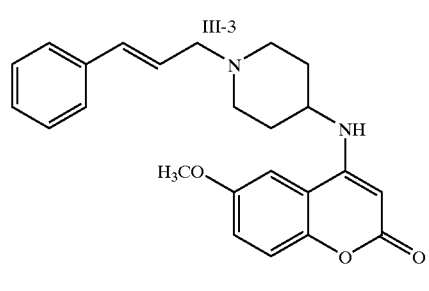

III-4

TABLE 3-continued
Examples of Compounds of Formula III
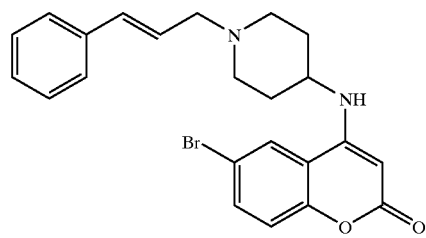
III-5
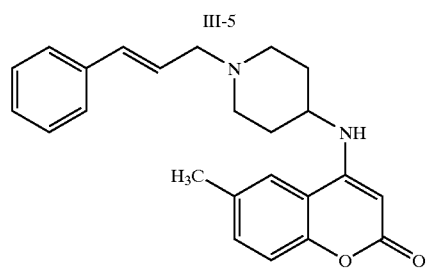
III-6
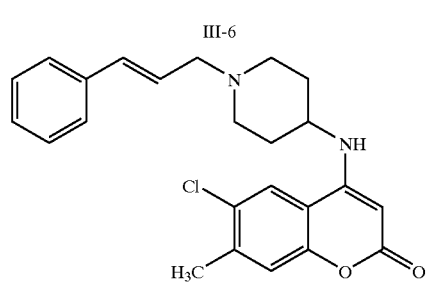
III-7
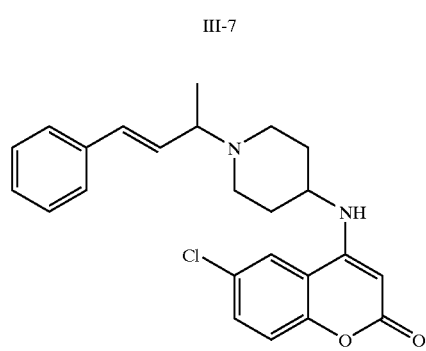
III-8
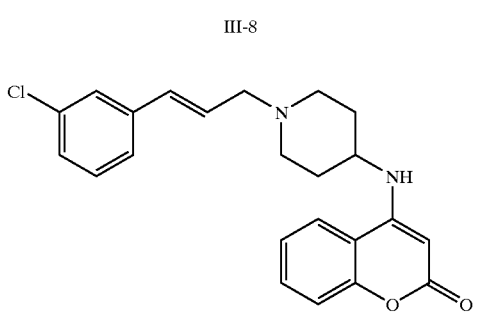
III-9
TABLE 3-continued
Examples of Compounds of Formula III
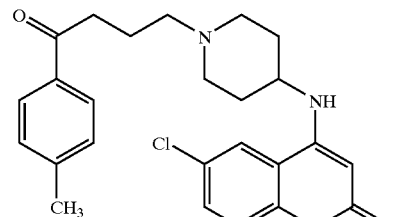
III-10
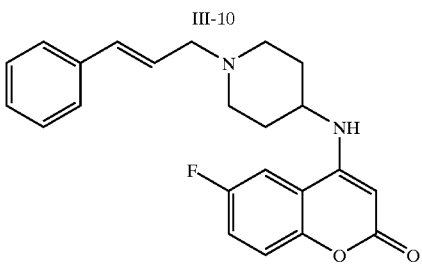
III-11
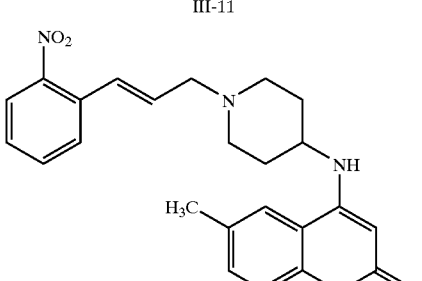
III-12
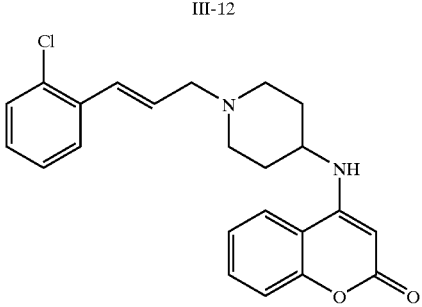
III-13
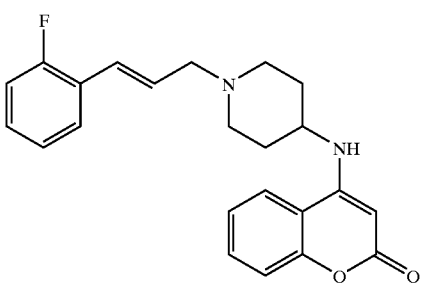
III-14

TABLE 3-continued
Examples of Compounds of Formula III
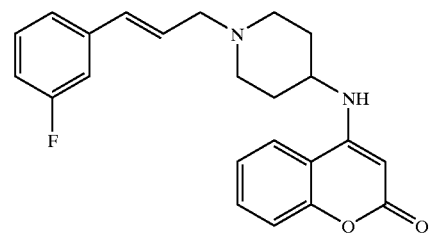
III-15
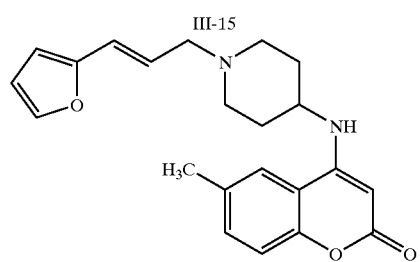
III-16
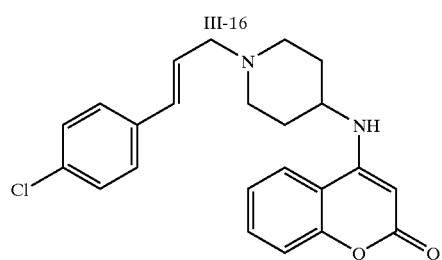
III-17
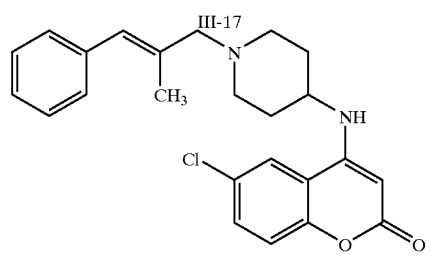
III-18
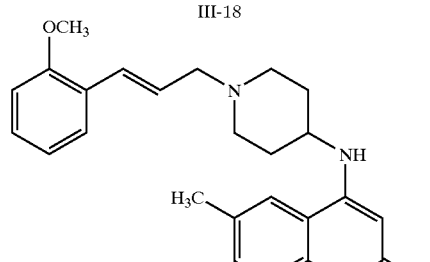
III-19
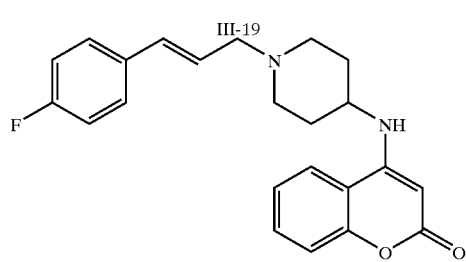
III-20
TABLE 3-continued
Examples of Compounds of Formula III
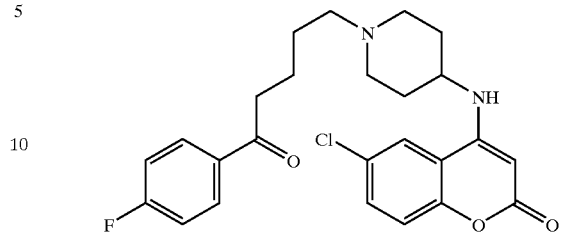
III-21
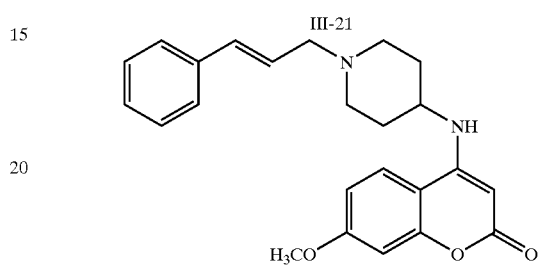
III-22
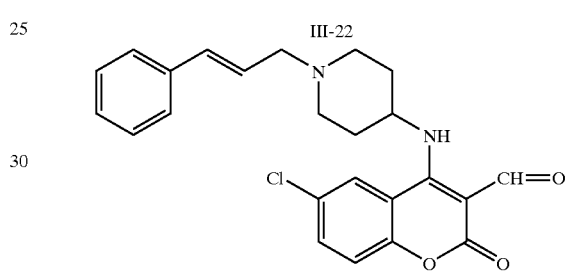
III-23
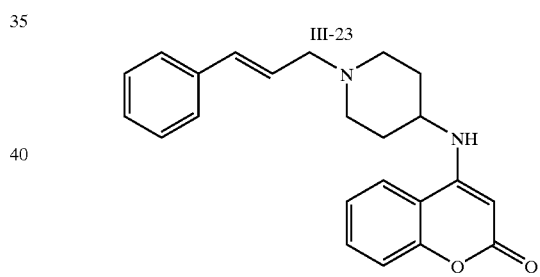
III-24
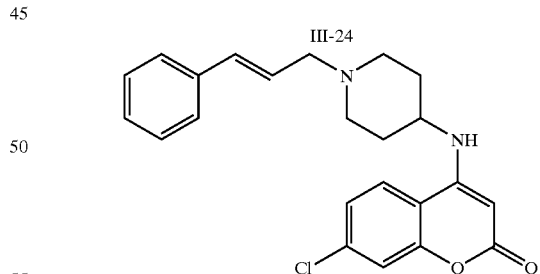
III-25
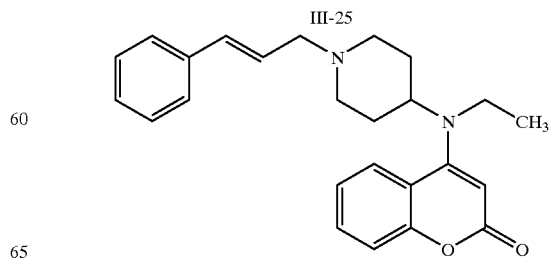
III-26

TABLE 3-continued
Examples of Compounds of Formula III
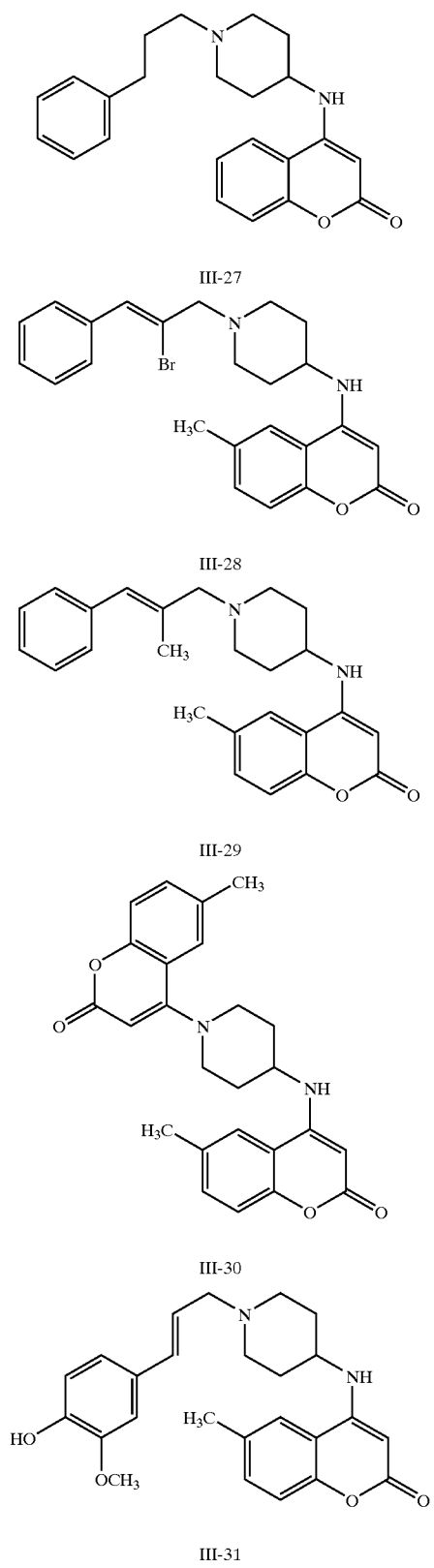
III-27
III-28
III-29
III-30
III-31
TABLE 3-continued
Examples of Compounds of Formula III
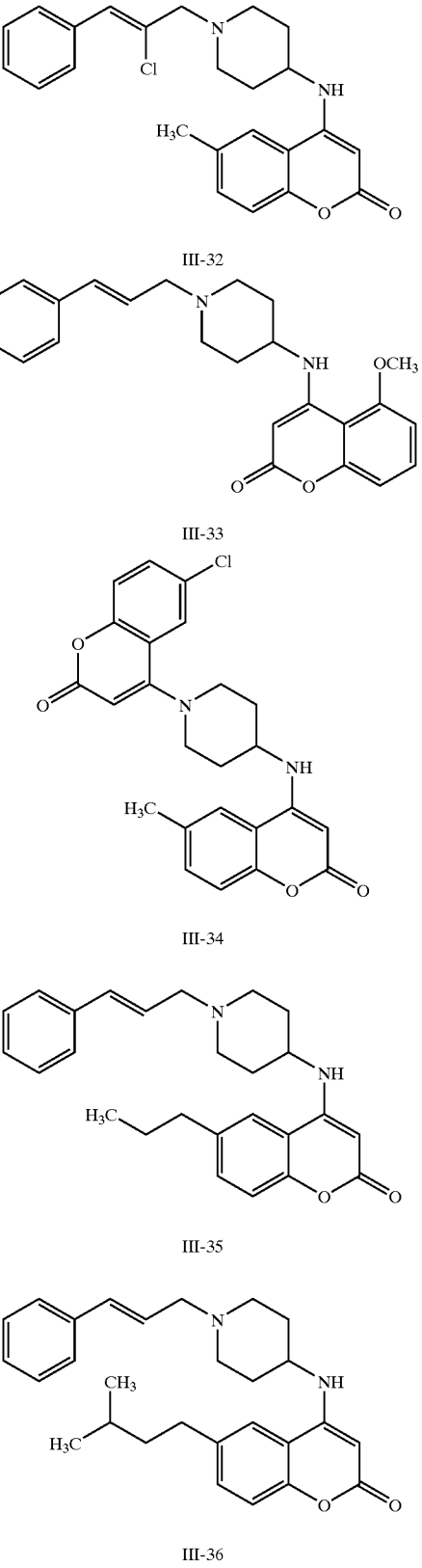
III-32
III-33
III-34
III-35
III-36

TABLE 3-continued
Examples of Compounds of Formula III
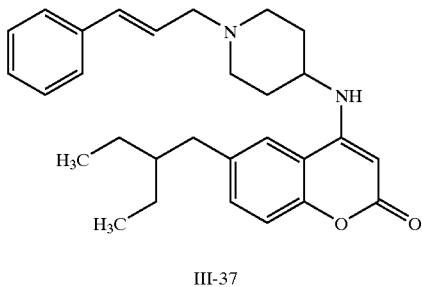
III-37
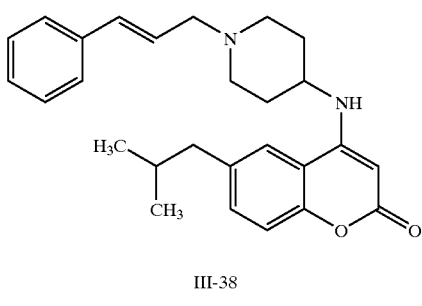
III-38
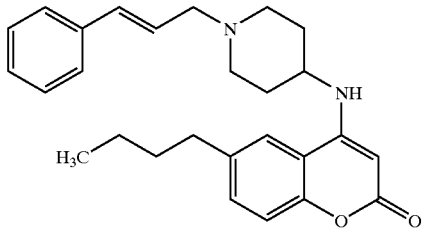
III-39
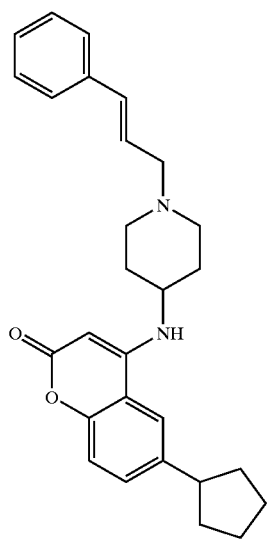
III-40
TABLE 3-continued
Examples of Compounds of Formula III
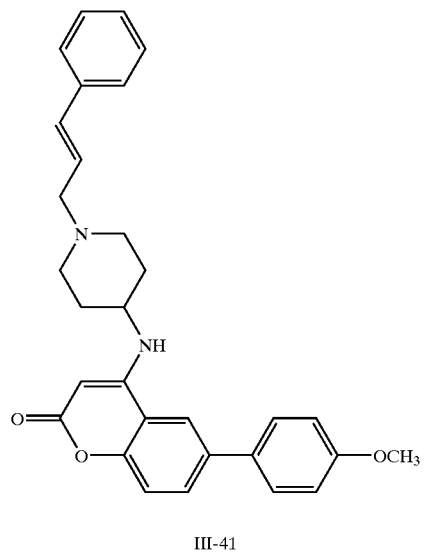
III-41
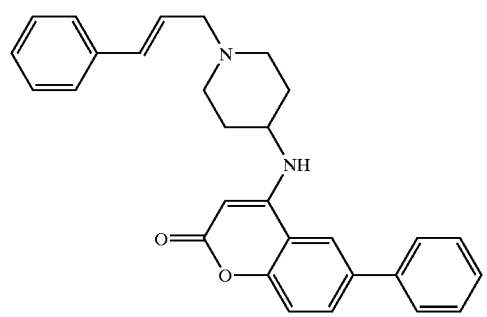
III-42
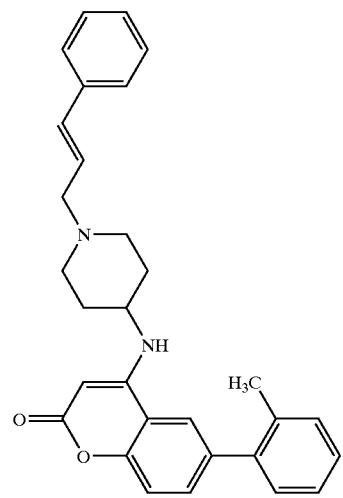
III-43

TABLE 3-continued
Examples of Compounds of Formula III
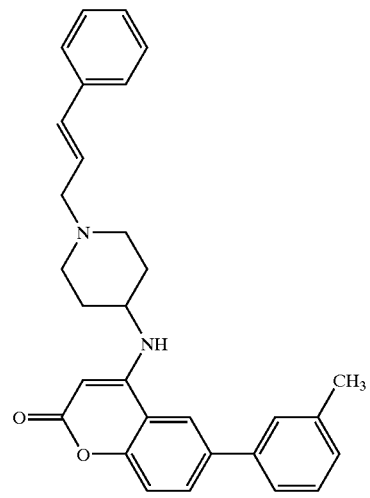
III-44
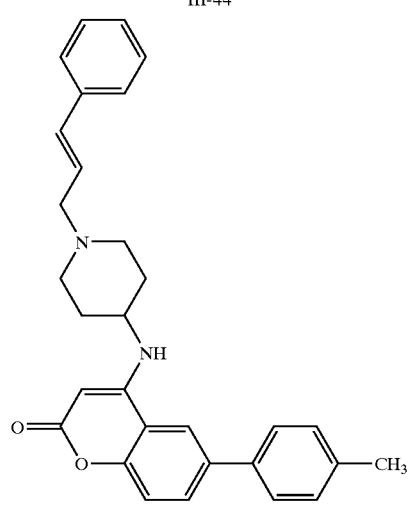
III-45
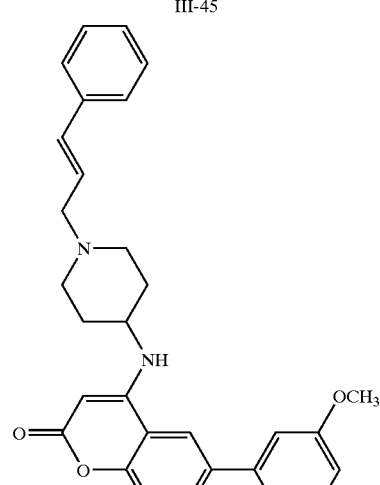
III-46
TABLE 3-continued
Examples of Compounds of Formula III
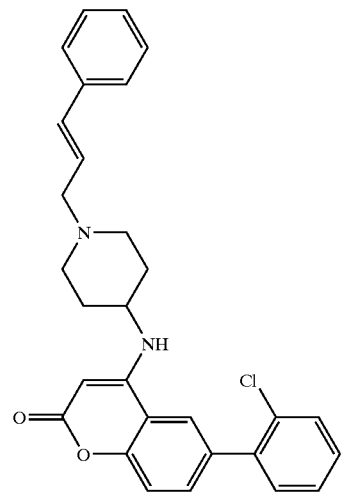
III-47
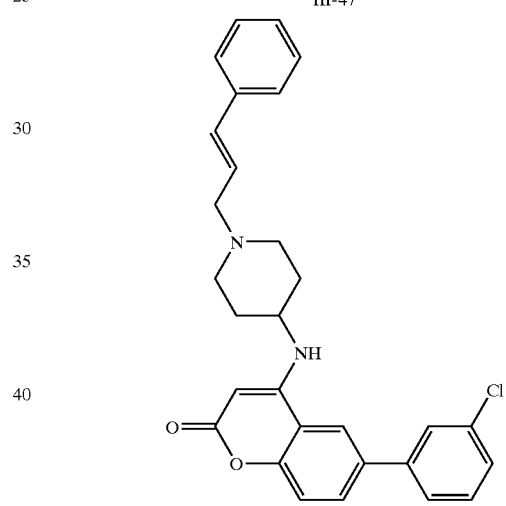
III-48
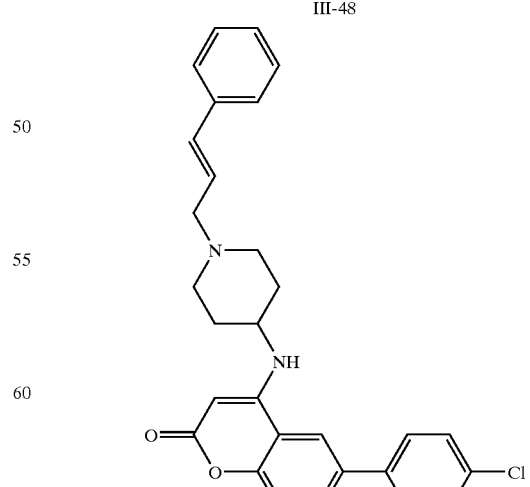
III-49

TABLE 3-continued
Examples of Compounds of Formula III
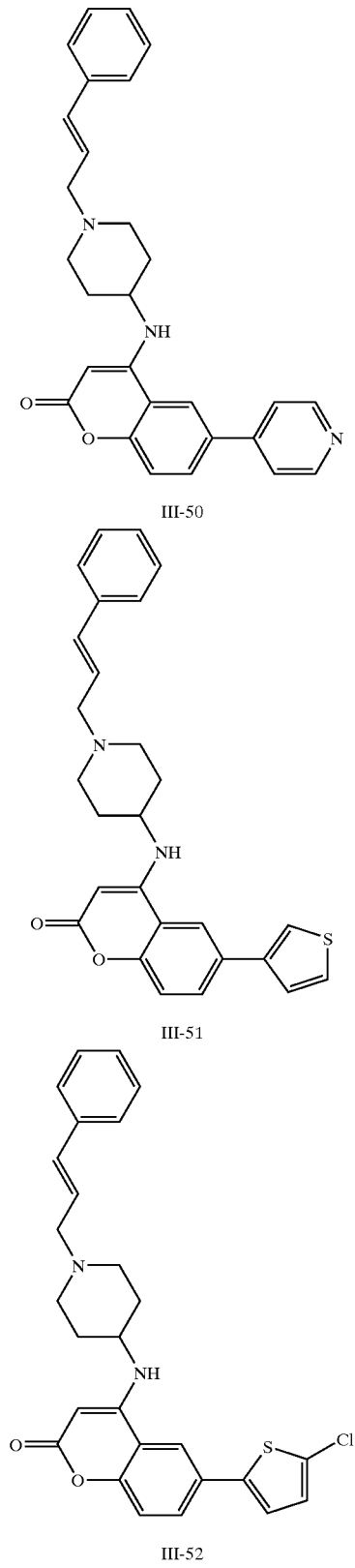
III-50
III-51
III-52
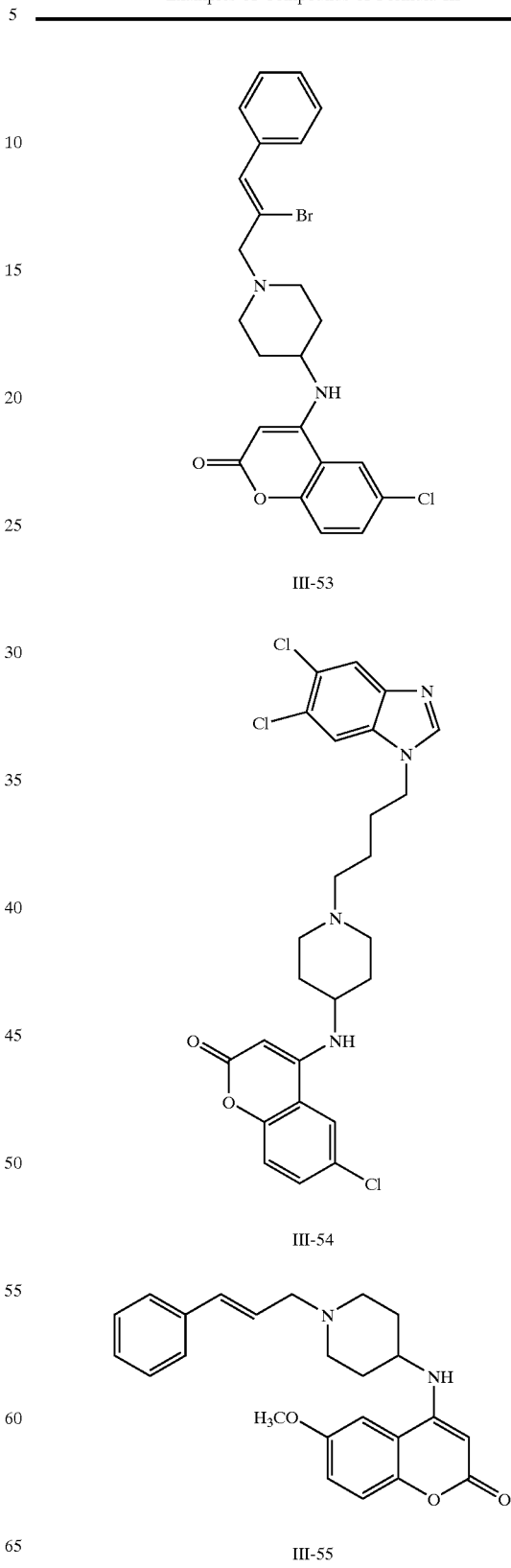
III-53
III-54
III-55

TABLE 3-continued

Examples of Compounds of Formula III

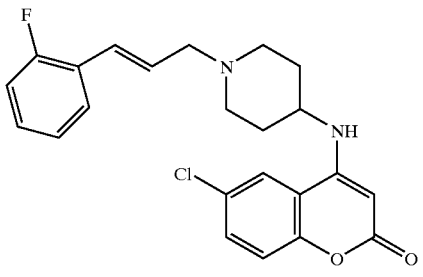

III-56

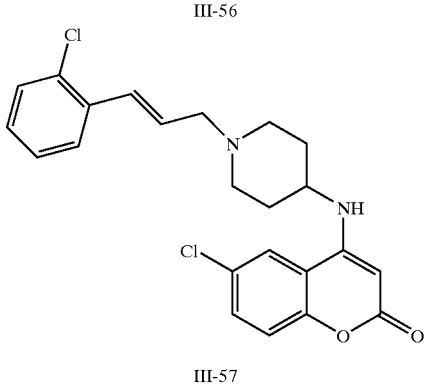

III-57

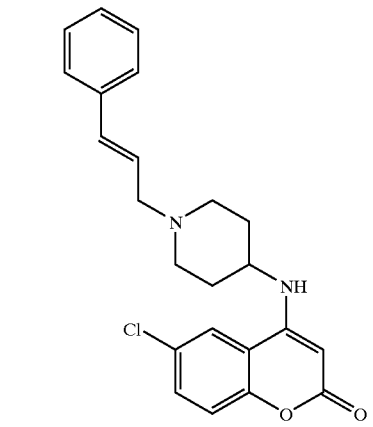

III-58

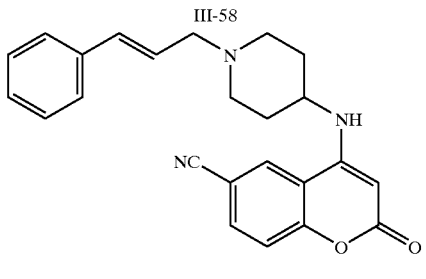

III-59

The compounds in Table 3 above may also be identified by the following chemical names:

III-1: 6-Methoxy-4-[1-(3-phenyl-allyl)-piperidin-4-ylamino]-chromen-2-one;
III-2: 6-Chloro-4-{1-[3-(2-chloro-phenyl)-allyl]-piperidin-4-ylamino}-chromen-2-one;
III-3: 6-Chloro-4-[1-(3-phenyl-allyl)-piperidin-4-ylamino]-chromen-2-one;
III-4: 6-Methoxy-4-[1-(3-phenyl-allyl)-piperidin-4-ylamino]-chromen-2-one;
III-5: 6-Bromo-4-[1-(3-phenyl-allyl)-piperidin-4-ylamino]-chromen-2-one;
III-6: 6-Methyl-4-[1-(3-phenyl-allyl)-piperidin-4-ylamino]-chromen-2-one;
III-7: 6-Chloro-7-methyl-4-[1-(3-phenyl-allyl)-piperidin-4-ylamino]-chromen-2-one;
III-8: 6-Chloro-4-[1-(4-phenyl-but-3-enyl)-piperidin-4-ylamino]-chromen-2-one;
III-9: 4-{1-[3-(3-Chloro-phenyl)-allyl]-piperidin-4-ylamino}-chromen-2-one;
III-10: 6-Chloro-4-[1-(4-oxo-4-p-tolyl-butyl)-piperidin-4-ylamino]-chromen-2-one;
III-11: 6-Fluoro-4-[1-(3-phenyl-allyl)-piperidin-4-ylamino]-chromen-2-one;
III-12: 6-Methyl-4-{1-[3-(2-nitro-phenyl)-allyl]-piperidin-4-ylamino}-chromen-2-one;
III-13: 4-{1-[3-(2-Chloro-phenyl)-allyl]-piperidin-4-ylamino}-chromen-2-one;
III-14: 4-{1-[3-(2-Fluoro-phenyl)-allyl]-piperidin-4-ylamino}-chromen-2-one;
III-15: 4-{1-[3-(3-Fluoro-phenyl)-allyl]-piperidin-4-ylamino}-chromen-2-one;
III-16: 4-[1-(3-Furan-2-yl-allyl)-piperidin-4-ylamino]-6-methyl-chromen-2-one;
III-17: 4-{1-[3-(4-Chloro-phenyl)-allyl]-piperidin-4-ylamino}-chromen-2-one;
III-18: 6-Chloro-4-[1-(2-methyl-3-phenyl-allyl)-piperidin-4-ylamino]-chromen-2-one;
III-19: 4-{1-[3-(2-Methoxy-phenyl)-allyl]-piperidin-4-ylamino}-6-methyl-chromen-2-one;
III-20: 4-{1-[3-(4-Fluoro-phenyl)-allyl]-piperidin-4-ylamino}-chromen-2-one;
III-21: 6-Chloro-4-{1-[5-(4-fluoro-phenyl)-5-oxo-pentyl]-piperidin-4-ylamino}-chromen-2-one;
III-22: 7-Methoxy-4-[1-(3-phenyl-allyl)-piperidin-4-ylamino]-chromen-2-one;
III-23: 6-Chloro-2-oxo-4-[1-(3-phenyl-allyl)-piperidin-4-ylamino]-2H-chromene-3-carbaldehyde;
III-24: 4-[1-(3-Phenyl-allyl)-piperidin-4-ylamino]-chromen-2-one;
III-25: 7-Chloro-4-[1-(3-phenyl-allyl)-piperidin-4-ylamino]-chromen-2-one;
III-26: 4-{Ethyl-[1-(3-phenyl-allyl)-piperidin-4-yl]-amino}-chromen-2-one;
III-27: 4-[1-(3-Phenyl-propyl)-piperidin-4-ylamino]-chromen-2-one;
III-28: 4-[1-(2-Bromo-3-phenyl-allyl)-piperidin-4-ylamino]-6-methyl-chromen-2-one;
III-29: 6-Methyl-4-[1-(2-methyl-3-phenyl-allyl)-piperidin-4-ylamino]-chromen-2-one;
III-30: 6-methyl-4-(4-((6-methyl-2-oxo-2H-chromen-4-yl)amino)piperidin-1-yl)-2H-chromen-2-one;
III-31: 4-{1-[3-(4-Hydroxy-3-methoxy-phenyl)-allyl]-piperidin-4-ylamino}-6-methyl-chromen-2-one;
III-32: 4-[1-(2-Chloro-3-phenyl-allyl)-piperidin-4-ylamino]-6-methyl-chromen-2-one;
III-33: 5-Methoxy-4-[1-(3-phenyl-allyl)-piperidin-4-ylamino]-chromen-2-one;
III-34: 6-chloro-4-(4-((6-methyl-2-oxo-2H-chromen-4-yl)amino)piperidin-1-yl)-2H-chromen-2-one;

III-35: 4-[1-(3-Phenyl-allyl)-piperidin-4-ylamino]-6-propyl-chromen-2-one;

III-36: 6-(3-Methyl-butyl)-4-[1-(3-phenyl-allyl)-piperidin-4-ylamino]-chromen-2-one;

III-37: 6-(2-Ethyl-butyl)-4-[1-(3-phenyl-allyl)-piperidin-4-ylamino]-chromen-2-one;

III-38: 6-Isobutyl-4-[1-(3-phenyl-allyl)-piperidin-4-ylamino]-chromen-2-one;

III-39: 6-Butyl-4-[1-(3-phenyl-allyl)-piperidin-4-ylamino]-chromen-2-one;

III-40: 6-Cyclopentyl-4-[1-(3-phenyl-allyl)-piperidin-4-ylamino]-chromen-2-one;

III-41: 6-(4-Methoxy-phenyl)-4-[1-(3-phenyl-allyl)-piperidin-4-ylamino]-chromen-2-one;

III-42: 6-Phenyl-4-[1-(3-phenyl-allyl)-piperidin-4-ylamino]-chromen-2-one;

III-43: 4-[1-(3-Phenyl-allyl)-piperidin-4-ylamino]-6-o-tolyl-chromen-2-one;

III-44: 4-[1-(3-Phenyl-allyl)-piperidin-4-ylamino]-6-m-tolyl-chromen-2-one;

III-45: 4-[1-(3-Phenyl-allyl)-piperidin-4-ylamino]-6-p-tolyl-chromen-2-one;

III-46: 6-(3-Methoxy-phenyl)-4-[1-(3-phenyl-allyl)-piperidin-4-ylamino]-chromen-2-one;

III-47: 6-(2-Chloro-phenyl)-4-[1-(3-phenyl-allyl)-piperidin-4-ylamino]-chromen-2-one;

III-48: 6-(3-Chloro-phenyl)-4-[1-(3-phenyl-allyl)-piperidin-4-ylamino]-chromen-2-one;

III-49: 6-(4-Chloro-phenyl)-4-[1-(3-phenyl-allyl)-piperidin-4-ylamino]-chromen-2-one;

III-50: 4-[1-(3-Phenyl-allyl)-piperidin-4-ylamino]-6-pyridin-4-yl-chromen-2-one;

III-51: 4-[1-(3-Phenyl-allyl)-piperidin-4-ylamino]-6-thiophen-3-yl-chromen-2-one;

III-52: 6-(5-Chloro-thiophen-2-yl)-4-[1-(3-phenyl-allyl)-piperidin-4-ylamino]-chromen-2-one;

III-53: 4-[1-(2-Bromo-3-phenyl-allyl)-piperidin-4-ylamino]-6-chloro-chromen-2-one;

III-54: 6-Chloro-4-{1-[4-(5,6-dichloro-benzoimidazol-1-yl)-butyl]-piperidin-4-ylamino}-chromen-2-one;

III-55: 6-Methoxy-4-[1-(3-phenyl-allyl)-piperidin-4-ylamino]-chromen-2-one;

III-56: 6-Chloro-4-{1-[3-(2-fluoro-phenyl)-allyl]-piperidin-4-ylamino}-chromen-2-one;

III-57: 6-Chloro-4-{1-[3-(2-chloro-phenyl)-allyl]-piperidin-4-ylamino}-chromen-2-one;

III-58: 6-Chloro-4-[1-(3-phenyl-allyl)-piperidin-4-ylamino]-chromen-2-one; and

III-59: 2-Oxo-4-[1-(3-phenyl-allyl)-piperidin-4-ylamino]-2H-chromene-6-carbonitrile.

Certain compounds of formula I that are useful in treating an MCH receptor-1 mediated disease are new. Accordingly, one aspect of this invention relates to such compounds, as represented by formula I:

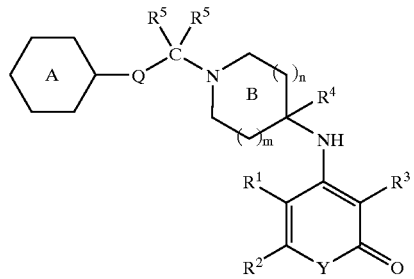

I or a pharmaceutically-acceptable salt or prodrug thereof, wherein:

m is zero or one;

n is zero, one or two;

Ring A is selected from the group consisting of phenyl, $C_{3-8}$ carbocyclyl, 5–6 membered heteroaryl and 5–6 membered heterocyclyl, wherein said Ring A is optionally fused to a 5–7 membered saturated, unsaturated or partially unsaturated ring having 0–2 heteroatoms selected from N, O, or S, and wherein the Ring A system is substituted or unsubstituted;

Y is oxygen or —N($R^9$)—;

Q is absent or —CH=CH—;

$R^1$ and $R^2$ taken together with their intervening atoms form a fused, unsaturated or partially unsaturated, substituted or unsubstituted, 5–7 membered ring having 0–2 heteroatoms selected from O, N or S;

R is hydrogen, $C^{1-10}$ aliphatic, aryl, aralkyl, heteroaryl, heteroaralkyl, heterocyclyl or heterocyclylalkyl;

$R^3$ is selected from R, —CN, $CO_2R$, —C(O)R, —$CH_2N$($R^8$)$_2$, or —C(O)N($R^8$)$_2$;

$R^4$ is selected from hydrogen, $C_{1-6}$ aliphatic, —CN, —$CO_2R$, —C(O)R, or —C(O)N($R_8$)$_2$;

each $R^5$ is independently selected from the group consisting of hydrogen, $C_{1-6}$ aliphatic, —CN, —$CO_2R$, —C(O)R, and —CON($R^8$)$_2$, or two $R^5$ groups taken together with their intervening carbon form an optionally substituted 3–6 membered ring having 0–2 heteroatoms selected from O, N, or S;

Ring B is optionally substituted by one or more $R^6$;

each $R^6$ is independently selected from one or more $C_{1-6}$ aliphatic, hydroxyl, alkoxy, oxo, halo, —SR, —CN, —N($R^8$)$_2$, —NHC(O)R, —N($R^8$)CON($R^8$)$_2$, —N($R^8$)COR, —$NHCO_2$($C_{1-8}$ aliphatic), —$CO_2R$, —C(O)R, —CON($R^8$)$_2$, —S(O)$_2$R, —S(O)R, —$SO_2$N($R^8$)$_2$, or —N($R^8$)S(O)$_2$R, or two $R^6$ taken together with their intervening atoms form a 5–7 membered ring having 0–2 heteroatoms selected from N, O, or S;

each $R^7$ is independently selected from hydrogen, $C_{1-10}$ aliphatic, —OR, —SR, —CN, —N($R^8$)$_2$, —NHC(O)R, —N($R^8$)CON($R^8$)$_2$, —N($R^8$)COR, —$NHCO_2$R—, —$CO_2R$, —C(O)R, —CON($R^8$)$_2$, —S(O)$_2$R, —S(O)R, —$SO_2$N($R^8$)$_2$, or —N($R^8$)S(O)$_2$R, or two $R^7$ groups taken together form =O, =N—OR, =N—N($R^8$)$_2$, =N—NHC(O)R, =N—$NHCO_2$R, or two $R^7$ groups taken together with their intervening carbon form an optionally substituted 3–6 membered ring having 0–2 heteroatoms selected O, N, or S;

each $R^8$ is independently selected from R, $-CO_2R$, $-C(O)R$, $-C(O)N(C_{1-6}$ aliphatic$)_2$, $-C(O)NH(C_{1-6}$ aliphatic), $-S(O)_2R$, $-S(O)R$, or $-SO_2N(C_{1-6}$ aliphatic$)_2$, $-SO_2NH(C_{1-6}$ aliphatic), or two $R^8$ groups on the same nitrogen taken together with the nitrogen form a 5–7 membered heterocyclyl ring; and $R^9$ is hydrogen, $C_{1-6}$ aliphatic, $C_{1-6}$ haloaliphatic, aralkyl, heteroaralkyl, $C_{1-6}$ aminoalkyl, or mono- or dialkylaminoalkyl.

Another embodiment of this invention relates to compounds of formula I wherein $R^1$ and $R^2$ are taken together to form a benzo ring. Such compounds contain a coumarin ring when Y is oxygen as shown below in formula IV or a quinolone ring when Y is $N(R^9)$ as shown below in formula V.:

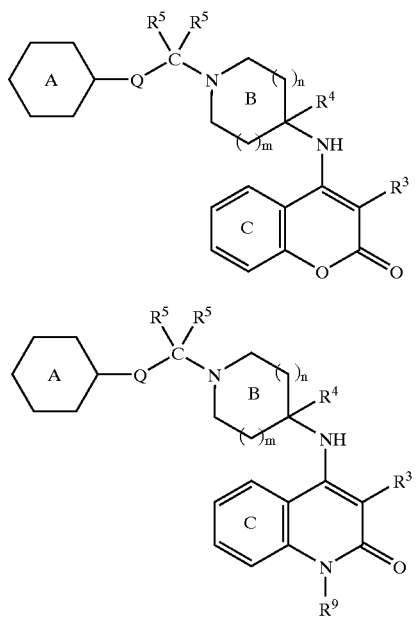

where m, n, Q, Ring A, $R^3$, $R^4$ and $R^5$ are as described above. Ring C is optionally substituted by 0–2 $R^{10}$ groups, which are described below.

Preferred compounds of formulae IV and V are compounds of formulae IV-A or IV-B and V-A or V-B:

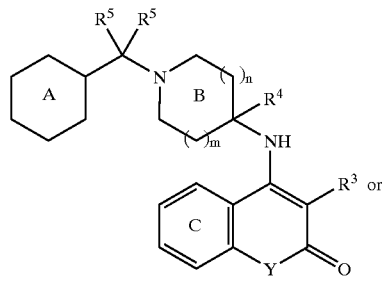

IV-A (Y = O)
V-A (Y = N—$R^9$)

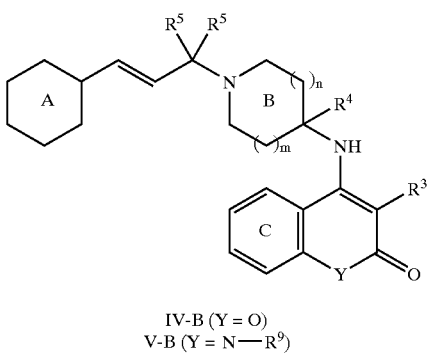

IV-B (Y = O)
V-B (Y = N—$R^9$)

Ring C of the coumarin or quinolone ring system may be substituted or unsubstituted by 0–2 $R^{10}$ groups. Examples of suitable $R^{10}$ substituents include halo, $C_{1-6}$ aliphatic, alkoxy, haloalkoxy, $C_{1-6}$ haloaliphatic, alkylcarbonyl, cyano, amino, mono- or dialkylamino, mono- or dialkylaminocarbonyl, aminocarbonyl, alkoxycarbonyl, alkoxycarbonylamino, mono- or dialkylaminosulfonyl, aminosulfonyl, alkylsulfonyl, carboxy, carboxyalkyl, phenyl, phenalkyl, 5–8 membered heteroaryl or heteroaralkyl, 3–8 membered heterocyclyl or heterocyclylalkyl, cyanoalkyl, aminoalkyl, mono- or dialkylaminoalkyl, alkoxycarbonylalkyl, thioalkyl, and alkoxysulfonyl. It is preferred that the alkyl moieties of the Ring A substituents have 1–6 carbons. The alkyl moieties may be interrupted by a heteroatom selected from NH, N(alkyl), O, or S or a carbonyl. Preferred Ring C substituents are halo, cyano, $C_{1-6}$ alkyl, $C_{1-6}$ alkoxy, phenyl or substituted phenyl, or $C_{5-6}$ heteroaryl.

Representative examples of compounds of formula V are shown in Table 4.

TABLE 4

Examples of Compounds of Formula V

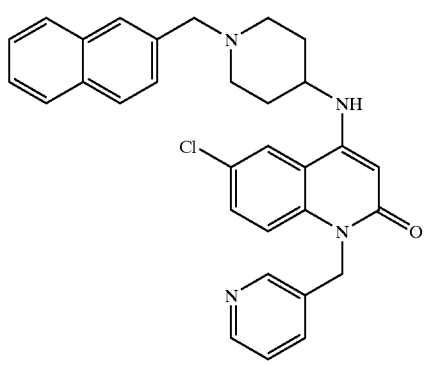

V-1

TABLE 4-continued
Examples of Compounds of Formula V
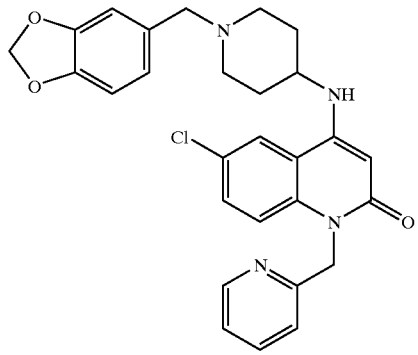
V-2
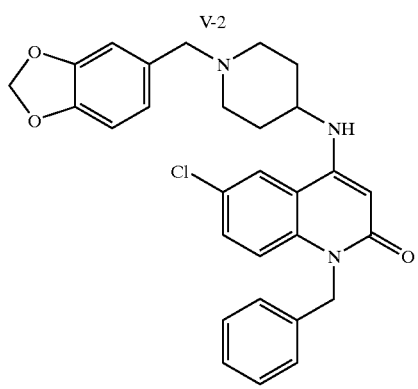
V-3
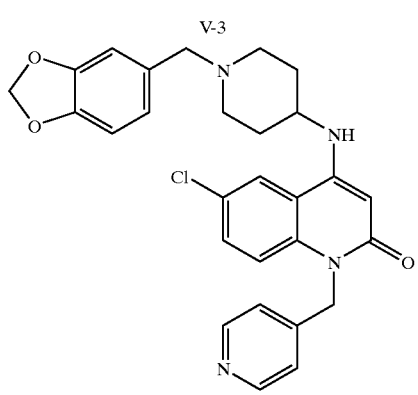
V-4
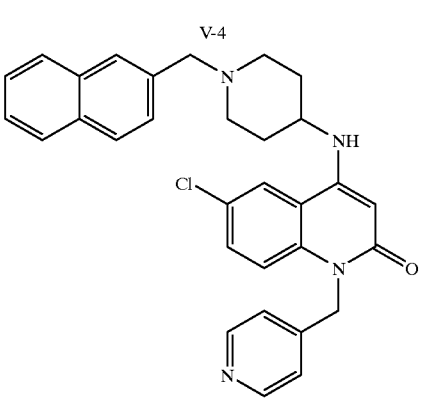
V-5
TABLE 4-continued
Examples of Compounds of Formula V
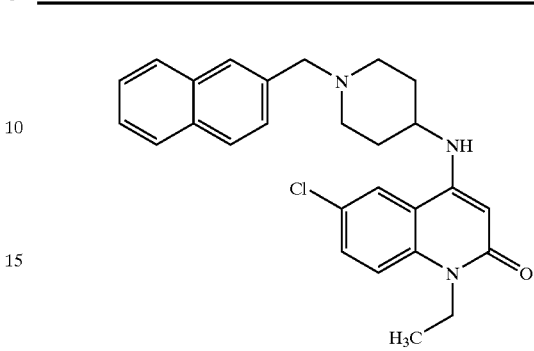
V-6
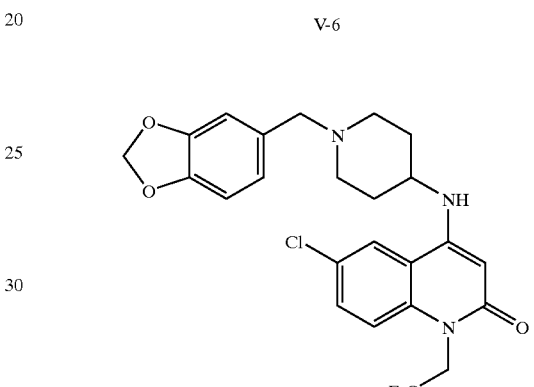
V-7
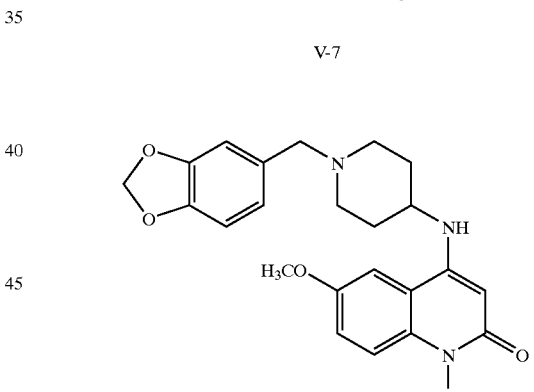
V-8
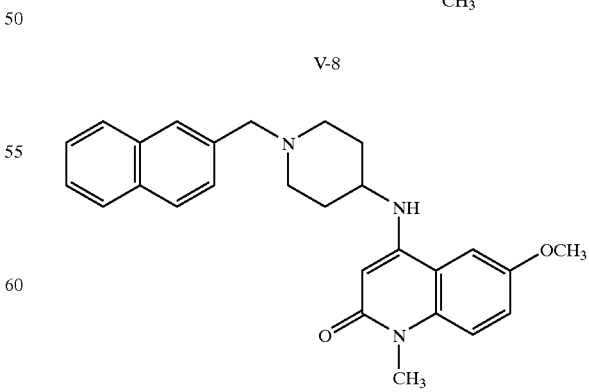
V-9

TABLE 4-continued
Examples of Compounds of Formula V
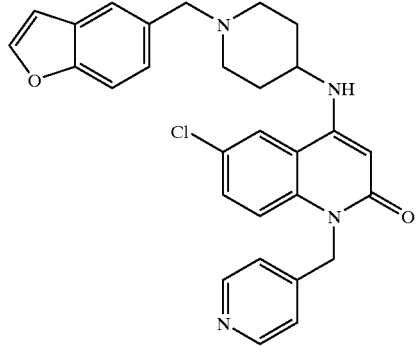
V-10
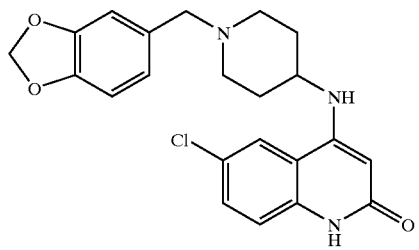
V-11
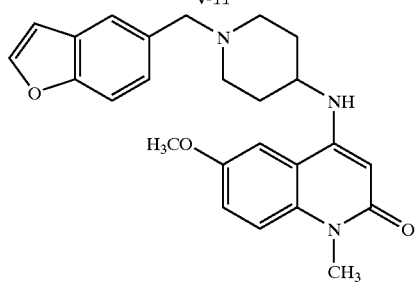
V-12
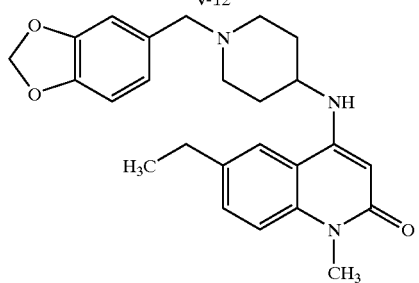
V-13
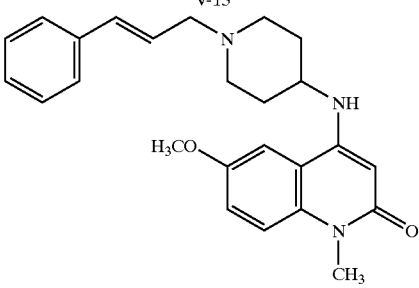
V-14
TABLE 4-continued
Examples of Compounds of Formula V
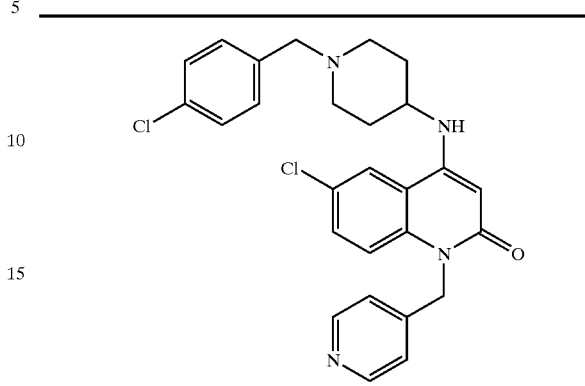
V-15
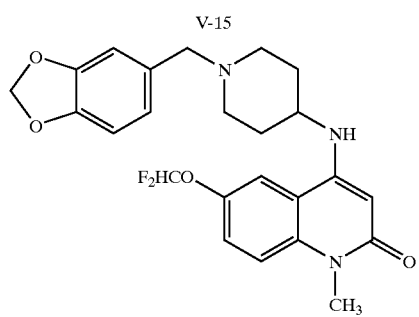
V-16
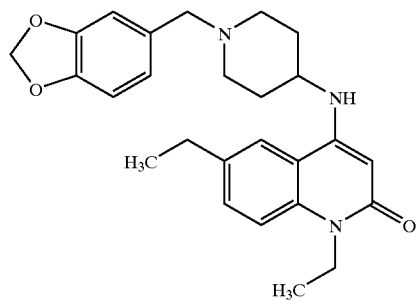
V-17
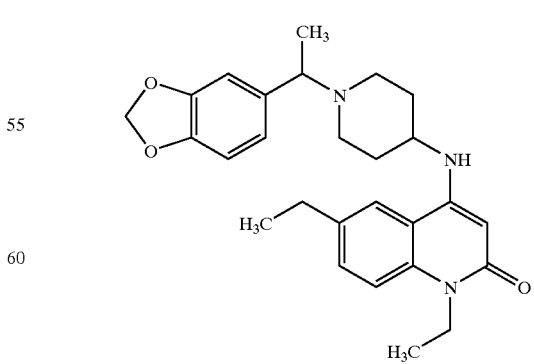
V-18

TABLE 4-continued
Examples of Compounds of Formula V
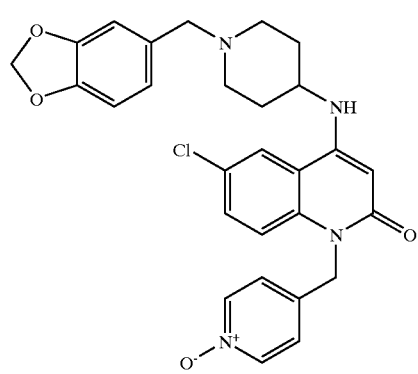
V-19
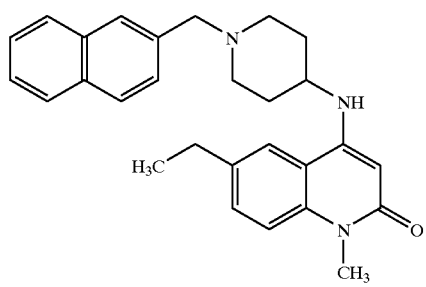
V-20
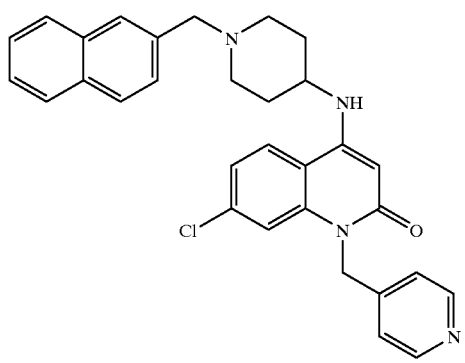
V-21
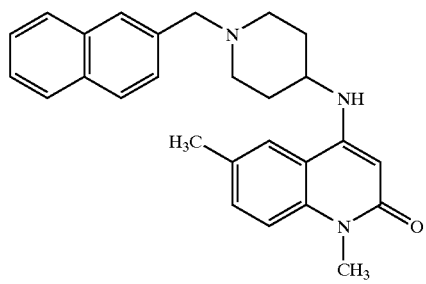
V-22
TABLE 4-continued
Examples of Compounds of Formula V
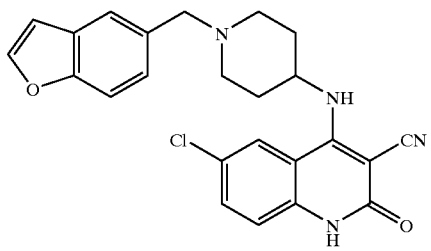
V-23
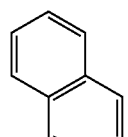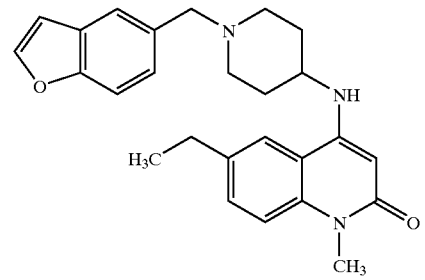
V-24
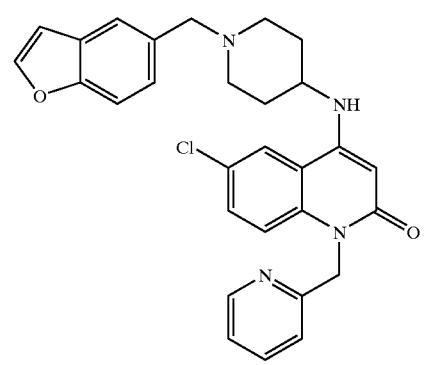
V-25
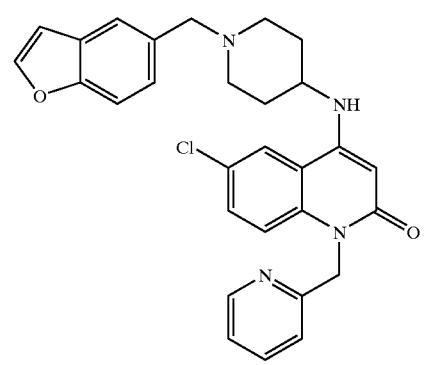
V-26

TABLE 4-continued
Examples of Compounds of Formula V
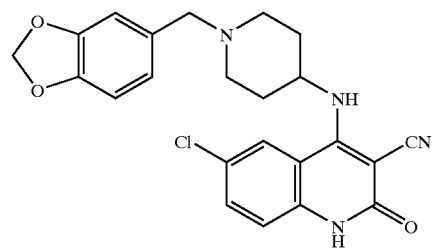
V-27
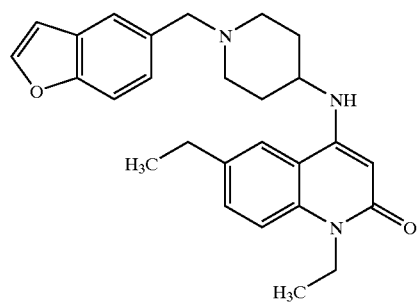
V-28
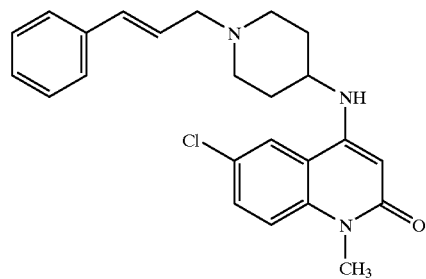
V-29
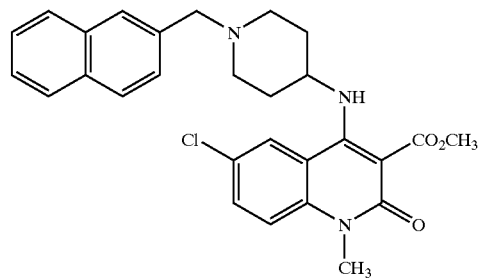
V-30
TABLE 4-continued
Examples of Compounds of Formula V
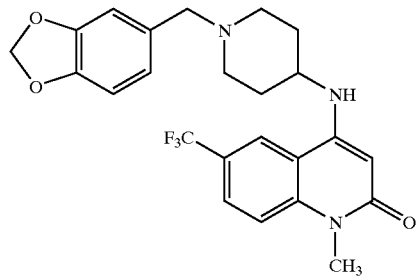
V-31
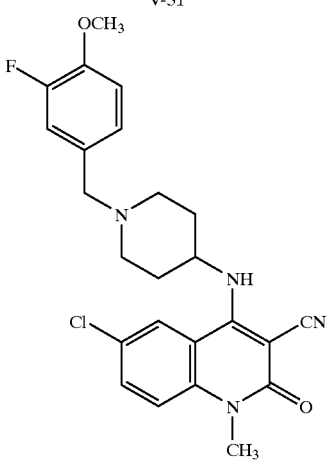
V-32
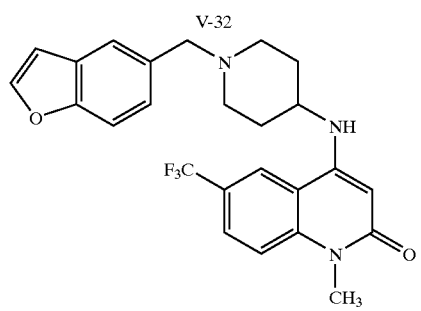
V-33
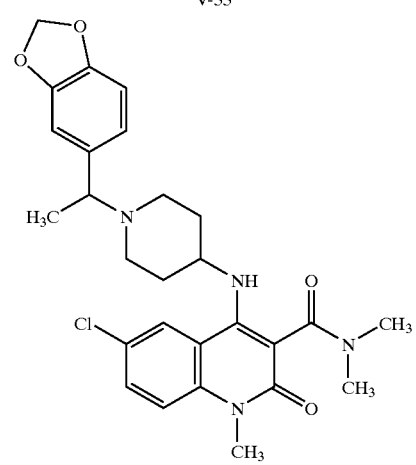
V-34

TABLE 4-continued
Examples of Compounds of Formula V
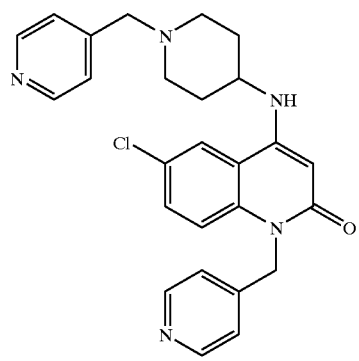
V-35
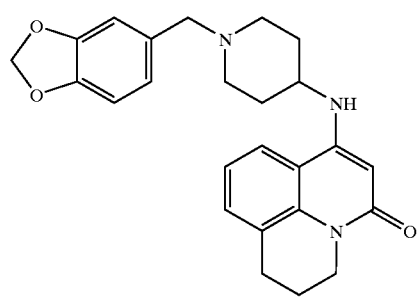
V-36
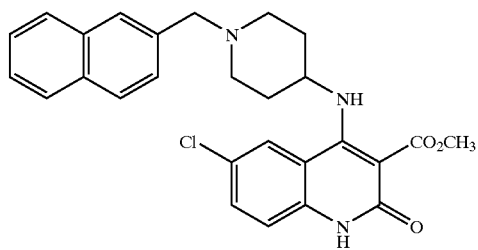
V-37
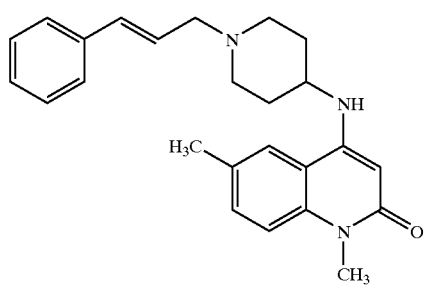
V-38
TABLE 4-continued
Examples of Compounds of Formula V
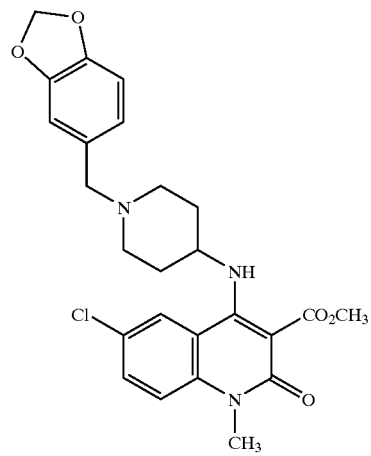
V-39
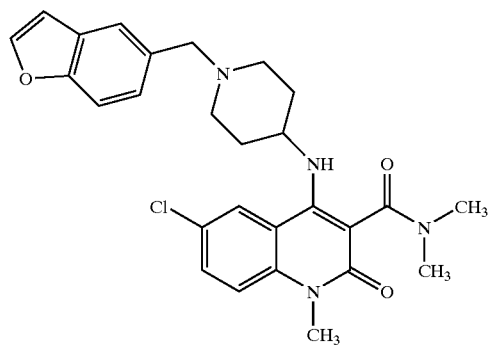
V-40
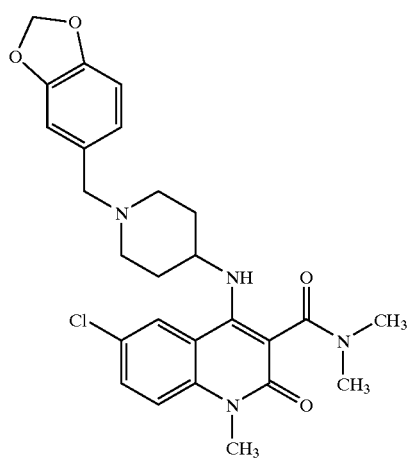
V-41

TABLE 4-continued
Examples of Compounds of Formula V
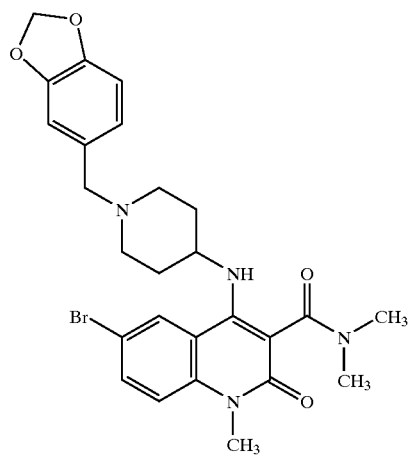
V-42
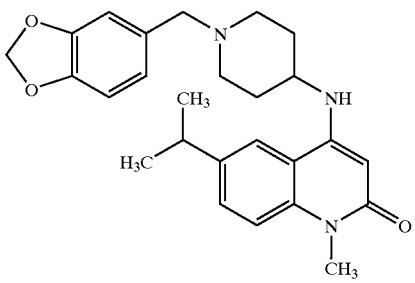
V-43
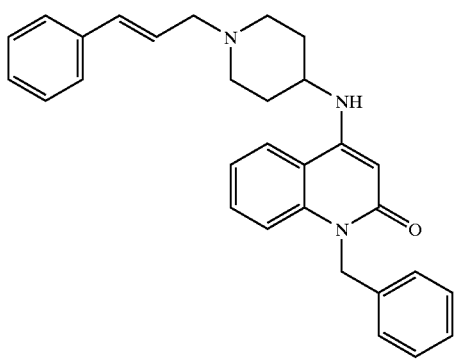
V-44
TABLE 4-continued
Examples of Compounds of Formula V
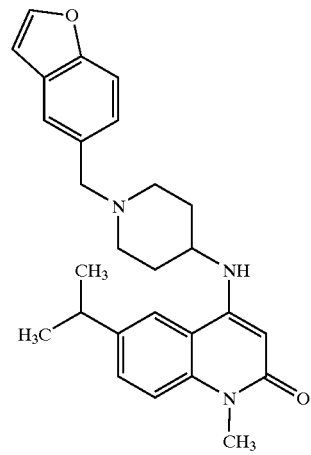
V-45
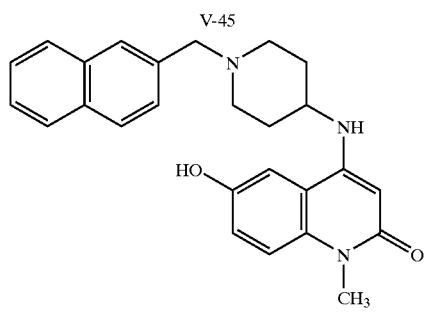
V-46
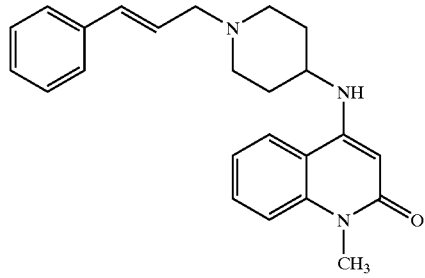
V-47
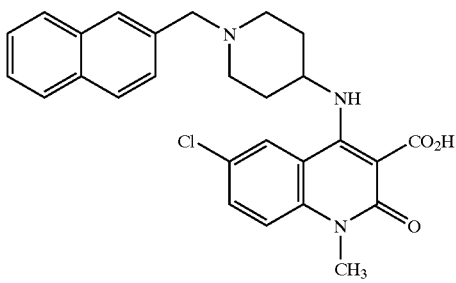
V-48

TABLE 4-continued
Examples of Compounds of Formula V
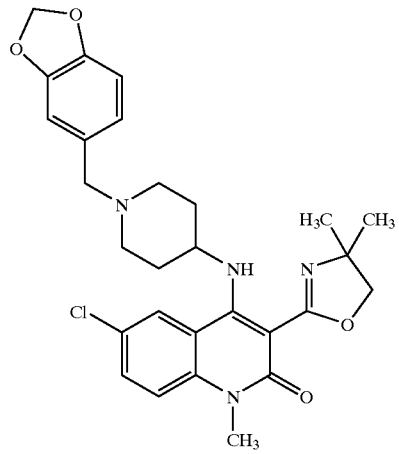
V-49
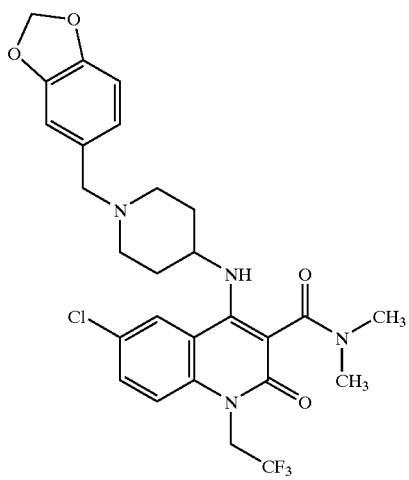
V-50
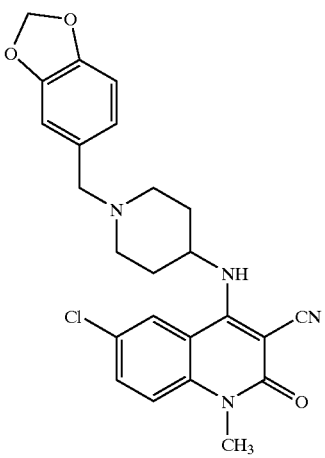
V-51
TABLE 4-continued
Examples of Compounds of Formula V
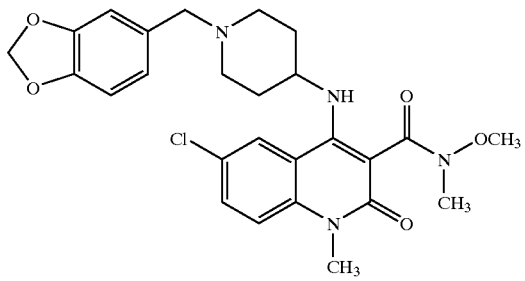
V-52
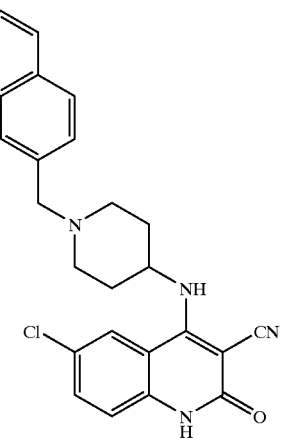
V-53
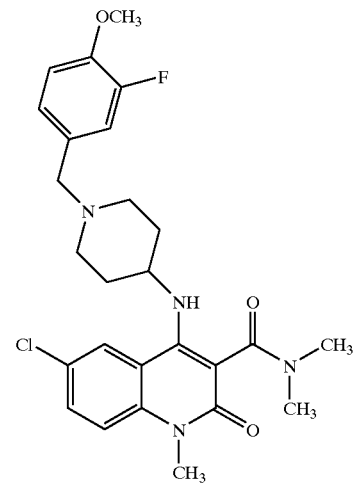
V-54
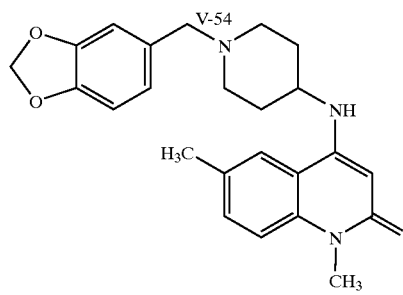
V-55

TABLE 4-continued
Examples of Compounds of Formula V
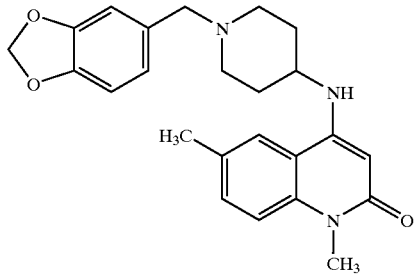
V-56
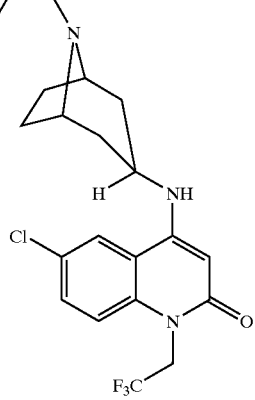
V-57
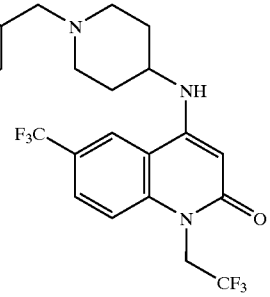
V-58
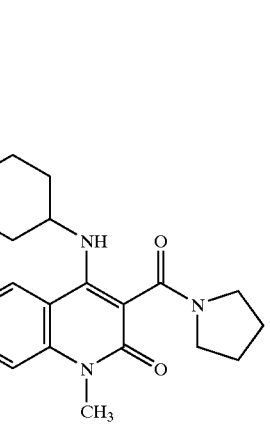
V-59
TABLE 4-continued
Examples of Compounds of Formula V
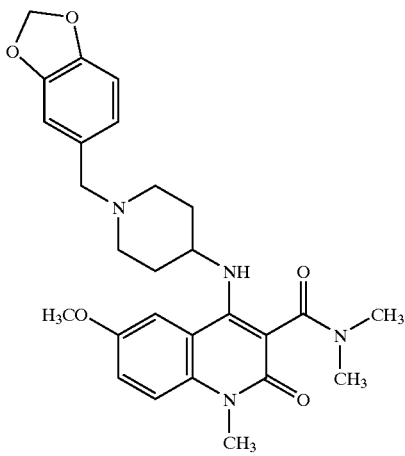
V-60
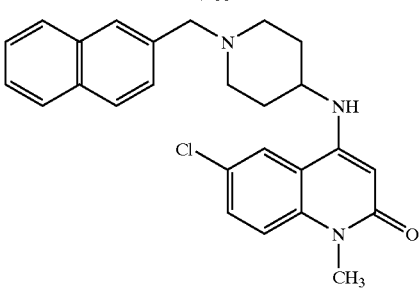
V-61
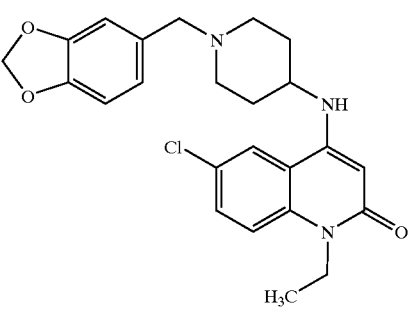
V-62
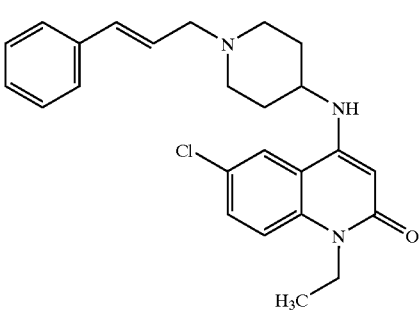
V-63

TABLE 4-continued

Examples of Compounds of Formula V

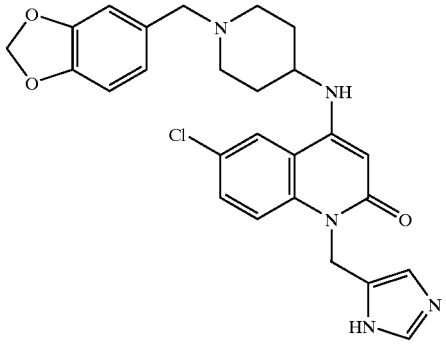

V-64

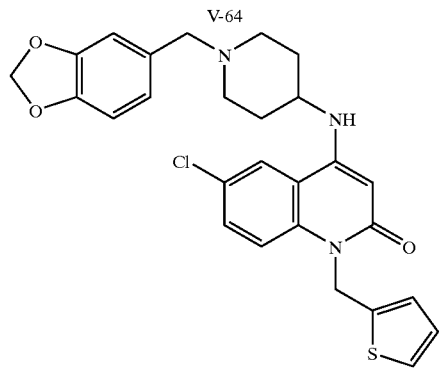

V-65

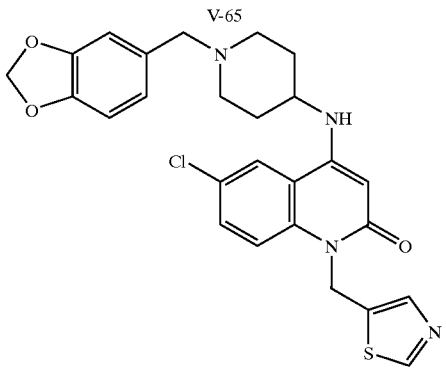

V-66

The compounds in Table 3 above may also be identified by the following chemical names:

V-1: 6-Chloro-4-(1-naphthalen-2-ylmethyl-piperidin-4-ylamino)-1-pyridin-3-ylmethyl-1H-quinolin-2-one;

V-2: 4-(1-Benzo[1,3]dioxol-5-ylmethyl-piperidin-4-ylamino)-6-chloro-1-pyridin-2-ylmethyl-1H-quinolin-2-one;

V-3: 4-(1-Benzo[1,3]dioxol-5-ylmethyl-piperidin-4-ylamino)-1-benzyl-6-chloro-1H-quinolin-2-one;

V-4: 4-(1-Benzo[1,3]dioxol-5-ylmethyl-piperidin-4-ylamino)-6-chloro-1-pyridin-4-ylmethyl-1H-quinolin-2-one;

V-5: 6-Chloro-4-(1-naphthalen-2-ylmethyl-piperidin-4-ylamino)-1-pyridin-4-ylmethyl-1H-quinolin-2-one;

V-6: 6-Chloro-1-ethyl-4-(1-naphthalen-2-ylmethyl-piperidin-4-ylamino)-1H-quinolin-2-one;

V-7: 4-(1-Benzo[1,3]dioxol-5-ylmethyl-piperidin-4-ylamino)-6-chloro-1-(2,2,2-trifluoro-ethyl)-1H-quinolin-2-one;

V-8: 4-(1-Benzo[1,3]dioxol-5-ylmethyl-piperidin-4-ylamino)-6-methoxy-1-methyl-1H-quinolin-2-one;

V-9: 6-Methoxy-1-methyl-4-(1-naphthalen-2-ylmethyl-piperidin-4-ylamino)-1H-quinolin-2-one;

V-10: 4-(1-Benzofuran-5-ylmethyl-piperidin-4-ylamino)-6-chloro-1-pyridin-4-ylmethyl-1H-quinolin-2-one;

V-11: 4-(1-Benzo[1,3]dioxol-5-ylmethyl-piperidin-4-ylamino)-6-chloro-1H-quinolin-2-one;

V-12: 4-(1-Benzofuran-5-ylmethyl-piperidin-4-ylamino)-6-methoxy-1-methyl-1H-quinolin-2-one;

V-13: 4-(1-Benzo[1,3]dioxol-5-ylmethyl-piperidin-4-ylamino)-6-ethyl-1-methyl-1H-quinolin-2-one;

V-14: 6-Methoxy-1-methyl-4-[1-(3-phenyl-allyl)-piperidin-4-ylamino]-1H-quinolin-2-one;

V-15: 6-Chloro-4-[1-(4-chloro-benzyl)-piperidin-4-ylamino]-1-pyridin-4-ylmethyl-1H-quinolin-2-one;

V-16: 4-(1-Benzo[1,3]dioxol-5-ylmethyl-piperidin-4-ylamino)-6-difluoromethoxy-1-methyl-1H-quinolin-2-one;

V-17: 4-(1-Benzo[1,3]dioxol-5-ylmethyl-piperidin-4-ylamino)-1,6-diethyl-1H-quinolin-2-one;

V-18: 4-[1-(1-Benzo[1,3]dioxol-5-yl-ethyl)-piperidin-4-ylamino]-1,6-diethyl-1H-quinolin-2-one;

V-19: 4-(1-Benzo[1,3]dioxol-5-ylmethyl-piperidin-4-ylamino)-6-chloro-1-(1-oxy-pyridin-4-ylmethyl)-1H-quinolin-2-one;

V-20: 6-Ethyl-1-methyl-4-(1-naphthalen-2-ylmethyl-piperidin-4-ylamino)-1H-quinolin-2-one;

V-21: 7-Chloro-4-(1-naphthalen-2-ylmethyl-piperidin-4-ylamino)-1-pyridin-4-ylmethyl-1H-quinolin-2-one;

V-22: 1,6-Dimethyl-4-(1-naphthalen-2-ylmethyl-piperidin-4-ylamino)-1H-quinolin-2-one;

V-23: 4-(1-Benzofuran-5-ylmethyl-piperidin-4-ylamino)-6-chloro-2-oxo-1,2-dihydro-quinoline-3-carbonitrile;

V-24: 6-Chloro-1-methyl-4-(1-naphthalen-2-ylmethyl-piperidin-4-ylamino)-2-oxo-1,2-dihydro-quinoline-3-carboxylic acid dimethylamide;

V-25: 4-(1-Benzofuran-5-ylmethyl-piperidin-4-ylamino)-6-ethyl-1-methyl-1H-quinolin-2-one;

V-26: 4-(1-Benzofuran-5-ylimethyl-piperidin-4-ylamino)-6-chloro-1-pyridin-2-ylmethyl-1H-quinolin-2-one;

V-27: 4-(1-Benzo[1,3]dioxol-5-ylmethyl-piperidin-4-ylamino)-6-chloro-2-oxo-1,2-dihydro-quinoline-3-carbonitrile;

V-28: 4-(1-Benzofuran-5-ylmethyl-piperidin-4-ylamino)-1,6-diethyl-1H-quinolin-2-one;

V-29: 6-Chloro-1-methyl-4-[1-(3-phenyl-allyl)-piperidin-4-ylamino]-1H-quinolin-2-one;

V-30: 6-Chloro-1-methyl-4-(1-naphthalen-2-ylmethyl-piperidin-4-ylamino)-2-oxo-1,2-dihydro-quinoline-3-carboxylic acid methyl ester;

V-31: 4-(1-Benzo[1,3]dioxol-5-ylmethyl-piperidin-4-ylamino)-1-methyl-6-trifluoromethyl-1H-quinolin-2-one;

V-32: 6-Chloro-4-[1-(3-fluoro-4-methoxy-benzyl)-piperidin-4-ylamino]-1-methyl-2-oxo-1,2-dihydro-quinoline-3-carbonitrile;

V-33: 4-(1-Benzofuran-5-ylmethyl-piperidin-4-ylamino)-1-methyl-6-trifluoromethyl-1H-quinolin-2-one;

V-34: 4-[1-(1-Benzo[1,3]dioxol-5-yl-ethyl)-piperidin-4-ylamino]-6-chloro-1-methyl-2-oxo-1,2-dihydro-quinoline-3-carboxylic acid dimethylamide;

V-35: 6-Chloro-1-pyridin-4-ylmethyl-4-(1-pyridin-4-ylmethyl-piperidin-4-ylamino)-1H-quinolin-2-one;

V-36: 1-(1-Benzo[1,3]dioxol-5-ylmethyl-piperidin-4-ylamino)-6,7-dihydro-5H-pyrido[3,2,1-ij]quinolin-3-one;

V-37: 6-Chloro-4-(1-naphthalen-2-ylmethyl-piperidin-4-ylamino)-2-oxo-1,2-dihydro-quinoline-3-carboxylic acid methyl ester;

V-38: 1,6-Dimethyl-4-[1-(3-phenyl-allyl)-piperidin-4-ylamino]-1H-quinolin-2-one;

V-39: 4-(1-Benzo[1,3]dioxol-5-ylmethyl-piperidin-4-ylamino)-6-chloro-1-methyl-2-oxo-1,2-dihydro-quinoline-3-carboxylic acid methyl ester;

V-40: 4-(1-Benzofuran-5-ylmethyl-piperidin-4-ylamino)-6-chloro-1-methyl-2-oxo-1,2-dihydro-quinoline-3-carboxylic acid dimethylamide;

V-41: 4-(1-Benzo[1,3]dioxol-5-ylmethyl-piperidin-4-ylamino)-6-chloro-1-methyl-2-oxo-1,2-dihydro-quinoline-3-carboxylic acid dimethylamide;

V-42: 4-(1-Benzo[1,3]dioxol-5-ylmethyl-piperidin-4-ylamino)-6-bromo-1-methyl-2-oxo-1,2-dihydro-quinoline-3-carboxylic acid dimethylamide;

V-43: 4-(1-Benzo[1,3]dioxol-5-ylmethyl-piperidin-4-ylamino)-6-isopropyl-1-methyl-1H-quinolin-2-one;

V-44: 1-Benzyl-4-[1-(3-phenyl-allyl)-piperidin-4-ylamino]-1H-quinolin-2-one;

V-45: 4-(1-Benzofuran-5-ylmethyl-piperidin-4-ylamino)-6-isopropyl-1-methyl-1H-quinolin-2-one;

V-46: 6-Hydroxy-1-methyl-4-(1-naphthalen-2-ylmethyl-piperidin-4-ylamino)-1H-quinolin-2-one;

V-47: 1-Methyl-4-[1-(3-phenyl-allyl)-piperidin-4-ylamino]-1H-quinolin-2-one;

V-48: 6-Chloro-1-methyl-4-(1-naphthalen-2-ylmethyl-piperidin-4-ylamino)-2-oxo-1,2-dihydro-quinoline-3-carboxylic acid;

V-49: 4-(1-Benzo[1,3]dioxol-5-ylmethyl-piperidin-4-ylamino)-6-chloro-3-(4,4-dimethyl-4,5-dihydro-oxazol-2-yl)-1-methyl-1H-quinolin-2-one;

V-50: 4-(1-Benzo[1,3]dioxol-5-ylmethyl-piperidin-4-ylamino)-6-chloro-2-oxo-1-(2,2,2-trifluoro-ethyl)-1,2-dihydro-quinoline-3-carboxylic acid dimethylamide;

V-51: 4-(1-Benzo[1,3]dioxol-5-ylmethyl-piperidin-4-ylamino)-6-chloro-1-methyl-2-oxo-1,2-dihydro-quinoline-3-carbonitrile;

V-52: 4-(1-Benzo[1,3]dioxol-5-ylmethyl-piperidin-4-ylamino)-6-chloro-1-methyl-2-oxo-1,2-dihydro-quinoline-3-carboxylic acid methoxy-methyl-amide;

V-53: 6-Chloro-4-(1-naphthalen-2-ylmethyl-piperidin-4-ylamino)-2-oxo-1,2-dihydro-quinoline-3-carbonitrile;

V-54: 6-Chloro-4-[1-(3-fluoro-4-methoxy-benzyl)-piperidin-4-ylamino]-1-methyl-2-oxo-1,2-dihydro-quinoline-3-carboxylic acid dimethylamide;

V-55: 4-(1-Benzo[1,3]dioxol-5-ylmethyl-piperidin-4-ylamino)-1,6-dimethyl-1H-quinolin-2-one;

V-56: 6-Chloro-1-methyl-4-(1-naphthalen-2-ylmethyl-piperidin-4-ylamino)-2-oxo-1,2-dihydro-quinoline-3-carbonitrile;

V-57: 4-(8-Benzo[1,3]dioxol-5-ylmethyl-8-aza-bicyclo[3.2.1]oct-3-ylamino)-6-chloro-1-(2,2,2-trifluoro-ethyl)-1H-quinolin-2-one;

V-58: 4-(1-Benzo[1,3]dioxol-5-ylmethyl-piperidin-4-ylamino)-1-(2,2,2-trifluoro-ethyl)-6-trifluoromethyl-1H-quinoline-2-one;

V-59: 4-(1-Benzo[1,3]dioxol-5-ylmethyl-piperidin-4-ylamino)-6-chloro-1-methyl-3-(pyrrolidine-1-carbonyl)-1H-quinolin-2-one;

V-60: 4-(1-Benzo[1,3]dioxol-5-ylmethyl-piperidin-4-ylamino)-6-methoxy-1-methyl-2-oxo-1,2-dihydro-quinoline-3-carboxylic acid dimethylamide;

V-61: 6-Chloro-1-methyl-4-(1-naphthalen-2-ylmethyl-piperidin-4-ylamino)-1H-quinolin-2-one;

V-62: 4-(1-Benzo[1,3]dioxol-5-ylmethyl-piperidin-4-ylamino)-6-chloro-1-ethyl-1H-quinolin-2-one;

V-63: 6-Chloro-1-ethyl-4-[1-(3-phenyl-allyl)-piperidin-4-ylamino]-1H-quinolin-2-one;

V-64: 4-(1-Benzo[1,3]dioxol-5-ylmethyl-piperidin-4-ylamino)-6-chloro-1-thiophen-2-ylmethyl-1H-quinolin-2-one;

V-65: 4-(1-Benzo[1,3]dioxol-5-ylmethyl-piperidin-4-ylamino)-6-chloro-1-(3H-imidazol-4-ylmethyl)-1H-quinolin-2-one; and V-66: 4-(1-Benzo[1,3]dioxol-5-ylmethyl-piperidin-4-ylamino)-6-chloro-1-thiazol-5-ylmethyl-1H-quinolin-2-one.

Another embodiment of the invention relates to compounds of formula VI:

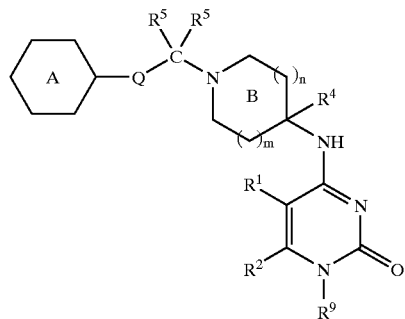

VI or a pharmaceutically-acceptable salt or prodrug thereof, wherein:

m is zero or one;

n is zero, one or two;

Ring A is selected from the group consisting of phenyl, $C_{3-8}$ carbocyclyl, 5–6 membered heteroaryl and 5–6 membered heterocyclyl, wherein said Ring A is optionally fused to a 5–7 membered saturated, unsaturated or partially unsaturated ring having 0–2 heteroatoms selected from N, O, or S, and wherein the Ring A system is substituted or unsubstituted;

Q is absent or is a $C_{3-6}$ cycloalk-1,2-diyl, —CHN($R^8$)$_2$—, or a saturated or unsaturated carbon chain having 1–5 chain atoms, wherein each hydrogen-bearing carbon of said chain is optionally and independently substituted by a $C_{1-6}$ aliphatic group, and one saturated carbon of said chain along with the hydrogen atoms attached thereto is optionally replaced by —C($R^7$)$_2$—, —O—, —S—, —S(O)—, —S(O)$_2$—, or —N($R^8$)—;

$R^1$ is selected from R, —CN, $CO_2R$, —C(O)R, or —CON($R^8$)$_2$;

R is hydrogen, $C_{1-10}$ aliphatic, aryl, aralkyl, heteroaryl, heteroaralkyl, heterocyclyl or heterocyclylalkyl;

$R^2$ is selected from hydrogen, $C_{1-10}$ aliphatic, aryl, aralkyl, heteroaryl, heteroaralkyl, heterocyclyl, or heterocyclylalkyl, or R¹ and R² taken together with their intervening atoms form a fused, unsaturated or partially unsaturated, substituted or unsubstituted, 5–7 membered ring having 0–2 heteroatoms selected from O, N or S;

$R^4$ is selected from hydrogen, $C_{1-10}$ aliphatic, —CN, —CO₂R, —C(O)R, or —C(O)N($R^8$)₂;

each $R^5$ is independently selected from the group consisting of hydrogen, $C_{1-6}$ aliphatic, —CN, —CO₂R, —C(O)R, and —CON($R^8$)₂, or two $R^5$ groups taken together with their intervening carbon form an optionally substituted 3–6 membered ring having 0–2 heteroatoms selected from O, N, or S;

Ring B is optionally substituted by one or more $R^6$;

each $R^6$ is independently selected from one or more $C_{1-6}$ aliphatic, hydroxyl, alkoxy, oxo, halo, —SR, —CN, —N($R^8$)₂, —NHC(O)R, —N($R^8$)CON($R^8$)₂, —N($R^8$)COR, —NHCO₂($C_{1-8}$ aliphatic), —CO₂R, —C(O)R, —CON($R^8$)₂, —S(O)₂R, —S(O)R, —SO₂N($R^8$)₂, or —N($R^8$)S(O)₂R, or two $R^6$ taken together with their intervening atoms form a 5–7 membered ring having 0–2 heteroatoms selected from N, O, or S;

each $R^7$ is independently selected from hydrogen, $C_{1-10}$ aliphatic, halo, —OR, —SR, —CN, —N($R^8$)₂, —NHC(O)R, —N($R^8$)CON($R^8$)₂, —N($R^8$)COR, —NHCO₂R—, —CO₂R, —C(O)R, —CON($R^8$)₂, —S(O)₂R, —S(O)R, —SO₂N($R^8$)₂, or —N($R^8$)S(O)₂R, or two $R^7$ groups taken together form =O, =N—OR, =N—N($R^8$)₂, =N—NHC(O)R, =N—NHCO₂R, or two $R^7$ groups taken together with their intervening carbon form an optionally substituted 3–6 membered ring having 0–2 heteroatoms selected O, N, or S;

each $R^8$ is independently selected from R, —CO₂R, —C(O)R, —C(O)N($C_{1-6}$ aliphatic)₂, —C(O)NH($C_{1-6}$ aliphatic), —S(O)₂R, —S(O)R, or —SO₂N($C_{1-6}$ aliphatic)₂, —SO₂NH($C_{1-6}$ aliphatic), or two $R^8$ groups on the same nitrogen taken together with the nitrogen form a 5–7 membered heterocyclyl ring; and $R^9$ is hydrogen, $C_{1-10}$ aliphatic, aralkyl, heteroaralkyl, or heterocyclylalkyl.

In compounds of formula VI, each of the variables Ring A, Q, $R^1$, $R^2$, $R^4$, $R^5$, $R^9$, m, and n are equivalent in function to the corresponding variables in the compounds of formula I. Accordingly, the teachings and descriptions provided above for each of these variables may be applied to the compounds of formula VI.

Preferred examples of the Ring A system in formula VI compounds are shown in Table 1 above. When Ring A is monocyclic, a preferred Ring A is phenyl. Examples of suitable substituents on the Ring A moiety include include halo, $C_{1-6}$ aliphatic, alkoxy, haloalkoxy, $C_{1-6}$ haloaliphatic, alkylcarbonyl, cyano, amino, mono- or dialkylamino, mono- or dialkylaminocarbonyl, aminocarbonyl, alkoxycarbonyl, alkoxycarbonylamino, mono- or dialkylaminosulfonyl, aminosulfonyl, alkylsulfonyl, carboxy, carboxyalkyl, phenyl, phenalkyl, 5–8 membered heteroaryl or heteroaralkyl, 3–8 membered heterocyclyl or heterocyclylalkyl, cyanoalkyl, aminoalkyl, mono- or dialkylaminoalkyl, alkoxycarbonylalkyl, thioalkyl, and alkoxysulfonyl. It is preferred that the alkyl moieties of the Ring A substituents have 1–6 carbons. The alkyl moieties may be interrupted by a heteroatom selected from NH, N(alkyl), O, S, SO₂, or a carbonyl. When Ring A is a phenyl ring, examples of particular substituted phenyl groups include 4-chlorophenyl, 3-acetylphenyl, 4-acetylphenyl and 4-fluoro-3-methoxyphenyl.

In compounds of formula VI, $R^9$ is preferably hydrogen, $C_{1-3}$ alkyl, 2,2,2-trifluoroethyl, benzyl, CH₂-imidazolyl, CH₂-thiazolyl, CH₂-thienyl and CH₂-pyridyl.

In compounds of formula VI, $R^1$ and $R^2$ are preferably taken together with their intervening atoms to form a fused benzo ring. The benzo ring so formed may be substituted or unsubstituted. Examples of preferred substituents on the benzo ring, when present, include halo, alkoxy, aliphatic, haloalkoxy, haloaliphatic, aryl, aralkyl, 5–6 membered heteroaryl, alkylcarbonyl, alkylcarboxy, amino, mono- or dialkylamino, alkoxycarbonyl, cyano, aminocarbonyl, mono- or dialkylaminocarbonyl, alkylsulfonyl, alkoxycarbonylamino, and mono- or dialkylaminosulfonyl. When $R^1$ and $R^2$ form a benzo ring, the 6-position is a preferred position of substitution on either the resulting coumarin ring (where Y is oxygen,) or quinolinone ring (where Y is nitrogen).

In compounds of formula VI, $R^4$ is preferably hydrogen, $C_{1-6}$ aliphatic, —CN, —CO₂R, —C(O)R, or —CON($R^8$)₂. More preferably $R^4$ is hydrogen or $C_{1-3}$ aliphatic, and most preferably $R^4$ is hydrogen.

In compounds of formula VI, Ring B is optionally substituted by one or more $R^6$. The $R^6$ substituent may be independently selected from one or more $C^{1-6}$ aliphatic, hydroxyl, alkoxy, =O, halo, —SR, —CN, —N($R^8$)₂, —NHC(O)R, —N($R^8$)CON($R^8$)₂, —N($R^8$)COR, —NHCO₂R, —CO₂R, —C(O)R, —CON($R^8$)₂, —S(O)₂R, —S(O)R, —SO₂N($R^8$)₂, or —N($R^8$)S(O)₂R, or two $R^6$ taken together with their intervening atoms form a 5–7 membered ring having 0–2 heteroatoms selected from N, O, or S. Ring B is preferably a piperidine ring (where m is one and n is one). The piperidine ring is preferably unsubstituted or substituted with one or more $C_{1-6}$ aliphatic groups, or two $R^6$ groups are taken together to form a ring. An 8-azabicyclo[3.2.1]octane is an example of a Ring B piperidine where two $R^6$ groups are taken together. The azabicyclooctane may be exo or endo, with the exo configuration preferred.

In compounds of formula VI, preferably each $R^5$ is independently selected from hydrogen or $C_{1-6}$ aliphatic, particularly methyl.

In compounds of formula VI, Q is preferably absent or —CH═CH— wherein the vinylic hydrogen closest to Ring B is optionally replaced by an alkyl or halo group. More preferably Q is absent or —CH═CH—.

In compounds of formula VI, preferred examples of the Ring A system wherein Ring A is a monocyclic ring include substituted or unsubstituted phenyl or a 5–6 membered heteroaryl or heterocyclyl ring, such as pyridyl, furanyl, thienyl, or pyrrolyl, that is optionally fused to a 5–6 membered aromatic ring having 0–2 heteroatoms. More preferred Ring A monocyclic rings are phenyl and furanyl.

One embodiment of the invention relates to a method of treating an MCH-R1-mediated disease comprising administering to a subject a compound of formula VI having one or more features selected from the group consisting of: (a) m is one and n is one; (b) Ring A is a phenyl or a 5–6 membered heteroaryl or heterocyclyl ring that is optionally fused to a 5–6 membered aromatic ring having 0–2 heteroatoms; (c) Q is absent or —CH═CH—; (d) $R^1$ and $R^2$ are taken together with their intervening atoms to form a fused benzo ring; (e) Y is oxygen, —NH—, —N(CH₃)—, —N(CH₂CF₃)—, or —N(CH₂-pyridyl)-; (f) $R^4$ is hydrogen; and (h) each $R^5$ is independently selected from hydrogen or CH₃. A more preferred method of this invention relates to the use of compounds of formula VI having all of these features.

One embodiment of this invention relates to compounds of formula VI wherein Q is absent providing compounds of formula VII. Another embodiment relates to compounds of formula VII wherein $R^1$ and $R^2$ are taken together to form a benzo ring to provide compounds of formula VIII as shown below. Ring C is optionally substituted by 0–2 $R^{10}$ groups, which are described below.
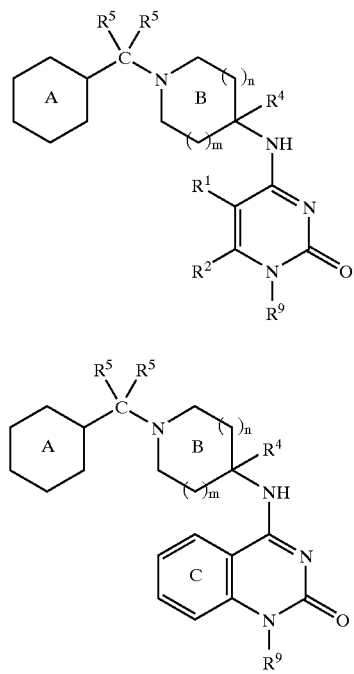
VII
VIII
Examples of specific compounds of formula VI are shown below in Table 5.
TABLE 5
Examples of Compounds of Formula VI
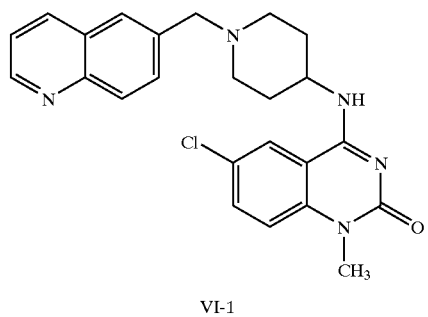
VI-1
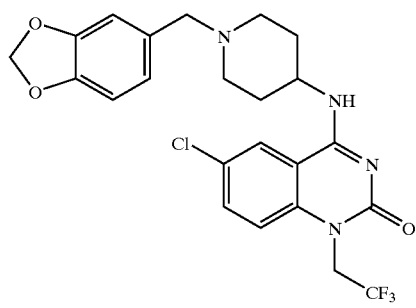
VI-2
TABLE 5-continued
Examples of Compounds of Formula VI
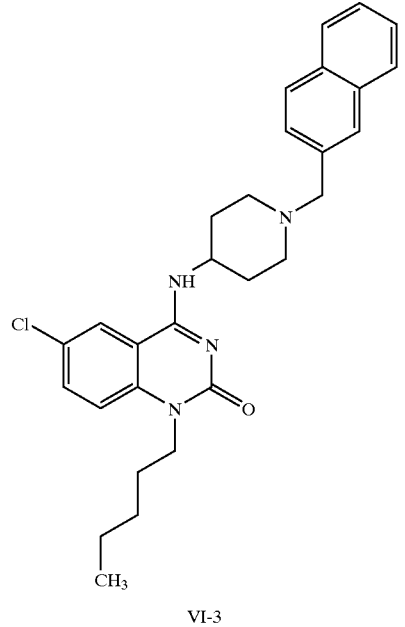
VI-3
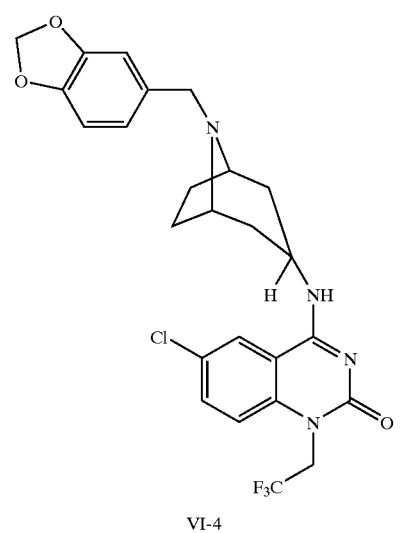
VI-4
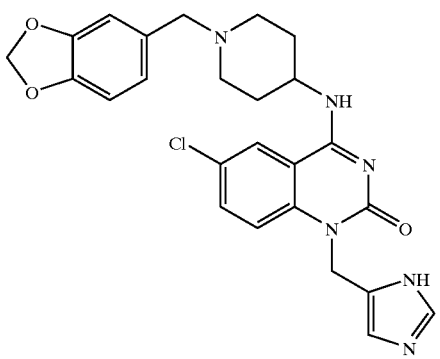
VI-5

TABLE 5-continued

Examples of Compounds of Formula VI

VI-6

The compounds shown in Table 5 may also be identified by the following chemical names:

VI-1: 6-Chloro-1-methyl-4-(1-quinolin-6-ylmethyl-piperidin-4-ylamino)-1H-quinazolin-2-one;

VI-2: 4-(1-Benzo[1,3]dioxol-5-ylmethyl-piperidin-4-ylamino)-6-chloro-1-(2,2,2-trifluoro-ethyl)-1H-quinazolin-2-one;

VI-3: 6-Chloro-4-(1-naphthalen-2-ylmethyl-piperidin-4-ylamino)-1-pentyl-1H-quinazolin-2-one;

VI-4: 4-(8-Benzo[1,3]dioxol-5-ylmethyl-8-aza-bicyclo[3.2.1]oct-3-ylamino)-6-chloro-1-(2,2,2-trifluoro-ethyl)-1H-quinazolin-2-one;

VI-5: 4-(1-Benzo[1,3]dioxol-5-ylmethyl-piperidin-4-ylamino)-6-chloro-1-(3H-imidazol-4-ylmethyl)-1H-quinazolin-2-one; and VI-6: 4-(1-Benzo[1,3]dioxol-5-ylmethyl-piperidin-4-ylamino)-6-chloro-1-thiazol-5-ylmethyl-1H-quinazolin-2-one.

The compounds of this invention may be prepared by methods known to those skilled in the art for analogous compounds, as illustrated by the general schemes below, and by reference to the preparative examples shown below.

The compounds and processes of the present invention will be better understood in connection with the following synthetic schemes and methods which illustrate a means by which the compounds of the invention can be prepared. Abbreviations which have been used in the descriptions of the scheme and the examples that follow are; DMSO for dimethylsulfoxide; DCM for dichloromethane; DMF for N,N-dimethylformamide; MP-BH$_3$CN for macroporous cyanoborohydride TFA for trifluoroacetic acid; THF for tetrahydrofuran.

Scheme I

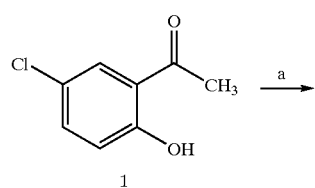

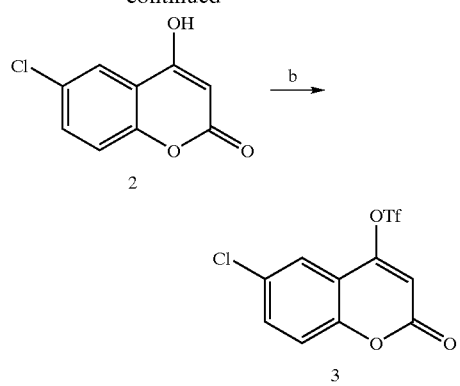

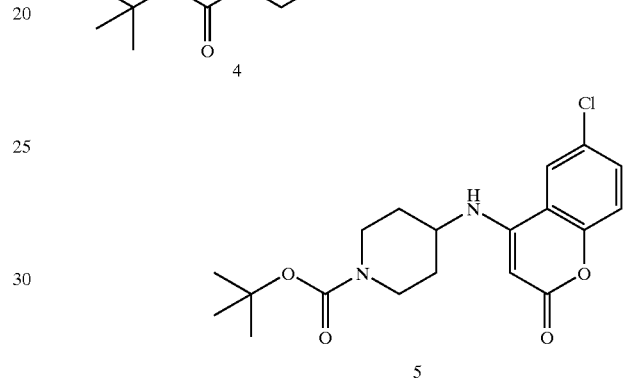

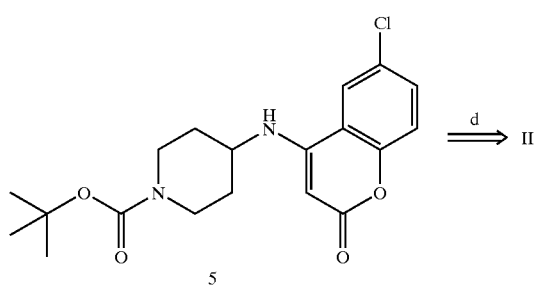

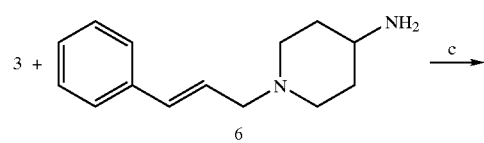

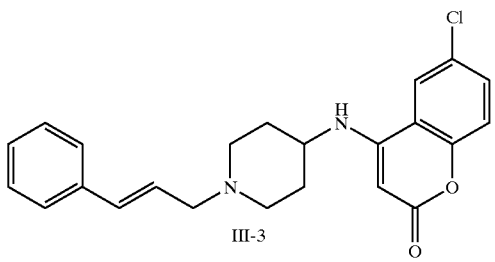

Reagents and conditions: (a) Na, diethylcarbonate, 130° C.; (b) Tf$_2$O, CH$_2$Cl$_2$, 0° C.; (c) diisopropylethylamine, room temperature; (d) see Procedures A and B in the Synthetic Examples below Scheme I above shows a general route to compounds of formulae II and III. A 4-hydroxy-chromenone compound 2 may be obtained by treating the starting material compound 1 with diethylcarbonate under strong basic conditions. Step (b) shows the conversion of compound 2 to the triflate compound 3 which may be performed in dichloromethane or another suitable organic solvent. The triflate group of compound 3 may be displaced by an aminopiperidine such as the Boc-protected compound 4 to provide the intermediate compound 5 or by a 4-amino-1-cinnamylpiperidine compound 6 to provide compounds of formula III. Step (c) is carried out in the presence of a suitable base such as diisopropylethylamine or another trialkylamine base such as triethylamine. Suitable solvents include DMF, acetonitrile and the like. While the tert-butoxycarbonyl (Boc) protecting group is shown in Scheme I for illustrative purposes, other amino protecting groups are well known that may also be used. See Greene, "Protecting Groups in Organic Chemistry" 3$^{rd}$ ed. (1999) Wiley & Sons, Inc.

The Boc protecting group in intermediate compound 5 may be removed using trifluoroacetic acid in dichloromethane or an aqueous acid in organic solvent such as 4N HCl in dioxane. The deprotection provides a versatile intermediate that may then be alkylated at the piperidinyl nitrogen to provide compounds of this invention. For example, by following the general procedures A and B in the synthetic examples below one may obtain compounds of formula II. It will be apparent to one skilled in the art that a number of other aminopiperidines may be used in place of compound 4 to provide other compounds of this invention. For example, the treatment of compound 3 with substituted or unsubstituted 4-amino-1-arylmethyl-piperidines, such as 4-amino-1-benzyl-piperidines, also provides compounds of formula II.

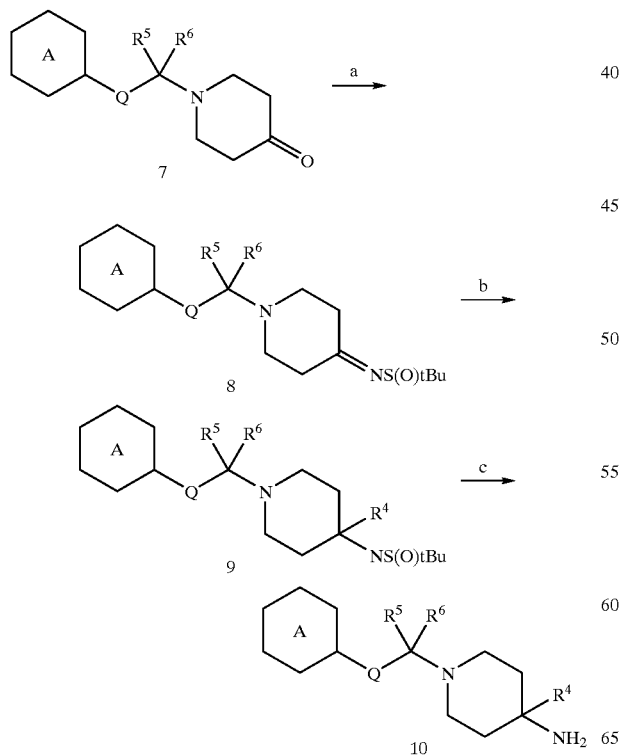

Scheme II

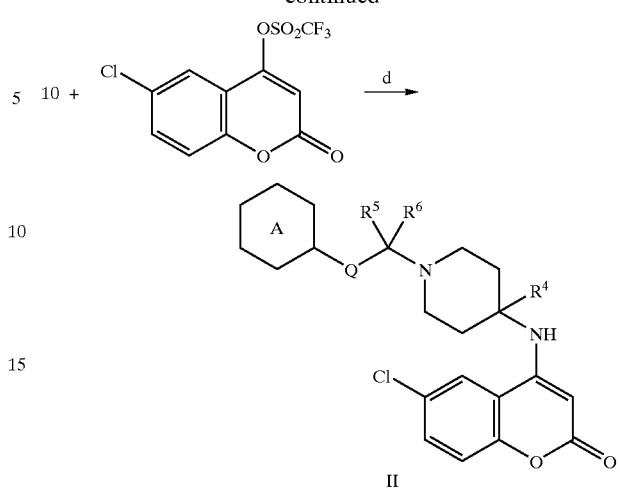

Reagents and conditions: (a) H$_2$NS(O)tBu, Ti(OEt)$_4$; (b) R$_4$Li, Al(CH$_3$)$_3$; (c) aqueous HCl; (d) Et$_3$N, heat Scheme II above shows a route to the present compounds starting from a 1-substituted-4-piperidinone compound 7. The piperidinone ring of compound 7 is converted through steps a–c to provide a 4-amino-4-substituted piperidine compound 10.

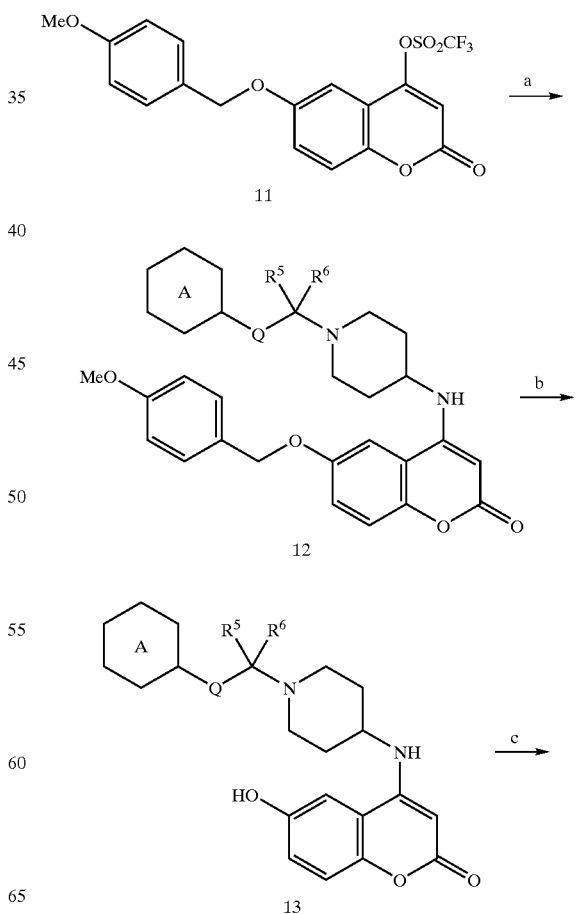

Scheme III

-continued

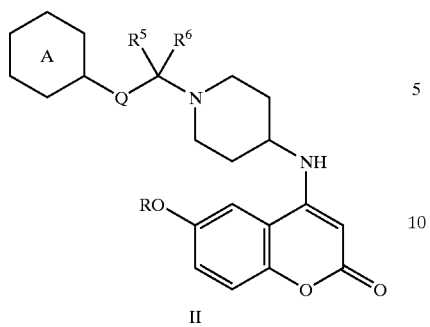

Reagents and conditions: (a) see step (d) of Scheme II; (b) HCl; (c) R—X, base

Scheme III above shows a route to compounds of the present invention that allows for the preparation of various substituents on the coumarin moiety.

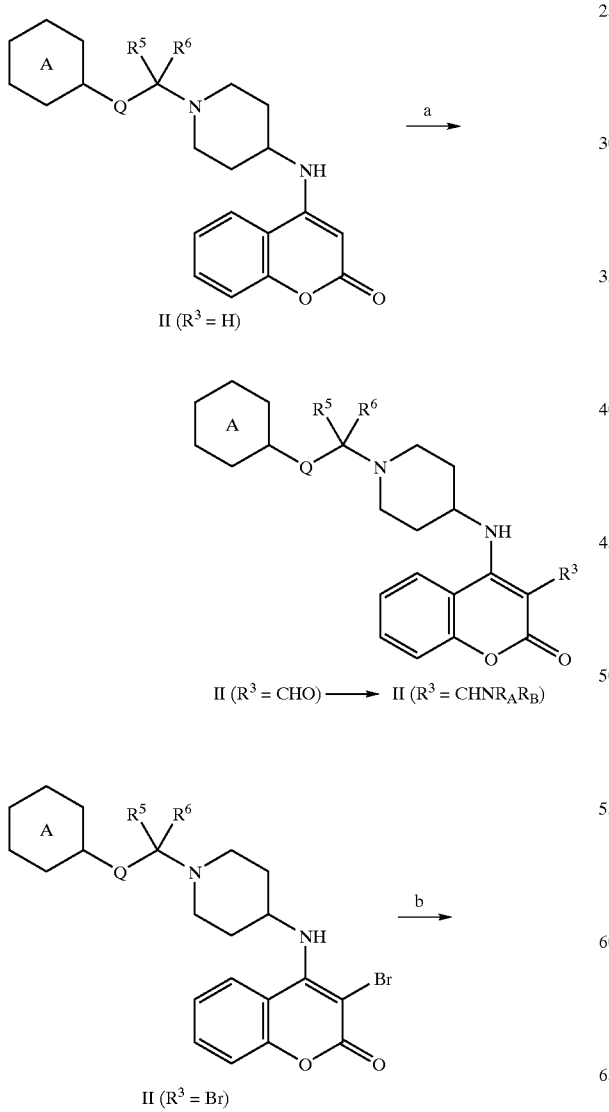

Scheme IV above shows how the present compounds may be prepared having various $R^3$ substituents. A formylation reaction (step a) may be employed to provide II where $R^3$ is CHO. A variety of synthetic procedures known in the art may then be used to convert the formyl group to other $R^3$ substituents. For example, reductive amination with MP-NaCNBH$_3$ provides II where $R^3$ is a disubstituted aminomethyl. Alternatively, a bromo at $R^3$ may be introduced using N-bromosuccinimide and acetic acid. The bromo substituent may then be replaced by a variety of other groups using palladium catalyzed coupling reactions known in the art (step b).

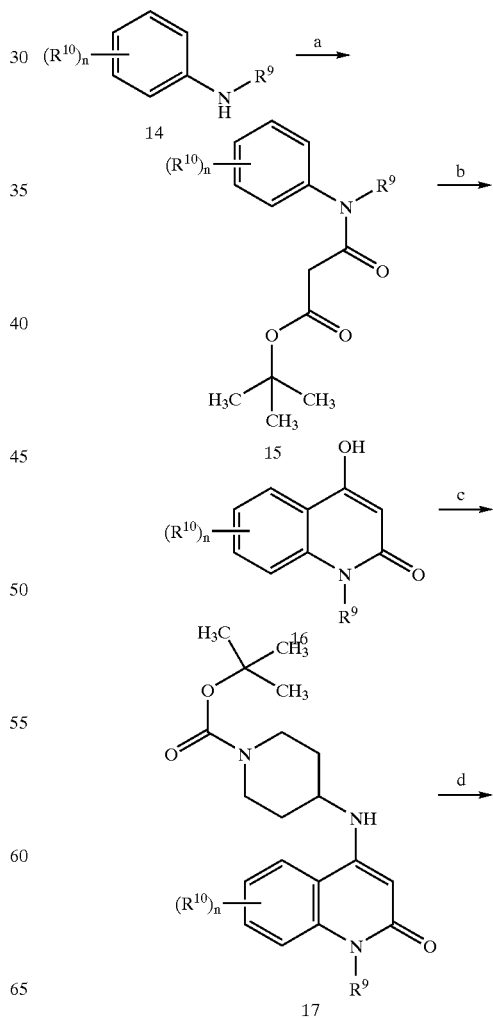

Scheme VI

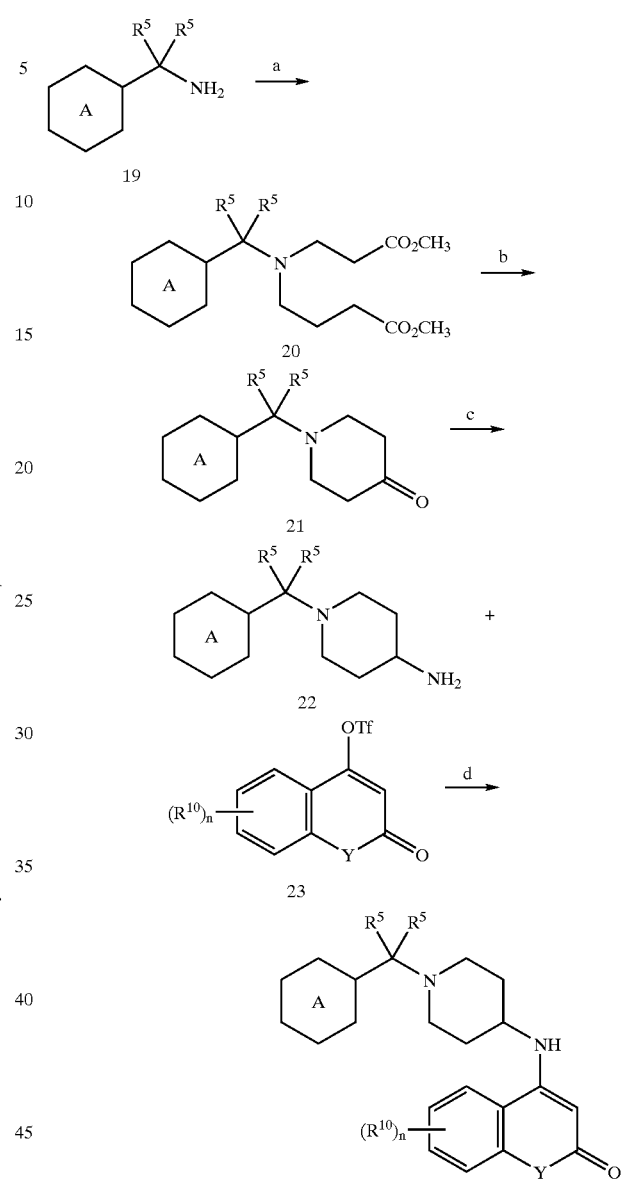

Reagents and conditions: (a) CH$_2$=CHCO$_2$Me, acetic acid; (b) NaH, toluene, then, 10% HCl; (c) NH$_2$OH•HCl, pyridine, EtOH, then, LiAlH$_4$, Et$_2$O, reflux; (d) diisopropylethylamine, THF

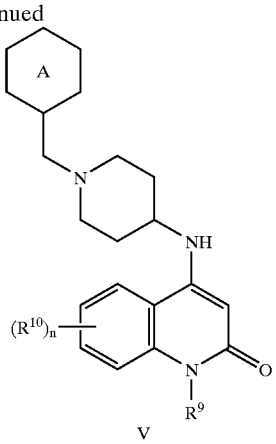

V

Reaction and conditions: (a) HO$_2$CCH$_2$CO$_2$ (t-Bu), Et—C≡N≡C—(CH$_2$)$_3$NMe$_2$•HCl, CH$_2$Cl$_2$; (b) CH$_3$SO$_3$H, P$_2$O$_5$; (c) acetonitrile, NaH, (CF$_3$SO$_2$)$_2$N—Ph, then, 4-aminopiperidine-1-carboxylic acid t-butyl ester; (d) CF$_3$CO$_2$H, CH$_2$Cl$_2$, then, acetonitrile, Na$_2$CO$_3$, Et$_3$N, BrCH$_2$-(Ring A).

Scheme V above shows a general route to making quinolone compounds of the present invention, where Ring A and R$^9$ are as described above, R$^{10}$ is halo, alkoxy, aliphatic, haloalkoxy, haloaliphatic, aryl, aralkyl, 5–6 membered heteroaryl, alkylcarbonyl, alkylcarboxy, amino, mono- or dialkylamino, alkoxycarbonyl, cyano, aminocarbonyl, mono- or dialkylaminocarbonyl, alkylsulfonyl, alkoxycarbonylamino, or mono- or dialkylaminosulfonyl, and n is 0–2. According to step (c), the hydroxy-quinolone compound 16 is first converted to a triflate, which is then displaced by an aminopiperidine to provide the useful intermediate compound 17. In this reaction the piperidine nitrogen is conveniently protected by t-butoxycarbonyl. This protecting group (Pg) may be replaced by any suitable protecting known to those skilled in the art. Examples of such protecting groups include other alkoxycarbonyl groups, benzyl groups, and those found in Greene and Wuts, *Protective Groups in Organic Synthesis*, 3$^{rd}$ edition, John Wiley & Sons, New York, 1999, and Harrison and Harrison et al., *Compendium of Synthetic Organic Methods*, Vols. 1–8 (John Wiley and Sons, 1971–1996), which are incorporated herein by reference. Accordingly, the following compounds are useful for preparing the MCH-R1 inhibitors of this invention:

18

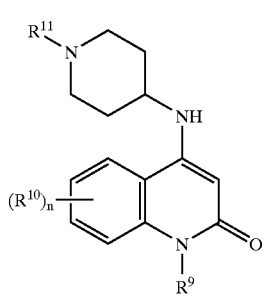

where R$^9$ is as described above; n is an integer of 0 to 2; R$^{10}$ is halo, alkoxy, aliphatic, haloalkoxy, haloaliphatic, aryl, aralkyl, 5–6 membered heteroaryl, alkylcarbonyl, alkylcarboxy, amino, mono- or dialkylamino, alkoxycarbonyl, cyano, aminocarbonyl, mono- or dialkylaminocarbonyl, alkylsulfonyl, alkoxycarbonylamino, or mono- or dialkylaminosulfonyl; and R$^{11}$ is hydrogen or a nitrogen protecting group.

Scheme VI above shows a general route to compounds of this invention wherein the N-substituted piperidine moiety is prepared early on. The scheme is shown for Q being absent, and Y, R$^5$, R$^{10}$ and n are as described above. This route is particularly useful when at least one of the R$^5$ groups is other than hydrogen.

Scheme VII

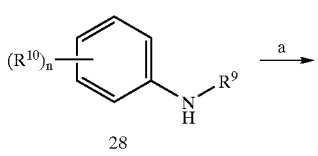

28 a

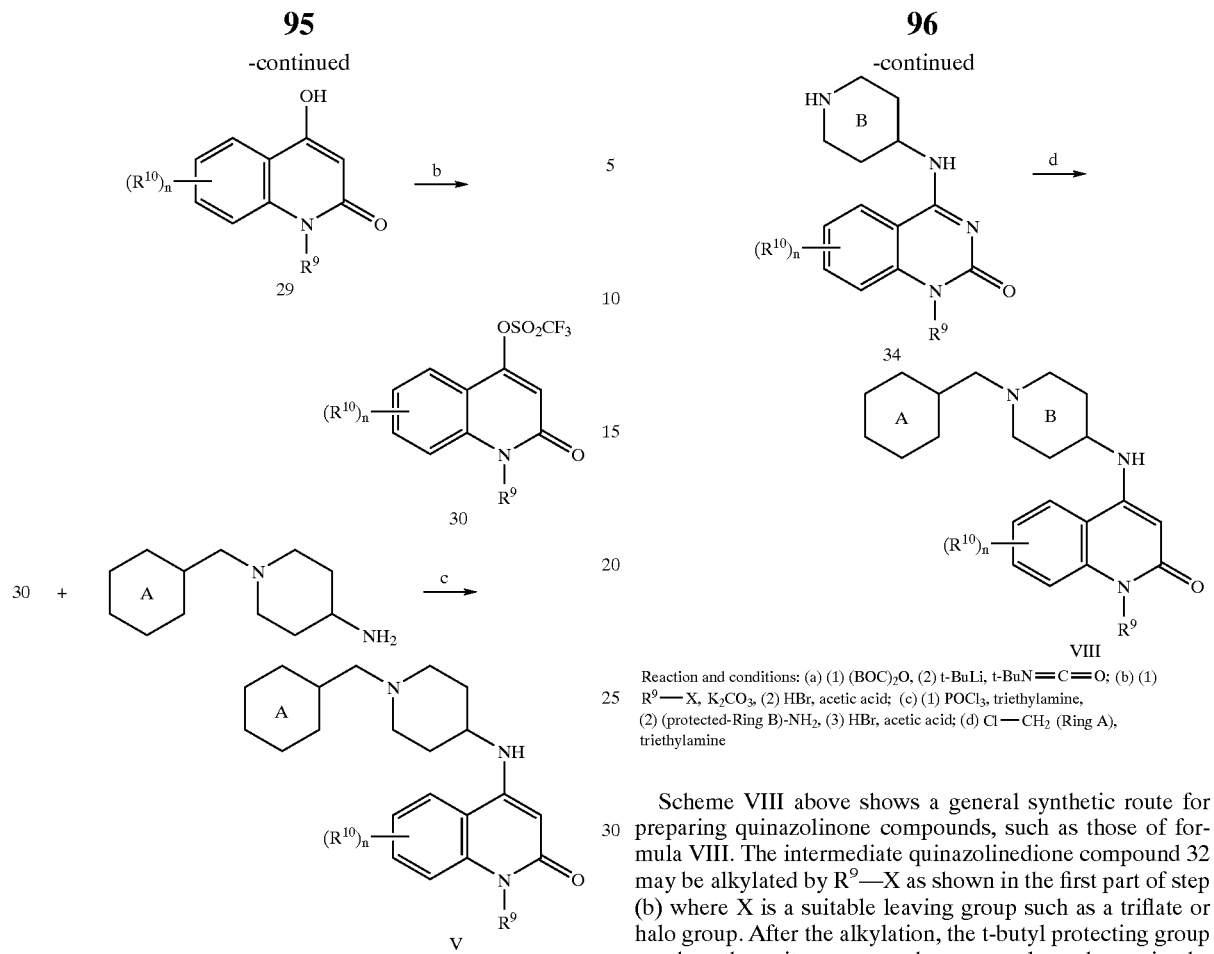

Reaction and conditions: (a) POCl₃, CH₂(CO₂H)₂; (b) NaH, (CF₃SO₂)₂N—Ph, acetonitrile; (c) diisopropylethylamine, reflux Scheme VII above shows an alternative general route for preparing quinolone compounds of this invention.

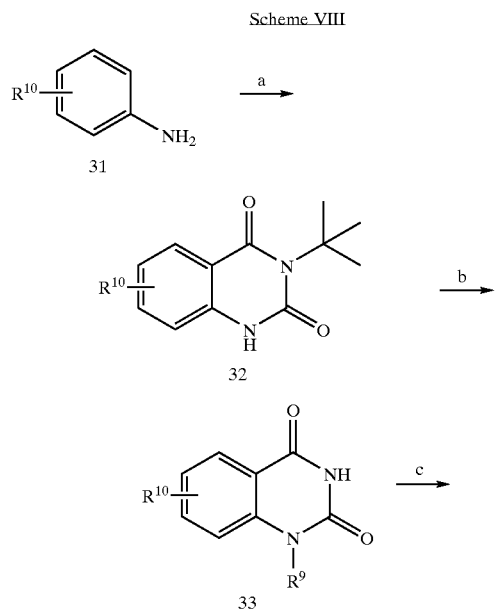

Reaction and conditions: (a) (1) (BOC)₂O, (2) t-BuLi, t-BuN═C═O; (b) (1) R⁹—X, K₂CO₃, (2) HBr, acetic acid; (c) (1) POCl₃, triethylamine, (2) (protected-Ring B)-NH₂, (3) HBr, acetic acid; (d) Cl—CH₂ (Ring A), triethylamine Scheme VIII above shows a general synthetic route for preparing quinazolinone compounds, such as those of formula VIII. The intermediate quinazolinedione compound 32 may be alkylated by R⁹—X as shown in the first part of step (b) where X is a suitable leaving group such as a triflate or halo group. After the alkylation, the t-butyl protecting group on the other nitrogen may be removed as shown in the second part of step (b). The first part of step (c) converts the 4-carbonyl to a 4-chloro group that is then displaced by a (protected-Ring B) —NH₂ group such as 4-amino-piperidine-1-carboxylic acid ethyl ester or 3-amino-8-aza-bicyclo[3.2.1]octane-8-carboxylic acid ethyl ester. After removal of the alkoxycarbonyl protecting group in step (c)(3), the Q-(Ring A) moiety is introduced as shown in step (d) where Q is CH₂.

The compounds of this invention are designed to be antagonists of the MCH receptor. Antagonists are meant to include compounds which reduce the stimulatory effects of agonists (e.g., MCH), reduce intracellular signaling mediated by MCH receptor, and/or reduce GDP/GTP exchange of receptor activity (e.g., antagonists, inverse agonists, neutral antagonists). Therefore, the compounds of this invention may be assayed for their ability to bind the MCH receptor or mediate MCH receptor activity directly. Assays for each of the activities are described below in the Testing section and/or are known in the art. One embodiment of this invention relates to a composition comprising a compound of this invention or a pharmaceutically acceptable salt thereof, and a pharmaceutically acceptable carrier. It will be appreciated that the compounds of this invention may be derivatized at functional groups to provide prodrug derivatives which are capable of conversion back to the parent compounds in vivo. Examples of such prodrugs include the physiologically acceptable and metabolically labile ester derivatives, such as methoxymethyl esters, methylthiomethyl esters, or pivaloyloxymethyl esters derived from a hydroxyl group of the compound or a carbamoyl moiety derived from an amino group of the compound. Additionally, any physiologically acceptable equivalents of the present compounds, similar to the metabolically labile esters or carbamates, which are capable of producing the parent compounds described herein in vivo, are within the scope of this invention.

If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, the basic nitrogen-containing groups may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility,to allow administration by injection, alter metabolism and alter rate of excretion.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being. Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers.

Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The above-described compositions are particularly useful in therapeutic applications relating to an MCH-R1-mediated disorder. As used herein, the term "MCH-R1 mediated disorder" includes a disorder, disease or condition which is caused or characterized by an abnormal metabolism (i.e., the chemical changes in living cells by which energy is provided for vital processes and activities), regulation of energy balance and/or response to stress, in a patient or subject. Metabolic disorders include diseases, disorders, or conditions associated with aberrant feeding activity or aberrant neuronal (e.g., hypothalamic neuronal cell) signaling or function. Metabolic disorders can be characterized by a dysregulation(e.g., upregulation) of MCH-R1 activity. Metabolic disorders can detrimentally affect cellular functions such as cellular proliferation, growth, differentiation, or migration, cellular regulation of homeostasis, inter- or intra-cellular communication; tissue function, such as liver function, muscle function, or adipocyte function; systemic responses in an organism, such as hormonal responses (e.g., insulin and/or leptin response) or satiety responses.

Examples of MCH-R1 mediated disorders include, metabolic disorders (e.g., obesity, weight regulation, diabetes, hyperphagia, endocrine abnormalities, triglyceride storage disease, Bardet-Biedl syndrome, Lawrence-Moon syndrome, and Prader-Labhart-Willi syndrome), stress-related disorders (e.g., anxiety), neurological or psychological disorders (e.g., schizophrenia, depression, Parkinson's disease, Huntington's Chorea, epilepsy), regulation of sexual activity, and treatment of memory and cognitive functions.

A preferred use of the compounds of the invention is in the therapeutic applications relating to metabolic disorders, e.g., obesity. Obesity is defined as a body mass index (BMI) of 30 kg/$^2$m or more (National Institute of Health, Clinical Guidelines on the Identification, Evaluation, and Treatment of Overweight and Obesity in Adults (1998)). However, the present invention is also intended to include a disease, disorder, or condition that is characterized by a body mass index (BMI) of 25 kg/$^2$m or more, 26 kg/$^2$m or more, 27 kg/$^2$m or more, 28 kg/$^2$m or more, 29 kg/$^2$m or more, 29.5 kg/$^2$m or more, or 29.9 kg/$^2$m or more, all of which are typically referred to as overweight (National Institute of Health, Clinical Guidelines on the Identification, Evaluation, and Treatment of Overweight and Obesity in Adults (1998)).

The amount of compound present in the above-described compositions should be sufficient to cause a detectable decrease in the severity of the disorder or in MCH receptor activity, as measured by the assays described in the examples or known in the art.

The amount of MCH receptor antagonist needed will depend on the effectiveness of the antagonist for the given cell type and the length of time required to treat the disorder. According to another embodiment, the compositions of this invention may further comprise another therapeutic agent. When a second agent is used, the second agent may be administered either as a separate dosage form or as part of a single dosage form with the compounds or compositions of this invention.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular compound and other therapeutic agent, if present, in the composition.

In a preferred embodiment, the invention provides a method of treating a mammal, having one of the aforementioned diseases, comprising the step of administering to said mammal a pharmaceutically acceptable composition described above. In this embodiment, if the patient is also administered another therapeutic agent or MCH receptor antagonist, it may be delivered together with the compound of this invention in a single dosage form, or, as a separate dosage form. When administered as a separate dosage form, the other MCH receptor antagonist or agent may be administered prior to, at the same time as, or following administration of a pharmaceutically acceptable composition comprising a compound of this invention.

In order that this invention be more fully understood, the following preparative and testing examples are set forth. These examples are for the purpose of illustration only and are not to be construed as limiting the scope of the invention in any way.

SYNTHETIC EXAMPLES

Example 1

6-chloro-4-hydroxycoumarin (2)

To a cooled (0° C.) suspension of sodium in toluene (7.7 g of the 30% by weight suspension, 100 mmol) in a flame dried flask was added dropwise 2-hydroxy-5-chloroacetophenone (1.7 g, 10 mmol) in 40 mL diethylcarbonate over a period of 25 minutes. The reaction mixture was allowed to warm to room temperature and then heated to reflux (about 130° C.) for 4 h. The reaction was monitored by LC-MS, the product was detected in negative ion mode. The cooled reaction mixture was quenched with MeOH (15 mL), then poured over ice water (150 mL) and extracted with ether (3×50 mL). The aqueous phase was acidified to pH 1.0 by slow dropwise addition of concentrated HCl (20 mL) (vigorous gas evolution) until a creamy white precipitate was formed. The precipitate was filtered off and dried affording the title compound 1.3 g, (66%) as an off white solid that was used directly in the next step. $^1$H NMR (300 MHz, MeOD-d$_4$) δ 5.651 (1H, s), 7.316–7.346 (1H, d, j=9.0 Hz), 7.585–7.623 (1H, dd, j=2.4, 9.0 Hz), 7.838–7.847 (1H, d, j=2.52 Hz.).

Example 2

4-hydroxy-6-methoxycoumarin

This was prepared in 82% yield in a manner similar to that described in Example 1. $^1$HNMR (300 MHz, MeOD-d$_4$) δ 4.019 (3H, s), 5.587 (1H, s), 7.076–7.333 (3H, m)

Example 3

Trifluoro-methanesulfonic acid 6-chloro-2-oxo-2H-chromen-4-yl ester (3)

To a cooled (0° C.) solution of 6-chloro-4-hydroxycoumarin (1.3 g, 6.6 mmol) and triethylamine (1.84 mL, 13.2 mmol) in dichloromethane (40 mL) was added dropwise triflic anhydride (1.33 mL, 7.9 mmol). The reaction was stirred at 0° C. for 2 hours. The reaction mixture was then washed with water and brine, dried over $MgSO_4$, and evaporated to afford a dark residue which was purified by chromatography on silica gel eluting with ethyl acetate/hexanes (1:9) to give the title compound (1.1 g, 51%) as a white powder. $^1$H NMR (300 MHz, MeOD-$d_4$) δ 6.557 (1H, s), 7.259 (1H, s), 7.366–7.398 (1H, d, j=9.5 Hz), 7.627–7.652 (1H, d, j=8.7 Hz).

Example 4

Trifluoromethanesulfonic acid 6-methoxy-2-oxo-2H-chromen-4-yl ester

This was prepared similarly in 76% in a manner similar to that described in Example 3. $^1$H NMR (300 MHz, MeOD-$d_4$) δ 3.876 (3H, s), 6.507 (1H, s), 7.066–7.077 (1H, d, j=3.3 Hz), 7.259–7.270 (1H, d, j=3.3 Hz), 7.344–7.376 (1H, d, j=9.4 Hz).

Example 5

4-N-Boc-1-cinnamylpiperidine

To a solution of 4-N-Boc-Amino-piperidine (5.0 g, 25 mmol) in DMF (25 mL) was added $K_2CO_3$ (10.35 g, 74.25 mmol) and cinnamyl chloride (3.3 mL, 24.75 mmol). The reaction stirred at room temperature for 2.5 hrs, and was diluted with diethyl ether and washed with water and brine. The organic layer was dried over $Na_2SO_4$, and concentrated to afford a white solid, which was used directly in the next step. MS (ESI(+)Q1MS m/z 317 (M+H)$^+$; $^1$H NMR (300 MHz, DMSO) δ ppm 1.37 (s, 9H), 1.4–1.5 (m, 2H), 1.67–1.69 (br d, 2H), 1.94 (br t, 2H), 2.63 (br d, 2H), 3.05 (br. d, 2H), 3.2 (m, 1H), 6.23–6.32 (m, 1H), 6.5 (d, 1H), 6.74 (br d, 1H), 7.20–7.44 (5H, m).

Example 6

4-amino-1-cinnamylpiperidine (4)

To a solution of compound 3 (1.85 g, 5.9 mmol) in about 30 mL of $CH_2Cl_2$ was added about 5 mL of 4.0N HCl in dioxane. The reaction was stirred overnight at room temperature. The solvent was then evaporated off to afford a white solid. The solid was diluted with $CH_2Cl_2$ and basified with 1N NaOH. The organic phase was dried over $MgSO_4$ and evaporated to afford 910 mg of a pale yellow solid (72%). $^1$H NMR (300 MHz, MeOD-$d_4$) δ 1.3–1.5 (2H, m), 1.7–1.9 (2H, m), 1.9–2.1 (2H, m), 2.6–2.8 (1H, m), 2.8–3.0 (2H, m), 3.1–3.2 (2H, m), 6.2–6.4 1H, m), 6.4–6.6 (1H, d, J=16.0 Hz), 7.2–7.4 (5H, m).

Example 7

6-Chloro-4-[1-(3-phenyl-allyl)-piperidin-4-ylamino]-chromen-2-one (5) (III-8)

To a solution of 1-(3-Phenyl-allyl)-piperidin-4-ylamine (4) (1.01 g,4.65 mmol) and diisopropylethylamine (1.63 mL, 9.3 mmol) in 10 mL $CHCl_3$ was added a solution of compound 3 (1.1 g, 5.6 mmol) in 10 mL $CHCl_3$. The reaction was stirred at room temperature for about 3 hours. The reaction mixture was then washed with water and brine and dried with $MgSO_4$. The yellow residue was triturated with a small volume of dichloromethane and filtered. The final product was converted to the HCl salt by addition of 4.0N HCl in dioxane to a suspension of the compound in dichloromethane. The solvent was removed by evaporation and the residue triturated with methanol to give the title compound (780 mg, 39%). $^1$H NMR (300 MHz, MeOD-$d_4$) δ 1.92–2.22 (2H, m), 2.35–2.45 (2H, bd, J=11.8 Hz), 3.15–3.35 (2H, m), 3.65–3.75 (2H, bd, j=12.3), 3.85–4.0 (1H, m), 3.90–4.00 (2H, d, J=6.9 Hz), 5.46 (1H, s), 6.32–6.43 (1H, p, J=7.7 Hz), 6.92–6.98 (1H, d, J=16.2 Hz), 7.31–7.41 (4H, m), 7.52–7.54 (2H, m), 7.58–7.62 (1H, dd, J=2.0, 8.8 Hz), 8.148 (1H, s).

Example 8

6-Methoxy-4-[1-(3-phenyl-allyl)-piperidin-4-ylamino] chromen-2-one (III-1)

This was prepared similarly in 54% yield in a manner similar to that described in Example 7 above. 1H NMR (300 MHz, MeOD-$d_4$) δ 1.60–1.75 (2H, m), 2.10–2.25 (4H, m), 2.95–3.05 (2H, bd, J=12.2 Hz), 3.19–3.21 (2H, d, j=6.4 Hz), 3.40–3.55 (1H, m), 3.87 (3H, s), 4.89–4.91 (1H, d, J=7.0 Hz), 5.30 (1H, s), 6.20–6.33 (1H, m), 6.47–6.57 (1H, m), 6.84–6.85 (1H, d, J=2.7 Hz), 7.09–7.13 (1H, dd, J=3.0, 9.0 Hz), 7.20–7.45 (6H, m).

Example 9

6-Chloro-4-(piperidin-4-ylamino)-chromen-2-one

A suspension of 4-Amino-1-N-Boc piperidine (0.25 g, 1.25 mmol), 6-chloro-4-hydroxycoumarin (0.27 g, 1.37 mmol) and TEA (0.35 mL, 2.5 mmol) in N-methylpyrrolidone (NMP, 1 mL) was heated in a microwave at 220° C. for 20 min. It was then cooled and carried forward to the next step. The reaction mixture was transferred to a 25 mL flask, diluted with 3 mL $CH_2Cl_2$ and cooled to 0° C. Trifluoroacetic acid (TFA, 4 mL) was added dropwise and the reaction allowed to warm up to room temperature and then stirred at room temperature for 4 h. The mixture was concentrated and the residual oil was purified on a C-18 RP HPLC system to give compound 3 (0.189 g, 30%, Bis TFA salt) as a off-white solid. $^1$H NMR (300 MHz, MeOH) δ ppm 8.15 (d, J=3, 1H), 7.61 (dd, J=3, 9, 1H), 7.34 (d, J=9, 1H), 5.47 (s, 1H), 3.82–3.95 (m, 1H), 3.46–3.55 (m, 2H), 3.18–3.25 (m, 2H), 2.26–2.36 (m, 2H), 1.81–1.95 (m, 2H); MS (ESI+Q1MS) m/z 279 [M+H]$^+$ General Procedures for the N-alkylation of a 4-(piperidin-4-ylamino)-chromen-2-one Procedure A. Reductive Amination $MP-BH_3CN$ (0.085 g, 0.216 mmol, loading 2.55 mmol/g) is added to a suspension of 4-(piperidin-4-ylamino)-chromen-2-one (0.030 g, 0.06 mmol) and the corresponding aldehyde (0.216 mmol) in 1:1 MeOH:$CH_2Cl_2$ (2 mL) and shaken at room temperature for 1 d. $PS-TsNHNH_2$ (0.084 g, 0.216 mmol, loading 2.56 mmol/g) is then added to scavenge unreacted aldehyde and the reaction mixture was shaken for 2 h, filtered, concentrated, and the residual oil was purified on a C-18 RP HPLC system to afford the title compound, usually as an off-white solid.

Procedure B. Nucleophilic Displacement of Alkyl Halides

The 4-(piperidin-4-ylamino)-chromen-2-one (0.025, 0.05 mmol) is added to a suspension of the corresponding alkyl halide (0.1 mmol) and K2CO3 (0.12 mmol) in DMF (1 mL). The reaction mixture is heated at 50–75° C. for 1 d. The reaction mixture is then filtered, concentrated and purified on a C-18 RP HPLC system to afford the title compound, usually as a white solid.

The following compounds were prepared according to a procedure similar to one of the procedures described above or in an analogous manner.

Example 10

4-(1-Benzo[1,3]dioxol-5ylmethyl-piperidin-4-ylamino)-6-chloro-chromen-2-one (II-4)

According to Procedure A above, 6-chloro-4-(piperidin-4-ylamino)-chromen-2-one and piperonal (0.032 g, 0.216 mmol) were allowed to react to give the title compound (0.0123 g, 39%, mono-TFA salt) as an off-white solid. $^1$H NMR (400 MHz, MeOH) δ ppm 8.12 (br s, 1H), 7.61 (d, J=8, 1H), 7.33 (d, J=8, 1H), 7.00 (m, 2H), 6.93 (dd, J=4, 8, 1H), 6.03 (s, 2H), 5.44 (s, 1H), 4.26 (s, 2H), 3.79–3.90 (m, 1H), 3.62–3.56 (m, 2H), 3.11–3.22 (m, 2H), 2.29–2.40 (m, 2H), 1.85–1.99 (m, 2H); MS (ESI+Q1MS) m/z 413 [M]$^+$

Example 11

4-[1-(2-Bromo-3-phenyl-allyl)-piperidin-4-ylamino]-6-chloro-chromen-2-one (III-53)

According to Procedure A above, 6-chloro-4-(piperidin-4-ylamino)-chromen-2-one and 2-bromo-3-phenyl-propenal (0.046 g, 0.216 mmol) were allowed to react to give the title compound (0.0088 g, 25.1%, mono-TFA salt) as a off-white solid. $^1$H NMR (400 MHz, MeOH) δ ppm 8.15 (d, J=4, 1H), 7.72 (dd, J=4, 8, 1H), 7.60 (dd, J=4, 8, 1H), 7.39–7.49 (m, 4H), 7.33 (d, J=8, 2H), 5.47 (s, 1H), 4.40 (s, 2H), 3.86–3.97 (m, 1H), 3.64–3.78 (m, 2H), 3.27–3.41 (partially buried m, 2H), 2.30–2.44 (m, 2H), 2.01–2.18 (m, 2H); MS (ESI+Q1MS) m/z 475 [M+H]$^+$

Example 12

6-Chloro-4-[1-(2-methyl-3-phenyl-allyl)-piperidin-4-ylamino]-chromen-2-one (III-8)

According to Procedure A above, 6-chloro-4-(piperidin-4-ylamino)-chromen-2-one and 2-methyl-3-phenyl-propenal (0.031 g, 0.216 mmol) were allowed to react to give the title compound (0.008 g, 25.8%, mono-TFA salt) as a off-white solid. $^1$H NMR (400 MHz, DMSO) δ ppm 8.35 (d, J=3, 1H), 7.66 (dd, J=3, 9, 1H), 7.32–7.47 (m, 6H), 6.76 (br s, 1H), 5.46 (s, 1H), 3.94–3.99 (m, 1H), 3.86 (d, J=3, 9, 1H), 3.53–3.60 (m, 2H), 3.05–3.20 (m, 2H), 2.18–2.28 (m, 2H), 2.05–2.15 (m, 1H), 2.01 (s, 3H), 1.82–1.91 (m, 2H); MS (ESI+Q1MS) m/z 409 [M]$^+$

Example 13

6-Chloro-4-{1-[5-(4-fluoro-phenyl)-5-oxo-pentyl]-piperidin-4-ylamino}-chromen-2-one (III-21)

According to Procedure B above, 6-chloro-4-(piperidin-4-ylamino)-chromen-2-one (0.025 g, 0.05 mmol) and 1-(4-fluorophenyl)-5-chloro-1-oxopentane (0.024 g, 0.11 mmol) were allowed to react to give the title compound (0.0078 g, 27.4%, mono-TFA salt) as a off-white solid. $^1$H NMR (300 MHz, MeOH) δ ppm 8.05–8.15 (m, 3H), 7.62 (dd, J=3, 9, 1H), 7.35 (d, J=9, 1H), 7.20–7.28 (m, 2H), 5.47 (s, 1H), 3.82–3.92 (m, 1H), 3.67–3.75 (m, 2H), 3.11–3.25 (m, 5H), 2.32–2.43 (m, 2H), 2.15–2.25 (m, 1H), 1.87–2.03 (m, 2H), 1.79–1.87 (m, 4H); MS (ESI+Q1MS) m/z 457 [M]$^+$

Example 14

6-Chloro-4-{1-[4-(5,6-dichloro-benzoimidazol-1-yl)-butyl]-piperidin-4-ylamino}-chromen-2-one (III-54)

According to Procedure B above, 6-chloro-4-(piperidin-4-ylamino)-chromen-2-one (0.020 g, 0.04 mmol) and 5,6-dichloro-1-(4-chlorobutyl)-1H-benzimidaole hydrochloride hydrate (0.023 g, 0.07 mmol) were allowed to react to give the title compound (0.012 g, 40.1%, mono-TFA salt) as a off-white solid. $^1$H NMR (500 MHz, MeOH) δ ppm 8.53 (br s, 1H), 8.11 (d, J=5, 1H), 7.99 (br s, 1H), 7.90 (br s, 1H), 7.61 (dd, J=5, 10, 1H), 7.33 (d, J=10, 1H), 5.44 (s, 1H), 4.42 (apparent t, J=10, 2H), 3.81–3.89 (m, 1H), 3.64–3.69 (m, 2H), 3.12–3.20 (m, 4H), 2.35 (apparent d, J=15, 2H), 1.97–2.03 (m, 2H), 1.89–1.96 (m, 2H), 1.76–1.82 (m, 2H); MS (ESI+Q1MS) m/z 521 [M+H]$^+$

Example 15

6-Methoxy-4-[1-(3-trifluoromethoxy-benzyl)-piperidin-4-ylamino]-chromen-2-one (II-20)

According to Procedure A above, 6-methoxy-4-(piperidin-4-ylamino)-chromen-2-one and 3trifluoromethoxybenzaldehyde were allowed to react to give the title compound. MS (DCI/NH$_3$) m/z 449 [M+H]$^+$; $^1$H NMR (500 MHz, DMSO) δ ppm 7.66 (m, 2H), 7.59 (m, 2H), 7.51 (m, 1H), 7.27 (m, 2H), 7.22 (m, 1H), 5.39 (m, 1H), 4.40 (m, 2H), 3.83 (m, 4H), 3.51 (m, 2H), 3.12 (m, 2H), 2.20 (m, 2H), 1.84 (m, 2H).

Example 16

4-(1-Benzo[1,3]dioxol-5-ylmethyl-piperidin-4-ylamino)-6-methoxy-chromen-2-one (II-1)

The title compound was prepared according to the procedure described in Example 15 substituting piperonal for 3-trifluoromethoxybenzaldehyde. MS (DCI/NH$_3$) m/z 409 [M+H]$^+$; $^1$H NMR (300 MHz, DMSO) δ ppm 7.66 (m, 1H), 7.26 (m, 3H), 7.10 (m, 1H), 7.03 (m, 2H), 6.10 (m, 2H), 5.39 (m, 1H), 4.24 (m, 2H), 3.83 (m, 3H), 3.74 (m, 1H), 3.28 (m, 2H), 3.07 (m, 2H), 2.18 (m, 2H), 1.80 (m, 2H).

Example 17

4-[1-(3,5-Dichloro-benzyl)-piperidin-4-ylamino]-6-methoxy-chromen-2-one (II-21)

The titled compound was prepared according to the procedure described in Example 15 substituting 3,5-dichlorobenzaldehyde for 3-trifluoromethoxybenzaldehyde. MS (DCI/NH$_3$) m/z 433 [M+H]$^+$; $^1$H NMR (500 MHz, DMSO) δ ppm 7.80 (m, 1H), 7.66 (m, 3H), 7.25 (m, 3H), 5.37 (m, 1H), 4.34 (m, 2H), 3.83 (m, 3H), 3.73 (m, 1H), 3.51 (m, 2H), 3.12 (m, 2H), 2.18 (m, 2H), 1.81 (m, 2H).

Example 18

4-{1-[5-(2-Chloro-phenyl)-furan-2-ylmethyl]-piperidin-4-ylamino}-6-methoxy-chromen-2-one (II-22)

The title compound was prepared according to the procedure described in Example 15 substituting 5-(2-chlorophenyl)-2-furancarboxaldehyde for 3-trifluoromethoxybenzaldehyde. MS (DCI/NH$_3$) m/z 465 [M+H]$^+$; $^1$H NMR (500 MHz, DMSO) δ ppm 7.92 (m, 1H), 7.63 (m, 2H), 7.50 (m, 1H), 7.42 (m, 1H), 7.23 (m, 4H), 6.91

(m, 1H), 5.41 (m, 1H), 4.54 (m, 2H), 3.84 (m, 4H), 3.79 (m, 1H), 3.59 (m, 2H), 3.19 (m, 1H), 2.21 (m, 2H), 1.85 (m, 2H).

Example 19

4-[1-(3-Hydroxy-benzyl)-piperidin-4-ylamino]-6-methyl-chromen-2-one (II-12)

According to Procedure A above, 6-methyl-4-(piperidin-4-ylamino)-chromen-2-one and 3-hydroxybenzaldehyde were processed to give the title compound. MS (DCI/NH$_3$) m/z 465 [M+H]$^+$; $^1$H NMR (500 MHz, DMSO) δ ppm 9.41–9.63 (m, 1H), 7.94 (m, 1H), 7.40 (m, 1H), 7.29 (m, 2H), 7.20 (m, 1H), 6.90 (m, 3H), 5.36 (m, 1H), 4.22 (m, 2H), 3.74 (m, 1H), 3.48 (m, 2H), 3.09 (m, 2H), 2.37 (m, 3H), 2.18 (m, 2H), 1.80 (m, 2H).

Example 20

6-Methyl-4-[1-(4-phenoxy-benzyl)-piperidin-4-ylamino]-chromen-2-one (II-13)

The title compound was prepared according to the procedure described in Example 19 substituting 4-phenoxybenzaldehyde for 3-hydroxybenzaldehyde. $^1$H NMR (500 MHz, DMSO) δ ppm 7.95 (m, 1H), 7.53 (m, 2H), 7.44 (m, 3H), 7.30 (m, 1H), 7.21 (m, 2H), 7.08 (m, 4H), 5.38 (m, 1H), 4.31 (m, 2H), 3.75 (m, 1H), 3.49 (m, 2H), 3.08 (m, 2H), 2.38 (m, 3H), 2.17 (m, 2H), 1.81 (m, 2H).

Example 21

6-Methoxy-4-{1-[5-(2-trifluoromethyl-phenyl)-furan-2-ylmethyl]-piperidin-4-ylamino}-chromen-2-one (II-23)

The title compound was prepared according to the procedure described in Example 15 substituting 5-(2-trifluoromethylphenyl)-2-furancarboxaldehyde for 3-trifluoromethoxybenzaldehyde. MS (DCI/NH$_3$) m/z 441 [M+H]$^+$; $^1$H NMR (500 MHz, DMSO) δ ppm 7.90 (m, 2H), 7.82 (m, 1H), 7.66 (m, 2H), 7.25 (m, 3H), 6.90 (m, 2H), 5.40 (m, 1H), 4.51 (m, 2H), 3.84 (m, 4H), 3.78 (m, 2H), 3.20 (m, 2H), 2.20 (m, 2H), 1.86 (m, 2H).

Example 22

4-{1-[5-(3-Chloro-phenyl)-furan-2-ylmethyl]-piperidin-4-ylamino}-6-methyl-chromen-2-one (II-24)

The title compound was prepared according to the procedure described in Example 19 substituting 5-(3-chlorophenyl)-2-furancarboxaldehyde for 3-hydroxybenzaldehyde. MS (DCI/NH$_3$) m/z 450 [M+H]$^+$; $^1$H NMR (500 MHz, DMSO) δ ppm 7.95 (m, 1H), 7.84 (m, 1H), 7.76 (m, 1H), 7.52 (m, 1H), 7.41 (m, 2H), 7.30 (m, 1H), 7.21 (m, 2H), 6.88 (m, 1H), 5.37 (m, 1H), 4.51 (m, 2H), 3.78 (m, 1H), 3.57 (m, 2H), 3.17 (m, 2H), 2.37 (m, 3H), 2.19 (m, 2H), 1.85 (m, 2H).

Example 23

4-(1-Benzo[1,3]dioxol-5-ylmethyl-piperidin-4-ylamino)-6-methyl-chromen-2-one (II-3)

The title compound was prepared according to the procedure described in Example 19 substituting piperonal for 3-hydroxybenzaldehyde. MS (DCI/NH$_3$) m/z 393 [M+H]$^+$; $^1$H NMR (300 MHz, DMSO) δ ppm 7.94 (m, 1H), 7.41 (m, 1H), 7.30 (m, 1H), 7.20 (m, 1H), 7.12 (m, 1H), 7.02 (m, 2H), 6.11 (m, 2H), 5.38 (m, 1H), 4.21 (m, 2H), 3.72 (m, 1H), 3.47 (m, 2H), 3.10 (m, 2H), 2.38 (m, 3H), 2.17 (m, 2H), 1.82 (m, 2H).

Example 24

4-[1-(3-Furan-2-yl-allyl)-piperidin-4-ylamino]-6-methyl-chromen-2-one (III-16)

The titled compound was prepared according to the procedure described in Example 19 substituting 2-furylacrolein for 3-hydroxybenzaldehyde. $^1$H NMR (500 MHz, DMSO-d$_6$) δ ppm 7.95 (br s, 1H), 7.74 (br s, 1H), 7.42 (m, 1H), 7.33 (m, 1H), 7.21 (m, 1H), 6.77 (m, 1H), 6.62 (m, 1H), 6.56 (m, 1H), 6.12 (m, 1H), 5.37 (s, 1H), 3.90 (m, 2H), 3.80 (m, 1H), 3.55 (m, 2H), 3.12 (m, 2H), 2.39 (s, 3H), 2.17 (m, 2H), 1.82 (m, 2H); MS (DCI/NH$_3$) m/z 365 [M+H]$^+$.

Example 25

4-{1-[3-(2-Methoxy-phenyl)-allyl]-piperidin-4-ylamino}-6-methyl-chromen-2-one (III-19)

The title compound was prepared according to the procedure described in Example 19 substituting 2-methoxycinnamaldehyde for 3-hydroxybenzaldehyde. $^1$H NMR (500 MHz, DMSO-d$_6$) δ ppm 7.96 (m, 1H), 7.59 (m, 1H), 7.42 (m, 1H), 7.34 (m, 2H), 7.20 (m, 1H), 7.07 (m, 2H), 6.99 (m, 1H), 6.35 (m, 1H), 5.38 (s, 1H), 3.92 (m, 2H), 3.85 (s, 3H), 3.79 (m, 1H), 3.58 (m, 2H), 3.15 (m, 2H), 2.37 (s, 3H), 2.19 (m, 2H), 1.85 (m, 2H); MS (DCI/NH$_3$) m/z 405 [M+H]$^+$.

Example 26

4-(1-Benzyl-piperidin-4-ylamino)-6-methyl-chromen-2-one (II-9)

The title compound was prepared according to the procedure described in Example 19 substituting benzaldehyde for 3-hydroxybenzaldehyde. $^1$H NMR (500 MHz, DMSO-d$_6$/D$_2$O) δ ppm 7.90 (br s, 1H), 7.53 (m, 5H), 7.45 (m, 1H), 7.23 (m, 1H), 5.36 (s, 1H), 4.32 (s, 2H), 3.77 (m, 1H), 3.47 (m, 2H), 3.15 (m, 2H), 2.38 (s, 3H), 2.20 (m, 2H), 1.84 (m, 2H); MS (DCI/NH$_3$) m/z 349 [M+H]$^+$.

Example 27

6-Methyl-4-[1-(2-methyl-3-phenyl-allyl)-piperidin-4-ylamino]-chromen-2-one (III-29)

The titled compound was prepared according to the procedure described in Example 19 substituting 2-methylcinnamaldehyde for 3-hydroxybenzaldehyde. $^1$H NMR (500 MHz, DMSO-d$_6$) δ ppm 7.96 (m, 1H), 7.29–7.54 (m, 7H), 7.21 (m, 1H), 6.76 (m, 1H), 5.38 (s, 1H), 3.87 (m, 2H), 3.77 (m, 1H), 3.58 (m, 2H), 3.15 (m, 2H), 2.38 (s, 3H), 2.22 (m, 2H), 2.03 (s, 3H), 1.91 (m, 2H); MS (DCI/NH$_3$) m/z 389 [M+H]$^+$.

Example 28

4-Amino-1-cinnamylpiperidine

To a solution of 4-N-Boc-1-cinnamylpiperidine (8.0 g, 25 mmol) in CH$_2$Cl$_2$ (50 mL) at 0° C. was added 25 mL of 50% TFA in CH$_2$Cl$_2$. The reaction was warmed to room temperature and stirred for an additional 3.5 hrs. The solution was diluted with ethyl acetate and washed with 1 N NaOH solution, dried over Na$_2$SO$_4$, and concentrated to afford a white solid in quantitative yield. MS (ESI (+)) m/e 217 (M+H)$^+$; $^1$H NMR (300 MHz, DMSO) δ ppm 1.47–1.56 (m, 2H), 1.84 (br d, 2H), 1.99 (t, 2H), 2.87–3.00 (m, 3H), 3.08 (d, 2H), 6.23–6.33 (m, 1H), 6.84 (d, 1H), 7.21–7.45 (m, 5H), 7.61 (br s, 2H).

Example 29

Trifluoro-methanesulfonic acid 6-bromo-2-oxo-2H-chromen-4-yl ester

To a cooled (–10° C.) solution of 6-bromo-4-hydroxycoumarin (1.8 g, 7.5 mmol) and dry triethylamine (2.1 mL, 15 mmol) in dry CH$_2$Cl$_2$ was added trifluoromethane sulfonic anhydride (1.5 mL, 9 mmol) dropwise over 10 minutes. The solution was allowed to stir for 2 hrs at –10° C. and was warmed to room temperature and diluted with 100 mL of 1:1 hexane:diethylether solution. The reddish brown solution was filtered through silica gel aided by another 300 mL of 1:1 hexane:diethylether solution and was concentrated to give 2.4 g (86%) of a pure yellow solid. $^1$H NMR (300 MHz, DMSO) δ ppm 6.97 (s, 1H), 7.57 (d, 1H), 7.80 (d, 1H), 7.98 (dd, 1H).

Example 30

6-Bromo-4-[1-(3-phenyl-allyl)-piperidine-4-ylamino]-chromen-2-one (III-5)

To a solution of 4-amino-1-cinnamylpiperidine (1.3 g, 6 mmol) and triethylamine (1.6 mL, 7.2 mmol) in dry acetonitrile (125 mL) was added trifluoromethanesulfonic acid 6-bromo-2-oxo-2H-chromen-4-yl ester (2.23 g, 6 mmol). About 5 mL of solution was added to each of 25 dry microwave vials equipped with stir bars. The vials were capped and each was heated at 150° C. for 5 minutes in the microwave. The solutions were combined, concentrated and dissolved in chloroform. The solution was washed with water and brine and dried over Na$_2$SO$_4$, and concentrated. The residue was purified by flash chromatography through a silica gel column with dichloromethane and methanol (95:5 v/v) to provide the desired compound (900 mg, 34%) as a yellow solid. MS (ESI(+)Q1MS m/z 440 (M+2H)$^+$; $^1$H NMR (300 MHz, DMSO) δ ppm 1.57–1.67 (m, 2H), 1.89–1.95 (m, 2H), 2.13 (m, 2H), 2.92 (m, 2H), 3.13 (m, 2H), 3.50 (m, 1H), 5.28 (sd, 1H), 6.35 (dt, 1H), 6.56 (d, 1H), 7.24–7.47 (m. 7H), 7.74 (dd, 1H), 8.45 (d, 1H).

Example 31

6-Propyl-4-[1-(3-phenyl-allyl)-piperidine-4-ylamino]-chromen-2-one (III-35)

Into a dry microwave vial under nitrogen was added 6-bromo-4-[1-(3-phenyl-allyl)-piperidine-4-ylamino]-chromen-2-one (20 mg, 0.046 mmol), Pd(dppf)Cl$_2$ (about 5 mol %), and CuI (about 6 mol %) in dry THF (0.5 mL) followed by n-propyl zinc bromide (0.273 mL, 0.138 mmol (0.5M in THF)) dropwise. The solution was heated in the microwave for 10 minutes at 160° C., filtered, and was purified by Prep HPLC to give 13.6 mg (57%) of the desired compound as the TFA salt. MS (ESI(+)Q1MS m/z 403 (M+H)$^+$; $^1$H NMR (300 MHz, MeOH) δ ppm 0.96 (t, 3H), 1.70 (m, 2H), 1.98–2.01 (m, 2H), 2.39 (br d, 2H), 2.69 (t, 2H), 3.23 (br t, 2H), 3.72 (m, 2H), 3.88–3.98 (m, 3H), 5.42 (s, 1H), 6.30–6.40 (m, 1H), 6.95 (d, 1H), 7.24–7.54 (m 0.8H), 7.85 (s, 1H).

Example 32

6-(3-methylbutyl)-4-[1-(3-phenyl-allyl)-piperidine-4-ylamino]-chromen-2-one (III-36)

Into a dry microwave vial under N$_2$ was added 6-bromo-4-[1-(3-phenyl-allyl)-piperidine-4-ylamino]-chromen-2-one (20 mg, 0.046 mmol), Pd(dppf)Cl$_2$ (about 5 mol %), and CuI (about 6 mol %) in dry THF (0.5 mL) followed by 3-methylbutyl zinc bromide (0.273 mL, 0.138 mmol (0.5M in THF)) dropwise. The solution was heated in the microwave for 10 minutes at 160° C., filtered, and was purified by Prep HPLC to give 6.2 mg (25%) of the desired compound as the TFA salt. MS (ESI(+)Q1MS m/z 431 (M+H)$^+$; $^1$H NMR (300 MHz, MeOH) δ ppm 0.97 (d, 6H), 1.52–1.64 (m, 3H), 1.97 (br q, 2H), 2.40 (br d, 2H), 2.72 (br t, 2H), 3.23 (br t, 2H), 3.73 (d, 2H), 3.93–3.97 (m, 3H), 5.42 (s, 1H), 6.30–6.40 (m, 1H), 6.95 (d, 1H), 7.23–7.54 (m. 8H), 7.86 (d, 1H).

Example 33

6-(2-ethylbutyl)-4-[1-(3-phenyl-allyl)-piperidine-4-ylamino]-chromen-2-one (III-37)

Into a dry microwave vial under N$_2$ was added 6-Bromo-4-[1-(3-phenyl-allyl)-piperidine-4-ylamino]-chromen-2-one (20 mg, 0.046 mmol), Pd(dppf)Cl$_2$ (about 5 mol %), and CuI (about 6 mol %) in dry THF (0.5 mL) followed by 2-ethylbutyl zinc bromide (0.273 mL, 0.138 mmol (0.5M in THF)) dropwise. The solution was heated in the microwave for 10 minutes at 160° C., filtered, and was purified by Prep HPLC to give 4.7 mg (18%) of the desired compound as the TFA salt. MS (ESI(+)Q1MS m/z 445 (M+H)$^+$; $^1$H NMR (300 MHz, MeOH) δ ppm 0.90 (t, 6H), 1.29–1.38 (m, 4H), 1.60 m, 1H), 1.99 (m, 2H), 2.39 (br d, 2H), 2.60 (m, 2H), 3.24 (br t, 2H), 3.72 (br d, 2H), 3.97 (m, 3H), 5.42 (s, 1H), 6.31–6.40 (m, 1H), 6.95 (d, 1H), 7.24–7.54 (m. 8H), 7.84 (d, 1H).

Example 34

6-(2-methylpropyl)-4-[1-(3-phenyl-allyl)-piperidine-4-ylamino]-chromen-2-one (III-38)

Into a dry microwave vial under N$_2$ was added 6-Bromo-4-[1-(3-phenyl-allyl)-piperidine-4-ylamino]-chromen-2-one (20 mg, 0.046 mmol), Pd(dppf)Cl$_2$ (~5 mol %), and CuI (~6 mol %) in dry THF (0.5 mL) followed by 2-methylpropyl zinc bromide (0.273 mL, 0.138 mmol (0.5M in THF)) dropwise. The solution was heated in the microwave for 10 minutes at 160° C., filtered, and was purified by Prep HPLC to give 3.6 mg (15%) of the desired compound as the TFA salt. MS (ESI(+)Q1MS m/z 417 (M+H)$^+$; $^1$H NMR (300 MHz, MeOH) δ ppm 0.93 (d, 6H), 1.91–2.03 (m, 3H), 2.41 (br d, 2H), 2.58 (d, 2H), 3.23 (br t, 2H), 3.72 (br d, 2H), 3.96 (m, 3H), 5.42 (s, 1H), 6.29–6.40 (m, 1H), 6.95 (d, 1H), 7.24–7.54 (m. 8H), 7.83 (d, 1H).

Example 35

6-(n-butyl)-4-[1-(3-phenyl-allyl)-piperidine-4-ylamino]-chromen-2-one (III-39)

Into a dry microwave vial under N$_2$ was added 6-Bromo-4-[1-(3-phenyl-allyl)-piperidine-4-ylamino]-chromen-2-one (20 mg, 0.046 mmol), Pd(dppf)Cl$_2$ (~5 mol %), and CuI (~6 mol %) in dry THF (0.5 mL) followed by n-butyl zinc bromide (0.273 mL, 0.138 mmol (0.5M in THF)) dropwise. The solution was heated in the microwave for 10 minutes at 160° C., filtered, and was purified by Prep HPLC to give 2.5 mg (10%) of the desired compound as the TFA salt. MS (ESI(+)Q1MS m/z 417 (M+H)$^+$; $^1$H NMR (300 MHz, MeOH) δ ppm. 96 (t, 3H), 1.33–1.42 (m, 2H), 1.61–1.69 (m, 2H), 1.91–2.03 (m, 2H), 2.41 (br d, 2H), 2.72 (t, 2H), 3.24 (br t, 2H), 3.73 (br d, 2H), 3.96 (m, 3H), 5.42 (s, 1H), 6.30–6.40 (m, 1H), 6.95 (d, 1H), 7.23–7.54 (m, 8H), 7.86 (d, 1H).

Example 36

6-(cyclopentyl)-4-[1-(3-phenyl-allyl)-piperidine-4-ylamino]-chromen-2-one (III-40)

Into a dry microwave vial under $N_2$ was added 6-Bromo-4-[1-(3-phenyl-allyl)-piperidine-4-ylamino]-chromen-2-one (20 mg, 0.046 mmol), Pd(dppf)Cl$_2$ (about 5 mol %), and CuI (about 6 mol %) in dry THF (0.5 mL) followed by cyclopentyl zinc bromide (0.273 mL, 0.138 mmol (0.5M in THF)) dropwise. The solution was heated in the microwave for 10 minutes at 160° C., filtered, and was purified by Prep HPLC to give 4.4 mg (18%) of the desired compound as the TFA salt. MS (ESI(+)Q1MS m/z 429 (M+H)$^+$; $^1$H NMR (300 MHz, MeOH) δ ppm. 1.62–2.13 (m, 10H), 2.40 (br d, 2H), 3.06–3.12 (m, 1H), 3.24(br t, 2H), 3.72 (br d, 2H), 3.96 (m, 3H), 5.42 (s, 1H), 6.31–6.40 (m, 1H), 6.96 (d, 1H), 7.23–7.54 (m. 8H), 7.90 (d, 1H).

Example 37

6-Phenyl-4-[1-(3-phenyl-allyl)-piperidine-4-ylamino]-chromen-2-one (III-42)

Into a dry microwave vial under $N_2$ was added 6-bromo-4-[1-(3-phenyl-allyl)-piperidine-4-ylamino]-chromen-2-one (20 mg, 0.046 mmol), Pd(PPh$_3$)Cl$_2$ (about 1 mol %), and Cs$_2$CO$_3$ (17.8 mg, 0.0547 mmol) in DME/H$_2$O/EtOH (7/3/2, 0.5 mL). Phenyl boronic acid (5.6 mg, 0.046 mmol) was added and the solution was heated in the microwave for 5 minutes at 160° C., filtered, and was purified by Prep HPLC to give 5.86 mg (23%) of the desired compound as the TFA salt. MS (ESI(+)Q1MS m/z 435 (M–H)$^+$; $^1$H NMR (300 MHz, DMSO) δ ppm 1.83–1.91 (m, 2H), 2.24 (br d, 2H), 3.15–3.23 (m, 2H), 3.61 (br d, 2H), 3.82–3.97 (m, 3H), 5.45 (s, 1H), 6.36–6.42 (m, 1H), 6.90 (d, 1H), 7.34–7.56 (m. 10H), 7.74 (d, 2H), 7.89 (dd, 1H), 8.40 (d, 1H).

Example 38

6-(o-Tolyl)-4-[1-(3-phenyl-allyl)-piperidine-4-ylamino]-chromen-2-one (III-43)

Into a dry microwave vial under $N_2$ was added 6-Bromo-4-[1-(3-phenyl-allyl)-piperidine-4-ylamino]-chromen-2-one (20 mg, 0.046 mmol), Pd(PPh$_3$)Cl$_2$ (~1 mol %), and Cs$_2$CO$_3$ (17.8 mg, 0.0547 mmol) in DME/H$_2$O/EtOH (7/3/2, 0.5 mL). O-tolyl boronic acid (6.3 mg, 0.046 mmol) was added and the solution was heated in the microwave for 5 minutes at 160° C., filtered, and was purified by Prep HPLC to give 6 mg (23%) of the desired compound as the TFA salt. MS (ESI(+)Q1MS m/z 451 (M–H)$^+$; $^1$H NMR (300 MHz, DMSO) δ ppm 1.78–1.86 (m, 2H), 2.19 (br d, 2H), 2.22 (s, 3H), 3.13–3.19 (m, 2H), 3.58 (br d, 2H), 3.81–3.92 (m, 3H), 5.43 (s, 1H), 6.34–6.40 (m, 1H), 6.88 (d, 1H), 7.23–7.43 (m. 10H), 7.54 (m, 2H), 8.14 (d, 1H).

Example 39

6-(3-chlorophenyl)-4-[1-(3-phenyl-allyl)-piperidine-4-ylamino]-chromen-2-one (III-48)

Into a dry microwave vial under $N_2$ was added 6-Bromo-4-[1-(3-phenyl-allyl)-piperidine-4-ylamino]-chromen-2-one (20 mg, 0.046 mmol), Pd(PPh$_3$)Cl$_2$ (about 1 mol %), and Cs$_2$CO$_3$ (17.8 mg, 0.0547 mmol) in DME/H$_2$O/EtOH (7/3/2, 0.5 mL). 3-Chlorophenyl boronic acid (6.3 mg, 0.046 mmol) was added and the solution was heated in the microwave for 5 minutes at 160° C., filtered, and was purified by Prep HPLC to give 3 mg (11%) of the desired compound as the TFA salt. MS (ESI(+)Q1MS m/z 469 (M–H)$^+$; $^1$H NMR (300 MHz, DMSO) δ ppm 1.84–1.91 (m, 2H), 2.25 (br d, 2H), 3.16–3.23 (m, 2H), 3.61 (br d, 2H), 3.84–4.01 (m, 3H), 5.43 (s, 1H), 6.37–6.43 (m, 1H), 6.89 (d, 1H), 7.34–7.94 (m. 12H), 8.41 (d, 1H).

Example 40

6-(3-thiophene)-4-[1-(3-phenyl-allyl)-piperidine-4-ylamino]-chromen-2-one (III-51)

Into a dry microwave vial under $N_2$ was added 6-Bromo-4-[1-(3-phenyl-allyl)-piperidine-4-ylamino]-chromen-2-one (20 mg, 0.046 mmol), Pd(PPh$_3$)Cl$_2$ (~1 mol %), and Cs$_2$CO$_3$ (17.8 mg, 0.0547 mmol) in DME/H$_2$O/EtOH (7/3/2, 0.5 mL). 3-thiophene boronic acid (6.3 mg, 0.046 mmol) was added and the solution was heated in the microwave for 5 minutes at 160° C., filtered, and was purified by Prep HPLC to give 5.1 mg (20%) of the desired compound as the TFA salt. MS (ESI(+)Q1MS m/z 443 (M+H)$^+$; $^1$H NMR (300 MHz, DMSO) δ ppm 1.83–1.91 (m, 2H), 2.26 (br d, 2H), 3.16–3.23 (m, 2H), 3.62 (br d, 2H), 3.83–3.94 (m, 3H), 5.44 (s, 1H), 6.37–6.43 (m, 1H), 6.90 (d, 1H), 7.34–7.95 (m. 11H), 8.40 (d, 1H).

Example 41

6-(2-chloro-3-thiophene)-4-[1-(3-phenyl-allyl)-piperidine-4-ylamino]-chromen-2-one (III-52)

Into a dry microwave vial under $N_2$ was added 6-Bromo-4-[1-(3-phenyl-allyl)-piperidine-4-ylamino]-chromen-2-one (20 mg, 0.046 mmol), Pd(PPh$_3$)Cl$_2$ (about 1 mol %), and Cs$_2$CO$_3$ (17.8 mg, 0.0547 mmol) in DME/H$_2$O/EtOH (7/3/2, 0.5 mL). 2-chloro-3-thiophene boronic acid (6.3 mg, 0.046 mmol) was added and the solution was heated in the microwave for 5 minutes at 160° C., filtered, and was purified by Prep HPLC to give 3.7 mg (14%) of the desired compound as the TFA salt. MS (ESI(+)Q1MS m/z 475 (M–2H)$^+$; $^1$H NMR (300 MHz, DMSO) δ ppm 1.82–1.89 (m, 2H), 2.25 (br d, 2H), 3.15–3.22 (m, 2H), 3.61 (br d, 2H), 3.78–4.01 (m, 3H), 5.45 (s, 1H), 6.36–6.42 (m, 1H), 6.90 (d, 1H), 7.21–7.82 (m, 10H), 8.30 (d, 1H).

Example 42

N-(4-Chlorophenyl)-trifluoroacetamide

4-Chloroaniline (2.55 g, 20 mmol) and triethylamine (3.5 mL, 25 mmol) were dissolved in THF (100 mL) and cooled in an ice bath under argon with stirring prior to slow addition of a solution of trifluoroacetic anhydride (3.0 mL, 21.2 mmol) in THF (20 mL). The reaction was found to be complete by TLC in 30 minutes. The reaction mixture was quenched with 1 N HCl (50 mL) and diluted with ethyl acetate. The organic layer was washed with additional 1 N HCl and dried with magnesium sulfate prior to evaporation under reduced pressure to give N-(4-chlorophenyl)-trifluoroacetamide (4.05 g). $^1$H NMR (300 MHz, CDCl$_3$) δ ppm 7.36 (2H, m), 7.51 (2H, m), 8.11 (1H, br s).

Example 43

(4-Chlorophenyl) (2,2,2-trifluoroethyl) amine

N-(4-Chlorophenyl)-trifluoroacetamide (2.22 g, 10 mmol) was dissolved in THF (100 mL) and treated with powdered lithium aluminum hydride (0.57 g, 15 mmol) under argon. The mixture was heated with stirring to reflux for 12 hours at which point both TLC and LC/MS analysis indicated the reaction was complete. The suspension was cooled in an ice bath prior to quenching with saturated aqueous sodium sulfate solution. The solution was dried with excess sodium sulfate and concentrated under reduced pressure to give 1.84 g of a viscous oil which was used without further purification. $^1$H NMR (300 MHz, CDCl$_3$) δ ppm 3.70 (2H, dt, J=8.96, 15.81 Hz), 3.91 (1H, br s), 6.58 (2H, m), 7.13 (2H, m).

Example 44

N-(4-Chlorophenyl)-N-(2,2,2-trifluoroethyl) malonamic acid t-butyl ester (4-Chlorophenyl) (2,2,2-trifluoroethyl)amine (1.84 g, 8.8 mmol) and mono-t-butyl malonate (1.37 mL, 8.9 mmol) were dissolved in DCM (50 mL) and the solution cooled in an ice bath prior to portion wise addition of 1-[3-(dimethylamino)propyl]-3-ethylcarbodiimide hydrochloride (1.71 g, 8.9 mmol). After one hour the reaction was complete by TLC and was diluted with ethyl acetate and sequentially washed with 1 N NaOH, 1N HCl, and brine. The organic layer was dried with MgSO4 and concentrated under reduced pressure to give a white solid which was used without further purification. $^1$H NMR (300 MHz, CDCl$_3$) δ ppm 1.40 (9H, s), 3.13 (2H, s), 4.34 (2H, q, J=8.7 Hz), 7.22 (2H, m), 7.41 (2H, m).

Example 45

6-Chloro-4-hydroxy-1-(2,2,2-trifluoroethyl)-1H-quinolin-2-one

N-(4-Chlorophenyl)-N-(2,2,2-trifluoroethyl)malonamic acid t-butyl ester (2.86 g, 8.1 mmol) was dissolved in methane sulfonic acid (50 mL) under argon with stirring prior to treatment with phosphorus pentoxide (0.51 g). The mixture was heated to 100° C. for 25 minutes. Analysis by LC/MS indicated the reaction was complete and the solution was cooled in an ice bath before quenching with ice and deionized water. The product precipitated and was collected by filtration. The filter cake was washed with ice water followed by cold chloroform and dried on high vacuum to give the title compound (1.83 g). $^1$H NMR (300 MHz, DMSO-d6) δ ppm 5.10 (2H, q, J=9.0 Hz), 5.97 (1H, s), 7.63 (2H, m), 7.79 (1H, m), 12.09 (1H, br s).

Example 46

4-(6-Chloro-2-oxo-1-(2,2,2-trifluoroethyl)-1,2-dihydroquinolin-4-ylamino)-piperidine-1-carboxylic acid ethyl ester 6-Chloro-4-hydroxy-1-(2,2,2-trifluoroethyl)-1H-quinolin-2-one (0.996 g, 3.6 mmol) was suspended in dry acetonitrile (50 mL) under argon and treated with sodium hydride (0.16 g, 60% wt in mineral oil, 4 mmol). After stirring for 10 minutes, 1,1,1-trifluoro-N-phenyl-N-[(trifluoromethyl)sulfonyl]methanesulfonamide (1.36 g, 3.8 mmol) was added and the mixture heated to 50° C. for 6 hours. Analysis by LC/MS indicated the starting quinolone had been completely consumed and 4-aminopiperidine-1-carboxylic acid ethyl ester (770 µL, 4.5 mmol) was added. The reaction was heated to reflux for 18 hours at which time LC/MS analysis indicated complete consumption of the intermediate triflate. The solution was diluted with ethyl acetate and washed with 1 N NaOH. The organic layer was dried with sodium sulfate and concentrated under reduced pressure to give the crude product. This material was purified by silica chromatography using DCM and methanol eluent gave the title compound (0.91 g). $^1$H NMR (300 MHz, CDCl$_3$) δ ppm 1.31 (5H, t, J=7.03 Hz), 2.02 (2H, m), 2.85 (2H, m), 3.50 (1H, m), 4.05 (2H, q, J=7.02 Hz), 4.80–5.11 (4H, m), 5.78 (1H, s), 7.28 (2H, m), 7.52 (2H, m).

Example 47

4-(1-Benzo[1,3]dioxol-5-ylmethylpiperidin-4-ylamino)-6-chloro-1-(2,2,2-trifluoroethyl)-1H-quinolin-2-(V-7)

4-(6-Chloro-2-oxo-1-(2,2,2-trifluoroethyl)-1,2-dihydroquinolin-4-ylamino)-piperidine-1-carboxylic acid ethyl ester (0.86 g, 2.0 mmol) was dissolved in glacial acetic acid (10 mL) and treated with hydrogen bromide (30% wt in acetic acid, 5 mL) in a pressure vessel and heated to 100° C. for 30 minutes. The solution was evaporated and redissolved in acetonitrile (50 mL). Triethylamine (2 mL) and sodium carbonate (1.06 g) were added and the solution was stirred for 5 minutes prior to addition of piperonyl chloride (50% wt in DCM, 550 µL). The mixture was stirred heated to 60° C. under argon for 1 hour before diluting with ethyl acetate and washing with 1N NaOH. Concentration under reduced pressure gave the crude product which was purified by silica chromatography using DCM and methanol eluent to give the title compound (0.78 g). $^1$H NMR (300 MHz, CDCl$_3$) δ ppm 1.61 (2H, m), 2.00–2.19 (4H, m), 2.87 (2H, m), 3.34–3.51 (3H, m), 4.78–5.05 (3H, m), 5.74 (1H, s), 5.94 (2H, m), 6.74 (2H, m), 6.85 (1H, m), 7.29 (1H, m), 7.51 (2H, m).

Example 48

N-(4-Chlorophenyl)-4-(aminomethyl)pyridine

4-Chloroaniline (2.55 g, 20 mmol) and 4-pyridinecarboxaldehyde (1.9 mL, 20 mmol) were dissolved in dichloroethane (80 mL) prior to addition of glacial acetic acid (5 mL). The solution was stirred for 15 minutes before portionwise addition of sodium triacetoxyborohydride (4.23 g, 20 mmol). Analysis by TLC showed the reaction was complete after stirring at room temperature for 3 hours. The reaction was diluted with ethyl acetate, washed several times with 1N NaOH, and dried with sodium sulfate. Evaporation at reduced pressure gave the title amine (3.61 g). $^1$H NMR (300 MHz, CDCl$_3$) δ ppm 4.27 (2H, d, J=5.89), 6.42 (2H, m), 7.02 (2H, m), 7.19 (2H, m), 8.45 (2H, m).

Example 49

N-(4-Chlorophenyl)-N-4-(aminomethyl) pyridinylmalonamic acid t-butyl ester

N-(4-Chlorophenyl)-4-(aminomethyl)pyridine (2.18 g, 10 mmol) and mono-t-butyl malonate (1.54 mL, 10 mmol) were dissolved in DCM (50 mL) and the solution cooled in an ice bath prior to portionwise addition of 1-[3-(dimethylamino) propyl]-3-ethylcarbodiimide hydrochloride (1.92 g, 10 mmol). After one hour the reaction was complete by TLC analysis, and was diluted with ethyl acetate and washed with 1 N NaOH and brine. The organic layer was dried with sodium sulfate and concentrated under reduced pressure to give the crude product. Further purification by silica chromatography using hexane and ethyl acetate eluent gave the title compound (3.05 g). $^1$H NMR (300 MHz, CDCl$_3$) δ ppm 1.37 (9H, s), 3.14 (2H, s), 4.84 (2H, s), 6.99 (2H, m), 7.18 (2H, m), 7.27 (2H, m), 8.48 (2H, m).

Example 50

6-Chloro-4-hydroxy-1-pyridin-4-ylmethyl-1H-quinolin-2-one

N-(4-Chlorophenyl)-N-4-(aminomethyl)pyridinyl- malonamic acid t-butyl ester (3.00 g, 8.3 mmol) was dissolved in methane sulfonic acid (50 mL) under argon with stirring prior to treatment with phosphorus pentoxide (0.50 g). The mixture was heated to 100° C. for 15 minutes. Analysis by LC/MS indicated the reaction was complete and the solution was cooled in an ice bath before quenching with ice and deionized water. The solution was treated with tribasic sodium phosphate (9.5 g) and the pH adjusted to 7.0 by addition of 1 N NaOH. The neutral slurry was extracted with ethyl acetate followed by DCM. The combined organic extracts were evaporated under reduced pressure to give the crude product as a brown solid. The crude material was tritrated with chloroform and filtered to give the title compound as a white powder (1.68 g).

Example 51

4-(6-Chloro-2-oxo-1-pyridin-4-ylmethyl-1,2-dihydroquinolin-4-ylamino)-piperidine-1-carboxylic acid t-butyl ester 6-Chloro-4-hydroxy-1-pyridin-4-ylmethyl-1H-quinolin-2-one (0.891 g, 3.1 mmol) was suspended in dry acetonitrile (50 mL) under argon and treated with sodium hydride (0.14 g, 60% wt in mineral oil, 3.5 mmol). After stirring for 10 minutes, 1,1,1-trifluoro-N-phenyl-N-[(trifluoromethyl)sulfonyl]methanesulfonamide (1.18 g, 3.3 mmol) was added and the mixture heated to 50° C. for 1 hour. Analysis by LC/MS indicated the starting quinolone had been completely consumed and the reaction was transferred to a pressure vessel containing 4-aminopiperidine-1-carboxylic acid t-butyl ester (0.80 g, 4 mmol). The pressure vessel was sealed and heated to 100° C. for 7 hours. After cooling, the solution was diluted with ethyl acetate, washed with 1N NaOH, and dried with sodium sulfate before concentrating to give the crude product. Purification by silica chromatography using DCM and methanol eluent gave the title compound (1.22 g). $^1$H NMR (300 MHz, CDCl$_3$) δ ppm 1.41 (11H, m), 2.03 (2H, m), 2.83 (2H, m), 3.50 (1H, m), 4.05 (2H, m), 5.39 (3H, m), 5.77 (1H, s), 6.87 (1H, d, J=9.04 Hz), 6.90 (2H, m), 7.23 (1H, m), 7.66 (1H, m), 8.40 (2H, m).

Example 52

4-(1-Benzo[1,3]dioxol-5-ylmethylpiperidin-4-ylamino)-6-chloro-1-pyridin-4-ylmethyl-1H-quinolin-2-one (V-4)

4-(6-Chloro-2-oxo-1-pyridin-4-ylmethyl-1,2-dihydroquinolin-4-ylamino)-piperidine-1-carboxylic acid t-butyl ester (1.22 g, 2.6 mmol) was dissolved in DCM (10 mL) and treated with trifluoroacetic acid (5 mL). The solution was stirred for 15 minutes before evaporating under reduced pressure. The crude amine was dissolved in acetone (25 mL), treated with cesium carbonate (1.26 g) and stirred for 15 minutes prior to addition of piperonyl chloride (50% wt solution in DCM, 1.4 mL). The mixture was heated to 50° C. for 8 hours at which time LC/MS analysis indicated the reaction was complete. The reaction was diluted with ethyl acetate and washed with 1 N NaOH. The organic layer was dried with sodium sulfate and concentrated to give the crude product which was purified by silica chromatography using DCM and methanol eluent to give the title compound (0.91 g). $^1$H NMR (300 MHz, CDCl$_3$) δ ppm 2.07 (2H, m), 2.23 (2H, m), 2.67 (2H, m), 3.19 (2H, m), 3.67 (1H, m), 3.81 (2H, s), 5.44 (3H, br s), 5.81 (1H, s), 5.95 (2H, s), 6.77 (1H, d, J=7.91 Hz), 6.93 (1H, m), 7.04 (4H, m), 7.30 (1H, m), 7.81 (1H, m), 8.48 (2H, m).

Example 53

6-Chloro-4-(1-naphthalen-2-ylmethyl-piperidin-4-ylamino)-1-pyridin-4-ylmethyl-1H-quinolin-2-one (V-5)

4-(6-Chloro-2-oxo-1-pyridin-4-ylmethyl-1,2-dihydroquinolin-4-ylamino)-piperidine-1-carboxylic acid t-butyl ester (0.58 g, 1.2 mmol) was dissolved in DCM (10 mL) and treated with trifluoroacetic acid (5 mL). The solution was stirred for 15 minutes before evaporating under reduced pressure. The crude amine was dissolved in acetonitrile (25 mL) prior to addition of sodium carbonate (1.22 g) and a drop of triethylamine. The mixture was stirred for 5 minutes before addition of 2-(bromomethyl)naphthalene (0.31 g, 1.4 mmol). After 2 hours the reaction was found to be complete by TLC analysis and the mixture was diluted with ethyl acetate, washed with 1N NaOH, and dried with sodium sulfate. Evaporation under reduced pressure gave the crude product which was purified by silica chromatography using DCM and methanol eluent to give the title compound (0.42 g). $^1$H NMR (300 MHz, CDCl$_3$) δ ppm 2.04 (2H, m), 2.22 (2H, m), 2.67 (2H, m), 3.23 (2H, m), 3.67 (1H, m), 4.02 (2H, s), 5.20 (1H, m), 5.47 (2H, m), 5.82 (1H, s), 6.93 (1H, d, J=8.96 Hz), 7.05 (2H, m), 7.32 (1H, m), 7.46–7.52 (2H, m), 7.65 (1H, m), 7.72 (1H, m), 7.84 (3H, m), 7.91 (1H, m), 8.48 (2H, m).

Example 54

6-(1-Bromoethyl)-quinoline

To a solution of 1-quinolin-6-yl-ethanol (0.4 g, 2.3 mmol) in dry CH$_2$Cl$_2$ (20 mL) was added PBr$_3$ (0.22 mL, 2.3 mmol). The reaction mixture was allowed to stir at room temperature for 12 h, and then was treated slowly with a saturated solution of NaHCO$_3$ (100 mL) until basic. The CH$_2$Cl$_2$ layer was removed, product was extracted from the aqueous layer with ethyl acetate (100 mL), and the combined organic layers were dried over MgSO$_4$, filtered and concentrated in vacuo to afford 0.4 g (72%) of a pale yellow oil. $^1$H NMR (300 MHz, CDCl$_3$) δ ppm 8.89–8.96 (m, 1H), 8.11–8.20 (m, 2H), 7.82–7.89 (m, 2H), 7.41–7.49 (m, 1H), 5.39 (dt, 1H), 2.15 (d, 3H).

Example 55

6-Chloro-4-[1-(1-quinolin-6-yl-ethyl)-piperidin-4-ylamino]-chromen-2-one (II-106)

To a solution of 6-(1-bromoethyl)-quinoline (0.44 g, 1.86 mmol) and 6-chloro-4-(piperidin-4-ylamino)-chromen-2-one (0.35 g, 1.24 mmol) in DMF (10 mL) was added K$_2$CO$_3$ (0.26 g, 1.86 mmol). The reaction mixture was allowed to stir at room temperature for 12 h, and was then treated with H$_2$O (100 mL) to provide 0.52 g (96%) of a white precipitate after filtration. MS (ESI(+)Q1MS) m/z 435 (M+H)$^+$; $^1$H NMR (300 MHz, DMSO) δ ppm 8.82–8.88 (m, 1H), 8.30–8.37 (m, 2H), 7.97–8.02 (m, 1H), 7.76–7.89 (m, 2H), 7.58–7.64 (m, 1H), 7.47–7.55 (m, 1H), 7.22–7.34 (m, 2H), 5.23 (s, 1H), 3.76 (dt, 1H), 3.37–3.52 (m, 1H), 2.96–3.04 (m, 1H), 2.80–2.89 (m, 1H), 2.09–2.21 (m, 2H), 1.82–1.98 (m, 2H), 1.50–1.71 (m, 2H), 1.40 (d, 3H). The pure racemic mixture was separated into enantiomers by prep HPLC chiral chromatography using a CHIRALPAK AD column: 7.5/7.5/85 MeOH/EtOH/Hexane. Enantiomers had retention times of 4.1 and 6.3 minutes. The optical rotations of the enantiomers were [α]$_D$ (90:10 CH$_2$Cl$_2$:MeOH, 25° C.)=+19.2 and −14.7, respectively.

Example 56

1-[4-(1-Hydroxyethyl)-phenyl]-ethanone

To a solution of 1-(4-acetylphenyl)-ethanone (1.0 g, 6.2 mmol) in dry methanol (30 mL) at 0° C. was slowly added NaBH$_4$ (0.07 g, 1.9 mmol). The reaction mixture was allowed to stir at 0° C. for 4 h, at which time silica gel TLC in hexanes and ethyl acetate (1:1 v/v, rf=0.5 desired product) showed a mixture of starting material, desired product, and the double-reduction side product. The reaction mixture was treated slowly with 1 N HCl solution (1 mL) at 0° C. until bubbling was no longer observed. Methanol was removed in vacuo to provide an orange residue, which was then partitioned between ethyl acetate (100 mL) and 1 N HCl (100 mL). The organic layer was washed with the 1 N HCl followed by a saturated NaCl solution (100 mL), dried over $MgSO_4$, filtered and concentrated in vacuo to afford an orange oil. The crude product was purified by flash chromatography through a silica gel column with hexanes and ethyl acetate (65:35 v/v) to provide the desired compound (0.55 g, 54%) as a clear oil. $^1$H NMR (300 MHz, $CDCl_3$) δ ppm 7.97 (d, 2H), 7.50 (d, 2H), 5.00 (dt, 1H), 2.61 (s, 3H), 1.52 (d, 3H).

Example 57

4-{1-[1-(4-acetylphenyl)-ethyl]-piperidin-4-ylamino}-6-chlorochromen-2-one (II-116)

To a solution of 1-[4-(1-bromoethyl)-phenyl]-ethanone (0.35 g, 1.54 mmol) and 6-chloro-4-(piperidin-4-ylamino)-chromen-2-one (0.42 g, 1.50 mmol) in dry THF (15 mL) was added $Cs_2CO_3$ (2.44 g, 7.50 mmol). The reaction mixture was allowed to stir at room temperature for 12 h, after which time THF was removed in vacuo and the white residue was partitioned between $H_2O$ (250 mL) and ethyl acetate (250 mL). After removal of the organic layer, the aqueous layer was washed with an addition portion of ethyl acetate (250 mL), and the combined organic layers were dried over MgSO4, filtered and concentrated in vacuo to provide a yellow oil. The crude product was purified by flash chromatography through a silica gel column with dichloromethane and methanol (95: 5 v/v). The resulting yellow residue was then treated with 4 M HCl in dioxane, solvent was removed in vacuo to provide a yellow solid. Crystallization from dichloromethane provided the HCl salt of the desired compound (0.027 g, 4%) as a white solid MS (ESI(+)Q1MS) m/z 425 (M+H)$^+$; $^1$H NMR (300 MHz, DMSO) δ ppm 10.84–10.97 (m, 1H), 8.32–8.38 (m, 1H), 8.00–8.08 (m, 2H), 7.75–7.84 (m, 2H), 7.58–7.63 (m, 1H), 7.48–7.54 (m, 1H), 7.30–7.35 (m, 1H), 5.39 (s, 1H), 4.51–4.63 (m, 1H), 3.60–3.77 (m, 2H), 3.24–3.40 (m, 1H), 2.73–2.95 (m, 2H), 2.59 (s, 3H), 1.95–2.14 (m, 4H), 1.72 (d, 3H). The pure racemic mixture was separated into enantiomers by prep HPLC chiral chromatography using a CHIRALPAK AD column: 7.5/7.5/85 MeOH/EtOH/Hexanes at 0.8 ml/min. Enantiomers had retention times of 4.2 and 6.4 minutes.

Example 58

(S)-Methyl-3-[(2-methoxycarbonylethyl)-(1-naphthalen-2-yl-ethyl)-amino]-propanoate (S)-(−)-1-(2-Naphthyl)ethylamine (2.28 g, 13 mmol) was added dropwise to a solution of methyl acrylate (5 mL, 55 mmol) and acetic acid (0.26 mL) with stirring in a sealed tube. A white crystalline solid precipitated out of solution. The temperature was then elevated to 80° C., at which time a clear solution was formed again. Stirring was continued for 18 hours. Excess methyl acrylate and acetic acid were removed under reduced pressure. The crude oil was purified by chromatography on silica gel with ethyl acetate/hexanes (1:4) to give the title compound (3.6 g, 77%) as a pale yellow oil. $^1$H NMR (300 MHz, $CDCl_3$) δ 1.45 (3H, d, J=6.78 Hz), 2.45 (4H, t, J=7.35 Hz), 2.73–2.94 (4H, m), 3.62 (6H, s), 4.00 (1H, q, J=6.78 Hz), 7.41–7.53 (3H, m), 7.70–7.84 (4H, m).

Example 59

(S)-1-(1-Naphthalen-2-yl-ethyl)-piperidin-4-one

To a solution of (S)-methyl-3-[(2-methoxycarbonylethyl)-(1-naphthalen-2-yl-ethyl)-amino]-propanoate (3.6 g, 10 mmol) in toluene (20 mL), NaH (0.5 g, 13 mmol) was added and the mixture was refluxed in an oil bath kept at 150° C. for 6 hours. After cool, the reaction mixture was acidified with AcOH and extracted with benzene. The organic layer was dried over $MgSO_4$, and concentrated to afford a crude oil. The oil was boiled with 10% HCl (20 mL) for 18 hours. The aqueous solution was basified with $K_2CO_3$ and extracted with ethyl acetate. The organic layer was dried over $MgSO_4$ and evaporated. The crude oil was purified by chromatography on silica gel with ethyl acetate/hexanes (1:4) to give the title compound (1.2 g, 47%). $^1$H NMR (300 MHz, $CDCl_3$) δ 1.51 (3H, d, J=6.59 Hz), 2.44 (4H, t, J=6.03 Hz), 2.71–2.90 (4H, m), 3.79 (1H, q, J=6.78 Hz), 7.42–7.60 (3H, m), 7.72–7.86 (4H, m).

Example 60

(S)-1-(1-Naphthalen-2-yl-ethyl)-piperidin-4-ylamine

A solution of (S)-1-(1-naphthalen-2-yl-ethyl)-piperidin-4-one (1.2 g, 4.7 mmol), hydroxylamine hydrochloride (0.47 g, 6.8 mmol), and pyridine (0.49 mL) in EtOH (8 mL) was heated under reflux for 1 hour. After evaporation, the residue was treated with ethyl acetate and aqueous NaOH (1M). The organic layer was separated, dried over $MgSO_4$ and evaporated to give the crude oxime.

To a solution of the oxime in ether (15 mL) and THF (5 mL) was added into a stirred suspension of 1M $LiAlH_4$ in THF (12.2 mL, 12.2 mmol) and ether (10 mL) via an additional funnel. The mixture was brought to a gentle reflux. After an hour, aqueous NaOH (1M, 0.16 mL) followed by water were added, and the mixture was filtered. The filtrate was transferred to a separatory funnel and extracted with dichloromethane. The organic layer was separated, dried over $MgSO_4$ and evaporated to give the title compound (1.14 g, 90%). $^1$H NMR (300 MHz, $CDCl_3$) δ 1.25–1.48 (2H, m), 1.45 (3H, d, J=6.78 Hz), 1.66–1.89 (2H, m), 1.94–2.11 (2H, m), 2.53–2.65 (1H, m), 2.75–2.84 (1H, m), 2.99–3.09 (1H, m), 3.56 (1H, q, J=6.78 Hz), 7.39–7.55 (3H, m), 7.66–7.86 (4H, m).

Example 61(a)

(S)-6-Chloro-4-[1-(1-naphthalen-2-yl-ethyl)-piperdin-4-ylamino]-chromen-2-one (II-120)

To a mixture of (S)-1-(1-naphthalen-2-yl-ethyl)-piperidin-4-ylamine (0.24 g, 0.94 mmol) and diisopropylethylamine (0.34 mL, 2 mmol) in 5 mL THF was added trifluoromethanesulfonic acid 6-chloro-2-oxo-2H-chromen-4-yl ester (0.30 g, 0.93 mmol). The reaction was stirred at room temperature for about 3 hours. The reaction mixture was then washed with water, dried with $MgSO_4$ and evaporated. The residue was purified by chromatography on silica gel with methanol/dichloromethane (2:98) to give the title compound (0.1 g, 25%). The final product was converted to the mono-HCl salt by addition of 1.0N HCl in ether to a suspension of the compound in dichloromethane. The solvent was removed by evaporation. $^1$H NMR of the mono- HCl salt (300 MHz, DMSO-d$_6$) δ 1.20–1.28 (2H, m), 1.81 (3H, d, J=6.97 Hz), 1.74–2.18 (4H, m), 2.83–3.05 (2H, m), 3.30–3.80 (2H, m), 4.65–4.78 (1H, br), 5.37 (1H, s), 7.30–7.79 (5H, m), 7.92–8.16 (4H, m), 8.32 (1H, d, J=2.64 Hz), 10.09 (1H, br, s).

Example 61(b)

(R)-6-Chloro-4-[1-(1-naphthalen-2-yl-ethyl)-piperdin-4-ylamino]-chromen-2-one (II-119)

Was similarly prepared starting from (R)-1-(1-naphthalen-2-yl-ethyl)-piperidin-4-ylamine.

Example 62

(4-Difluoromethoxyphenyl)methylamine

To a solution of ethyl(4-difluoromethoxyphenyl) carbamate (7.5 g, 32 mmol) in 100 mL of THF was added LiAlH$_4$ (1M, 66 mL) dropwise. The reaction mixture was stirred at room temperature for 4 hours, and heated at 50° C. After 18 hours, the reaction was cooled to room temperature. Few drops of MeOH were added into the reaction mixture followed by water. The reaction mixture was washed with aqueous NaOH (1M) and extracted with dichloromethane. The organic layer was separated, dried over MgSO$_4$ and evaporated to give the title compound (5.2 g, 94%). $^1$H NMR (300 MHz, CDCl$_3$) δ 2.79 (3H, s), 3.67 (1H, br), 6.35 (1H, t, J=75.01 Hz), 6.50–6.57 (2H, m), 6.91–6.99 (2H, m).

Example 63

6-Difluoromethoxy-4-hydroxy-1-methyl-1H-quinolin-2-one

To a mixture of (4-difluoromethoxyphenyl)methylamine (2.4 g, 14 mmol) and malonic acid (3.0 g, 29 mmol) was added POCl$_3$ (14 mL). After heating at 90° C. for 1.5 hours, the reaction mixture was poured over ice and basified with 6N NaOH to a pH of 14. The solution was then filtered and the filtrate was acidified with 6N HCl to pH 3. The precipitate was filtered and dried to afford a brown solid (0.45 g, 13%). MS (ESI(+)QIMS m/z 242 (M+H)$^+$

Example 64

4-(1-Benzo[1,3]dioxol-5-ylmethyl-piperidine-4-ylamino)-5-difluoromethoxy-1-methyl-1H-quinolin-2-one (V-16)

To a solution of 6-difluoromethoxy-4-hydroxy-1-methyl-1H-quinolin-2-one (0.45 g, 1.9 mmol) in acetonitrile (10 mL) was added NaH (0.077 g, 1.9 mmol). After bubbling stopped, N-phenyltrifluoromethane sulfonamide (0.68 g, 1.9 mmol) was added, and the reaction mixture was refluxed. After 30 minutes, 1-benzo[1,3]dioxol-5-ylmethyl-piperidin-4-ylamine dihydrochloride (0.57 g, 1.9 mmol) and diisopropylethylamine (1.6 mL, 9.2 mmol) were added, and the mixture was stirred for 18 hours. The reaction mixture was then washed with sodium bicarbonate solution, brine, dried with MgSO$_4$ and concentrated. The residue was purified on a C-18 RP LC-MS system to afford the title compound (0.029 mg, 3%, mono-formate salt) as a white solid. $^1$H NMR (300 MHz, DMSO-d$_6$) δ 1.53–1.71 (2H, m), 1.88–2.03 (2H, m), 2.07–2.24 (2H, m), 2.81–2.94 (2H, m), 3.12–3.59 (1H, m), 3.48 (2H, s), 3.52 (3H, s), 5.57 (1H, s), 6.02 (2H, s), 6.50–7.06 (4H, m), 7.24 (1H, s), 7.42–7.61 (2H, m), 8.02 (1H, s), 8.17 (1H, s).

Example 65

4-Hydroxy-6-methoxy-1-methyl-1H-quinolin-2-one

To a mixture of N-methyl-p-anisidine (2.8 g, 20 mmol) and malonic acid (4.3 g, 40 mmol) was added POCl$_3$ (17 mL). After heating at 90° C. for 1.5 hr, the reaction mixture was poured over ice and basified with 6N NaOH to a pH of 14. The solution was then filtered and the filtrate was acidified with 6N HCl to pH 3. The precipitate was filtered and dried to afford a brown solid (1.8 g, 50%). $^1$H NMR (300 MHz, MeODd$_4$) δ 3.65 (3H, s), 3.86 (3H, s), 5.97 (1H, s), 7.28 (1H, dd, J=2.8, 9.3 Hz), 7.49 (2H, d, J=9.3 Hz).

Example 66

4-(6-Methoxy-1-methyl-2-oxo-1,2-dihydro-quinolin-4-ylamino)-piperidine-1-carboxylic acid ethyl ester To a suspension of 4-Hydroxy-6-methoxy-1-methyl-1H-quinolin-2-one (1.8 g, 10 mmol) in DMF (30 mL) was added sodium hydride (385 mg, 10 mmol, 60% dispersion in mineral oil). After stirring for 5 minutes, N-phenyltrifluoromethanesulfonamide (3.4 g, 10 mmol) was added and the reaction was stirred and monitored by TLC to completion (20 minutes). 4-amino-piperidine-1-carboxylic acid ethyl ester was then added and the reaction mixture was heated at 60° C. over night. The reaction mixture was then diluted up with EtOAc and washed with water, NaHCO$_3$, and brine. The organic portion was dried over MgSO$_4$ and evaporated to afford a residue which was purified by flash chromatography through a silica gel column with dichloromethane and methanol (95:5 v/v) to provide the title compound (445 mg, 12%). $^1$H NMR (300 MHz, CDCl$_3$) δ 1.27 (2H, t, J=7.11 Hz), 1.22–1.35 (2H, m), 1.40–1.55 (2H, m), 2.10–2.20 (2H, m), 2.90–3.05 (2H, m), 3.50–3.70 (1H, m), 3.64 (3H, s), 3.87 (3H, s), 4.14 (2H, q, J=7.10), 4.50 (1H, br d, J=7.3 Hz), 5.29 (1H, s), 6.95 (1H, d; J=2.31 Hz), 7.17 (1H, dd, J=2.31, 9.03 Hz), 7.30 (1H, d, J=8.94 Hz).

Example 67

6-Methoxy-1-methyl-4-(piperidin-4-ylamino)-1H-quinolin-2-one 4-(6-Methoxy-1-methyl-2-oxo-1,2-dihydro-quinolin-4-ylamino)-piperidine-1-carboxylic acid ethyl ester (445 mg, 1.2 mmol) was dissolved in HBr/Acetic acid (30% by weight HBr in Acetic Acid) and heated at 90° C. for 1 hr. The solvent was then evaporated to afford an orange solid (~500 mg, 100%) which was carried onto the next step without any characterization.

Example 68

4-(1-Benzo[1,3]dioxol-5-ylmethyl-piperidin-4-ylamino)-6-methoxy-1-methyl-1H-quinolin 2-one (V-8)

To a solution of 6-methoxy-1-methyl-4-(piperidin-4-ylamino)-1H-quinolin-2-one (300 mg, 0.8 mmol) and diisopropylethylamine (705 uL, 4 mmol) in DMF (5 mL) was added a solution of 3,4 methylenedioxybenzyl chloride in methylene chloride (231 uL, 0.9 mmol, 50% by weight in CH$_2$Cl$_2$). After stirring at room temperature for 2 hours, the reaction mixture was diluted up with methylene chloride, washed with brine and dried with MgSO$_4$. The residue was purified by flash chromatography through a silica gel column with dichloromethane and methanol (95:5 v/v) to provide the title compound (66.4 mg, 20%): $^1$H NMR (300 MHz, CDCl$_3$) δ 1.58–1.72 (2H, m), 2.10–2.23 (4H, m), 2.88–2.98 (2H, m), 3.40–3.50 (1H, m), 3.48 (3H, s), 3.64 (3H, s), 4.58 (1H, bd, J=7.5), 5.75 (1H, s), 5.95 (2H, s), 6.77 (2H, s), 6.89 (1H, s), 7.25 (1H, d; J=1.89 Hz), 7.26 (1H, s), 7.40 (1H, dd, j=1.79, 8.75 Hz).

Example 69

6-Chloro-4-hydroxy-2-oxo-1,2-dihydro-quinoline-3-carboxylic acid methyl ester To a solution of dimethylmalonate (1.5 mL, 10 mmol) in anhydrous toluene (10 mL) was added sodium hydride (404 mg, 10 mmol, 60% dispersion in mineral oil). The sodium salt of the dimethylmalonate precipitated out as a chloroisatoic anhydride (2.0 g, 10 mmol) in DMF (20 mL) under argon. The reaction mixture was refluxed at 120° C. for 3 h. The resulting white precipitate was filtered and washed with ether multiple times. The white solid was then dissolved in water (400 mL) and filtered again. The filtrate was acidified with concentrated HCl to a pH of 1. The white precipitate was filtered and dried to afford the title compound (1.2 g, 47%). $^1$H NMR (300 MHz, DMSO) δ 3.83 (3H, s), 7.27 (1H, d, J=8.5 Hz), 7.64 (1H, t, J=10.2 Hz), 7.87 (1H, d, J=6.1 Hz).

Example 70

6-Chloro-4-(1-ethoxycarbonyl-piperidin-4-ylamino)-2-oxo-1,2-dihydro-quinoline-3-carboxylic acid methyl ester To a suspension of 6-Chloro-4-hydroxy-2-oxo-1,2dihydro-quinoline-3-carboxylic acid methyl ester (445 mg, 1.8 mmol) and diisopropylethylamine (607 uL, 3.5 mmol) in acetonitrile (30 mL) was added p-toluenesulfonyl chloride (400 mg, 2.1 mmol). The reaction was stirred at room temperature and monitored by TLC to completion (2 h). 4-amino-piperidine-1-carboxylic acid ethyl ester was then added to the reaction mixture which was stirred at 50° C. for 8 h. The reaction mixture was then diluted up with CH$_2$Cl$_2$ and washed with water. The organic portion was dried with MgSO$_4$ and evaporated. The residue was purified by flash chromatography through a silica gel column with dichloromethane and methanol (95:5 v/v) to provide a white solid (235 mg, 32%) which was carried onto the next step without characterization.

Example 71

6-Chloro-4-(piperidin-4-ylamino)-1H-quinolin-2one

6-Chloro-4-(1-ethoxycarbonyl-piperidin-4-ylamino)2-oxo-1,2-dihydro-quinoline-3-carboxylic acid methyl ester (235 mg) was dissolved in HBr and acetic acid (1 mL, 30% by weight) and heated at 90° C. for 1 hr. The solvent was then evaporated to afford an orange solid (109 mg, 53%) which was carried onto the next step without characterization.

Example 72

4-(1-Benzo[1,3]dioxol-5-ylmethyl-piperidin-4-ylamino)-6-chloro-1H-quinolin-2-one (V-11)

To a suspension of 6-Chloro-4-(piperidin-4-ylamino)-1H-quinolin-2-one (109 mg, 0.32 mmol) and cesium carbonate (127 mg, 0.39 mmol) in acetone (2 mL) was added in 3,4 methylenedioxybenzyl chloride in methylene chloride (84 uL, 0.32 mmol, 50% by weight in CH$_2$Cl$_2$). The reaction was stirred overnight at 40° C. The reaction mixture was then diluted up with CH$_2$Cl$_2$ (and a little MeOH) and washed with water. The organic portion was dried with MgSO$_4$ and evaporated. The resulting residue was chromatographed with a gradient from 0% MeOH 100% CH$_2$Cl$_2$ to 5% MeOH 95% CH$_2$Cl$_2$ to afford 30 mg of a white solid. The final product was converted to the HCl salt by addition of 4.0 N HCl in dioxane and methylene chloride and evaporation of the white suspension to afford a white solid (42 mg, 30%). $^1$H NMR (300 MHz, MeOD-d$_4$) δ 2.60–2.75 (2H, m), 2.98–3.08 (2H, m), 3.12–3.24 (2H, m), 3.90–4.00 (2H, m), 4.15–4.30 (1H, m), 4.47 (3H, s), 6.53 (1H, s), 6.90 (2H, s), 7.75–7.78 (2H, m), 7.85 (1H, d, J=1.28 Hz), 8.24 (1H, d, J=8.96 Hz), 8.45 (1H, dd, J=2.18, 8.85 Hz), 9.07 (1H, d, J=2.05 Hz).

Example 73

2-(3,4-Dichloro-phenoxy)-but-2-enedioic acid.

Benzyltrimethylammonium hydroxide (1.5 mL of a 40% weight aqueous solution, 1.2%) was added to a solution of 3,4-dichlorophenol (20.0 g, 123 mmol), dimethyl acetylenedicarboxylate (16.6 mL, 135 mmol), and dioxane (230 mL) The dark, homogeneous mixture was heated at 90° C. for 1.5 h before the solution was cooled to ambient temperature, combined with 20% aqueous NaOH (100 mL), and warmed to 90° C. After an hour, the mixture was cooled to ambient temperature and combined with 2N aqueous HCl until the pH of the solution was neutral. White sediment was removed by filtration. The filtrate was combined with 2N aqueous HCl until acidic (pH=2). The resulting precipitate was collected by filtration, washed with copious water, and air-dried to provide the product (18.0 g, 53%) as a yellow solid. MS (APCI) m/z 275 [M–H]$^+$; $^1$H NMR (300 MHz, DMSO-D$_6$) δ ppm 6.64 (s, 1H) 6.95 (dd, J=8.82, 2.71 Hz, 1H) 7.25 (d, J=3.05 Hz, 1H) 7.57 (d, J=8.82 Hz, 1H).

Example 74

6,7-Dichloro-4-oxo-4H-chromene-2-carboxylic acid 2-(3,4-Dichloro-phenoxy)-but-2-enedioic acid (17.98 g, 64.9 mmol) was combined with Eaton's Reagent (140 ml). The mixture was heated at 70° C overnight. After 14 h, the mixture was cooled to ambient temperature and added to ice (600 g). The resulting white precipitate was collected by filtration, washed with copious water, and air-dried. The white solid (16.8 g) was dissolved in hot DMSO and cooled slowly to ambient temperature. The supernatant was recovered and concentrated, and the process was repeated to provide the desired compound (4.96 g, 29%) as a white solid. The crystalline material proved to be the undesired 5,6-dichloro isomer. MS (APCI) m/z 259 [M+H]$^+$; $^1$H NMR (300 MHz, DMSO-D$_6$) δ ppm 6.96 (s, 1H) 8.16 (s, 1H) 8.26 (s, 1H).

Example 75

4,6,7-Trichlorochromen-2-one 6,7-Dichloro-4-oxo-4H-chromene-2-carboxylic acid (19.1 mmol) and thionyl chloride (20 mL) were carefully combined. DMF (0.2 mL) was added, and the dark, hetereogeneous solution was warmed to 70° C. After 16 h, the black homogeneous solution was cooled to ambient temperature and concentrated to a dark residue. The residue was diluted with CH$_2$Cl$_2$ (75 mL), washed with saturated aqueous NaHCO$_3$ (2×75 mL), washed with brine (1×50 mL), dried (MgSO$_4$), filtered, and concentrated to an orange residue that was passed through a plug of silica gel (1:1 hexane:EtOAc). The filtrate was concentrated to a beige solid (3.2 g) that was recrystallized from CH$_3$CN to provide the desired solid (2.6 g, 55%) as off-white crystals. MS (APCI) m/z 273 [M+Na]$^+$; $^1$H NMR (300 MHz, DMSO-D6) δ ppm 7.06 (s, 1H) 7.99 (s, 1H) 8.06 (s, 1H).

Example 76

(4-Benzo[1,3]dioxol-5-ylmethyl-piperidin-4-ylamino)-6,7-dichloro-chromen-2-one (II-117)

4,6,7-Trichlorochromen-2-one (25 mg, 0.100 mmol) was combined with the hydrochloride salt of 1-benzo[1,3]dioxol-5-yl-piperdin-4-ylamine (30 mg, 0.110 mmol), cesium carbonate (98 mg, 0.300 mmol), and DMF (0.5 mL). After 16 h, the yellow, heterogeneous solution was diluted with $CH_2Cl_2$ (20 mL), washed with water (1×20 mL), washed with brine (1×20 mL), dried ($MgSO_4$), filtered, and concentrated to a pale yellow solid (120 mg) that was purified by preparative HPLC. The desired fractions were combined, diluted with saturated aqueous $K_2CO_3$, and extracted with EtOAc. The EtOAc extract was washed with brine, dried ($MgSO_4$), filtered, and concentrated to provide the desired compound (13 mg, 29%) as a white solid. MS (APCI) m/z 446 $[M-H]^+$, 481 $[M+Cl]^+$; $^1H$ NMR (300 MHz, DMSO-D6) δ ppm 1.60 (m, J=2.71 Hz, 2H) 1.88 (m, 2H) 2.07 (m, 2H) 2.81 (m, J=11.19 Hz, 2H) 3.39 (s, 2H) 3.48 (m, 1H) 5.28 (s, 1H) 5.98 (s, 2H) 6.74 (dd, J=7.80, 1.36 Hz, 1H) 6.84 (d, J=7.80 Hz, 2H) 7.34 (d, J=7.46 Hz, 1H) 7.70 (s, 1H) 8.51 (s, 1H).

Example 77

2-(4-Trifluoromethyl-phenoxy)-but-2-enedioic acid 2-(4-Trifluoromethyl-phenoxy)-but-2-enedioic acid was prepared according to the procedure described in Example 73, except that 4-hydroxybenzotrifluoride (10 g, 61.7 mmol) was used in place of 3,4-dichlorophenol, to provide the desired cis isomer as a white solid (11.7 g, 69%). $^1H$ NMR (300 MHz, DMSO-$D_6$) δ ppm 6.67 (s, 1H) 7.11 (d, J=8.48 Hz, 2H) 7.69 (d, J=8.48 Hz, 2H).

Example 78

4-Oxo-6-trifluoromethyl-4H-chromene-2-carboxylic acid

4-Oxo-6-trifluoromethyl-4H-chromene-2-carboxylic acid was prepared according to the procedure described in Example 74, except that 2-(4-trifluoromethyl-phenoxy)-but-2-enedioic acid (1.00 g, 3.62 mmol) was used in place of 2-(3,4-Dichloro-phenoxy)-but-2-enedioic acid, to provide the desired compound as a white solid (700 mg, 75%). MS (APCI) m/z 259 $[M+H]^+$, 281 $[M+Na]^+$, 257 $[M-H]^+$; $^1H$ NMR (300 MHz, DMSO-$D_6$) δ ppm 7.00 (s, 1H) 7.97 (d, J=8.82 Hz, 1H) 8.20 (dd, J=8.82, 2.71 Hz, 1H) 8.29 (d, J=1.70 Hz, 1H).

Example 79

4-Chloro-6-trifluoromethyl-chromen-2-one

4-Chloro-6-trifluoromethyl-chromen-2-one was prepared according to the procedure described in Example 75, except that 4-Oxo-6-trifluoromethyl-4H-chromene-2-carboxylic acid (700 mg, 2.71 mmol) was used in place of 6,7-dichloro-4-oxo-4H-chromene-2-carboxylic acid, to provide a mixture of two compounds as a white solid (478 mg) that was used in the next step without additional purification. MS (APCI) m/z 249 $[M+H]^+$, 247 $[M-H]^+$.

Example 80

4-(Piperdin-4-ylamino)-6-trifluoromethyl-chromen-2-one 4-(Piperdin-4-ylamino)-6-trifluoromethyl-chromen-2-one was prepared according to the procedure described in Example 76, except that crude 4-chloro-6-trifluoromethyl-chromen-2-one (423 mg, 1.7 mmol) and 4-amino-1-N-Boc-piperidine (359 mg, 1.79 mmol) were used in place of 4,6,7-trichlorochromen-2-one and 1-benzo[1,3]dioxol-5-yl-piperdin-4-ylamine, to give a white solid (521 mg). Removal of the BOC protecting group provided the free base as a white solid (272 mg, 69%). MS (APCI) m/z 313 $[M+H]^+$, 311 $[M-H]^+$; $^1H$ NMR (300 MHz, DMSO-$D_6$) δ ppm 1.81 (m, 2H) 2.10 (m, 2H) 3.03 (m, J=2.37 Hz, 2H) 3.39 (m, 2H) 3.84 (m, 1H) 5.50 (s, 1H) 7.52 (d, J=8.48 Hz, 1H) 7.68 (d, J=7.80 Hz, 1H) 7.95 (d, J=8.82 Hz, 1H) 8.66 (s, 1H) 8.72 (s, 2H).

Example 81

4-(1-Benzo[1,3]dioxol-5-ylmethyl-piperidin-4-ylamino)-6-trifluoromethyl-chromen-2-one (II-82)

4-(1-Benzo[1,3]dioxol-5-ylmethyl-piperidin-4-ylamino)-6-trifluoromethyl-chromen-2-one was prepared according to a reductive amination procedure using 4-(piperdin-4-ylamino)-6-trifluoromethyl-chromen-2-one (116 mg, 0.373 mmol) and piperonal (62 mg, 0.411 mmol) to provide the title product as a white solid (73 mg, 44%). MS (APCI) m/z 447 $[M+H]^+$, 445 $[M-H]^+$, 481 $[M+Cl]^+$; $^1H$ NMR (300 MHz, DMSO-$D_6$) δ ppm 1.64 (m, 2H) 1.92 (m, J=9.83 Hz, 2H) 2.09 (m, 2H) 2.84 (m, J=11.53 Hz, 2H) 3.51 (m, 1H) 5.34 (s, 1H) 5.99 (s, 2H) 6.76 (d, J=6.44 Hz, 1H) 6.85 (d, J=8.82 Hz, 2H) 7.51 (t, J=9.32 Hz, 2H) 7.92 (dd, J=8.82, 1.70 Hz, 1H) 8.63 (s, 1H).

Example 82

4-(1-Benzo[1,3]dioxol-5ylmethyl-piperidin-4-ylamino)-6-trifluoromethoxy-chromen-2-one (II-96)

To a suspension of 4-chloro-6-trifluoromethoxycoumarin (0.04 g, 0.15 mmol) in 1 ml N-methylpyrrolidone in a Smith reaction vial was added 1-benzo[1,3]dioxol-5-ylmethyl-piperidin-4-ylamine (0.039 g, 0.16 mmol) followed by 0.042 ml of triethylamine. The reaction vessel was sealed with a crimper and the reaction heated at 220° C. for 20 minutes in a Smith Synthesizer. The reaction was diluted with 20 ml water and extracted with 3×10 ml ethyl acetate. The combined organic layers were dried over $MgSO_4$, filtered, evaporated and chromatographed using 2% $CH_3OH:DCM$ to afford 36.4 mg (52%) of a white solid. MS (ESI (+)) m/e 463 $(M+H)^+$; $^1H$ NMR (300 MHz, $MeOD_4$) δ ppm 1.65–1.75 (m, 2H), 2.0–2.1 (m, 2H), 2.25 (m, 2H), 3.0 (m, 2H), 3.5 (s, 2H), 3.6 (m, 1H), 5.37 (s, 1H), 5.9 (s, 2H), 6.75 (m, 2H), 6.9 (m, 1H), 7.45 (m, 1H), 7.55 (m, 1H), 8.10 (br s, 1H).

Example 83

4-(1-Benzo[1,3]dioxol-5-ylmethyl-piperidin-4-ylamino)-3-chloro-6-methoxy-chromen-2-one (II-90)

The 4-(1-Benzo[1,3]dioxol-5-ylmethyl-piperidin-4-ylamino)-6-methoxy-chromen-2-one para-toluene sulfonic acid salt (0.025 g, 0.043 mmol), N-chlorosuccinimide (0.0061 g, 0.046 mmol), and 0.2 mL Acetic Acid were shaken at room temperature overnight. Solution was diluted with Acetonitrile and purified on a C-18 RP HPLC. Product fractions were combined, treated with $K_2CO_3$, extracted with $CH_2Cl_2$, dried over sodium sulfate and concentrated to dryness to give the title compound as an off white solid. MS ESI(+)Q1MS m/z 451 $(M-H)^+$; $^1H$ NMR (300 MHz, CDCl$_3$) δ ppm partially buried 1.47–1.78 (m, 2H), 2.03–2.21 (m, 4H), 2.8–2.91 (br d, 2H), 3.39–3.46 (s, 2H), 3.8–3.87 (s, 3H), 4.01–4.13 (m, 1H), 4.83–4.91 (br s, 1H), 5.93–5.97 (s, 2H), 6.71–6.78 (m, 2H), 6.83–6.86 (s, 1H), 7.05–7.16 (m, 2H), 7.27–7.36 (d, 1H).

Example 84

4-{[1-(1-benzothien-4-ylmethyl)piperidin-4-yl]amino}-6-methoxy-2H-chromen-2-one (II-101)

6-Methoxy-4-(piperidine-4ylamino)-chromen-2-one and thianaphthene-3-carboxaldehyde were subjected to a reductive amination to provide title compound. MS ESI(+)Q1MS m/z 421 (M+H)$^+$; $^1$H NMR (300 MHz, CDCl$_3$) δ ppm 1.80–2.15 (m, 4H), 2.28–2.40 (m, 4H), 3.62–3.71 (m, 1H), 3.87 (s, 3H), 4.72 (s, 1H), 4.85 (s, 2H), 5.41 (s, 1H), 7.20–7.29 (m, 2H), 7.42–7.47 (m, 2H), 7.53 (d, 1H), 7.65 (s, 1H), 7.88–7.96 (m, 2H).

Example 85

6-Methoxy-4-[1-benzo[1,3]dioxol-5-ylmethyl-piperidin-(trans)-3-methyl-4-ylamino]chromen-2-one (II-38 trans)

A solution of 4-amino-1-benzyl-3-methylpiperidine (550 mg, 2.69 mmol) in 6 mL of acetonitrile under nitrogen was treated with diisopropylethylamine (562 uL, 3.2 mmol) and then with trifluoromethanesulfonic acid 6-methoxy-2-oxo-2H-chromen-4-yl ester (900 mg, 2.69 mmol, as prepared in example 4) in 5 mL of acetonitrile. This light brown, heterogeneous reaction was stirred at room temperature for 40 hours, diluted with dichloromethane, washed with 1 M K$_2$CO$_3$, dried (Na$_2$SO$_4$) and concentrated to give 860 mg (86%) of a beige foam that was a mixture of the four possible stereoisomers. A solution of this beige foam (280 mg, 0.74 mmol) in methanol (4 mL) and distilled water (0.4 mL) under nitrogen was treated with ammonium formate (700 mg, 11.1 mmol) followed by 10% palladium on carbon (100 mg). After 24 hours, another aliquot of ammonium formate (700 mg) and 10% palladium on carbon (100 mg) added. After a total of 46 hours at room temperature, the reaction was filtered, the black solid rinsed with 90:10 CH$_2$Cl$_2$:MeOH, the filtrate washed with 1 M K$_2$CO$_3$, dried (Na$_2$SO$_4$), filtered and concentrated. Some of this de-benzylated material (165 mg, 0.57 mmol) was dissolved in 2.2 mL of 50:50 dichloromethane:methanol containing 1% acetic acid and treated with piperonal (103 mg, 0.69 mmol) followed by sodium cyanoborohydride (50 mg, 0.8 mmol). After five days, the reaction was quenched by dropwise addition of 1M HCl, stirred for five minutes, diluted with dichloromethane, washed with 1 M K$_2$CO$_3$, dried (Na$_2$SO$_4$), filtered through a plug of silica (10 g SepPak), rinsed through with 90:10 CH$_2$Cl$_2$:MeOH and concentrated to give a yellow foam (227 mg). This foam was purified by flash silica gel chromatography (gradient elution 0 to 10% MeOH in CH$_2$Cl$_2$) to give the racemic cis and trans diastereomers. Trans diastereomer (racemic): Rf=0.35 (90:10 CH$_2$Cl$_2$:MeOH), $^1$H NMR (300 MHz,ppm, DMSO-d$_6$) δ 0.84 (d, J=6.45 Hz, 3H), 1.55 (m, 1H), 1.8 (m, 1H), 1.9 (m, 2H), 2.05 (m, 1H), 2.83 (m, 2H), 3.2 (m, 1H), 3.40 (bs, 2H), 3.83 (s, 3H), 5.25 (s, 1H), 5.99 (s, 2H), 6.75 (m, 1H), 6.85 (m, 2H), 7.19–7.23 (m, 3H), 7.66 (d, J=2.71 Hz, 1H). MS(ESI) 423 (M+H), 421 (M–H).

Example 86

6-Methoxy-4-[1-benzo[1,3]dioxol-5-ylmethyl-piperidin-(cis)-3-methyl-4-ylamino]chromen-2-one (II-38 cis)

This was prepared and purified as shown above. Cis diastereomer: (racemic) Rf=0.42 (90:10 CH2Cl2:MeOH), 1H NMR (300 MHz, DMSO-d$_6$) δ 0.97 (d, J=6.9 Hz, 3H), 1.6 (m, 1H), 2.1 (m, 2H), 2.2 (m, 2H), 2.64 (m, 1H), 2.81 (m, 1H), 3.3–3.5 (m, 2H), 3.64 (m, 1H), 3.84 (s, 3H), 5.19 (s, 1H), 5.99 (s, 2H), 6.77 (m, 1H), 6.84–6.87 (m, 2H), 7.02 (bd, J=7.1 Hz, 1H), 7.18–7.26 (m, 2H), 7.77 (d, J=2.7 Hz, 1H). MS(ESI) 423 (M+H), 421 (M–H).

Example 87

(d)-6-Methoxy-4-[1-benzo[1,3]dioxol-5-ylmethyl-piperidin-(trans)-3-methyl-4-ylamino]chromen-2-one (II-38, resolution of trans isomer)

The racemic trans diastereomer prepared and isolated in Example 85 was purified on a Chiralcel OD column (21.2×250 mm) with gradient elution (0 to 60% ethanol in hexanes over 45 minutes, 15 mL/min) to produce the two trans enantimers. Dextrorotary enantimer: [α]D=+63.6° (c=0.195 MeOH, 23.9° C.), Rf=0.35 (90:10 CH$_2$Cl$_2$:MeOH), $^1$H NMR (300 MHz, ppm, DMSO-d$_6$) δ 0.84 (d, J=6.45 Hz, 3H), 1.55 (m, 1H), 1.8 (m, 1H), 1.9 (m, 2H), 2.05 (m, 1H), 2.83 (m, 2H), 3.2 (m, 1H), 3.40 (bs, 2H), 3.83 (s, 3H), 5.25 (s, 1H), 5.99 (s, 2H), 6.75 (m, 1H), 6.85 (m, 2H), 7.19–7.23 (m, 3H), 7.66 (d, J=2.71 Hz, 1H) MS(ESI) 423 (M+H), 421 (M–H).

Example 88

(l)-6-Methoxy-4-[1-benzo[1,3]dioxol-5-ylmethyl-piperidin-(trans)-3-methyl-4-ylamino]chromen-2-one (II-38, resolution of trans isomer)

The racemic trans diastereomer prepared and isolated in Example 85 was purified on a Chiralcel OD column (21.2×250 mm) with gradient elution (0 to 60% ethanol in hexanes over 45 minutes, 15 mL/min) to produce the two trans enantimers. Levorotary enantimer: [α]D=−61.2° (c=0.17 MeOH, 24° C.), Rf=0.35 (90:10 CH$_2$Cl$_2$:MeOH), $^1$H NMR (300 MHz, ppm, DMSO-d$_6$) δ 0.84 (d, J=6.45 Hz, 3H), 1.55 (m, 1H), 1.8 (m, 1H), 1.9 (m, 2H), 2.05 (m, 1H), 2.83 (m, 2H), 3.2 (m, 1H), 3.40 (bs, 2H), 3.83 (s, 3H), 5.25 (s, 1H), 5.99 (s, 2H), 6.75 (m, 1H), 6.85 (m, 2H), 7.19–7.23 (m, 3H), 7.66 (d, J=2.71 Hz, 1H) MS(ESI) 423 (M+H), 421 (M–H).

Example 89.

(d)-6-Methoxy-4-[1-benzo[1,3]dioxol-5-ylmethyl-piperidin-(cis)-3-methyl-4-ylamino]chromen-2-one (II-38, resolution of cis isomer)

The racemic cis diastereomer prepared and isolated in Example 86 was purified on a Chiralcel OD column (21.2×250 mm) with gradient elution (0 to 60% ethanol in hexanes over 45 minutes, 15 mL/min) to produce the two cis enantiomers. Dextrotary enantimer: [α]D=+44.6° (c=0.13 MeOH, 23° C.), Rf=0.42 (90:10 CH$_2$Cl$_2$:MeOH), $^1$H NMR (300 MHz, ppm, DMSO-d$_6$) δ 0.97 (d, J=6.9 Hz, 3H), 1.6 (m, 1H), 2.1 (m, 2H), 2.2 (m, 2H), 2.64 (m, 1H), 2.81 (m, 1H), 3.3–3.5 (m, 2H), 3.64 (m, 1H), 3.84 (s, 3H), 5.19 (s, 1H), 5.99 (s, 2H), 6.77 (m, 1H), 6.84–6.87 (m, 2H), 7.02 (bd, J=7.1 Hz, 1H), 7.18–7.26 (m, 2H), 7.77 (d, J=2.7 Hz, 1H) MS(ESI) 423 (M+H), 421 (M–H).

Example 90

(l)-6-Methoxy-4-[1-benzo[1,3]dioxol-5-ylmethyl-piperidin-(cis)-3-methyl-4-ylamino] chromen-2-one (II-38, resolution of cis isomer)

The racemic cis diastereomer prepared and isolated in Example 86 was purified on a Chiralcel OD column (21.2×

250 mm) with gradient elution (0 to 60% ethanol in hexanes over 45 minutes, 15 mL/min) to produce the two cis enantiomers. Levorotary enantiomer: [α]D=−32° (c=0.155 MeOH, 23° C.), Rf=0.42 (90:10 $CH_2Cl_2$:MeOH), $^1$H NMR (300 MHz, ppm, DMSO-$d_6$) δ 0.97 (d, J=6.9 Hz, 3H), 1.6 (m, 1H), 2.1 (m, 2H), 2.2 (m, 2H), 2.64 (m, 1H), 2.81 (m, 1H), 3.3–3.5 (m, 2H), 3.64 (m, 1H), 3.84 (s, 3H), 5.19 (s, 1H), 5.99 (s, 2H), 6.77 (m, 1H), 6.84–6.87 (m, 2H), 7.02 (bd, J=7.1 Hz, 1H), 7.18–7.26 (m, 2H), 7.77 (d, J=2.7 Hz, 1H) MS(ESI) 423 (M+H), 421 (M−H).

Example 91

6-Methoxy-4-[N-methylindole-5-ylmethyl-piperidin-4-ylamino]chromen-2-one (II-111)

6-Methoxy-4-(piperidin-4-ylamino)-chromen-2-one and indole-5-carboxaldehyde were allowed to react under reductive alkylation conditions to give a crude beige product. After trituration of the crude product with hot ethyl acetate, filtration and concentration, the resulting partially-purified white powder was carried on to the subsequent alkylation step. A solution of this material (202 mg, 0.5 mmol) in 2 mL DMF under nitrogen at 0° C., was treated with NaH (60% dispersion in mineral oil, 50 mg, 12.5 mmol). After 45 minutes, methyl iodide (33 uL, 0.525 mmol) was added via syringe. The reaction was stirred at 0° C. for two hours, and then allowed to warm to room temperature and stirred overnight. After 17 hours, the reaction was quenched by slow addition of distilled water, diluted with $CH_2Cl_2$/MeOH (95:5), washed with distilled water, dried ($Na_2SO_4$) and concentrated to give a yellow oil. Purification by flash silica gel chromatography (0 to 5% MeOH in $CH_2Cl_2$) gave the titled compound as a yellow foam (80 mg). $^1$H NMR (300 MHz, ppm, DMSO-$d_6$) δ 1.57–1.71 (m, 2H), 1.86–1.96 (m, 2H), 2.04–2.15 (m, 2H), 2.73 (m, 2H), 3.46–3.58 (m, 3H), 3.77 (s, 3H), 3.83 (s, 3H), 5.21 (s, 1H), 6.38 (d, J=3.1 Hz, 1H), 7.10–7.23 (m, 3H), 7.29 (d, J=3.1 Hz, 1H), 7.37 (d, J=8.4 Hz, 1H), 7.45 (s, 1H), 7.63 (d, J=2.8 Hz, 1H) MS(ESI) 418 (M+H), 416 (M−H).

Example 92

6-Methoxy-4-[N-ethylindole-5-ylmethyl-piperidin-4-ylamino]-chromen-2-one (II-33)

The partially purified indole reductive alkylation product described in Example 91 (202 mg, 0.5 mmol) in 2 mL DMF under nitrogen at 0° C., was treated with NaH (60% dispersion in mineral oil, 50 mg, 12.5 mmol). After 45 minutes, ethyl iodide (42 uL, 0.525 mmol) was added via syringe. The reaction was stirred at 0° C. for two hours, and then allowed to warm to room temperature and stirred overnight. After 22 hours, the reaction was quenched by slow addition of distilled water, diluted with $CH_2Cl_2$/MeOH (95:5), washed with 1M K2CO3, dried (Na2SO4) and concentrated to give a brown oil. Purification by reverse phase silica gel chromatography (Zorbax C18, 21.2×250 mm column, 15 mL/min, 0 to 60% acetonitrile in water containing 0.1% trifluoroacetic acid) followed by extraction into $CH_2Cl_2$/MeOH (95.5), washed with 1M K2CO3, dried ($Na_2SO_4$) and concentrated to give the titled compound as a white foam (53 mg). $^1$H NMR (300 MHz, ppm, DMSO-$d_6$) δ 1.35 (t, J=7.2 Hz, 3H), 1.65 (m, 2H), 1.89 (m, 2H), 2.1 (m, 2H), 2.88 (m, 2H), 3.42–3.55 (m, 3H), 3.83 (s, 3H), 4.18 (q, J=7.2 Hz, 2H), 5.21 (s, 1H), 6.38 (d, J=3.2 Hz, 1H), 7.10 (dd, J=1.35, 8.48 Hz, 1H), 7.14–7.25 (m, 3H), 7.36 (d, J=3.1 Hz, 1H), 7.41 (d, J=8.4 Hz, 1H), 7.44 (s, 1H), 7.63 (d, J=2.7 Hz, 1H) MS(ESI) 432 (M+H), 430 (M−H).

Example 93

8-Bromo-6-chloro-4-[1-benzo[1,3]dioxol-5-ylmethyl-piperidin-4-ylamino]chromen-2-one 8-bromo-6-chloro-4-(piperidin-4-ylamino)-chromen-2-one and piperonal were allowed to react under reductive alkylation conditions for 44 hours at room temperature, then treated with 1 M $K_2CO_3$, extracted with $CH_2Cl_2$, filtered through silica gel (5 g SepPak), rinsed with 95:5 $CH_2Cl_2$:MeOH, and concentrated. Purification by silica gel preparatory plate (0.25 mm×20 cm×20 cm) developed with 95:5 $CH_2Cl_2$:MeOH to give the title compound as a white solid (6 mg). $^1$H NMR (300 MHz, ppm, DMSO-$d_6$) δ 1.6 (m, 2H), 1.9 (m, 2H), 2.1 (m, 2H), 2.8 (m, 2H), 3.4–3.5 (m, 3H), 5.33 (s, 1H), 5.99 (s, 2H), 6.77 (m, 1H), 6.85 (m, 2H), 7.38 (m, 1H), 8.05 (d, J=2 Hz, 1H), 8.36 (d, J=2 Hz, 1H). MS(ESI) 493 (M+H), 491 (M−H).

Example 94

8-Pyrrolidinyl-6-chloro-4-[1-benzo[1,3]dioxol-5-ylmethyl-piperidin-4-ylamino]chromen-2-one (II-81)

A solution of 8-Bromo-6-chloro-4-[1-benzo[1,3]dioxol-5-ylmethyl-piperidin-4-ylamino]chromen-2-one (30 mg, 0.061 mmol) in 0.3 mL toluene under nitrogen was treated with K2CO3 (20 mg, 0.13 mmol), about 3 mg CuI (0.016 mmol), 2-pyrrolidinone (10 uL, 0.13 mmol), followed by N,N'-dimethylethylenediamine (3 uL, 0.025 mmol) and heated to reflux. After 16 hours, the reaction was allowed to cool to room temperature, diluted with $CH_2Cl_2$, washed with distilled water, dried ($Na_2SO_4$) and concentrated. Purification by reverse phase HPLC (Zorbax C18, 21.2×250 mm column, 15 mL/min, 0 to 60% acetonitrile:water with 0.1% trifluoroacetic acid) followed by extraction into $CH_2Cl_2$ after basification with 1 M $K_2CO_3$, dried ($Na_2SO_4$) and concentrated to give the title compound (6 mg, 20%). $^1$H NMR (300 MHz, ppm, DMSO-$d_6$) δ 1.6 (m, 2H), 1.8 (m, 2H), 2.1 (m, 4H), 2.7 (m, 2H), 3.4–3.5 (m, 3H), 3.72 (t, J=7 Hz, 2H) 5.23 (s, 1H), 5.92 (s, 2H), 6.68–6.80 (m, 3H), 7.27 (m, 1H), 7.62 (d, J=2.3 Hz, 1H), 8.20 (d, J=2.4 Hz, 1H). MS(ESI) 496 (M+H), 494 (M−H).

Example 95

6-Chloro-4-[1-(2,3-dihydro-benzofuran-5-ylmethyl)-piperidin-4-ylamino]-chromen-2-one (II-78)

Prepared from 6-Chloro-4-(piperidin-4-ylamino)-chromen-2-one and 2,3-dihydro-benzofuran-5-carbaldehyde in a manner analogous to that described above. $^1$H NMR (500 MHz, MeOD-$d_4$) δ ppm 8.13 (s, 1H), 7.61 (d, 1H), 7.33–7.36 (m, 2H), 7.84 (d, 1H), 7.24 (s, 1H), 5.45 (s, 1H), 4.61 (t, 2H), 4.26 (s, 2H), 3.85 (br t, 1H), 3.58 (br d, 2H), 3.26 (t, 2H), 3.16(br t, 2H), 3.35 (br d, 2H), 1.93 (m, 2H).

Example 96

6-Chloro-4-[1-(3,4-dimethyl-benzyl)-piperidin-4-ylamino]-chromen-2-one (II-71)

Prepared from 6-Chloro-4-(piperidin-4-ylamino)-chromen-2-one and 3,4-dimethyl benzaldehyde in a manner analogous to that described above. MS (ESI) m/e 397.1 (M+H)$^+$. $^1$H NMR (500 MHz, MeOD-$d_4$) δ ppm 8.12 (d, 1H), 7.60 (dd, 1H), 7.21–7.34 (m, 4H), 5.44 (s, 1H), 4.27 (s, 2H), 3.83–3.87 (m, 1H), 3.55–3.60 (m, 2H), 3.16–3.20 (m, 2H), 2.30–2.38 (m, 2H), 2.33 (s, 3H), 2.31 (s, 3H), 1.89–1.96 (m, 2H).

Example 97

6-Chloro-4-hydroxy-3-nitro-chromen-2-one

Red fuming nitric acid (10 mL) was added to a stirred suspension of 6-Chloro-4-hydroxy-chromen-2-one (2.0 g, 10.17 mmol) in chloroform (200 mL) at 0° C. The resultant solution was stirred at 0° C. for 1.5 h, quenched with water (80 mL), the organics separated and treated with saturated NaHCO$_3$ when a thick yellow solid fell out of solution. The solid was filtered and the filtrate acidified with 3N HCl (pH 2) and extracted with chloroform. The organic extracts were dried to a yellow powder and all solids were combined and identified as 6-chloro-4-hydroxy-3-nitro-chromen-2-one. $^1$H NMR (300 MHz, DMSO-d$_6$) δ ppm 7.78 (d, 1H), 7.55 (dd, 1H), 7.23 (d, 1H).

Example 98

4-(1-Benzo[1,3]dioxol-5-ylmethyl-piperidin-4-ylamino)-6-chloro-3-nitro-chromen-2-one Triflic anhydride (0.47 mL, 2.8 mmol) was added to a 0° C. solution of 6-Chloro-4-hydroxy-3-nitro-chromen-2-one (0.45 g, 1.86 mmol) and triethylamine (0.52 mL, 3.72 mmol) in dichloromethane (10 mL). The reaction was stirred at 0° C. for 1 h, diluted with a 1:1 mixture of diethyl ether/hexanes (30 mL) and then filtered through a pad of silica gel eluting with 1:1:1 mixture of diethylether/dichloromethane/hexanes (350 mL). The organics were concentrated and used directly in the next step.

1-Benzo[1,3]dioxol-5-ylmethyl-piperidin-4-ylammonium chloride (0.34 g, 1.27 mmol) was added to a stirred suspension of the triflate (0.45 g, 1.21 mmol) and triethylamine (0.33 mL, 2.42 mmol) in acetonitrile (10 mL) and 1-methyl-2-pyrrolidinone (4 mL). The reaction was stirred at rt for 3 d, diluted with dichloromethane (10 mL) and quenched with saturated NaHCO$_3$ (25 mL) and water (25 mL). The mixture was extracted with dichloromethane (3×25 mL), dried (Na$_2$SO$_4$), concentrated and purified by RP-HPLC to give the title compound. MS (ESI) m/e 458.0 (M+H)$^+$.

Example 99

N-[4-(1-Benzo[1,3]dioxol-5-ylmethyl-piperidin-4-ylamino)-6-chloro-2-oxo-2H-chromen-3-yl]-acetamide (II-42)

Iron powder (0.067 g, 1.2 mmol) was added to a suspension of ammonium chloride (0.006 g, 0.12 mmol) and 4-(1-Benzo[1.3]dioxol-5-ylmethyl-piperidin-4-ylamino)-6-chloro-3-nitro-chromen-2-one (0.055 g, 0.12 mmol) in ethanol (5 mL) and water (2 mL) at room temperature. The reaction was heated at reflux for 1 d and then filtered through a pad of wet celite. The filtrate was treated with saturated NaHCO$_3$ (10 mL), extracted with dichloromethane (3×25 mL), dried (Na$_2$SO$_4$), concentrated, purified by RP-HPLC and the amine carried forward to the next step. MS (ESI) m/e 428.0 (M+H)$^+$.

The amine (0.055 g, 0.13 mmol) was placed in acetic anhydride (5 mL) and stirred at rt for 1 h. The acetic anhydride was removed as an azeotrope with toluene and the residue was washed with diethyl ether. The residue was then dissolved in dichloromethane, washed successively with saturated NaHCO$_3$, water and the organic layer concentrated to afford the target compound. MS (ESI) m/e 467.9 (M–H)$^+$. $^1$H NMR (500 MHz, DMSO-d$_6$) δ ppm 8.99 (br s, 1H), 8.34 (br s, 1H), 7.62 (d, 1H), 7.35 (d, 1H), 6.83–6.85 (m, 2H), 6.74 (d, 1H), 6.65 (d, 1H), 5.98 (s, 2H), 3.82–3.89 (m, 1H), 3.37 (s, 2H), 2.79–2.85 (m, 2H), 1.96 (s, 3H), 1.86–1.93 (m, 2H), 1.72–1.80 (m, 2H), 1.60–1.69 (m, 2H).

Example 100

6-Ethyl-4-(piperidin-4-ylamino)-chromen-2-one

To an oven dried 250 mL round bottom flask with a stir bar was added 1.37 g (7.21 mmol) of 4-hydroxy-6-ethylcoumarin and 36.0 mL of dry CH$_2$Cl$_2$. To this mixture was added 1.51 mL (10.8 mmol) of triethylamine, and the resultant solution cooled to −10° C. in an ice/saturated NaCl bath. Triflic anhydride was then added dropwise (1.58 mL, 9.39 mmol) and the reaction stirred at this temp under N$_2$ for 2 h. After this time, the reaction solution was allowed to warm to room temperature, and was then diluted with 120 mL of 1:1 ether/hexane. The mixture was then poured over a bed of silica gel to remove the fine white ppt and the cake rinsed with 1:1 ether/hexane. Evaporation of the filtrate afforded 2.18 g of a yellow solid. From this material, 0.400 g (1.24 mmol) was added to a 2–5 mL microwave process vial and 0.248 g (1.24 mmol) of 4-amino-piperidine-1-carboxylic acid tert-butyl ester was added followed by 3.50 mL of CH$_3$CN. After the addition of 0.500 mL (3.59 mmol) of triethylamine, the reaction vessel was sealed and heated to 150° C. for 300 s in the Smith microwave reactor. Upon cooling, filtration of the ppt afforded 0.980 g (2.63 mmol) of a white solid. This material was then added to a 10 mL rb flask and 3 mL of a 1:1 mixture of CH$_2$Cl$_2$/TFA was added. The reaction mixture was allowed to stand at rt for 2 h, and the cleavage cocktail evaporated down in a rotary evaporator. After co-evaporating with toluene (3×), the resultant white solid was triturated with EtOAc and filtered to afford 0.610 g (1.65 mmol) of the title compound as the TFA salt. $^1$H NMR (300 MHz, DMSO-D$_6$) δ ppm 1.21 (m, 3H) 1.77 (m, 2H) 2.09 (m, 2H) 2.68 (q, 2H) 3.07 (m, 2H) 3.41 (m, 3H) 3.80 (m, 1H) 5.37 (s, 1H) 7.23 (m, 1H) 7.32 (m, 1H) 7.45 (m, 1H) 7.97 (m, 1H); MS (DCI/NH$_3$) m/z 273 [M+H]$^+$.

Example 101

4-(1-Benzo{1,3}dioxol-5-ylmethyl-piperidin-4-ylamino)-6-ethyl-chromen-2-one (II-63)

Prepared from 6-Ethyl-4-(piperidin-4-ylamino)-chromen-2-one and piperonal in a manner analogous to that described above. $^1$H NMR (300 MHz, MeOD-d$_4$) δ ppm 1.28 (t, J=7.63 Hz, 3H) 1.92 (m, 2H) 2.34 (m, 2H) 2.74 (q, J=7.46 Hz, 2H) 3.22 (m, 2H) 3.60 (m, 2H) 3.86 (m, 1H) 4.26 (s, 2H) 5.40 (s, 1H) 6.04 (s, 2H) 6.94 (m, 2H) 7.01 (m, 2H) 7.25 (m, 1H) 7.48 (m, 1H) 7.86 (s, 1H); MS (DCI/NH$_3$) m/z 407 [M+H]$^+$.

Example 102

4-{1-(3,4-Dimethyl-benzyl)-piperidin-4-ylamino}-6-ethyl-chromen-2-one (II-103)

Prepared from 6-Ethyl-4-(piperidin-4-ylamino)-chromen-2-one and 3,4-dimethylbenzaldehyde in a manner analogous to that described above. $^1$H NMR (300 MHz, DMSO-D$_6$) δ ppm 1.21 (m, 3H) 1.77 (m, 2H) 2.16 (m, 2H) 2.27 (m, 6H) 2.66 (m, 2H) 3.07 (m, 2H) 3.45 (m, 2H) 3.73 (m, 1H) 4.23 (m, 2H) 5.36 (m, 1H) 7.25 (m, 5H) 7.44 (m, 1H) 7.95 (m, 1H); MS (DCI/NH$_3$) m/z 391 [M+H]$^+$.

Example 103

6-Chloro-4-{1-(4-chloro-benzyl)-piperidin-4-ylamino}-chromen-2-one (II-59)

Prepared from 6-Ethyl-4-(piperidin-4-ylamino)-chromen-2-one and 4-chlorobenzaldehyde in a manner analogous to that described above. ¹H NMR (300 MHz, DMSO-D₆) δ ppm 1.81 (m, 2H) 2.14 (m, 2H) 3.09 (m, 2H) 3.51 (m, 2H) 3.73 (m, 1H) 4.34 (m, 2H) 5.43 (s, 1H) 7.37 (m, 2H) 7.57 (m, 4H) 7.64 (m, 1H) 8.30 (m, 1H); MS (DCI/NH₃) m/z 403 [M+H]⁺.

Example 104

4-(1-Benzo{1,3}dioxol-5-ylmethyl-piperidin-4-ylamino)-3-fluoro-6-methoxychromene-2-one (II-26)

To an oven dried 100 mL round bottom flask with a stir bar was added 0.200 g of example 16 (0.490 mmol) and 7.60 mL of dry CH₃CN and the slurry allowed to stir at room temperature under N₂. To this was added 0.189 g (0.534 mmol) of 1-chloromethyl-4-fluoro-1,4-diazoniabicyclo[2.2.2]octane ditetrafluoroborate, and the reaction vessel heated to reflux in an oil bath. The reaction mixture was kept at this temperature for 18 h and then was cooled slowly to room temperature and then to 0° C. in an ice bath. The resultant white precipitate was then filtered and the filtrate evaporated to dryness. The residue was loaded on a reverse phase HPLC and the desired material isolated as a white solid. ¹H NMR (300 MHz, DMSO-D₆) δ ppm 1.72 (m, 2H) 1.92 (m, 2H) 2.01 (m, 2H) 2.85 (m, 2H) 3.40 (s, 3H) 3.79 (m, 1H) 3.84 (s, 2H) 5.99 (s, 2H) 6.65 (m, 1H) 6.75 (m, 1H) 6.85 (m, 2H) 7.19 (m, 1H) 7.30 (m, 1H) 7.68 (m, 1H); MS (DCI/NH₃) m/z 427 [M+H]⁺.

Example 105

4-(1-Benzo{1,3}dioxol-5-ylmethyl-piperidin-4-ylamino)-3-fluoro-6-methylchromene-2-one (II-89)

According to the procedure above, 4-(1-Benzo{1,3}dioxol-5-ylmethyl-piperidin-4-ylamino)-6-methylchromene-2-one and 1-chloromethyl-4-fluoro-1,4-diazoniabicyclo[2.2.2]octane ditetrafluoroborate were allowed to react to give the title compound. ¹H NMR (500 MHz, MeOD-d₄) δ ppm 1.96 (m, 2H) 2.36 (m, 2H) 2.44 (s, 3H) 3.16 (m, 2H) 3.42 (m, 1H) 3.57 (m, 2H) 4.25 (s, 2H) 6.03 (s, 2H) 6.93 (m, 1H) 7.00 (m, 2H) 7.24 (m, 1H) 7.42 (m, 1H) 7.85 (s, 1H); MS (DCI/NH₃) m/z 411 [M+H]⁺.

Example 106

4-(6-Bromo-2-oxo-2H-chromen-4-ylamino)-piperidin-1-carboxylic acid tert-butyl ester To an oven dried 250 mL round bottom flask with a stir bar was added 3.00 g (12.4 mmol) of 4-hydroxy-6-bromocoumarin and 25.0 mL of dry CH₂Cl₂. To this was added 2.25 mL(16.1 mmol) of triethylamine, and the resultant solution cooled to −10° C. in an ice/sat NaCl bath. Triflic anhydride was then added dropwise (2.80 mL, 16.6 mmol) and the reaction stirred at this temp under N₂ for 2 h. After this time, the reaction solution was allowed to warm to rt, and was then diluted with 120 mL of 1:1 ether/hexane. The mixture was then poured over a bed of silica gel to remove the fine white precipitate and the cake rinsed with 1:1 ether/hexane. Evaporation of the filtrate afforded 4.30 g of a yellow solid. This material was then added to a 500 mL rb flask with a stir bar and 100 mL THF was added. To this was added 2.40 g (12.0 mmol) of 4-amino-piperidine-1-carboxylic acid tert-butyl ester and the reaction mixture allowed to stir for 5 h. After this time the solvent was evaporated down and the resultant material taken up in 1:1 EtOAc/hexanes and loaded onto a plug of silica gel. Elution with the same mixture afforded the title product as a white solid. ¹H NMR (300 MHz, DMSO-D₆) δ ppm 1.42 (m, 11H) 1.89 (s, 2H) 2.89 (m, 2H) 3.75 (m, 1H) 3.99 (m, 2H) 5.37 (m, 1H) 7.29 (m, 2H) 7.74 (m, 1H) 8.40 (m, 1H); MS (DCI/NH₃) m/z 425 [M+H]⁺.

Example 107

4-(Piperidin-4-ylamino)-6-vinyl-chromen-2-one

To a 100 mL round bottom flask was added 2.00 g of 4-(6-Bromo-2-oxo-2H-chromen-4-ylamino)-piperidin-1-carboxylic acid tert-butyl ester (4.74 mmol), 0.540 g (0.468 mmol) of Pd(PPH₃)₄, and 20.0 mL of DMF. To this mixture was added 11.8 g (37.2 mmol) of tributyl-vinyl-stannane, and the reaction mixture heated to 80° C. in an oil bath. After stirring at this temp for 18 h, the reaction mixture was cooled to room temperature and the DMF removed. The residue was then loaded on a silica gel column and eluted with 50% EtOAc/hexanes to afford 1.90 grams of an oil. From this material, 0.400 g (1.08 mmol) was added to a 50 mL round bottom flask and 5 mL of 4N HCl/dioxane was slowly added. After stirring at room temperature for 3 days, the reaction mixture was basified with 50% NaOH. Extraction with CH₂Cl₂ and solvent evaporation afforded 0.290 mg (0.757 mmol) of the title compound as the TFA salt. ¹H NMR (300 MHz, DMSO-D₆) δ ppm 1.47 (m, 2H) 1.86 (m, 2H) 2.60 (m, 2H) 2.97 (m, 2H) 3.52 (m, 1H) 5.24 (s, 1H) 5.34 (m, 1H) 5.95 (m, 1H) 6.76 (m, 1H) 7.27 (m, 2H) 7.68 (m, 2H) 8.24 (m, 1H); MS (DCI/NH₃) m/z 271 [M+H]⁺.

Example 108

4-{1-(3,4-Dimethyl-benzyl)-piperidin-4-ylamino}-6-vinyl-chromen-2-one (II-46)

4-(Piperidin-4-ylamino)-6-vinyl-chromen-2-one and 3,4-dimethylbenzaldehyde were allowed to react in a manner analogous to that previously described to give the title compound. ¹H NMR (500 MHz, DMSO-D₆) δ ppm 1.65 (m, 2H) 1.92 (m, 2H) 2.08 (m, 2H) 2.20 (m, 6H) 2.84 (m, 2H) 3.42 (m, 2H) 3.50 (m, 1H) 5.23 (s, 1H) 5.34 (m, 1H) 5.94 (m, 1H) 6.76 (m, 1H) 7.01 (m, 1H) 7.07 (m, 2H) 7.24 (m, 2H) 7.69 (m, 1H) 8.20 (m, 1H); MS (DCI/NH₃) m/z 389 [M+H]⁺.

Example 109

4-{1-(2,3-Dihydrobenzo{1,4}dioxin-6-ylmethyl)-piperidin-4-ylamino}-6-vinyl-chromen-2-one (II-57)

4-(Piperidin-4-ylamino)-6-vinyl-chromen-2-one and 2,3-dihydro-benzo{1,4}dioxine-6-carbaldehyde were allowed to react in a manner analogous to that previously described to give the title compound. ¹H NMR (500 MHz, DMSO-D₆) δ ppm 1.64 (m, 2H) 1.92 (m, 2H) 2.08 (m, 2H) 2.83 (m, 2H) 3.38 (s, 2H) 3.49 (m, 1H) 4.22 (m, 4H) 5.23 (s, 1H) 5.34 (m, 1H) 5.95 (m, 1H) 6.77 (m, 4H) 7.25 (m, 2H) 7.69 (m, 1H) 8.21 (m, 1H); MS (DCI/NH₃) m/z 418 [M+H]⁺.

Example 110

4-{1-Benzooxazol-5-ylmethyl-piperidin-4-ylamino)-6-chloro-chromen-2-one (II-95)

6-Chloro-4-(piperidin-4-ylamino)-chromen-2-one and benzooxazole-5-carbaldehyde were allowed to react in a manner analogous to that previously described to give the title compound. ¹H NMR (500 MHz, DMSO-D₆) δ ppm 1.66 (m, 2H) 1.91 (m, 2H) 2.14 (m, J=10.29 Hz, 2H) 2.85

(m, 2H) 3.50 (m, 1H) 3.63 (s, 2H) 5.28 (s, 1H) 7.29 (m, 1H) 7.33 (m, 1H) 7.41 (m, 1H) 7.62 (m, 1H) 7.71 (m, 2H) 8.32 (m, 1H) 8.71 (s, 1H); MS (DCI/NH$_3$) m/z 410 [M+H9 $^+$.

Example 111

Procedure C. Exemplary Reductive Alkylation of 4-(Piperidin-4-ylamino)-chromen-2-one To a 4 mL screw cap vial charged with MP-BH$_3$CN resin (Argonaut Technologies, loading 2.32 mmol/g; 0.056 g; 2 eq.) and 6-methoxy-4-(piperidin-4-ylamino)-chromen-2-one hydrochloride (I)(0.020 g, 0.064 mmol) a solution of the corresponding aldehyde (1.5 eq.) in 1.0 mL of 1:1 MeOH:CH$_2$Cl$_2$(1% AcOH) was added. The resulting mixture was agitated at 60° C. for 12 h. Then, additional MP-BH$_3$CN resin (0.028 g; 1 eq.) was added followed by a solution of the aldehyde (0.75 eq.) in 0.5 mL of the same solvent. The resulting mixture was shaken at 60° C. for additional 12 h. The reaction mixture was then filtered and the resin washed with MeOH (1 mL, twice). The filtrate and the washes were combined, evaporated in vacuo and the residual oil was purified by reverse phase HPLC (TFA method).

Example 112

6-Methoxy-4-[1-(1-methyl-1H-indol-2-ylmethyl)-piperidin-4-ylamino]-chromen-2-one, trifluoroacetate (II-84)

According to Procedure C above, (I) and 1-methyl-1H-indole-2-carbaldehyde were allowed to react to give 5.7 mg (16.5%, as mono-TFA salt) of a yellow oil. MS (DCI/NH$_3$)(+)Q1MS m/z 418 (M+H)$^+$; $^1$H NMR (500 MHz, pyridine-d$_5$) δ ppm 1.64 (m, 2H), 2.05 (m, 4H), 2.90 (m, 2H), 3.42 (s, 3H), 3.54 (m, 1H), 3.61 (s, 5H), 6.52 (s, 1H), 7.15 (dd, J=8.73, 2.81 Hz, 1H), 7.23 (m, 1H), 7.29 (m, 1H), 7.36 (m, 2H), 7.54 (br d, J=7.49 Hz, N H), 7.68 (d, J=3.12 Hz, 1H), 7.75 (d, J=7.80 Hz, 1H).

Example 113.

4-[1-(3-Fluoro-4-methoxy-benzyl)-piperidin-4-ylamino]-6-methoxy-chromen-2-one trifluoroacetate (II-70)

According to Procedure C above, (I) and 3-fluoro-4-methoxybenzaldehyde were allowed to react to give 19.3 mg (56.4%, as mono-TFA salt) of a yellow oil. MS (DCI/NH$_3$)(+)Q1MS m/z 413 (M+H)$^+$; $^1$H NMR (500 MHz, pyridine-d$_5$) δ ppm 1.79 (m, 2H), 2.08 (m, 2H), 2.20 (m, 11.54 Hz, 2H), 2.98 (m, 2H), 3.40 (s, 3H), 3.56 (s, 2H), 3.58 (m, 1H), 3.75 (s, 3H), 5.71 (s, 1H), 7.01 (m, 2H), 7.11 (m, 1H), 7.15(dd, J=9.05, 2.81 Hz, 1H), 7.27 (m, 1H), 7.34 (d, J=9.05 Hz, 1H), 7.64 (br d, J=7.18 Hz, N H), 7.67 (d, J=2.81 Hz, 1H).

Example 114

4-[1-(2,3-Dihydro-benzo[1,4]dioxin-6-ylmethyl)-piperidin-4-ylamino]-6-methoxy-chromen-2-one trifluoroacetate (II-64)

According to Procedure C above, (I) and 2,3-dihydro-benzo[1,4]dioxine-6-carbaldehyde were allowed to react to give 18.1 mg (51.9%, as mono-TFA salt) of a yellow oil. MS (DCI/NH$_3$)(+)Q1MS m/z 423 (M+H)$^+$; $^1$H NMR (500 MHz, pyridine-d$_5$) δ ppm 1.87 (m, 2H), 2.09 (m, 2H), 2.32 (m, 2H), 3.11 (m, 2H), 3.40 (s, 3H), 3.61 (m, 1H), 3.68 (s, 2H) 4.15 (s, 4H), 5.70 (s, 1H), 6.95 (dd, J=8.11, 1.87 Hz, 1H), 7.00 (m, 1H), 7.15 (m, 2H), 7.33 (d, J=8.74 Hz, 1H), 7.66 (d, J=2.81 Hz, 1H), 7.68 (br d, J=7.49 Hz, N H).

Example 115

4-[1-(2,2-Difluoro-benzo[1,3]dioxol-5-ylmethyl)-piperidin-4-ylamino]-6-methoxy-chromen-2-one trifluoroacetate (II-68)

According to Procedure C above, (I) and 2,2-difluoro-benzo[1,3]dioxole-5-carbaldehyde were allowed to react to give 20.3 mg (55.9%, as mono-TFA salt) of a yellow oil. MS (DCI/NH$_3$)(+)Q1MS m/z 445 (M+H)$^+$; $^1$H NMR (500 MHz, pyridine-d$_5$) δ ppm 1.73 (m, 2H), 2.10 (m, 4H), 2.87 (m, 2H), 3.41 (s, 3H), 3.48 (s, 2H), 3.55 (m, 1H), 5.71 (s, 1H), 7.05 (m, 2H), 7.16 (dd, J=8.89, 2.96 Hz, 1H), 7.18 (m, 1H) 7.34 (d, J=9.05 Hz, 1H), 7.62 (br d, J=7.18 Hz, N H), 7.68 (d, J=2.81 Hz, 1H).

Example 116

6-Methoxy-4-[1-(4-methyl-benzyl)-piperidin-4-ylamino]-chromen-2-one trifluoroacetate (II-34)

According to Procedure C above, (I) and 4-methyl-benzaldehyde were allowed to react to give 18.9 mg (59.0%, as mono-TFA salt) of a yellow oil. MS (DCI/NH$_3$)(+)Q1MS m/z 379 (M+H)$^+$; $^1$H NMR (500 MHz, pyridine-d$_5$) δ ppm 1.93 (m, 2H), 2.11 (m, 2H), 2.24 (s, 3H), 2.38 (m, 2H), 3.14 (m, 2H), 3.41 (s, 3H), 3.62 (m, 1H), 3.78 (s, 2H), 5.69 (s, 1H), 7.15 (d, J=6.55 Hz, 3H), 7.34 (m, 3H), 7.67 (d, J=2.81 Hz, 1H), 7.73 (br d, J=7.18 Hz, N H).

Example 117

6-Methoxy-4-[1-(4-methoxy-benzyl)-piperidin-4-ylamino]-chromen-2-one trifluoroacetate (II-39)

According to Procedure C above, (I) and 4-methoxy-benzaldehyde were allowed to react to give 15.6 mg (47.2%, as mono-TFA salt) of a yellow oil. MS (DCI/NH$_3$)(+)Q1MS m/z 395 (M+H)$^+$; $^1$H NMR (500 MHz, pyridine-d$_5$) δ ppm 1.95 (m, 2H), 2.13 (m, 2H), 2.41 (m, 2H), 3.17 (m, 2H), 3.40 (s, 3H), 3.65 (m, 1H), 3.69 (s, 3H), 3.81 (m, 2H), 5.70 (s, 1H), 6.99 (m, 2H), 7.15 (dd, J=8.73, 2.81 Hz, 1H), 7.33 (d, J=9.05 Hz, 1H), 7.41 (m, 2H), 7.66 (d, J=2.81 Hz, 1H), 7.75 (br d, J=7.18 Hz, N H).

Example 118

4-[1-(4-Bromo-benzyl)-piperidin-4-ylamino]-6-methoxy-chromen-2-one trifluoroacetate (II-65)

According to Procedure C above, (I) and 4-bromo-benzaldehyde were allowed to react to give 17.9 mg (49.1%, as mono-TFA salt) of a yellow oil. MS (DCI/NH$_3$)(+)Q1MS m/z 443/445 (M+H)$^+$; $^1$H NMR (500 MHz, pyridine-d$_5$) δ ppm 1.75 (m, 2H), 2.09 (m, 4H), 2.89 (m, 2H), 3.40 (s, 3H), 3.48 (s, 2H), 3.54 (m, 1H), 5.71 (s, 1H), 7.15 (dd, J=9.05, 2.81 Hz, 1H) 7.24 (m, 2H) 7.34 (d, J=9.05 Hz, 1H) 7.51 (m, 2H) 7.63 (br d, J=7.49 Hz, N H) 7.67 (d, J=2.81 Hz, 1H).

Example 119

4-[1-(3,4-Dimethyl-benzyl)-piperidin-4-ylamino]-6-methoxy-chromen-2-one trifluoroacetate (II-29)

According to Procedure C above, (I) and 3,4-dimethyl-benzaldehyde were allowed to react to give 18.1 mg (55.0%, as mono-TFA salt) of a yellow oil. MS (DCI/NH$_3$)(+)Q1MS m/z 393 (M+H)$^+$; $^1$H NMR (500 MHz, pyridine-d$_5$) δ ppm 1.95 (m, 2H), 2.13 (m, 2H), 2.14 (s, 3H), 2.15 (s, 3H), 2.41 (m, 2H), 3.18 (m, 2H), 3.40 (s, 3H), 3.64 (m, 1H), 3.78 (s, 2H), 5.69 (s, 1H), 7.12 (m, 1H), 7.15 (dd, J=8.73, 2.81 Hz, 1H), 7.23 (m, 2H), 7.33 (d, J=9.05 Hz, 1 H), 7.66 (d, J=2.81 Hz, 1H), 7.74 (br d, J=7.18 Hz, N H).

Example 120

4-[1-(2,4-Dimethyl-benzyl)-piperidin-4-ylamino]-6-methoxy-chromen-2-one trifluoroacetate (II-25)

According to Procedure C above, (I) and 2,4-dimethyl-benzaldehyde were allowed to react to give 20.5 mg (62.3%, as mono-TFA salt) of a yellow oil. MS (DCI/NH$_3$)(+)Q1MS m/z 393 (M+H)$^+$; $^1$H NMR (500 MHz, pyridine-d$_5$) δ ppm 1.75 (m, 2H), 2.05 (m, 2H), 2.19 (m, 2H), 2.23 (s, 3H), 2.31 (s, 3H), 2.99 (m, 2H), 3.41 (s, 3H), 3.56 (s, 2H), 3.58 (m, 1H), 5.70 (s, 1H), 6.95 (s, 1H), 7.00 (d, J=7.80 Hz, 1H), 7.15 (dd, J=8.73, 2.81 Hz, 1H), 7.26 (d, J=7.80 Hz, 1H) 7.33 (d, J=9.05 Hz, 1H), 7.60 (m, N H), 7.66 (d, J=2.81 Hz, 1H).

Example 121

4-[1-(4-Butoxy-benzyl)-piperidin-4-ylamino]-6methoxy-chromen-2-one trifluoroacetate (II-50)

According to Procedure C above, (I) and 4-butoxy-benzaldehyde were allowed to react to give 19.9 mg (55.6%, as mono-TFA salt) of a yellow oil. MS (DCI/NH$_3$)(+)Q1MS m/z 437 (M+H)$^+$; $^1$H NMR (500 MHz, pyridine-d$_5$) δ ppm 0.87 (t, J=7.33 Hz, 3H), 1.42 (m, 2H), 1.69 (m, 2H), 1.95 (m, 2H), 2.13 (m, 2H), 2.40 (m, 2H), 3.17 (m, 2H), 3.39 (s, 3H), 3.64 (m, 1H), 3.79 (s, 2H), 3.91 (t, J=6.40 Hz, 2H), 5.70 (s, 1H), 7.03 (d, J=8.42 Hz, 2H), 7.15 (dd, J=8.73, 2.81 Hz, 1H), 7.33 (d, J=9.05 Hz, 1H), 7.42 (d, J=8.42 Hz, 2H), 7.66 (d, J=2.81 Hz, 1H), 7.74 (br d, J=7.49 Hz, N H).

Example 122

6-Methoxy-4-[1-(4-methoxy-3-methyl-benzyl)-piperidin-4-ylamino]-chromen-2-one trifluoroacetate (II-37)

According to Procedure C above, (I) and 4-methoxy-3-methyl-benzaldehyde were allowed to react to give 20.1 mg (59.2%, as mono-TFA salt) of a yellow oil. MS (DCI/NH$_3$)(+)Q1MS m/z 409 (M+H)$^+$; $^1$H NMR (500 MHz, pyridine-d$_5$) δ ppm 2.02 (m, 2H), 2.15 (m, 2H), 2.25 (s, 3H), 2.49 (m, 2H), 3.25 (m, 2H), 3.39 (s, 3H), 3.68 (m, 1H), 3.71 (s, 3H), 3.85 (s, 2H), 5.70 (s, 1H), 6.84 (d, J=8.11 Hz, 1H), 7.15(dd, J=9.05, 2.81 Hz, 1H), 7.31 (m, 3H), 7.66 (d, J=2.81 Hz, 1H), 7.78 (br d, J=7.18 Hz, N H).

Example 123

6-Methoxy-4-[1-(7-methyl-naphthalen-2-ylmethyl)-piperidin-4-ylamino]-chromen-2-one trifluoroacetate (II-27)

According to Procedure C above, (I) and 7-methyl-naphthalene-2-carbaldehyde were allowed to react to give 21.3 mg (60.4%, as mono-TFA salt) of a yellow oil. MS (DCI/NH$_3$)(+)Q1MS m/z 429 (M+H)$^+$; $^1$H NMR (500 MHz, pyridine-d$_5$) δ ppm 1.83 (m, 2H), 2.09 (m, 2H), 2.27 (m, 2H), 2.41 (s, 3H), 3.05 (m, 2H), 3.39 (s, 3H), 3.59 (m, 1H), 3.79 (s, 2H), 5.72 (s, 1H), 7.15 (dd, J=9.05, 2.81 Hz, 1H), 7.34 (m, 2H), 7.54 (m, 1H), 7.65 (m, 2H+N H), 7.83 (m, 3H).

Example 124

6-Methoxy-4-(1-naphthalen-2-ylmethyl-piperidin-4-ylamino)-chromen-2-one trifluoroacetate (II-19)

According to Procedure C above, (I) and naphthalene-2-carbaldehyde were allowed to react to give 8.1 mg (23.6%, as mono-TFA salt) of a yellow oil. MS (DCI/NH$_3$)(+)Q1MS m/z 415 (M+H)$^+$; $^1$H NMR (500 MHz, pyridine-d$_5$) δ ppm 1.83 (m, 2H), 2.08 (m, 2H), 2.26 (m, 2H), 3.03 (m, 2H), 3.40 (s, 3H), 3.59 (m, 1H), 3.79 (s, 2H), 5.71 (s, 1H), 7.15 (dd, J=9.05, 2.81 Hz, 1H), 7.33 (d, J=9.05 Hz, 1H), 7.51 (m, 2H), 7.58 (m, 1H), 7.66 (m, 1H+N H), 7.90 (m, 4H).

Example 125

Procedure D

Same as Procedure C, except starting with 0.025 g (0.080 mmol) of (I).

Example 126

4-(1-Benzyl-piperidin-4-ylamino)-6-methoxy-chromen-2-one trifluoroacetate (II-102)

According to Procedure D above, (I) and benzaldehyde were allowed to react to give 25.9 mg (66.8%, as mono-TFA salt) of a yellow oil. MS (DCI/NH$_3$)(+)Q1MS m/z 365 (M+H)$^+$; $^1$H NMR (500 MHz, pyridine-d$_5$) δ ppm 1.95 (m, 2H), 2.11 (m, 2H), 2.42 (m, 2H), 3.16 (m, 2H), 3.39 (s, 3H), 3.63 (m, 1H), 3.84 (s, 2H), 5.68 (s, 1H), 7.15 (dd, J=8.73, 2.81 Hz, 1H), 7.34 (m, 4H), 7.48 (m, 2H), 7.65 (d, J=2.81 Hz, 1H), 7.74 (br d, J=7.18 Hz, N H).

Example 127

4-[1-(3-Fluoro-benzyl)-piperidin-4-ylamino]-6-methoxy-chromen-2-one trifluoroacetate (II-79)

According to Procedure D above, (I) and 3-fluoro-benzaldehyde were allowed to react to give 25.0 mg (62.2%, as mono-TFA salt) of a yellow oil. MS (DCI/NH$_3$)(+)Q1MS m/z 383 (M+H)$^+$; $^1$H NMR (500 MHz, pyridine-d$_5$) δ ppm 1.70 (m, 2H), 2.07 (m, 4H), 2.86 (m, 2H), 3.40 (s, 3H), 3.50 (s, 2H), 3.53 (m, 1H), 5.70 (s, 1H), 7.06 (m, 1H), 7.15 (m, 2H), 7.21 (m, 1H), 7.29 (m, 1H), 7.34 (m, 1H), 7.66 (d, J=2.50 Hz, 1H).

Example 128

4-[1-(4-Difluoromethoxy-benzyl)-piperidin-4-ylamino]-6-methoxy-chromen-2-one trifluoroacetate (II-43)

According to Procedure D above, (I) and 4-difluoromethoxy-benzaldehyde were allowed to react to give 34.3 mg (78.8%, as mono-TFA salt) of a yellow oil. MS (DCI/NH$_3$)(+)Q1MS m/z 431 (M+H)$^+$; $^1$H NMR (500 MHz, pyridine-d$_5$) δ ppm 1.69 (m, 2H), 2.05 (m, 4H), 2.84 (m, 2H), 3.38 (s, 3H), 3.45 (s, 2H), 3.52 (m, 1H), 5.71 (s, 1H), 7.15(dd, J=8.89, 2.65 Hz, 1H), 7.21 (m, 2H), 7.35 (m, 3H), 7.59 (m, N H), 7.64 (d, J=2.50 Hz, 1H).

Example 129

6-Methoxy-4-[1-(3-methoxy-benzyl)-piperidin-4-ylamino]-chromen-2-one trifluoroacetate (II-76)

According to Procedure D above, (I) and 3-methoxy-benzaldehyde were allowed to react to give 32.8 mg (79.6%, as mono-TFA salt) of a yellow oil. MS (DCI/NH$_3$)(+)Q1MS m/z 395 (M+H)$^+$; $^1$H NMR (500 MHz, pyridine-d$_5$) δ ppm 1.78 (m, 2H), 2.06 (m, 2H), 2.21 (m, 2H), 3.00 (m, 2H), 3.39 (s, 3H), 3.56 (m, 1H), 3.63 (s, 2H), 3.70 (s, 3H), 5.70 (s, 1H), 6.95 (dd, J=8.27, 2.03 Hz, 1H), 7.03 (m, 1H), 7.15 (m, 2H), 7.32 (m, 2H), 7.62 (br d, J=7.18 Hz, N H), 7.65 (d, J=2.81 Hz, 1H).

Example 130

6-Methoxy-4-[1-(3-methyl-benzyl)-piperidin-4-ylamino]-chromen-2-one trifluoroacetate (II-92)

According to Procedure D above, (I) and 3-methyl-benzaldehyde were allowed to react to give 27.1 mg (67.9%, as mono-TFA salt) of a yellow oil. MS (DCI/NH$_3$)(+)Q1MS m/z 379 (M+H)$^+$; $^1$H NMR (500 MHz, pyridine-d$_5$) δ ppm 1.76 (m, 2H), 2.03 (m, 2H), 2.17 (m, 2H), 2.25 (s, 3H), 2.98 (m, 2H), 3.37 (s, 3H), 3.54 (m, 1H), 3.58 (s, 2H), 5.70 (s, 1H), 7.11 (m, 1H), 7.15 (dd, J=9.05, 2.81 Hz, 1H), 7.26 (m, 3H), 7.33 (d, J=9.05 Hz, 1H), 7.62 (br d, J=7.49 Hz, N H), 7.64 (d, J=2.81 Hz, 1H).

Example 131

4-[1-(4-Chloro-benzyl)-piperidin-4-ylamino]-6-methoxy-chromen-2-one trifluoroacetate (II-110)

According to Procedure D above, (I) and 4-Chloro-benzaldehyde were allowed to react to give 28.9 mg (69.6%, as mono-TFA salt) of a yellow oil. MS (DCI/NH$_3$)(+)Q1MS m/z 399 (M+H)$^+$; $^1$H NMR (500 MHz, pyridine-d$_5$) δ ppm 1.67 (m, 2H), 2.03 (m, 4H), 2.81 (m, 2H), 3.38 (s, 3H), 3.41 (s, 2H), 3.52 (m, 1H), 5.71 (s, 1H), 7.15 (dd, J=9.05, 2.81 Hz, 1 H), 7.27 (m, 2H), 7.35 (m, 3H), 7.65 (d, J=2.81 Hz, 1H).

Example 132

4-[1-(4-Ethoxy-benzyl)-piperidin-4-ylamino]-6-methoxy-chromen-2-one trifluoroacetate (II-80)

According to Procedure D above, (I) and 4-methoxy-benzaldehyde were allowed to react to give 31.7 mg (74.9%, as mono-TFA salt) of a yellow oil. MS (DCI/NH$_3$)(+)Q1MS m/z 409 (M+H)$^+$; $^1$H NMR (500 MHz, pyridine-d$_5$) δ ppm 1.28 (t, J=6.86 Hz, 3H), 1.72 (m, 2H), 2.12 (m, 4H), 2.93 (m, 2H), 3.37 (s, 3H), 3.51 (s, 2H), 3.53 (m, 1H), 3.93 (q, J=6.86 Hz, 2H), 5.71 (s, 1H), 6.99 (m, 2H), 7.15 (dd, J=8.73, 2.50 Hz, 1H), 7.33 (m, 3H), 7.60 (m, N H), 7.64 (d, J=2.81 Hz, 1H).

Example 133

6-Methoxy-4-(1-naphthalen-1-ylmethyl-piperidin-4-ylamino)-chromen-2-one trifluoroacetate (II-66)

According to Procedure D above, (I) and naphthalene-1-carbaldehyde were allowed to react to give 34.9 mg (81.5%, as mono-TFA salt) of a yellow oil. MS (DCI/NH$_3$)(+)Q1MS m/z 415 (M+H)$^+$; $^1$H NMR (500 MHz, pyridine-d$_5$) δ ppm 1.61 (m, 2H), 1.98 (m, 2H), 2.13 (m, 2H), 2.94 (m, 2H), 3.41 (s, 3H), 3.53 (m, 1H), 3.90 (s, 2H), 5.71 (s, 1H), 7.14 (dd, J=9.05, 2.81 Hz, 1H), 7.33 (m, 1H), 7.50 (m, 5H), 7.64 (d, J=2.81 Hz, 1H), 7.86 (m, N H), 7.91 (m, 1H), 8.41 (m, 1H).

Example 134

4-[1-(4-Chloro-3-fluoro-benzyl)-piperidin-4-ylamino]-6-methoxy-chromen-2-one trifluoroacetate (II-58)

According to Procedure D above, (I) and 4-chloro-3-fluoro-benzaldehyde were allowed to react to give 28.7 mg (66.7%, as mono-TFA salt) of a yellow oil. MS (DCI/NH$_3$)(+)Q1MS m/z 417 (M+H)$^+$; $^1$H NMR (500 MHz, pyridine-d$_5$) δ ppm 1.67 (m, 2H), 2.03 (m, 4H), 2.78 (m, 2H), 3.38 (s, 2H), 3.40 (s, 3H), 3.52 (m, 1H), 5.72 (s, 1H), 7.05 (m, 1H), 7.16 (dd, J=9.05, 2.81 Hz, 1H), 7.22 (m, 1H), 7.36 (m, 2H), 7.56 (m, N H), 7.67 (d, J=2.81 Hz, 1H).

Example 135

4-[1-(2-Fluoro-4-methoxy-benzyl)-piperidin-4-ylamino]-6-methoxy-chromen-2-one trifluoroacetate (II-62)

According to Procedure D above, (I) and 2-fluoro-4-methoxy-benzaldehyde were allowed to react to give 40.4 mg (94.7%, as mono-TFA salt) of a yellow oil. MS (DCI/NH$_3$)(+)Q1MS m/z 413 (M+H)$^+$; $^1$H NMR (500 MHz, pyridine-d$_5$) δ ppm 1.78 (m, 2H), 2.06 (m, 2H), 2.24 (m, 2H), 3.01 (d, 2H), 3.37 (s, 3H), 3.56 (m, 1H), 3.67 (s, 2H), 3.68 (s, 3H), 5.71 (s, 1H), 6.79 (m, 1H), 6.84 (m, 1H), 7.15 (dd, J=8.89, 2.96 Hz, 1H), 7.35 (m, 2H), 7.64 (m, 1H+N H).

Example 136

4-[1-(3-Fluoro-4-methyl-benzyl)-piperidin-4-ylamino]-6-methoxy-chromen-2-one trifluoroacetate (II-105)

According to Procedure D above, (I) and 3-fluoro-4-methyl-benzaldehyde were allowed to react to give 32.2 mg (77.9%, as mono-TFA salt) of a yellow oil. MS (DCI/NH$_3$)(+)Q1MS m/z 397 (M+H)$^+$; $^1$H NMR (500 MHz, pyridine-d$_5$) δ ppm 1.74 (m, 2H), 2.05 (m, 2H), 2.13 (m, 2H), 2.19 (s, 3H), 2.91 (m, 2H), 3.40 (s, 3H), 3.51 (s, 2H), 3.55 (m, 1H), 5.71 (s, 1H), 7.05 (m, 1H), 7.14 (m, 3H), 7.34 (d, J=8.73 Hz, 1H), 7.59 (m, N H), 7.66 (d, J=2.81 Hz, 1H).

Example 137

Procedure E

Same as Procedure C, starting from 0.0158 g (0.051 mmol) of (I).

Example 138

4-[1-(3-Ethoxy-benzyl)-piperidin-4-ylamino]-6-methoxy-chromen-2-one trifluoroacetate (II-97)

According to Procedure E above, (I) and 3-ethoxy-benzaldehyde were allowed to react to give 21.9 mg (72.3%, as mono-TFA salt) of a yellow oil. MS (DCI/NH$_3$)(+)Q1MS m/z 409 (M+H)$^+$; $^1$H NMR (500 MHz, pyridine-d$_5$) δ ppm 1.27 (t, J=7.02 Hz, 3H), 1.81 (m, 2H), 2.05 (m, 2H), 2.24 (m, 2H), 3.02 (m, 2H), 3.39 (s, 3H), 3.57 (m, 1H), 3.66 (s, 2H), 3.93 (q, J=6.97 Hz, 2H), 5.68 (s, 1H), 6.94 (dd, J=8.11, 2.50 Hz, 1H), 7.01 (m, 1H), 7.13 (m, 2H), 7.30 (m, 2H), 7.64 (m, 1H+N H).

Example 139

Dimethylamino-propoxy)-benzyl]-piperidin-4-ylamino}-6-methoxy-chromen-2-one; Double TFA Salt (II-91)

According to Procedure E above, (I) and 4-(3-dimethylamino-propoxy)-benzaldehyde were allowed to react to give 30.9 mg (92.8%, as double-TFA salt) of a yellow oil. MS (DCI/NH$_3$)(+)Q1MS m/z 466 (M+H)$^+$; $^1$H NMR (500 MHz, pyridine-d$_5$) δ ppm 2.12 (m, 2H) 2.19 (m, 2H) 2.28 (m, 2H) 2.65 (m, 2H) 2.82 (s, 6H) 3.27 (m, 2H) 3.35 (m, 2H) 3.41 (s, 3H) 3.73 (m, 1H) 4.01 (m, 4H) 5.68 (s, 1H) 6.98 (m, 2H) 7.15 (dd, J=8.89, 2.96 Hz, 1H) 7.33 (d, J=9.05 Hz, 1H) 7.48 (m, 2H) 7.68 (d, J=2.81 Hz, 1H) 7.68 (br d, J=2.81 Hz, N H).

Example 140

4-[1-(3-Fluoro-4-hydroxy-benzyl)-piperidin-4-ylamino]-6-methoxy-chromen-2-one hydrochloride (II-88)

According to Procedure C above, (I) (0.0223 g; 0.081 mmol) and 3-fluoro-4-hydroxy-benzaldehyde were allowed to react to give after the purification the corresponding mono-TFA salt. The product was then suspended in MeOH and hydrochloride salt was precipitated by addition of 4 N HCl solution in dioxane. The resulting white solid was triturated with $Et_2O$/MeOH (2:1), washed with $Et_2O$ and dried under high vacuum to afford 33.6 mg (95.4%) of the title compound. MS (DCI/NH3)(+)Q1MS m/z 399 (M+H)$^+$; $^1$H NMR (500 MHz, pyridine-$d_5$) δ ppm 1.94 (m, 2H), 2.10 (m, 2H), 2.27 (m, 2H), 3.06 (m, 2H), 3.42 (s, 3H), 3.61 (m, 1H), 3.65 (s, 2H), 5.71 (s, 1H), 7.15 (m, 2H), 7.24 (m, 1H), 7.33 (d, J=9.05 Hz, 1H), 7.39 (m, 1H), 7.69 (m, 1H+1N H).

Example 141

4-[4-(6-Chloro-2-oxo-2H-chromen-4-ylamino)-piperidin-1-ylmethyl]-benzoic Acid trifluoroacetate According to Procedure C above, 6-chloro-4-(piperidin-4-ylamino)-chromen-2-one (0.350 g of hydrochloride salt; 1.11 mmol) and 4-formyl-benzoic acid were allowed to react to afford 0.307 g (67.0%) of the title compound. MS (DCI/NH$_3$)(+)Q1MS m/z 413 (M+H)$^+$; $^1$H NMR (500 MHz, pyridine-$d_5$) δ ppm 1.78 (m, 2H), 2.10 (m, 4H), 2.90 (m, 2H), 3.54 (m, 1H), 3.57 (s, 2H), 5.69 (s, 1H), 7.28 (d, J=8.73 Hz, 1H), 7.45 (dd, J=8.73, 2.18 Hz, 1H), 7.51 (m, 2H), 8.26 (d, J=2.50 Hz, 1H), 8.42 (m, J=8.42 Hz, 2H).

Example 142

Procedure F. Method for Amidation of 4-[4-(6-Chloro-2-oxo-2H-chromen-4-ylamino)-piperidin-1-ylmethyl]-benzoic Acid To a 4 mL screw cap vial charged with the title compound from Example 141 (II) (0.020 g of mono-TFA salt; 0.038 mmol) and PS-carbodiimide resin (Argonaut Technologies, loading 1.33 mmol/g; 0.086 g; 3 eq.) a solution of triethylamine (0.021 mL, 4 eq.) in DMA (0.5 mL) was added followed by a solution of hydroxybenzotriazole hydrate (0.0051 g; 1 eq.) in DMA (0.5 mL). The resulting mixture was agitated at room temperature for 5 min. Then a solution of the requisite amine (1.5 eq.) in DMA (0.5 mL) was added and the mixture was agitated at 55° C. for 12 h. The mixture was then filtered and the resin was washed twice with 1 mL of DMA. The filtrate and the washes were combined and evaporated in vacuo. The residual oil was purified by reverse phase HPLC (TFA method).

Example 143

4-[4-(6-Chloro-2-oxo-2H-chromen-4-ylamino)-piperidin-1-ylmethyl]-N-(2-pyrrolidin-1-yl-ethyl)-benzamide; Double TFA Salt (II-55)

According to Procedure F above, (II) and 2-pyrrolidin-1-yl-ethylamine were allowed to react to afford 18.5 mg (66.0%, as double-TFA salt) of a yellow oil. MS (DCI/NH$_3$)(+)Q1MS m/z 509 (M+H)$^+$; $^1$H NMR (500 MHz, pyridine-$d_5$) δ ppm 1.77 (m, 6H), 2.08 (m, 4H), 2.86 (m, 2H), 3.31(br s, 4H), 3.48 (t, J=5.77 Hz, 2H), 3.52 (s, 3H), 4.01 (q, J=5.62 Hz, 2H), 5.68 (s, 1H), 7.28 (d, J=8.73 Hz, 1H), 7.46 (m, 3H+N H), 8.27 (d, J=2.18 Hz, 1H), 8.30 (d, J=8.11 Hz, 2H), 9.49 (m, N H).

Example 144

4-[4-(6-Chloro-2-oxo-2H-chromen-4-ylamino)-piperidin-1-ylmethyl]-N-(2-piperidin-1-yl-ethyl)-benzamide; Double TFA Salt (II-67)

According to Procedure F above, (II) and 2-piperidin-1-yl-ethylamine were allowed to react to afford 20.9 mg (73.2%, as double-TFA salt) of a yellow oil. MS (DCI/NH$_3$)(+)Q1MS m/z 523 (M+H)$^+$; $^1$H NMR (500 MHz, pyridine-$d_5$) δ ppm 1.33 (m, 2H), 1.73 (m, 6H), 2.08 (m, 4H), 2.88 (m, 2H), 3.07 (br s, 4H), 3.33 (t, J=6.08 Hz, 2H), 3.53 (m, 3H), 4.03 (q, J=5.93 Hz, 2H), 5.68 (s, 1H), 7.28 (d, J=8.73 Hz, 1H), 7.46 (m, 3H+N H), 8.27 (m, 3H), 9.47 (br t, J=5.30 Hz, N H).

Example 145

4-[4-(6-Methoxy-2-oxo-2H-chromen-4-ylamino)-piperidin-1-ylmethyl]-benzoic Acid Hydrochloride Salt According to Procedure C above, (I) (0.300 g of hydrochloride salt; 1.09 mmol) and 4-formyl-benzoic acid were allowed to react to afford after HPLC purification and precipitation with hydrochloric acid as described before, 0.182 g (35.4%) of the title compound. MS (DCI/NH$_3$)(+) Q1MS m/z 409 (M+H)$^+$; $^1$H NMR (500 MHz, pyridine-$d_5$) δ ppm 1.78 (m, 2H), 2.13 (m, 4H), 2.89 (m, 2H), 3.42 (s, 3H), 3.56 (m, 1H), 3.57 (s, 2H), 5.72 (s, 1H), 7.15 (dd, J=9.05, 2.81 Hz, 1H), 7.34 (d, J=9.05 Hz, 1H), 7.53 (d, J=8.11 Hz, 2H), 7.62 (br d, J=7.18 Hz, N H), 7.70 (d, J=2.50 Hz, 1H) 8.41 (d, J=8.11 Hz, 2H).

Example 146

Procedure G

Same as Procedure F, starting with 4-[4-(6-Methoxy-2-oxo-2H-chromen-4-ylamino)-piperidin-1-ylmethyl]-benzoic acid as the mono-TFA salt (III), (0.015 g of mono-TFA salt, 0.034 mmol).

Example 147

4-[4-(6-Methoxy-2-oxo-2H-chromen-4-ylamino)-piperidin-1-ylmethyl]-N-(2-pyridin-2-yl-ethyl)-benzamide; Double TFA Salt (II-83)

According to Procedure G above, (III) (0.015 g of mono-TFA salt; 0.0335 mmol) and 2-pyridin-2-yl-ethylamine were allowed to react to afford 23.2 mg (92.1%, as double-TFA salt) of a yellow oil. MS (DCI/NH$_3$)(+)Q1MS m/z 513 (M+H)$^+$; $^1$H NMR (500 MHz, pyridine-$d_5$) δ 1.93 (m, 2H), 2.10 (m, 2H), 2.40 (m, 2H), 3.11 (m, 2H), 3.29 (t, J=6.86 Hz, 2H), 3.42 (s, 3H), 3.64 (m, 1H), 3.82 (s, 2H), 4.13 (m, 2H), 5.69 (s, 1H), 7.05 (m, 1H), 7.15 (dd, J=9.05, 2.81 Hz, 1H), 7.19 (d, J=7.80 Hz, 1H), 7.33 (d, J=8.74 Hz, 1H), 7.50 (m, 3H), 7.68 (d, J=2.81 Hz, 1H), 7.75 (br d, J=7.18 Hz, N H), 8.20 (d, J=8.11 Hz, 2H), 8.60 (m, J=4.06 Hz, 1H), 9.16 (br t, J=5.46 Hz, N H).

Example 148

4-[4-(6-Methoxy-2-oxo-2H-chromen-4-ylamino)-piperidin-1-ylmethyl]-N-(2-piperidin-1-yl-ethyl)-benzamide; Double TFA Salt (II-69)

According to Procedure G above, (III) (0.015 g of mono-TFA salt; 0.0335 mmol) and 2-piperidin-1-yl-ethylamine were allowed to react to afford 24.3 mg (95.7%, as double-TFA salt) of a yellow oil. MS (DCI/NH$_3$)(+)Q1MS m/z 519 (M+H)$^+$; $^1$H NMR (500 MHz, pyridine-d$_5$) δ 1.34 (m, 2H), 1.81 (m, 6H), 2.07 (m, 2H), 2.24 (m, 2H), 2.98 (m, 2H), 3.23 (br s, 4H), 3.42 (s, 3H), 3.45 (t, J=6.08 Hz, 2H), 3.58 (m, 1H), 3.67 (s, 2H), 4.07 (q, J=5.82 Hz, 2H), 5.70 (s, 1H), 7.15(dd, J=8.89, 2.65 Hz, 1H), 7.33 (d, J=9.05 Hz, 1H), 7.50 (d, J=8.11 Hz, 2H), 7.66 (d, J=7.18 Hz, N H), 7.69 (d, J=2.81 Hz, 1H), 8.28 (d, J=8.11 Hz, 2H), 9.60 (t, J=5.62 Hz, N H).

Example 149

4-[4-(6-Methoxy-2-oxo-2H-chromen-4-ylamino)-piperidin-1-ylmethyl]-N-(2-pyrrolidin-1-yl-ethyl)-benzamide; Double TFA Salt (II-86)

According to Procedure G above, (III) (0.050 g of hydrochloride salt; 0.112 mmol) and 2-pyrrolidin-1-yl-ethylamine were allowed to react to afford 73.3 mg (89.3%, as double-TFA salt) of a yellow oil. MS (DCI/NH$_3$)(+)Q1MS m/z 505 (M+H)$^+$; $^1$H NMR (500 MHz, pyridine-d$_5$) δ 1.76 (m, 2H), 1.84 (m, 4H), 2.05 (m, 2H), 2.14 (m, 2H), 2.90 (m, 2H), 3.37 (br s, 4H), 3.41 (s, 3H), 3.55 (m, 5H), 4.03 (q, J=5.93 Hz, 2H), 5.71 (s, 1H), 7.15 (dd, J=8.73, 2.81 Hz, 1H), 7.34 (d, J=8.73 Hz, 1H), 7.47 (d, J=8.42 Hz, 2H), 7.61(br d, J=7.17 Hz, N H), 7.68 (d, J=2.81 Hz, 1H), 8.29 (d, J=8.42 Hz, 2H), 9.55 (br t, J=5.61 Hz, 1H).

Example 150

4-{1-[4-(4-Benzyl-piperazine-1-carbonyl)-benzyl]-piperidin-4-ylamino}-6-methoxy-chromen-2-one; Double TFA Salt (II-94)

According to Procedure G above, (IV) (0.0164 g of hydrochloride salt; 0.0367 mmol) and 1-benzyl-piperazine were allowed to react to afford 23.6 mg (80.3%, as double-TFA salt) of a yellow oil. MS (DCI/NH$_3$)(+)Q1MS m/z 567 (M+H)$^+$; $^1$H NMR (500 MHz, pyridine-d$_5$) δ 1.77 (m, 2H), 2.05 (m, 2H), 2.16 (m, 2H), 2.35 (br s, 4H), 2.95 (m, 2H), 3.38 (s, 3H), 3.46 (s, 2H), 3.56 (m, 1H), 3.62 (s, 2H), 3.87 (br s, 4H), 5.71 (s, 1H), 7.15 (dd, J=9.05, 2.81 Hz, 1H), 7.33 (m, 2H), 7.40 (m, 3H+N H), 7.47 (d, J=8.11 Hz, 2H), 7.58 (m, 2H), 7.64 (m, 2H).

Example 151

Methanesulfonic Acid 3-piperidin-1-yl-propyl ester. Procedure H

In a 20 mL scintillation vial equipped with a stirring bar and a septum screw cap, a solution of 3-piperidin-1-yl-propan-1-ol (0.500 g, 3.49 mmol) in DCM (5 mL) was cooled down to 0° C. Then, triethylamine (10 eq.) was added to the vial via a syringe followed by a solution of methanesulfonyl chloride (5 eq.) in DCM (1 mL). The resulting reaction mixture was allowed to slowly warm up to room temperature and stirring was maintained for additional 2 h. The volatiles were removed in vacuo and the resulting crude methanesulfonic acid 3-piperidin-1-yl-propyl ester was used in the next step of the synthesis without further purification (the material was found to contain 30% of the title compound by weight according to $^1$H NMR).

Example 152

4-{1-[3-Fluoro-4-(3-piperidin-1-yl-propoxy)-benzyl]-piperidin-4-ylamino}-6-methoxy-chromen-2-one; Double TFA Salt (II-47)

To a 4 mL screw cap vial equipped with a magnetic stirring bar containing a solution of 4-[1-(3-Fluoro-4-hydroxy-benzyl)-piperidin-4-ylamino]-6-methoxy-chromen-2-one hydrochloride in DMF (1.0 mL), solid cesium carbonate (0.163 g; 10 eq.) was added. The resulting suspension was stirred for 5 min. Then, a suspension of methanesulfonic acid 3-piperidin-1-yl-propyl ester from Procedure H (0.110 g, 3 eq.) in DMF (1 mL) was added and the resulting mixture was stirred at 55° C. for 10 h. The reaction mixture was then diluted with water and extracted with EtOAc. Organic layers were combined, washed with saturated aqueous Na$_2$CO$_3$, water, and evaporated to dryness in vacuo. The residue was purified by reverse phase HPLC (TFA method) to afford 26.6 mg (70.8%, as double-TFA salt) of a yellow oil. MS (DCI/NH$_3$)(+)Q1MS m/z 524 (M+H)$^+$; $^1$H NMR (500 MHz, pyridine-d$_5$) δ 1.35 (br s, 2H), 1.74 (m, 6H), 2.07 (m, 2H), 2.20 (m, 2H), 2.33 (m, 2H), 2.55–3.25 (m, 6H), 3.20 (m, 2H), 3.39 (s, 3H), 3.56 (s, 2H), 3.61 (m, 1H), 4.09 (t, J=5.93 Hz, 2H), 5.71 (s, 1H), 7.04 (m, J=8.42, 8.42 Hz, 1H), 7.15 (m, 2H), 7.29 (m, 1H), 7.34 (m, 1H), 7.64 (br d, J=7.80 Hz, N H), 7.67 (d, J=2.81 Hz, 1H).

Example 153

6-Chloro-4-{1-[4-(3-piperidin-1-yl-propoxy)-benzyl]-piperidin-4-ylamino}-chromen-2-one; Double TFA Salt (II-49)

The product was obtained as a yellow oil in a manner analogous to that described above for similar compounds in a yield of 21.7 mg (61.2%, as double-TFA salt). MS (DCI/NH$_3$)(+)Q1MS m/z 510 (M+H)$^+$; $^1$H NMR (500 MHz, pyridine-d$_5$) δ 1.36 (br s, 2H), 1.73 (b s, 4H), 1.88 (m, 2H), 2.11 (m, 2H), 2.27 (m, 4H), 3.06 (m, 8H), 3.59 (m, 1H), 3.64 (s, 2H), 4.01 (t, J=5.93 Hz, 2H), 5.68 (s, 1H), 7.00 (d, J=8.42 Hz, 2H), 7.28 (d, J=8.73 Hz, 1H), 7.39 (d, J=8.42 Hz, 2H), 7.45 (dd, J=8.73, 2.50 Hz, 1H), 7.57 (m, N H), 8.25 (d, J=2.50 Hz, 1H).

Example 154

4-[1-(3-Chloro-4-hydroxy-benzyl)-piperidin-4-ylamino]-6-methoxy-chromen-2-one. Procedure M According to Procedure C above, 6-methyl-4-(piperidin-4-ylamino)-chromen-2-one (0.316 g of hydrochloride salt; 1.11 mmol) and 3-chloro-4-hydroxy-benzaldehyde were allowed to react to afford after HPLC purification 0.344 g of mono-TFA salt, (74.9%) of the title compound. MS (DCI/NH$_3$)(+)Q1MS m/z 415 (M+H)$^+$.

Example 155

4-{1-[3-Chloro-4-(3-piperidin-1-yl-propoxy)-benzyl]-piperidin-4-ylamino}-6-methoxy-chromen-2-one; Double TFA Salt (II-115)

The product was obtained as a yellow oil in a manner analogous to that described above for similar compounds in a yield of 30.3 mg (82.2%, as double-TFA salt). MS (DCI/NH$_3$)(+)Q1MS m/z 540 (M+H)$^+$; $^1$H NMR (500 MHz, pyridine-d$_5$) δ 1.36 (s, 2H), 1.78 (m, 6H), 2.08 (m, 2H), 2.22 (m, 2H), 2.36 (m, 2H), 2.75–3.20 (m, 6H), 3.25 (m, 2H), 3.40 (s, 3H), 3.59 (m, 3H), 4.07 (t, J=5.93 Hz, 2H), 5.71 (s, 1H), 6.98 (d, J=8.42 Hz, 1H), 7.16 (dd, J=9.04, 2.81 Hz, 1H), 7.28 (m, 1H), 7.34 (m, 1H), 7.55 (m, 1H), 7.64 (br d, J=7.17 Hz, N H), 7.67 (d, J=2.81 Hz, 1H).

Example 156

3-Hydroxy-8-aza-bicyclo[3.2.1]octane-8-carboxylic acid ethyl ester

To a solution of 3-oxo-8-aza-bicyclo[3.2.1]octane-8-carboxylic acid ethyl ester (3.0 g, 15.23 mmol) in methanol (20 mL) was added 5 mL Raney Nickel (50% aq slurry). The resultant mixture was degassed and charged with hydrogen (g) three times, heated to 70° C. and stirred for 12 hrs. The suspension was filtered through celite, and concentrated to provide a white solid (3.0 g, 100%). $^1$H NMR (300 MHz, CDCl$_3$) δ ppm 1.25 (t, J=7.0 Hz, 3H), 1.57 (m, 2H), 1.72 (app dd, J=1.4, 15.1 Hz, 2H), 1.94 (m, 2H), 2.12 (m 4H), 4.13 (q, J=7.1 Hz, 2H), 4.25 (m, 2H); MS (ESI+Q1MS) m/z 200 [M+H]$^+$ Example 157

3-Methanesulfonyloxy-8-aza-bicyclo[3.2.1]octane-8-carboxylic acid ethyl ester

To a solution of 3-hydroxy-8-aza-bicyclo[3.2.1]octane-8-carboxylic acid ethyl ester (1.250 g, 6.28 mmol) in dichloromethane (62 mL) was added triethylamine (1.40 mL, 10.0 mmol) and methanesulfonyl chloride (0.722 mL, 9.38 mmol) dropwise. The solution was stirred 2 hrs, washed with sodium bicarbonate, dried over MgSO$_4$, filtered, and concentrated. The crude oil (1.74 g) was taken on with no purification. $^1$H NMR (300 MHz, CDCl$_3$) δ ppm 1.26 (t, J=7.1 Hz, 3H), 2.04 (m, 6H), 2.18 (m, 2H), 3.02 (s, 3H), 4.14 (q, J=7.1 Hz, 2H), 4.29 (m, 2H), 5.02 (m, 1H); MS (ESI+Q1MS) m/z 278 [M+H]$^+$ Example 158

3-Azido-8-aza-bicyclo[3.2.1]octane-8-carboxylic acid ethyl ester

To a solution of 3-methanesulfonyloxy-8-aza-bicyclo [3.2.1]octane-8-carboxylic acid ethyl ester (1.74 g, 6.28 mmol) in DMF (62 mL) was added sodium azide (813 mg, 12.5 mmol) portion-wise. The mixture was heated to 100° C., stirred for 5 hrs, cooled, and diluted with ethyl acetate. The solution was washed three times with water, sodium bicarbonate, brine; dried over Na$_2$SO$_4$, filtered, and concentrated to provide a yellow oil (1.42 g). $^1$H NMR (300 MHz, CDCl$_3$) δ ppm 1.25 (t, J=7.1 Hz, 3H), 1.68 (m, 4H), 1.91 (m, 2H), 2.01 (m, 2H), 3.73 (m, 1H), 4.15 (q, J=7.0 Hz, 2H), 4.34 (m, 2H); MS (ESI+Q1MS) m/z 225 [M−H]$^+$ Example 159

3-Amino-8-aza-bicyclo[3.2.1]octane-8-carboxylic acid ethyl ester

To a solution of 3-azido-8-aza-bicyclo[3.2.1]octane-8-carboxylic acid ethyl ester (1.42 g, 6.28 mmol) in methanol (62 mL) was added Pd (10% weight on carbon, 100 mg). The mixture was degassed and charged with hydrogen (g) 3×, and stirred for 12 hrs. The mixture was filtered through celite and concentrated. The crude residue was purified by flash chromatography (gradient elution: 0→20% MeOH/dichloromethane) to provide 855 mg of a clear oil (68%, 3 steps). $^1$H NMR (300 MHz, CDCl3) ☐ ppm 1.26 (t, J=7.1 Hz, 3H), 1.66 (m, 4H), 1.83 (m, 2H), 1.95 (m, 2H), 3.16 (m, 1H), 4.13 (q, J=7.1 Hz, 2H), 4.27 (m, 2H); MS (ESI+Q1MS) m/z 199 [M+H]$^+$ Example 160

3-tert-Butyl-6-chloro-1H-quinazoline-2,4-dione

To a room temperature solution of 4-chloro-phenylamine (5.0 g, 39.19 mmol) was added di-tert-butyl dicarbonate (9.41 g, 43.11 mmol) portion-wise. The solution was heated to reflux, stirred for 2 hrs, cooled, concentrated, and dissolved in diethylether. The solution was washed with water, sodium bicarbonate and brine, dried over MgSO$_4$, filtered, and concentrated to provide (4-chloro-phenyl)-carbamic acid tert-butyl ester (8.5 g) as a white solid, which was used with no further purification. To a −78° C. solution of (4-chloro-phenyl)-carbamic acid t-butyl ester (5.046, 23.30 mmol) in THF (232 mL) was added 32.9 mL of t-BuLi (1.7 M in pentane, 55.92 mmol) via cannula. The solution was stirred 10 min, warmed to −20° C. and stirred 2 hours further. To the −20° C. red solution was added t-butyl isocyanate (3.33 mL, 29.13 mmol). The solution was stirred at −20° C. for 1 hr, warmed to room temperature, stirred 2 hrs, then heated to reflux and stirred for 12 hrs. The reaction was cooled to room temperature, concentrated and dissolved in diethylether. The solution was washed with water, sodium bicarbonate and brine, dried over MgSO$_4$, filtered, and concentrated to provide 5.87 g of white solid (100%). $^1$H NMR (300 MHz, CDCl3) δ ppm 1.76 (s, 9H), 6.91 (d, J=8.6 Hz, 1H), 7.48 (dd, J=2.2, 8.5 Hz, 1H), 7.97 (d, J=2.3 Hz, 1H), 9.22 (br s, 1H).

Example 161

6-Chloro-1-(2,2,2-trifluoro-ethyl)-1H-quinazoline-2,4-dione

To a solution of 3-tert-butyl-6-chloro-1H-quinazoline-2,4-dione (1.0 g, 3.97 mmol) in acetonitrile (40 mL) was added trifluoroethyl triflate (0.736 mL, 4.76 mmol) and potassium carbonate (821 mg, 5.95 mmol). The reaction was heated to 50° C. and stirred 48 hrs. The solution was cooled, concentrated, and dissolved in ethyl acetate. The solution was washed with sodium bicarbonate, brine, dried over Na$_2$SO$_4$, filtered, and concentrated. The crude residue was dissolved in acetic acid and treated with 4 mL HBr solution (30 weight % in AcOH). The reaction was stirred for 3 hours at room temperature, and concentrated to provide 1.1 g of yellow solid. $^1$H NMR (300 MHz, CD$_3$OD) δ ppm 4.96 (q, J=8.7 Hz, 2H), 7.53 (d, J=9.0 Hz, 1H), 7.75 (dd, J=2.6, 9.1 Hz, 1H), 8.07 (d, J=2.7 Hz, 1H); MS (ESI+Q1MS) m/z 279 [M+H]$^+$ Example 162

4-(8-Aza-bicyclo[3.2.1]oct-3-ylamino)-6-chloro-1-(2,2,2-trifluoro-ethyl)-1H-quinazolin-2-one To a solution of 6-chloro-1-(2,2,2-trifluoro-ethyl)-1H-quinazoline-2,4-dione (1.10 g, 3.97 mmol) in phosphorous oxychloride (15 mL) was added 1 mL triethylamine. The reaction was heated to 100° C., stirred for 4 hrs and concentrated. The crude residue was dissolved in chloroform, washed with 1 N aq sodium hydroxide, dried over Na$_2$SO$_4$, filtered, and concentrated. To a solution of the crude residue in DMF (50 mL), was added triethylamine (1 mL) and 3-amino-8-aza-bicyclo[3.2.1]octane-8-carboxylic acid ethyl ester (1.0 g, 5.50 mmol). The solution was heated to 50° C. and stirred for 12 hrs. The reaction was partitioned between ethyl acetate and water and the organic phase was washed an additional 2× with water and brine, dried over Na$_2$SO$_4$, filtered, and concentrated. The resultant yellow foam was treated with HBr solution (6 mL, 30 weight % in AcOH) in a pressure vessel at 100° C. After 4 hrs the solution was cooled and concentrated (1.1 g). $^1$H NMR (300 MHz, CD$_3$OD) δ ppm 2.20 (m, 8H), 4.16 (m, 2H), 4.65 (m, 1H), 5.04 (q, J=8.6 Hz, 2H), 7.62 (d, J=9.0 Hz, 1H), 7.83 (dd, J=2.2, 9.0 Hz, 1H), 8.47 (d, J=2.2 Hz, 1H); MS (ESI+Q1MS) m/z 388 [M+2H]$^+$ Example 163

4-(8-Benzo[1,3]dioxol-5-ylmethyl-8-aza-bicyclo [3.2.1]oct-3-ylamino)-6-chloro-1-(2,2,2-trifluoro-ethyl)-1H-quinazolin-2-one (VI-4)

To a solution of 4-(8-aza-bicyclo[3.2.1]oct-3-ylamino)-6-chloro-1-(2,2,2-trifluoro-ethyl)-1H-quinazolin-2-one (149 mg, 0.320 mmol) in DMF (10 mL) was added triethylamine (0.3 mL) and 5-Chloromethyl-benzo[1,3]dioxole (0.061 mL, 0.480 mmol). The solution was heated to 50° C. and stirred for 6 hrs. The reaction was partitioned between ethyl acetate and water and the organic phase was washed an additional 2x with water and brine, dried over $Na_2SO_4$, filtered, and concentrated. The crude residue was purified by flash chromatography (gradient elution: 0→20% MeOH/dichloromethane) to provide 99 mg white solid (60%). $^1$H NMR (300 MHz, $CDCl_3$) δ ppm 2.10 (m, 4H), 2.32 (m, 2H), 3.56 (m, 3H), 3.77 (s, 2H), 4.87 (m, 2H), 5.96 (s, 2H), 6.77 (d, J=8.0 Hz, 1H), 6.83 (m, 1H), 6.95 (d, J=8.1 Hz, 1H), 7.17 (m, 2H), 7.56 (dd, J=2.3, 8.9 Hz, 1H), 7.91 (s, 1H); MS (ESI+Q1MS) m/z 522 [M+2H]$^+$

Example 164

4-(8-Azabicyclo[3.2.1]oct-3-ylamino)-6-chloro-1-(2,2,2-trifluoroethyl)-1H-quinolin-2-one 6-Chloro-4-hydroxy-1-(2,2,2-trifluoroethyl)-1H-quinolin-2-one (0.841 g, 3 mmol) was suspended in dry acetonitrile (50 mL) under argon and treated with sodium hydride (0.14 g, 60% wt in mineral oil, 4 mmol). After stirring for 10 minutes, 1,1,1-trifluoro-N-phenyl-N-[(trifluoromethyl)sulfonyl]methanesulfonamide (1.14 g, 3.2 mmol) was added and the mixture heated to 50° C. for 6 hours. Analysis by LC/MS indicated the starting quinolone had been completely consumed and 3-amino-8-azabicyclo[3.2.1]octane-8-carboxylic acid ethyl ester (0.902 g, 4 mmol) was added. The reaction was heated to reflux for 18 hours at which time LC/MS analysis indicated complete consumption of the intermediate triflate. The solution was diluted with ethyl acetate and washed with 1 N NaOH. The organic layer was dried with sodium sulfate and concentrated under reduced pressure to give the crude product. Purification by silica chromatography using DCM/methanol eluent gave a yellow foam (0.59 g). This material was dissolved in acetic acid (10 mL) and treated with HBr (5 mL of 30% in acetic acid) in a pressure vessel at 100° C. After 3 hours, the solution was concentrated to give the title compound as an HBr salt. $^1$H NMR (300 MHz, $CD_3OD$) δ ppm 2.21 (8H, m), 4.11 (2H, m), 4.76–5.08 (3H, m), 5.86 (1H, s), 7.25 (1H, m), 7.61 (2H, m).

Example 165

4-(8-Benzo[1,3]dioxol-5-ylmethyl-8-azabicyclo[3.2.1]oct-3-ylamino-0-6-chloro-1-(2,2,2-trifluoroethyl)-1H-quinolin-2-one (V-57)

4-(8-Azabicyclo[3.2.1]oct-3-ylamino)-6-chloro-1-(2,2,2-trifluoroethyl)-1H-quinolin-2-one hydrobromide (0.51 g) was dissolved in acetonitrile (30 mL) prior to addition of sodium carbonate (0.96 g) and triethylamine (1.2 mL). After stirring for 5 minutes, piperonyl chloride (50% wt in DCM, 0.5 mL) was added and the mixture heated to 60° C. under argon for 8 hours. The reaction was diluted with ethyl acetate and washed with 1N NaOH. Concentration under reduced pressure gave the crude product which was purified by silica chromatography using DCM/methanol eluent to give the title compound (0.22 g). $^1$H NMR (300 MHz, $CD_3OD$) δ ppm 2.18–2.35 (5H, m), 2.49 (2H, m), 3.30 (1H, m), 4.0 (2H, br), 4.17 (2H, m), 5.17 (2H, m), 6.01 (2H, s), 6.90 (1H, m), 7.12 (1H, m), 7.25 (1H, m), 7.68 (2H, m), 8.24 (1H, m).

Example 166

3,3-Dimethyl-4-oxo-piperidine-1-carboxylic acid ethyl ester

To a solution of 1-carbethoxy-4-piperidone (5.00 mL, 33.1 mmol) at 0° C. in THF was added NaH (2.96 g, 74.0 mmol) and the suspension was stirred at this temperature 10 min before $CH_3I$ (4.10 mL, 65.9 mmol) was added. The suspension was allowed to stir at 25° C. overnight. After 16 h, the suspension was heated to reflux 2 h at which point the mixture was concentrated in vacuo and partitioned between EtOAc and saturated aqueous $NaHCO_3$. The aqueous layer was extracted with EtOAc (3x) and the combined organics were washed with saturated aqueous NaCl, dried over $MgSO_4$, filtered, and concentrated in vacuo. Silica gel chromatography eluting with a gradient of 0 to 50% EtOAc in hexanes afforded 2.02 g (31%) of the title compound as a pale yellow oil. $^1$H NMR (300 MHz, $CDCl_3$) δ ppm 1.11 (s, 6H), 1.29 (t, 3H, J=7.1 Hz), 2.46–2.55 (m, 2H), 3.42–3.52 (m, 2H), 3.72–3.81 (m, 2H), 4.19 (q, 2H, J=7.1 Hz); $^{13}$C NMR (60 MHz, $CDCl_3$) δ ppm 14.24, 22.01, 37.13, 43.31, 45.94, 53.98, 61.18, 155.2, 208.5, 212.0.

Example 167

4-Amino-3,3-dimethyl-piperidine-1-carboxylic acid ethyl ester

To a solution of 3,3-dimethyl-4-oxo-piperidine-1-carboxylic acid ethyl ester (2.02 g, 10.1 mmol) in $CH_3OH$ was added $NH_4OAc$ (7.82 g, 101 mmol) and the solution was stirred for 24 h before $NaBH_4$ (712 mg, 11.3 mmol) was added and the solution stirred 5 d. The solution was concentrated with nitrogen flow and partitioned between saturated aqueous $NaHCO_3$ and EtOAc. The layers were separated and the aqueous layer was extracted with EtOAc (3x) and the combined organics were washed with saturated aqueous NaCl, dried over $MgSO_4$, filtered, and concentrated in vacuo to produce 1.49 g (73%) of the title compound as a yellow oil. $^1$H NMR (300 MHz, $CDCl_3$) δ ppm 0.72–1.05 (m, 6H), 1.25 (t, 3H, J=7.1 Hz), 1.39–1.89 (m, 1H), 2.13–2.44 (m, 2H), 2.49–2.70 (m, 1H), 2.71–2.99 (m, 1H), 3.62–3.96 (m, 1H), 3.99–4.28 (m, 3H).

Example 168

4-(6-Chloro-2-oxo-2H-chromen-4-ylamino)-3,3-dimethyl-piperidine-1-carboxylic acid ethyl ester To a solution of the 4-amino-3,3-dimethyl-piperidine-1-carboxylic acid ethyl ester (131 mg, 0.654 mmol) in DMF was added NaH (36.4 mg, 0.910 mmol) under nitrogen, and the mixture was stirred 10 min before trifluoromethanesulfonic acid 6-chloro-2-oxo-2H-chromen-4-yl ester (prepared as before, 184 mg, 0.519 mmol) in DMF was added slowly, dropwise. The mixture was stirred 3 d before being concentrated with nitrogen flow to about half its original volume. The mixture was partitioned between EtOAc and $H_2O$ and the layers were separated. The aqueous was extracted with EtOAc (3x) and the combined organics were washed with $H_2O$, saturated aqueous NaCl, dried over $MgSO_4$, filtered, and concentrated in vacuo. Silica gel chromatography eluting with a gradient of 0 to 5% MeOH in $CH_2Cl_2$ afforded 119 mg (56%) of the title compound as a yellow solid. MS (ESI(+)Q1MS) m/z 379 (M+H)$^+$; $^1$H NMR (300 MHz, DMSO) δ ppm 0.83–0.93 (m, 6H), 1.19 (t, 3H, J=7.0 Hz), 1.50–1.63 (m, 1H), 1.70–1.91 (m, 1H), 2.67–3.07 (m, 2H), 3.58–3.84 (m, 2H), 3.92–4.14 (m, 3H), 5.55 (s, 1H), 6.77–6.88 (m, 1H), 7.30–7.40 (m, 1H), 7.60–7.69 (m, 1H), 8.40–8.48 (m, 1H).

Example 169

6-Chloro-4-(3,3-dimethyl-piperidin-4-ylamino)-chromen-2-one, di-HBr Salt

To 4-(6-chloro-2-oxo-2H-chromen-4-ylamino)-3,3-dimethyl-piperidine-1-carboxylic acid ethyl ester (101 mg, 0.267 mmol) was added HBr (30 wt. % solution in HOAc, 5.00 mL, 18.5 mmol) and the solution was heated to 90° C. 1 h before being concentrated with nitrogen flow to produce 103 mg of the title compound as an orange solid. MS (ESI(−)Q1MS) m/z 305 (M−H)$^-$; $^1$H NMR (300 MHz, DMSO) δ ppm 0.93 (s, 3H), 1.10 (s, 3H), 1.69–1.81 (m, 1H), 1.95–2.14 (m, 1H), 2.88–3.05 (m, 2H), 3.06–3.18 (m, 1H), 3.24–3.33 (m, 1H), 3.87–4.10 (m, 1H), 5.57 (s, 1H), 6.93–7.03 (m, 1H), 7.33–7.42 (m, 1H), 7.62–7.70 (m, 1H), 8.18 (bs, 1H), 8.44 (s, 1H), 8.81 (bs, 1H).

Example 170

4-(1-Benzo[1,3]dioxol-5-ylmethyl-3,3-dimethyl-piperidin-4-ylamino)-6-chloro-chromen-2-one (II-124)

To a mixture of 6-chloro-4-(3,3-dimethyl-piperidin-4-ylamino)-chromen-2-one, di-HBr salt (88 mg, 0.188 mmol) in THF was added Cs$_2$CO$_3$ (287 mg, 0.881 mmol) and the suspension was stirred for 5 min under nitrogen before 5-chloromethyl-benzo[1,3]dioxole (124 mg, 0.363 mmol) was added dropwise. The mixture was stirred for 70 h at 25° C. before being refluxed 24 h. The reaction was concentrated with nitrogen flow. The crude product was partitioned between saturated aqueous NaHCO$_3$ and EtOAc and the aqueous layer was extracted with EtOAc (3×). The combined organic layers were washed with saturated aqueous NaCl, dried over MgSO$_4$, filtered, concentrated, and purified by C-18 RP LC-MS chromatography to afford 33 mg (40%) of the title compound as a white solid. MS (ESI(+)Q1MS) m/z 442 (M+H)$^+$; $^1$H NMR (300 MHz, DMSO) δ ppm 0.80 (s, 3H), 1.06 (s, 3H), 1.52–1.62 (m, 1H), 1.84–2.14 (m, 3H), 2.37–2.55 (m, 1H), 2.80–2.90 (m, 1H), 3.25–3.37 (m, 1H), 3.39–3.52 (m, 2H), 5.44 (s, 1H), 5.97–6.02 (m, 2H), 6.73–6.90 (m, 4H), 7.31–7.38 (m, 1H), 7.60–7.67 (m, 1H), 8.45–8.50 (m, 1H).

Example 171

4,6-Dihydroxy-chromen-2-one

4-Hydroxy-6-methoxy-chromen-2-one (500 mg, 2.588 mmol) was suspended in CH$_2$Cl$_2$ (10 mL) and cooled to −78° C. under nitrogen. BBr$_3$ (1 M solution in CH$_2$Cl$_2$, 13 mL, 13 mmol) was added to this suspension dropwise. Following completion of the addition, the resulting suspension was stirred at 25° C. for 1 h before being quenched by the slow addition of H$_2$O. The product was extracted with EtOAc and the combined organic layers dried over Na$_2$SO$_4$ and concentrated to give 350 mg (75%) of the title compound as a tan solid. MS (ESI(+)Q1MS) m/z 179 (M+H)$^+$; $^1$H NMR (300 MHz, DMSO) δ ppm 9.71 (bs, 1H), 7.01–7.23 (m, 3H), 5.57 (s, 1H).

Example 172

6-Difluoromethoxy-4-(1-naphthalen-2-ylmethyl-piperidin-4-ylamino)-chromen-2-one (II-126)

4,6-Dihydroxy-chromen-2-one (500 mg, 2.790 mmol) was dissolved in $^i$PrOH (50 mL). KOH pellets (1.57 g, 27.90 mmol) were added and this mixture was stirred at 25° C. for 5 min. ClCHF$_2$ (g) was bubbled through the reaction mixture for 5 min. The reaction was stirred an additional 10 min. at 25° C. followed by stirring for 30 min. at 60° C. The reaction mixture was diluted with EtOAc and washed with 1 N HCl (aq). The organic layer was dried over Na$_2$SO$_4$, concentrated, and partially purified via silica gel chromatography (20% CH$_3$OH in CH$_2$Cl$_2$) to produce 490 mg of crude 6-difluoromethoxy-4-hydroxy-chromen-2-one. 626 mg of crude 6-difluoromethoxy-4-hydroxy-chromen-2-one was dissolved in CH$_2$Cl$_2$ (20 mL) under nitrogen, cooled to 0° C., and N,N-diisopropylethylamine (2.51 mL, 14.4 mmol) was added. Triflic anhydride (1.31 mL, 7.81 mmol) was added dropwise and the solution was stirred 30 min. at 0° C. The crude product was partially purified via silica gel chromatography (20% EtOAc in hexanes) to produce 682 mg of crude trifluoro-methanesulfonic acid 6-difluoromethoxy-2-oxo-2H-chromen-4-yl ester. 600 mg of crude trifluoro-methanesulfonic acid 6-difluoromethoxy-2-oxo-2H-chromen-4-yl ester was dissolved in CHCl$_3$ (15 mL). 1-Naphthalen-2-ylmethyl-piperidin-4-ylamine dihydrochloride salt (448 mg, 1.43 mmol) and N,N-diisopropylethylamine (0.75 mL, 4.30 mmol) were added and the resulting solution was stirred at 50° C. for 3 h. The reaction mixture was diluted with EtOAc and washed with H$_2$O (3×) followed by saturated aqueous NaCl (1×). The combined organics were dried over Na$_2$SO$_4$, concentrated, and purified on a C-18 RP HPLC system to afford 50 mg of the title compound as a white solid. MS (ESI(+)Q1MS) m/z 451 (M+H)$^+$; $^1$H NMR (300 MHz, CD$_3$OD) δ ppm 7.77–7.91 (m, 5H), 7.32–7.54 (m, 5H), 6.86 (t, J=73 Hz, 1H), 5.34 (s, 1H), 3.74 (s, 2H), 3.48–3.60 (m, 1H), 2.98–3.08 (m, 2H), 2.21–2.33 (m, 2H), 2.00–2.10 (m, 2H), 1.69–1.83 (m, 2H). Compound II-125 was prepared similarly.

Biological Testing

Assay for Release of Intracellular Calcium

Activation of the melanin concentrating hormone receptor (MCHR) by MCH induces the release of Ca$^{++}$ from intracellular stores. This intracellular calcium release is measured using a fluorometric imaging plate reader (FLIPR™, Molecular Devices Corp.) in conjunction with the Ca$^{++}$-sensitive dye Fluo-4. Release of Ca$^{++}$ from intracellular stores causes an increase in fluorescence of the dye that is proportional to Ca$^{++}$ concentration. Briefly, the assays are performed as follows. HEK293 cells expressing the murine MCHR are plated overnight at 50,000 cells/well in 96-well plates. The following day, culture medium is removed and replaced with 100 μl/well of D-PBS (+glucose and sodium pyruvate) containing 2.5 μM Fluo-4AM (Molecular Probes), 0.01% Pluronic F-127 and 2.5 mM probenecid. Cells are loaded with the Fluo-4 dye for at least one hour at room temp. After loading, the cells are washed gently to remove extracellular dye and 100 μl of D-PBS (+glucose and sodium pyruvate) is added to each well. Test compounds are prepared at 40 μM in 4% DMSO. The cell plate is placed in the FLIPR™ and 50 μl/well of test compound is delivered. The calcium signal is followed for 3 minutes to assay for potential agonist activity by the test compounds. Then 50 μl/well of 12 nM mouse MCH (in D-PBS containing 0.1% BSA) is added and the ligand-induced calcium signal is followed for an additional 3 minutes. Antagonist activity as determined by the test compounds ability to inhibit MCH induced Ca$^{++}$ flux is calculated as % inhibition as described by the following formula:

% inhibition=[1−((fTC−fB)÷(fMCH−fB))]×100, where fTC=MCH-induced fluorescence in the presence of test compound; fMCH=MCH-induced fluorescence in the absence of test compound; and fB=Baseline fluorescence.

MCH (3 nM) usually elicits a response of 30,000–40,000 relative fluorescence units (RFU) with a baseline of about 1000 RFU. Fluo-4 fluorescence is measured at 488 nm, with an exposure of 0.40 sec. and F-stop=2.0 and the laser set at 0.40–0.60 W constant light output.

The compounds of the present invention inhibit MCH induced fluorescence at a dose of 10 μM. For example, in this assay a number of the compounds tested provided 50% or better inhibition of MCH at a dose of 10 μM. Examples of such compounds include II-1, II-2, II-3, II-4, II-5, II-6, II-18, II-19, II-25, II-26, II-27, II-28, II-29, II-31, II-32, II-33, II-34, II-35, II-36, II-37, II-38, II-39, II-40, II-41, II-42, II-43, II-44, II-45, II-46, II-47, II-48, II-49, II-50, II-51, II-53, II-54, II-55, II-57, II-58, II-59, II-60, II-60, II-61, II-63, II-64, II-65, II-66, II-67, II-68, II-69, II-70, II-71, II-72, II-73, II-74, II-75, II-76, II-78, II-79, II-80, II-81, II-82, II-83, II-84, II-85, II-86, II-87, II-88, II-89, II-90, II-91, II-92, II-93, II-94, II-95, II-96, II-97, II-98, II-99, II-100, II-101, II-102, II-103, II-105, II-106, II-111, II-112, II-113, II-114, II-115, II-116, II-117, II-120, II-125, III-1, III-2, III-3, III-4, III-5, III-6, III-9, III-12, III-14, III-18, III-19, III-24, III-56, III-59, V-1, V-2, V-3, V-4, V-5, V-6, V-7, V-8, V-9, V-10, V-11, V-12, V-13, V-14, V-16, V-17, V-18, V-19, V-20, V-22, V-23, V-24, V-25, V-26, V-27, V-28, V-29, V-30, V-31, V32, V-33, V-34, V-35, V-36, V-37, V-38, V-39, V-40, V-42, V-43, V-44, V-46, V-47, V-49, V-51, V-52, V-53, V-54, V-57, V-58, V-59, V-60, and V-63.

In the above assay for the release of intracellular calcium, the present compounds that were tested typically had activity below 10.0 micromolar.

While we have described a number of embodiments of this invention, it is apparent that our basic examples may be altered to provide other embodiments, which utilize the compounds and methods of this invention. Therefore, it will be appreciated that the scope of this invention is to be defined by the appended claims rather than by the specific embodiments, which have been represented by way of example.

We claim:

1. A compound of formula I:

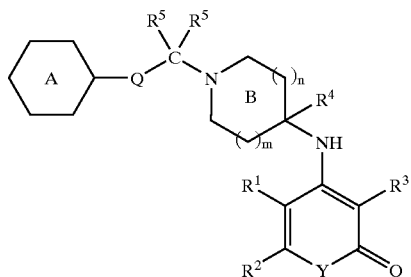

I or a pharmaceutically-acceptable salt; wherein:

m is zero or one;

n is zero, one or two;

Ring A is selected from the group consisting of $C_{3-8}$ carbocyclyl, 5–6 membered heteroaryl and 5–6 membered heterocyclyl, wherein said Ring A is optionally fused to a 5–7 membered saturated, unsaturated or partially unsaturated ring having 0–2 heteroatoms selected from N, O, or S, and wherein the Ring A system is substituted or unsubstituted, or substituted phenyl;

Y is oxygen or —N($R^9$)—;

Q is absent or is a $C_{3-6}$ cycloalk-1,2-diyl, —CHN($R^8$)$_2$—, or a saturated or unsaturated carbon chain having 1–5 chain atoms, wherein each hydrogen-bearing carbon of said chain is optionally and independently substituted by a $C_{1-6}$ aliphatic group, and one saturated carbon of said chain along with the hydrogen atoms attached thereto is optionally replaced by —C($R^7$)$_2$—, —O—, —S—, —S(O)—, —S(O)$_2$—, or —N($R^8$)—;

$R^1$ is selected from R, —CN, $CO_2R$, —C(O)R, or —CON($R^8$)$_2$;

R is hydrogen, $C_{1-10}$ aliphatic, aryl, aralkyl, heteroaryl, heteroaralkyl, heterocyclyl or heterocyclylalkyl;

$R^2$ is selected from hydrogen, $C_{1-10}$ aliphatic, aryl, aralkyl, heteroaryl, heteroaralykyl, heterocyclyl, or heterocyclylalkyl, or $R^1$ and $R^2$ taken together with their intervening atoms form a fused, unsaturated or partially unsaturated, substituted or unsubstituted, 5–7 membered ring having 0–2 heteroatoms selected from O, N or S;

$R^3$ is selected from R, —CN, $CO_2R$, —C(O)R, —$CH_2N$($R^8$)$_2$, or —C(O)N($R^8$)$_2$, heterocyclyl;

$R^4$ is selected from hydrogen, $C_{1-10}$ aliphatic, —CN, —$CO_2R$, —C(O)R, or, —C(O)N($R^8$)$_2$; each $R^5$ is independently selected from the group consisting of hydrogen, $C_{1-6}$ aliphatic, —CN, —$CO_2R$, —C(O)R, and —CON($R^8$)$_2$, or two $R^5$ groups taken together with their intervening carbon form an optionally substituted 3–6 membered ring having 0–2 heteroatoms selected from O, N, or S;

Ring B is optionally substituted by one or more $R^6$;

each $R^6$ is independently selected from $C_{1-6}$ aliphatic, hydroxyl, alkoxy, oxo, halo, —SR, —CN, —N($R^8$)$_2$, —NHC(O)R, —N($R^8$)CON($R^8$)$_2$, —N($R^8$)COR, —$NHCO_2$($C_{1-8}$ aliphatic), —$CO_2R$, —C(O)R, —CON($R^8$)$_2$, —S(O)$_2R$, —S(O)R, —$SO_2$N($R^8$)$_2$, or —N($R^8$)S(O)$_2R$, or two $R^6$ taken together with their intervening atoms form a 5–7 membered ring having 0–2 heteroatoms selected from N, O, or S;

each $R^7$ is independently selected from hydrogen, $C_{1-10}$ aliphatic, halo, —OR, —SR—CN, —N($R^8$)$_2$, —NHC(O)R, —N($R^8$)CON($R^8$)$_2$, —N($R^8$)COR, —$NHCO_2R$—, —$CO_2R$, —C(O)R, —CON($R^8$)$_2$, —S(O)$_2R$, —S(O)R, —$SO_2$N($R^8$)$_2$, or —N($R^8$)S(O)$_2R$, or two $R^7$ groups taken together form =O, =N—OR, =N—N($R^8$)$_2$, =N—NHC(O)R, =N—$NHCO_2R$, or two $R^7$ groups taken together with their intervening carbon form an optionally substituted 3–6 membered ring having 0–2 heteroatoms selected O, N, or S;

each $R^8$ is independently selected from R, —$CO_2R$, —C(O)R, —C(O)N($C_{1-6}$ aliphatic)$_2$, —C(O)NH($C_{1-6}$ aliphatic), —S(O)$_2R$, —S(O)R, or —$SO_2$N($C_{1-6}$ aliphatic)$_2$, —$SO_2$NH($C_{1-6}$ aliphatic), or two $R^8$ groups on the same nitrogen taken together with the nitrogen form a 5–7 membered heterocyclyl ring; and $R^9$ is hydrogen, $C_{1-10}$ aliphatic, aralkyl, heteroaralkyl, or heterocyclylalkyl.

2. The compound of claim 1 wherein Y is oxygen and $R^1$ and $R^2$ are taken together with their intervening atoms to form a fused benzo ring.

3. The compound of claim 2 having formula IV-A or IV-B:

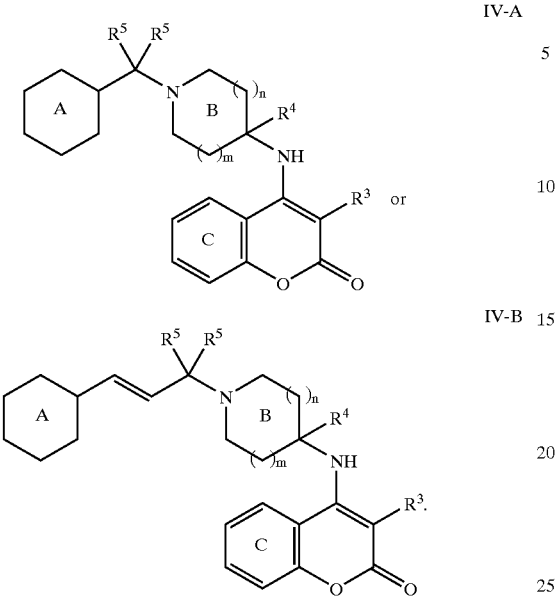

4. The compound of claim 3 having one or more features selected from the group consisting of:

(a) m is one and n is one;
(b) Q is absent or —CH=CH—;
(c) R³, R⁴, and R⁵ are each hydrogen; and
(d) Ring A is a substituted or unsubstituted pyridyl ring, substituted phenyl, or a substituted or unsubstituted ring selected from the group consisting of:

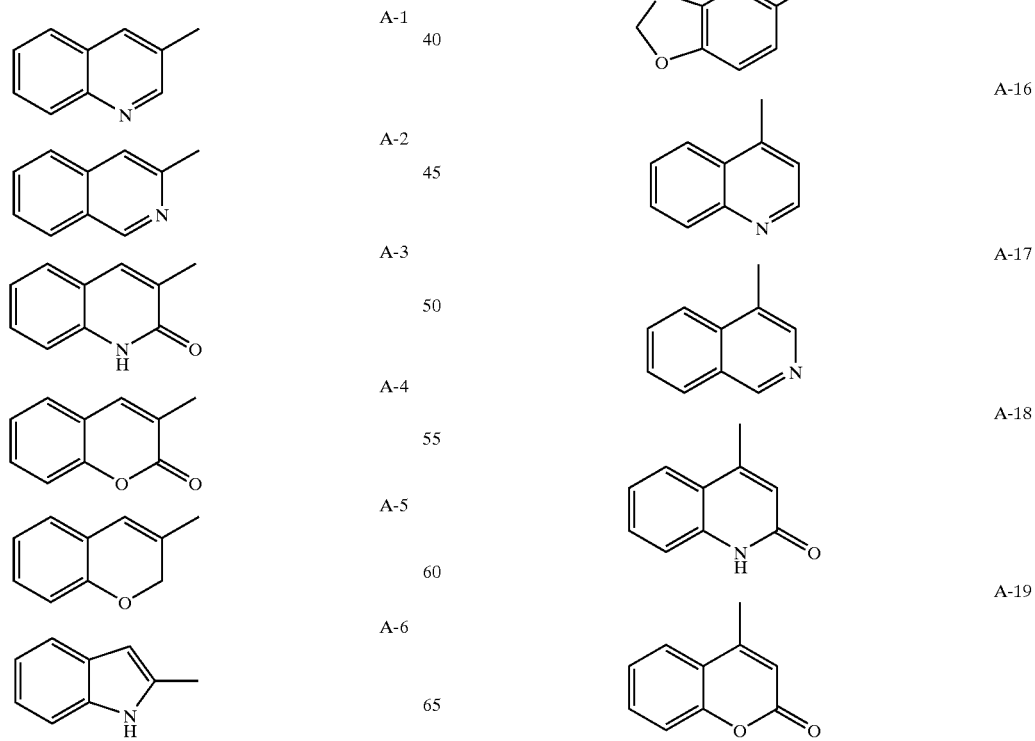

-continued

A-20 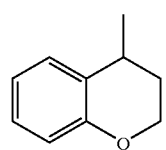

A-21 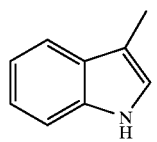

A-22 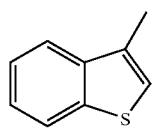

A-23 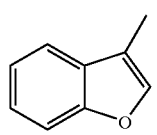

A-24 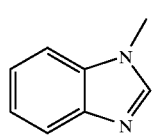

A-25 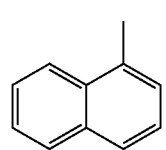

A-26 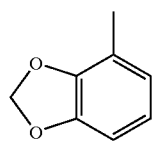

A-27 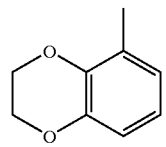

A-28 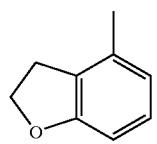

A-29 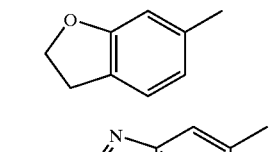

A-30

A-31 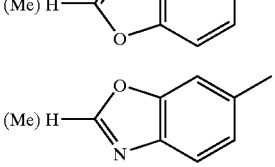

-continued

A-32 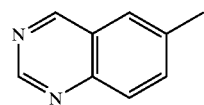

A-33 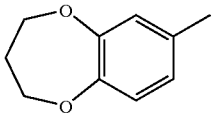

A-34 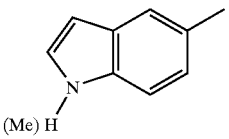

5. The compound of claim 4 having the features (a), (b), (c), and (d).

6. The compound of claim 4 wherein the Ring A system is substituted phenyl.

7. The compound of claim 1 wherein Y is —N(R$^9$)— and R$^1$ and R$^2$ are taken together with their intervening atoms to form a fused benzo ring.

8. The compound of claim 7 having formula V-A or V-B:

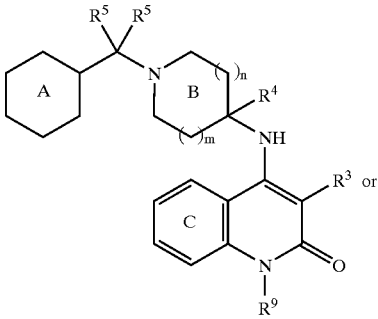

V-A

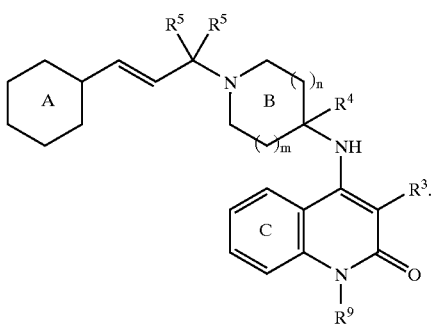

V-B

9. The compound of claim 7 having one or more features selected from the group consisting of:

(a) m is one and n is one;

(b) Q is absent or —CH═CH—;

(c) R$^3$, R$^4$, and R$^5$ are each hydrogen; and (d) Ring A is a substituted phenyl or a substituted or unsubstituted ring selected from the group consisting of:

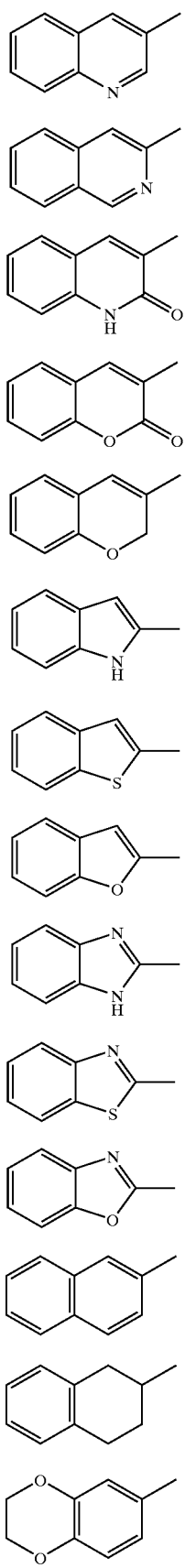
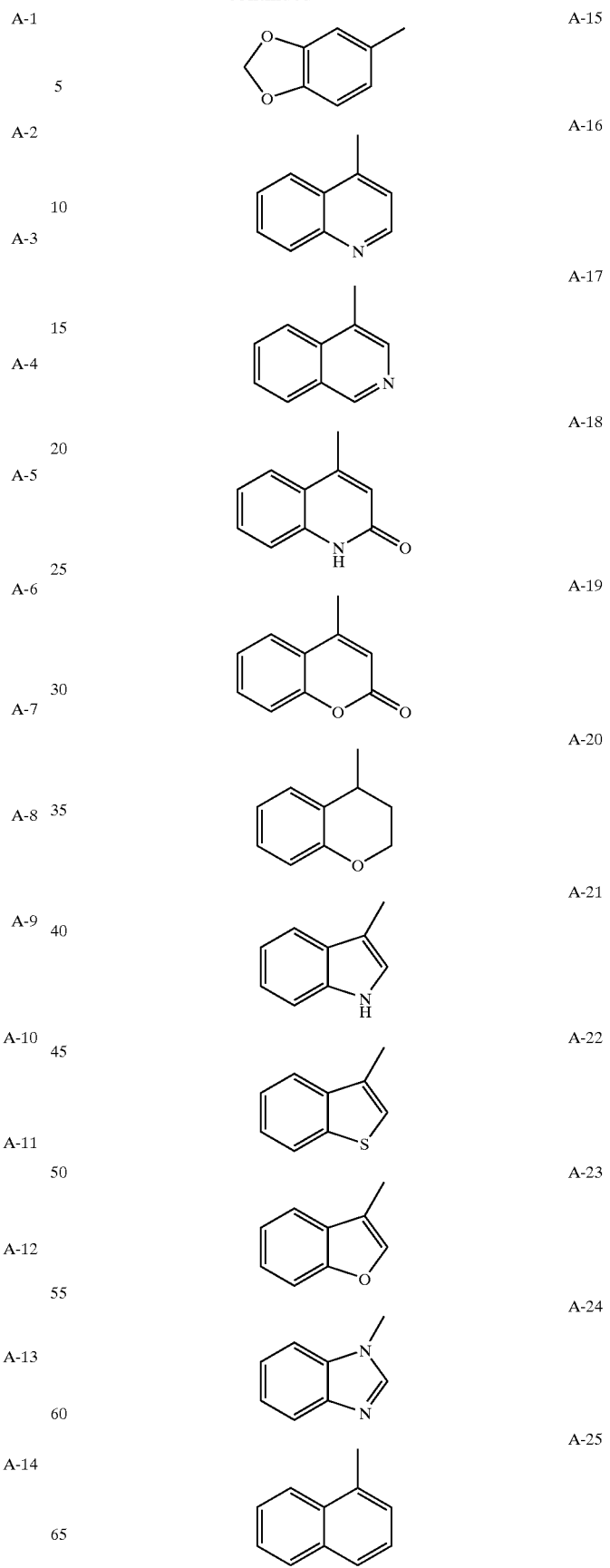

-continued

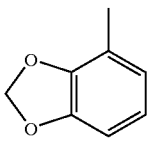
A-26

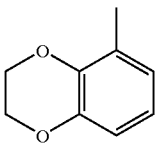
A-27

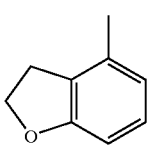
A-28

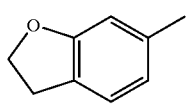
A-29

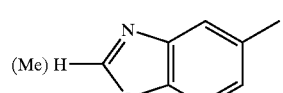
A-30

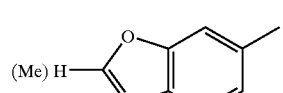
A-31

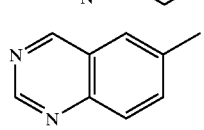
A-32

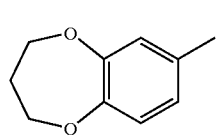
A-33

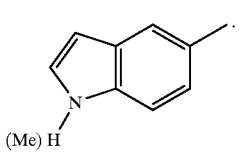
A-34

10. The compound of claim 9 having the features (a), (b), (c), and (d).

11. The compound of claim 9 wherein the Ring A system is substituted phenyl.

12. The compound of claim 10 wherein the Ring A system is substituted phenyl.

13. A compound selected from the group consisting of:

II-1: 4-(1-Benzo[1,3]dioxol-5-ylmethyl-piperidin-4-ylamino)-6-methoxy-chromen-2-one;

II-2: 6-Chloro-4-(1-naphthalen-2-ylmethyl-piperidin-4-ylamino)-chromen-2-one;

II-3: 4-(1-Benzo[1,3]dioxol-5-ylmethyl-piperidin-4-ylamino)-6-methyl-chromen-2-one;

II-4: 4-(1-Benzo[1,3]dioxol-5-ylmethyl-piperidin-4-ylamino)-6-chloro-chromen-2-one;

II-5: 6-Chloro-4-(1-naphthalen-1-ylmethyl-piperidin-4-ylamino)-chromen-2-one;

II-6: 4-(1-Benzo[b]thiophen-3-ylmethyl-piperidin-4-ylamino)-6-chloro-chromen-2-one;

II-7: 4-(1-Biphenyl-3-ylmethyl-piperidin-4-ylamino)-6-chloro-chromen-2-one;

II-8: 4-(1-Biphenyl-4-ylmethyl-piperidin-4-ylamino)-6-chloro-chromen-2-one;

II-9: 4-(1-Benzyl-piperidin-4-ylamino)-6-methyl-chromen-2-one;

II-10: 6-Chloro-4-(1-cyclohex-1-enylmethyl-piperidin-4-ylamino)-chromen-2-one;

II-6-Methyl-4-[1-(3-trifluoromethoxy-benzyl)-piperidin-4-ylamino]-chromen-2-one;

II-12: 4-[1-(3-Hydroxy-benzyl)-piperidin-4-ylamino]-6-methyl-chromen-2-one;

II-13: 6-Methyl-4-[1-(4-phenoxy-benzyl)-piperidin-4-ylamino]-chromen-2-one;

II-14: 4-{1-[5-(3-Chloro-phenyl)-furan-2-ylmethyl]-piperidin-4-ylamino}-6-methyl-chromen-2-one;

II-15: 4-[1-(4-tert-Butyl-benzyl)-piperidin-4-ylamino]-6-methyl-chromen-2-one;

II-16: 4-{1-[3-(4-Methoxy-phenoxy)-benzyl]-piperidin-4-ylamino}-6-methyl-chromen-2-one;

II-17: 4-(1-Benzo[b]thiophen-2-ymethyl-piperidin-4-ylamino)-6-chloro-chromen-2-one;

II-18: 4-(1-Benzofuran-2-ylmethyl-piperidin-4-ylamino)-6-chloro-chromen-2-one;

II-19: 6-Methoxy-4-(1-naphthalen-2-ylmethyl-piperidin-4-ylamino)-chromen-2-one;

II-20: 6-Methoxy-4-[1-(3-trifluoromethoxy-benzyl)-piperidin-4-ylamino]-chromen-2-one;

II-21: 4-[1-(3,5-Dichloro-benzyl)-piperidin-4-ylamino]-6-methoxy-chromen-2-one;

II-22: 4-{1-[5-(2-Chloro-phenyl)-furan-2-ylmethyl]-piperidin-4-ylamino}-6-methoxy-chromen-2-one;

II-23: 6-Methoxy-4-{1-[5-(2-trifluoromethyl-phenyl)-furan-2-ylmethyl]-piperidin-4-ylamino}-chromen-2-one;

II-24: 4-{1-[5-(3-Chloro-phenyl)-furan-2-ylmethyl]-piperidin-4-ylamino}-6-methyl-chromen-2-one;

II-25: 4-[1-(2,4-Dimethyl-benzyl)-piperidin-4-ylamino]-6-methoxy-chromen-2-one;

II-26: 4-(1-Benzo[1,3]dioxol-5-ylmethyl-piperidin-4-ylamino)-3-fluoro-6-methoxy-chromen-2-one;

II-27: 6-Methoxy-4-[1-(7-methyl-naphthalen-2-ylmethyl)-piperidin-4-ylamino]-chromen-2-one;

II-28: 4-[1-(1-Benzo[1,3]dioxol-5-yl-ethyl)-piperidin-4-ylamino]-6-chloro-chromen-2-one;

II-29: 4-[1-(3,4-Dimethyl-benzyl)-piperidin-4-ylamino]-6-methoxy-chromen-2-one;

II-30: 4-(1-Benzo[1,3]dioxol-5-ylmethyl-piperidin-4-ylamino)-6-chloro-chromen-2-one;

II-31: 6-Chloro-4-[1-(1H-indol-6-ylmethyl)-piperidin-4-ylamino]-chromen-2-one;

II-32: 6-Difluoromethoxy-4-(1-naphthalen-2-ylmethyl-piperidin-4-ylamino)-chomen-2-one;

II-33: 4-[1-(1-Ethyl-1H-indol-5-ylmethyl)-piperidin-4-ylamino]-6-methoxy-chromen-2-one;

II-34: 6-Methoxy-4-[1-(4-methyl-benzyl)-piperidin-4-ylamino]-chromen-2-one;

II-35: 4-(1-Benzo[1,3]dioxol-5-ylmethyl-piperidin-4-ylamino)-6-vinyl-chromen-2-one;

II-36: 4-(1-Benzofuran-6-ylmethyl-piperidin-4-ylamino)-6-chloro-chromen-2-one;

II-37: 6-Methoxy-4-[1-(4-methoxy-3-methyl-benzyl)-piperidin-4-ylamino]-chromen-2-one;

II-38: 4-(1-Benzo[1,3]dioxol-5-ylmethyl-3-methyl-piperidin-4-ylamino)-6-methoxy-chromen-2-one;

II-39: 6-Methoxy-4-[1-(4-methoxy-benzyl)-piperidin-4-ylamino]-chromen-2-one;

II-40: 6-Chloro-4-(1-quinolin-6-ylmethyl-piperidin-4-ylamino)-chromen-2-one;

II-41: 4-(1-Benzo[1,3]dioxol-5-ylmethyl-piperidin-4-ylamino)-8-bromo-6-chloro-chromen-2-one;

II-42: N-[4-(1-Benzo[1,3]dioxol-5-ylmethyl-piperidin-4-ylamino)-6-chloro-2-oxo-2H chromen-3-yl]-acetamide;

II-43: 4-[1-(4-Difluoromethoxy-benzyl)-piperidin-4-ylamino]-6-methoxy-chromen-2-one;

II-44: 4-(1-Benzooxazol-5-ylmethyl-piperidin-4-ylamino)-6-chloro-chromen-2-one;

II-45: 6-Chloro-4-{1-[1-(3-fluoro-4-methoxy-phenyl)-ethyl]-piperidin-4-ylamino}-chromen-2-one;

II-46: 4-[1-(3,4-Dimethyl-benzyl)-piperidin-4-ylamino]-6-vinyl-chromen-2-one;

II-47: 4-{1-[3-Fluoro-4-(3-piperidin-1-yl-propoxy)-benzyl]-piperidin-4-ylamino}-6-methoxy-chromen-2-one;

II-48: 4-[1-(4-Acetyl-benzyl)-piperidin-4-ylamino]-6-chloro-chromen-2-one;

II-49: 6-Chloro-4-{1-[4-(3-piperidin-1-yl-propoxy)-benzyl]-piperidin-4-ylamino}-chromen-2-one;

II-50: 4-[1-(4-Butoxy-benzyl)-piperidin-4-ylamino]-6-methoxy-chromen-2-one;

II-51: 6-Chloro-4-[1-(3,4-dihydro-2H-benzo[b][1,4]dioxepin-7-ylmethyl)-piperidin-4-ylamino]-chromen-2-one;

II-52: 6-Methoxy-4-[1-(1-naphthalen-2-yl-ethyl)-piperidin-4-ylamino]-chomen-2-one;

II-53: 4-(1-Benzo[1,3]dioxol-5-ylmethyl-3-methyl-piperidin-4-ylamino)-6-methoxy-chromen-2-one;

II-54: 4-[1-(1H-Indol-5-ylmethyl)-piperidin-4-ylamino]-6-methoxy-chromen-2-one;

II-55: 4-[4-(6-Chloro-2-oxo-2H-chromen-4-ylamino)-piperidin-1-ylmethyl]—N-(2-pyrrolidin-1-yl-ethyl)-benzamide;

II-56: 4-(1-Benzo[1,3]dioxol-5-ylmethyl-3-methyl-piperidin-4-ylamino)-6-methoxy-chromen-2-one;

II-57: 4-[1-(2,3-Dihydro-benzo[1,4]dioxin-6-ylmethyl)-piperidin-4-ylamino]-6-vinyl-chromen-2-one;

II-58: 4-[1-(4-Chloro-3-fluoro-benzyl)-piperidin-4-ylamino]-6-methoxy-chromen-2-one;

II-59: 6-Chloro-4-[1-(4-chloro-benzyl)-piperidin-4-ylamino]-chromen-2-one;

II-60: 4-[-(1-Benzo[1,3]dioxol-5-yl-ethyl)-piperidin-4-ylamino]-6-chloro-chromen-2-one;

II-61: 6-Chloro-4-[1-(2-methyl-benzofuran-5-ylmethyl)-piperidin-4-ylamino]-chromen-2-one;

II-62: 4[-(2-Fluoro-4-methoxy-benzyl)-piperidin-4-ylamino]-6-methoxy-chromen-2-one;

II-63: 4-(1-Benzo[1,3]dioxol-5-ylmethyl-piperidin-4-ylamino)-6-ethyl-chromen-2-one;

II-64: 4[-(2,3-Dihydro-benzo[1,4]dioxin-6-ylmethyl)-piperidin-4-ylamino]-6-methoxy-chromen-2-one;

II-65: 4-[1-(4-Bromo-benzyl)-piperidin-4-ylamino]-6-methoxy-chromen-2-one;

II-66: 6-Methoxy-4-(1-naphthalen-1-ylmethyl-piperidin-4-ylamino)-chromen-2-one;

II-67: 4-[4-(6-Chloro-2-oxo-2H-chromen-4-ylamino)-piperidin-1-ylmethyl]-N-(2-piperidin-1-yl-ethyl)-benzamide;

II-68: 4[-(2,2-Difluoro-benzo[1,3]dioxol-5-ylmethyl)-piperidin-4-ylamino]-6-methoxy-chromen-2-one;

II-69: 4-[4-(6-Methoxy-2-oxo-2H-chromen-4-ylamino)-piperidin-1-ylmethyl]-N-(2-piperidin-1-yl-ethyl)-benzamide;

II-70: 4[-(3-Fluoro-4-methoxy-benzyl)-piperidin-4-ylamino]-6-methoxy-chromen-2-one;

II-71: 6-Chloro-4-[1-(3,4-dimethyl-benzyl)-piperidin-4-ylamino]-chromen-2-one;

II-72: 4-(1-Benzo[1,3]dioxol-5-ylmethyl-3-methyl-piperidin-4-ylamino)-6-methoxy-chromen-2-one;

II-73: 6-Chloro-4-(1-isoquinolin-6-ylmethyl-piperidin-4-ylamino)-chromen-2-one;

II-74: 6-Chloro-4-{1-[1-(4-chloro-phenyl)-ethyl]-piperidin-4-ylamino}-chromen-2-one;

II-75: 4-(1-Benzo[1,3]dioxol-5-ylmethyl-piperidin-4-ylamino)-2-oxo-2H-chromene-6-carbonitrile;

II-76: 6-Methoxy-4-[1-(3-methoxy-benzyl)-piperidin-4-ylamino]-chromen-2-one;

II-77: 4-[1-(3-Acetyl-benzyl)-piperidin-4-ylamino]-6-chloro-chromen-2-one;

II-78: 6-Chloro-4-[1-(2,3-dihydro-benzofuran-5-ylmethyl)-piperidin-4-ylamino]-chromen-2-one;

II-79: 4-[1-(3-Fluoro-benzyl)-piperidin-4-ylamino]-6-methoxy-chromen-2-one;

II-80: 4-[1-(4-Ethoxy-benzyl)-piperidin-4-ylamino]-6-methoxy-chromen-2-one;

II-81: 1-[4-(1-Benzo[1,3]dioxol-5-ylmethyl-piperidin-4-ylamino)-6-chloro-2-oxo-2H-chromen-8-yl]-pyrrolidin-2-one;

II-82: 4-(1-Benzo[1,3]dioxol-5-ylmethyl-piperidin-4-ylamino)-6-trifluoromethyl-chromen-2-one;

II-83: 4-[4-(6-Methoxy-2-oxo-2H-chromen-4-ylamino)-piperidin-1-ylmethyl]-N-(2-pyridin-2-yl-ethyl)-benzamide;

II-84: 6-Methoxy-4-[1-(1-methyl-1H-indol-2-ylmethyl)-piperidin-4-ylamino]-chromen-2-one;

II-85: 6,8-Difluoro-4-(1-naphthalen-2-ylmethyl-piperidin-4-ylamino)-chromen-2-one;

II-86: 4-[4-(6-Methoxy-2-oxo-2H-chromen-4-ylamino)-piperidin-1-ylmethyl]-N-(2-pyrrolidin-1-yl-ethyl)-benzamide;

II-87: 4-[1-(2,3-Dihydro-benzofuran-5-ylmethyl)-piperidin-4-ylamino]-6-vinyl-chromen-2-one;

II-88: 4-[1-(3-Fluoro-4-hydroxy-benzyl)-piperidin-4-ylamino]-6-methoxy-chromen-2-one;

II-89: 4-(1-Benzo[1,3]dioxol-5-ylmethyl-piperidin-4-ylamino)-3-fluoro-6-methyl-chromen-2-one;

II-90: 4-(1-Benzo[1,3]dioxol-5-ylmethyl-piperidin-4-ylamino)-3-chloro-6-methoxy-chromen-2-one;

II-91: 4-{1-[4-(3-Dimethylamino-propoxy)-benzyl]-piperidin-4-ylamino}-6-methoxy-chromen-2-one;

II-92: 6-Methoxy-4-[1-(3-methyl-benzyl)-piperidin-4-ylamino]-chromen-2-one;

II-93: 6-Chloro-4-[1-(7-chloro-benzofuran-5-ylmethyl)-piperidin-4-ylamino]-chromen-2-one;

II-94: 4-{1-[4-(4-Benzyl-piperazine-1-carbonyl)-benzyl]-piperidin-4-ylamino}-6-methoxy-chromen-2-one;

II-95: 4-(1-Benzooxazol-5-ylmethyl-piperidin-4-ylamino)-6-chloro-chromen-2-one;
II-96: 4-(1-Benzo[1,3]dioxol-5-ylmethyl-piperidin-4-ylamino)-6-trifluoromethoxy-chromen-2-one;
II-97: 4-[1-(3-Ethoxy-benzyl)-piperidin-4-ylamino]-6-methoxy-chromen-2-one;
II-98: 4-(1-Benzo[1,3]dioxol-5-ylmethyl-piperidin-4-ylamino)-6,8-dimethyl-chromen-2-one;
II-99: 3-[4-(6-Chloro-2-oxo-2H-chromen-4-ylamino)-piperidin-1-ylmethyl]-benzamide;
II-100: 4-(1-Benzooxazol-5-ylmethyl-piperidin-4-ylamino)-6-vinyl-chromen-2-one;
II-101: 4-(1-Benzo[b]thiophen-4-ylmethyl-piperidin-4-ylamino)-6-methoxy-chromen-2-one;
II-102: 4-(1-Benzyl-piperidin-4-ylamino)-6-methoxy-chromen-2-one;
II-103: 4-[1-(3,4-Dimethyl-benzyl)-piperidin-4-ylamino]-6-ethyl-chromen-2-one;
II-104: 6-Chloro-4-[1-(1-naphthalen-2-yl-ethyl)-piperidin-4-ylamino]-chromen-2-one;
II-105: 4-[1-(3-Fluoro-4-methyl-benzyl)-piperidin-4-ylamino]-6-methoxy-chromen-2-one;
II-106: 6-Chloro-4-[1-(1-quinolin-6-yl-ethyl)-piperidin-4-ylamino]-chromen-2-one;
II-107: 4-(1-Benzo[1,3]dioxol-5-ylmethyl-3-methyl-piperidin-4-ylamino)-6-methoxy-chromen-2-one;
II-108: 6-Chloro-4-{1-[1-(4-chloro-phenyl)-ethyl]-piperidin-4-ylamino}-chromen-2-one;
II-109: 6-Methoxy-4-(1-naphthalen-2-ylmethyl-piperidin-4-ylamino)-chromen-2-one;
II-110: 4-[1-(4-Chloro-benzyl)-piperidin-4-ylamino]-6-methoxy-chromen-2-one;
II-111: 6-Metboxy-4-[1-(1-methyl-1H-indol-5-ylmethyl)-piperidin-4-ylamino]-chromen-2-one;
II-112: 6-Methoxy-4-(1-quinolin-6-ylmethyl-piperidin-4-ylamino)-chromen-2-one;
II-113: 6-Chloro-4-{1-[1-(3-fluoro-4-hydroxy-phenyl)-ethyl]-piperidin-4-ylamino }-chromen-2-one;
II-114: 4-(1-Benzofuran-5-ylmethyl-piperidin-4-ylamino)-2-oxo-2H-chromene-6-carbonitrile;
II-115: 4-{1-[3-Chloro-4-(3-piperidin-1-yl-propoxy)-benzyl]-piperidin-4-ylamino}-6-methoxy-chromen-2-one;
II-116: 4-{1-[1-(4-Acetyl-phenyl)-ethyl]-piperidin-4-ylamino }-6-chloro-chromen-2-one; and
II-117: 4-(1-Benzo[1,3]dioxol-5-ylmethyl-piperidin-4-ylamino)-6,7-dichloro-chromen-2-one.
14. A compound selected from the group consisting of:
III-1: 6-Methoxy-4-[1-(3-phenyl-allyl)-piperidin-4-ylamino]-chromen-2-one;
III-2: 6-Chloro-4-{1-[3-(2-chloro-phenyl)-allyl]-piperidin-4-ylamino}-chromen-2-one;
III-3: 6-Chloro-4-[1-(3-phenyl-allyl)-piperidin-4-ylamino]-chromen-2-one;
III-4: 6-Methoxy-4-[1-(3-phenyl-allyl)-piperidin-4-ylamino]-chromen-2-one;
III-5: 6-Bromo-4-[1-(3-phenyl-allyl)-piperidin-4-ylamino]-chromen-2-one;
III-6: 6-Methyl-4-[1-(3-phenyl-allyl)-piperidin-4-ylamino]-chromen-2-one;
III-7: 6-Chloro-7-methyl-4-[1-(3-phenyl-allyl)-piperidin-4-ylamino]-chromen-2-one;
III-8: 6-Chloro-4-[1-(4-phenyl-but-3-enyl)-piperidin-4-ylamino]-chromen-2-one;
III-9: 4-{1-[3-(3-Chloro-phenyl)-allyl]-piperidin-4-ylamino}-chromen-2-one;
III-10: 6-Chloro-4-[1-(4-oxo-4-p-tolyl-butyl)-piperidin-4-ylamino]-chromen-2-one;
III-11: 6-Fluoro-4-[1-(3-phenyl-allyl)-piperidin-4-ylamino]-chromen-2-one;
III-12: 6-Methyl-4-{1-[3-(2-nitro-phenyl)-allyl]-piperidin-4-ylamino}-chromen-2-one;
III-13: 4-{1-[3-(2-Chloro-phenyl)-allyl]-piperidin-4-ylamino}-chromen-2-one;
III-14: 4-{1-[3-(2-Fluoro-phenyl)-allyl]-piperidin-4-ylamino}-chromen-2-one;
III-15: 4-{1-[3-(3-Fluoro-phenyl)-allyl]-piperidin-4-ylamino }-chromen-2-one;
III-16: 4-[1-(3-Furan-2-yl-allyl)-piperidin-4-ylamino]-6-methyl-chromen-2-one;
III-17: 4-{1-[3-(4-Chloro-phenyl)-allyl]-piperidin-4-ylamino}-chromen-2-one;
III-18: 6-Chloro-4-[1-(2-methyl-3-phenyl-allyl)-piperidin-4-ylamino]-chromen-2-one;
III-19: 4-{1-[3-(2-Methoxy-phenyl)-allyl]-piperidin-4-ylamino}-6-methyl-chromen-2-one;
III-20: 4-{1-[3-(4-Fluoro-phenyl)-allyl]-piperidin-4-ylamino}-chromen-2-one;
III-21: 6-Chloro-4-{1-[5-(4-fluoro-phenyl)-5-oxo-pentyl]-piperidin-4-ylamino}-chromen-2-one;
III-22: 7-Methoxy-4-[1-(3-phenyl-allyl)-piperidin-4-ylamino]-chromen-2-one;
III-23: 6-Chloro-2-oxo-4-[1-(3-phenyl-allyl)-piperidin-4-ylamino]-2H-chromene-3-carbaldehyde;
III-24: 4-[1-(3-Phenyl-allyl)-piperidin-4-ylamino]-chromen-2-one;
III-25: 7-Chloro-4-[1-(3-phenyl-allyl)-piperidin-4-ylamino]-chromen-2-one;
III-26: 4-{Ethyl-[1-(3-phenyl-allyl)-piperidin-4-yl]-amino}-chromen-2-one;
III-27: 4-[1-(3-Phenyl-propyl)-piperidin-4-ylamino]-chromen-2-one;
III-28: 4-[1-(2-Bromo-3-phenyl-allyl)-piperidin-4-ylamino]-6-methyl-chromen-2-one;
III-29: 6-Methyl-4-[1-(2-methyl-3-phenyl-allyl)-piperidin-4-ylamino]-chromen-2-one;
III-30: 6-methyl-4-(4-((6-methyl-2-oxo-2H-chromen-4-yl)amino)piperidin-1-yl)-2H-chromen-2-one;
III-31: 4{-[3-(4-Hydroxy-3-methoxy-phenyl)-allyl]-piperidin-4-ylamino}-6-methyl-chromen-2-one;
III-32: 4-[1-(2-Chloro-3-phenyl-allyl)-piperidin-4-ylamino]-6-methyl-chromen-2-one;
III-33: 5-Methoxy-4-[1-(3-phenyl-allyl)-piperidin-4-ylamino]-chromen-2-one;
III-34: 6-chloro-4-(4-((6-methyl-2-oxo-2H-chromen-4-yl)amino)piperidin-1-yl)-2H-chromen-2-one;
III-35: 4-[1-(3-Phenyl-allyl)-piperidin-4-ylamino]-6-propyl-chromen-2-one;
III-36: 6-(3-Methyl-butyl)-4-[1-(3-phenyl-allyl)-piperidin-4-ylamino]-chromen-2-one;
III-37: 6-(2-Ethyl-butyl)-4-[1-(3-phenyl-allyl)-piperidin-4-ylamino]-chromen-2-one;
III-38: 6-Isobutyl-4-[1-(3-phenyl-allyl)-piperidin-4-ylamino]-chromen-2-one;

III-39: 6-Butyl-4-[1-(3-phenyl-allyl)-piperidin-4-ylamino]-chromen-2-one;
III-40: 6-Cyclopentyl-4-[1-(3-phenyl-allyl)-piperidin-4-ylamino]-chromen-2-one;
III-41: 6-(4-Methoxy-phenyl)-4-[1-(3-phenyl-allyl)-piperidin-4-ylamino]-chromen-2-one;
III-42: 6-Phenyl-4-[1-(3-phenyl-allyl)-piperidin-4-ylamino]-chromen-2-one;
III-43: 4-[1-(3-Phenyl-allyl)-piperidin-4-ylamino]-6-o-tolyl-chromen-2-one;
III-44: 4-[1-(3-Phenyl-allyl)-piperidin-4-ylamino]-6-m-tolyl-chromen-2-one;
III-45: 4-[1-(3-Phenyl-allyl)-piperidin-4-ylamino]-6-p-tolyl-chromen-2-one;
III-46: 6-(3-Methoxy-phenyl)-4-[1-(3-phenyl-allyl)-piperidin-4-ylamino]-chromen-2-one;
III-47: 6-(2-Chloro-phenyl)-4-[1-(3-phenyl-allyl)-piperidin-4-ylamino]-chromen-2-one;
III-48: 6-(3-Chloro-phenyl)-4-[1-(3-phenyl-allyl)-piperidin-4-ylamino]-chromen-2-one;
III-49: 6-(4-Chloro-phenyl)-4-[1-(3-phenyl-allyl)-piperidin-4-ylamino]-chromen-2-one;
III-50: 4-[1-(3-Phenyl-allyl)-piperidin-4-ylamino]-6-pyridin-4-yl-chromen-2-one;
III-51: 4-[1-(3-Phenyl-allyl)-piperidin-4-ylamino]-6-thiophen-3-yl-chromen-2-one;
III-52: 6-(5-Chloro-thiophen-2-yl)-4-[1-(3-phenyl-allyl)-piperidin-4-ylamino]-chromen-2-one;
III-53: 4-[1-(2-Bromo-3-phenyl-allyl)-piperidin-4-ylamino]-6-chloro-chromen-2-one;
III-54: 6-Chloro-4-{1-[4-(5,6-dichloro-benzoimidazol-1-yl)-butyl]-piperidin-4-ylamino}-chromen-2-one;
III-55: 6-Methoxy-4-[1-(3-phenyl-allyl)-piperidin-4-ylamino]-chromen-2-one;
III-56: 6-Chloro-4-{1-[3-(2-fluoro-phenyl)-allyl]-piperidin-4-ylamino}-chromen-2-one;
III-57: 6-Chloro-4-{1-[3-(2-chloro-phenyl)-allyl]-piperidin-4-ylamino}-chromen-2-one;
III-58: 6-Chloro-4-[1-(3-phenyl-allyl)-piperidin-4-ylamino]-chromen-2-one; and
III-59: 2-Oxo-4-[1-(3-phenyl-allyl)-piperidin-4-ylamino]-2H-chromene-6-carbonitrile.

15. A compound selected from the group consisting of:
V-1: 6-Chloro-4-(1-naphthalen-2-ylmethyl-piperidin-4-ylamino)-1-pyridin-3-ylmethyl-1H-quinolin-2-one;
V-2: 4-(1-Benzo[1,3]dioxol-5-ylmethyl-piperidin-4-ylamino)-6-chloro-1-pyridin-2-ylmethyl-1H-quinolin-2-one;
V-3: 4-(1-Benzo[1,3]dioxol-5-ylmethyl-piperidin-4-ylamino)-1-benzyl-6-chloro-1H-quinolin-2-one;
V-4: 4-(1-Benzo[1,3]dioxol-5-ylmethyl-piperidin-4-ylamino)-6-chloro-1-pyridin-4-ylmethyl-1H-quinolin-2-one;
V-5: 6-Chloro-4-(1-naphthalen-2-ylmethyl-piperidin-4-ylamino)-1-pyridin-4-ylmethyl-1H-quinolin-2-one;
V-6: 6-Chloro-1-ethyl-4-(1-naphthalen-2-ylmethyl-piperidin-4-ylamino)-1H-quinolin-2-one;
V-7: 4-(1-Benzo[1,3]dioxol-5-ylmethyl-piperidin-4-ylamino)-6-chloro-1-(2,2,2-trifluoroethyl)-1H-quinolin-2-one;
V-8: 4-(1-Benzo[1,3]dioxol-5-ylmethyl-piperidin-4-ylamino)-6-methoxy-1-methyl-1H-quinolin-2-one;
V-9: 6-Methoxy-1-methyl-4-(1-naphthalen-2-ylmethyl-piperidin-4-ylamino)-1H-quinolin-2-one;
V-10: 4-(1-Benzofuran-5-ylmethyl-piperidin-4-ylamino)-6-chloro-1-pyridin-4-ylmethyl-1H-quinolin-2-one;
V-11: 4-(1-Benzo[1,3]dioxol-5-ylmethyl-piperidin-4-ylamino)-6-chloro-1H-quinolin-2-one;
V-12: 4-(1-Benzofuran-5-ylmethyl-piperidin-4-ylamino)-6-methoxy-1-methyl-1H-quinolin-2-one;
V-13: 4-(1-Benzo[1,3]dioxol-5-ylmethyl-piperidin-4-ylamino)-6-ethyl-1-methyl-1-quinolin-2-one;
V-14: 6-Methoxy-1-methyl-4-[1-(3-phenyl-allyl)-piperidin-4-ylamino]-1H-quinolin-2-one;
V-15: 6-Chloro-4-[1-(4-chloro-benzyl)-piperidin-4-ylamino]-1-pyridin-4-ylmethyl-1H-quinolin-2-one;
V-6: 4-(1-Benzo[1,3]dioxol-5-ylmethyl-piperidin-4-ylamino)-6-difluoromethoxy-1-methyl-1H-quinolin-2-one;
V-17: 4-(1-Benzo[1,3]dioxol-5-ylmethyl-piperidin-4-ylamino)-1,6-diethyl-1H-quinolin-2-one;
V-18: 4-[1-(1-Benzo[1,3]dioxol-5-yl-ethyl)-piperidin-4-ylamino]-1,6-diethyl-1H-quinolin-2-one;
V-19: 4-(1-Benzo[1,3]dioxol-5-ylmethyl-piperidin-4-ylamino)-6-chloro-1-(1-oxy-pyridin-4-ylmethyl)-1H-quinolin-2-one;
V-20: 6-Ethyl-1-methyl-4-(1-naphthalen-2-ylmethyl-piperidin-4-ylamino)-1H-quinolin-2-one;
V-21: 7-Chloro-4-(1-naphthalen-2-ylmethyl-piperidin-4-ylamino)-1-pyridin-4-ylmethyl-1H-quinolin-2-one;
V-22: 1,6-Dimethyl-4-(1-naphthalen-2-ylmethyl-piperidin-4-ylamino)-1H-quinolin-2-one;
V-23: 4-(1-Benzofuran-5-ylmethyl-piperidin-4-ylamino)-6-chloro-2-oxo-1,2-dihydro-quinoline-3-carbonitrile;
V-24: 6-Chloro-1-methyl-4-(1-naphthalen-2-ylmethyl-piperidin-4-ylamino)-2-oxo-1,2-dihydro-quinoline-3-carboxylic acid dimethylamide;
V-25: 4-(1-Benzofuran-5-ylmethyl-piperidin-4-ylamino)-6-ethyl-1-methyl-1H-quinolin-2-one;
V-26: 4-(1-Benzofuran-5-ylmethyl-piperidin-4-ylamino)-6-chloro-1-pyridin-2-ylmethyl-1H-quinolin-2-one;
V-27: 4-(1-Benzo[1,3]dioxol-5-ylmethyl-piperidin-4-ylamino)-6-chloro-2-oxo-1,2-dihydro-quinoline-3-carbonitrile;
V-28: 4-(1-Benzofuran-5-ylmethyl-piperidin-4-ylamino)-1,6-diethyl-1H-quinolin-2-one;
V-29: 6-Chloro-1-methyl-4-[1-(3-phenyl-allyl)-piperidin-4-ylamino]-1H-quinolin-2-one;
V-30: 6-Chloro-1-methyl-4-(1-naphthalen-2-ylmethyl-piperidin-4-ylamino)-2-oxo-1,2-dihydro-quinoline-3-carboxylic acid methyl ester;
V-31: 4-(1-Benzo[1,3]dioxol-5-ylmethyl-piperidin-4-ylamino)-1-methyl-6-trifluoromethyl-1H-quinolin-2-one;
V-32: 6-Chloro-4-[1-(3-fluoro-4-methoxy-benzyl)-piperidin-4-ylamino]-1-methyl-2-oxo-1,2-dihydro-quinoline-3-carbonitrile;
V-33: 4-(1-Benzofuran-5-ylmethyl-piperidin-4-ylamino)-1-methyl-6-trifluoromethyl-1H-quinolin-2-one;
V-34: 4-[1-(1-Benzo[1,3]dioxol-5-yl-ethyl)-piperidin-4-ylamino]-6-chloro-1-methyl-2-oxo-1,2-dihydro-quinoline-3-carboxylic acid dimethylamide;
V-35: 6-Chloro-1-pyridin-4-ylmethyl-4-(1-pyridin-4-ylmethyl-piperidin-4-ylamino)-1H-quinolin-2-one;

V-36: 1-(1-Benzo[1,3]dioxol-5-ylmethyl-piperidin-4-ylamino)-6,7-dihydro-5H-pyrido[3,2,1-ij]quinolin-3-one;

V-37: 6-Chloro-4-(1-naphthalen-2-ylmethyl-piperidin-4-ylamino)-2-oxo-1,2-dihydro-quinoline-3-carboxylic acid methyl ester;

V-38: 1,6-Dimethyl-4-[1-(3-phenyl-allyl)-piperidin-4-ylamino]-1H-quinolin-2-one;

V-39: 4-(1-Benzo[1,3]dioxol-5-ylmethyl-piperidin-4-ylamino)-6-chloro-1-methyl-2-oxo-1,2-dihydro-quinoline-3-carboxylic acid methyl ester;

V-40: 4-(1-Benzofuran-5-ylmethyl-piperidin-4-ylamino)-6-chloro-1-methyl-2-oxo-1,2-dihydro-quinoline-3-carboxylic acid dimethylamide;

V-41: 4-(1-Benzo[1,3]dioxol-5-ylmethyl-piperidin-4-ylamino)-6-chloro-1-methyl-2-oxo-1,2-dihydro-quinoline-3-carboxylic acid dimethylamide;

V-42: 4-(1-Benzo[1,3]dioxol-5-ylmethyl-piperidin-4-ylamino)-6-bromo-1-methyl-2-oxo-1,2-dihydro-quinoline-3-carboxylic acid dimethylamide;

V-43: 4-(1-Benzo[1,3]dioxol-5-ylmethyl-piperidin-4-ylamino)-6-isopropyl-1-methyl-1-quinolin-2-one;

V-44: 1-Benzyl-4-[1-(3-phenyl-allyl)-piperidin-4-ylamino]-1H-quinolin-2-one;

V-45: 4-(1-Benzofuran-5-ylmethyl-piperidin-4-ylamino)-6-isopropyl-1-methyl-1H-quinolin-2-one;

V-46: 6-Hydroxy-1-methyl-4-(1-naphthalen-2-ylmethyl-piperidin-4-ylamino)-1H-quinolin-2-one;

V-47: 1-Methyl-4-[1-(3-phenyl-allyl)-piperidin-4-ylamino]-1H-quinolin-2-one;

V-48: 6-Chloro-1-methyl-4-(1-naphthalen-2-ylmethyl-piperidin-4-ylamino)-2-oxo-1,2-dihydro-quinoline-3-carboxylic acid;

V-49: 4-(1-Benzo[1,3]dioxol-5-ylmethyl-piperidin-4-ylamino)-6-chloro-3-(4,4-dimethyl-4,5-dihydro-oxazol-2-yl)-1-methyl-1H-quinolin-2-one;

V-50: 4-(1-Benzo[1,3]dioxol-5-ylmethyl-piperidin-4-ylamino)-6-chloro-2-oxo-1-(2,2,2-trifluoro-ethyl)-1,2-dihydro-quinoline-3-carboxylic acid dimethylamide;

V-51: 4-(1-Benzo[1,3]dioxol-5-ylmethyl-piperidin-4-ylamino)-6-chloro-1-methyl-2-oxo-1,2-dihydro-quinoline-3-carbonitrile;

V-52: 4-(1-Benzo[1,3]dioxol-5-ylmethyl-piperidin-4-ylamino)-6-chloro-1-methyl-2-oxo-1,2-dihydro-quinoline-3-carboxylic acid methoxy-methyl-amide;

V-53: 6-Chloro-4-(1-naphthalen-2-ylmethyl-piperidin-4-ylamino)-2-oxo-1,2-dihydro-quinoline-3-carbonitrile;

V-54: 6-Chloro-4-[1-(3-fluoro-4-methoxy-benzyl)-piperidin-4-ylamino]-1-methyl-2-oxo-1,2-dihydro-quinoline-3-carboxylic acid dimethylamide;

V-55: 4-(1-Benzo[1,3]dioxol-5-ylmethyl-piperidin-4-ylamino)-1,6-dimethyl-1H-quinolin-2-one;

V-56: 6-Chloro-1-methyl-4-(1-naphthalen-2-ylmethyl-piperidin-4-ylamino)-2-oxo-1,2-dihydro-quinoline-3-carbonitrile;

V-57: 4-(8-Benzo[1,3]dioxol-5-ylmethyl-8-aza-bicyclo[3.2.1]oct-3-ylamino)-6-chloro-1-(2,2,2-trifluoro-ethyl)-1H-quinolin-2-one;

V-58: 4-(1-Benzo[1,3]dioxol-5-ylmethyl-piperidin-4-ylamino)-1-(2,2,2-trifluoro-ethyl)-6-trifluoromethyl-1H-quinolin-2-one;

V-59: 4-(1-Benzo[1,3]dioxol-5-ylmethyl-piperidin-4-ylamino)-6-chloro-1-methyl-3-(pyrrolidine-1-carbonyl)-1H-quinolin-2-one;

V-60: 4-(1-Benzo[1,3]dioxol-5-ylmethyl-piperidin-4-ylamino)-6-methoxy-1-methyl-2-oxo-1,2-dihydro-quinoline-3-carboxylic acid dimethylamide;

V-61: 6-Chloro-1-methyl-4-(1-naphthalen-2-ylmethyl-piperidin-4-ylamino)-1H-quinolin-2-one;

V-62: 4-(1-Benzo[1,3]dioxol-5-ylmethyl-piperidin-4-ylamino)-6-chloro-1-ethyl-1-quinolin-2-one;

V-63: 6-Chloro-1-ethyl-4-[1-(3-phenyl-allyl)-piperidin-4-ylamino]-1H-quinolin-2-one; and V-64: 4-(1-Benzo[1,3]dioxol-5-ylmethyl-piperidin-4-ylamino)-6-chloro-1-thiophen-2-ylmethyl-1H-quinolin-2-one;

V-65: 4-(1-Benzo[1,3]dioxol-5-ylmethyl-piperidin-4-ylamino)-6-chloro-1-(3H-imidazol-4-ylmethyl)-1H-quinolin-2-one; and V-66: 4-(1-Benzo[1,3]dioxol-5-ylmethyl-piperidin-4-ylamino)-6-chloro-1-thiazol-5-ylmethyl-1H-quinolin-2-one.

16. A pharmaceutical composition comprising a compound according to any one of claims 1, 13, 14 or 15 and a pharmaceutically-acceptable carrier.

17. A compound of formula VI:

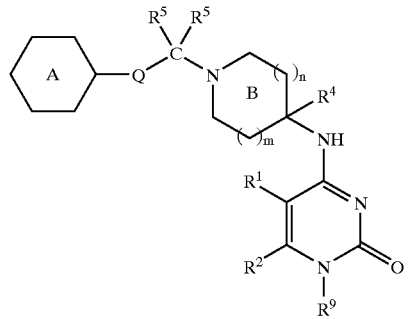

VI or a pharmaceutically-acceptable salt, wherein:

m is zero or one;

n is zero, one or two;

Ring A is selected from the group consisting of $C_{3-8}$ carbocyclyl, 5–6 membered heteroaryl and 5–6 membered heterocyclyl, wherein said Ring A is optionally fused to a 5–7 membered saturated, unsaturated or partially unsaturated ring having 0–2 heteroatoms selected from N, O, or S, and wherein the Ring A system is substituted or unsubstituted, or substituted phenyl;

Q is absent or is a $C_{3-6}$ cycloalk-1,2-diyl, —CHN($R^8$)$_2$—, or a saturated or unsaturated carbon chain having 1–5 chain atoms, wherein each hydrogen-bearing carbon of said chain is optionally and independently substituted by a $C_{1-6}$ aliphatic group, and one saturated carbon of said chain along with the hydrogen atoms attached thereto is optionally replaced by —C($R^7$)$_2$—, —O—, —S—, —S(O)—, —S(O)$_2$—, or —N($R^8$)—;

$R^1$ is selected from R, —CN, CO$_2$R, —C(O)R, or —CON($R^8$)$_2$;

R is hydrogen, $C_{1-10}$ aliphatic, aryl, aralkyl, heteroaryl, heteroaralkyl, heterocyclyl or heterocyclylalkyl;

$R^2$ is selected from hydrogen, $C_{1-10}$ aliphatic, aryl, aralkyl, heteroaryl, heteroaralkyl, heterocyclyl, or heterocyclylalkyl, or $R^1$ and $R^2$ taken together with their intervening atoms form a fused, unsaturated or partially unsaturated, substituted or unsubstituted, 5–7 membered ring having 0–2 heteroatoms selected from O, N or S;

R⁴ is selected from hydrogen, $C_{1-10}$ aliphatic, —CN, —$CO_2R$, —C(O)R, or —C(O)N(R⁸)₂;

each R⁵ is independently selected from the group consisting of hydrogen, $C_{1-6}$ aliphatic, —CN, —$CO_2R$, —C(O)R, and —C(O)N(R⁸)₂, or two R⁵ groups taken together with their intervening carbon form an optionally substituted 3–6 membered ring having 0–2 heteroatoms selected from O, N, or S;

Ring B is optionally substituted by one or more R⁶;

each R⁶ is independently selected from one or more $C_{1-6}$ aliphatic, hydroxyl, alkoxy, oxo, halo, —SR, —CN, —N(R⁸)₂, —NHC(O)R, —N(R⁸)CON(R⁸)₂, —N(R⁸)COR, —NHCO₂($C_{1-8}$ aliphatic), —$CO_2R$, —C(O)R, —CON(R⁸)₂, —S(O)₂R, —S(O)R, —SO₂N(R⁸)₂, or —N(R⁸)S(O)₂R, or two R⁶ taken together with their intervening atoms form a 5–7 membered ring having 0–2 heteroatoms selected from N, O, or S;

each R⁷ is independently selected from hydrogen, $C_{1-10}$ aliphatic, halo, —OR, —SR, —CN, —N(R⁸)₂, —NHC(O)R, —N(R⁸)CON(R⁸)₂, —N(R⁸)COR, —NHCO₂R—, —$CO_2R$, —C(O)R, —CON(R⁸)₂, —S(O)₂R, —S(O)R, —SO₂N(R⁸)₂, or —N(R⁸)S(O)₂R, or two R⁷ groups taken together form =O, =N—OR, =N—N(R⁸)₂, =N—NHC(O)R, =N—NHCO₂R, or two R⁷ groups taken together with their intervening carbon form an optionally substituted 3–6 membered ring having 0–2 heteroatoms selected O, N, or S;

each R⁸ is independently selected from R, —$CO_2R$, —C(O)R, —C(O)N($C_{1-6}$ aliphatic)₂, —C(O)NH($C_{1-6}$ aliphatic), —S(O)₂R, —S(O)R, or —SO₂N($C_{1-6}$ aliphatic)₂, —SO₂NH($C_{1-6}$ aliphatic), or two R⁸ groups on the same nitrogen taken together with the nitrogen form a 5–7 membered heterocyclyl ring; and R⁹ is hydrogen, $C_{1-10}$ aliphatic, aralkyl, heteroaralkyl, or heterocyclylalkyl.

18. The compound of claim 17, wherein R¹ and R² are taken together with their intervening atoms to form a fused benzo ring.

19. The compound of claim 18 having one or more features selected from the group consisting of:

-continued

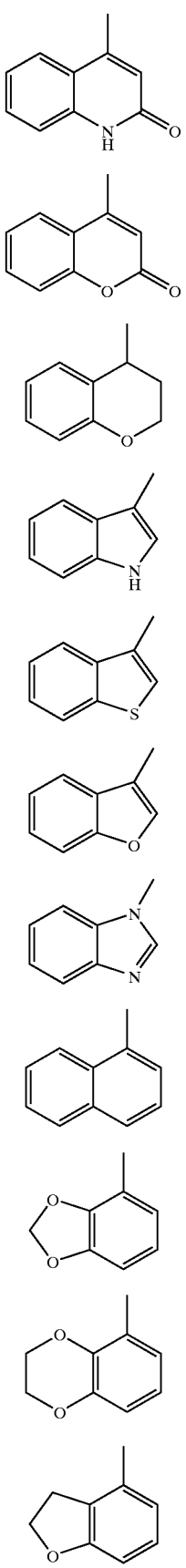

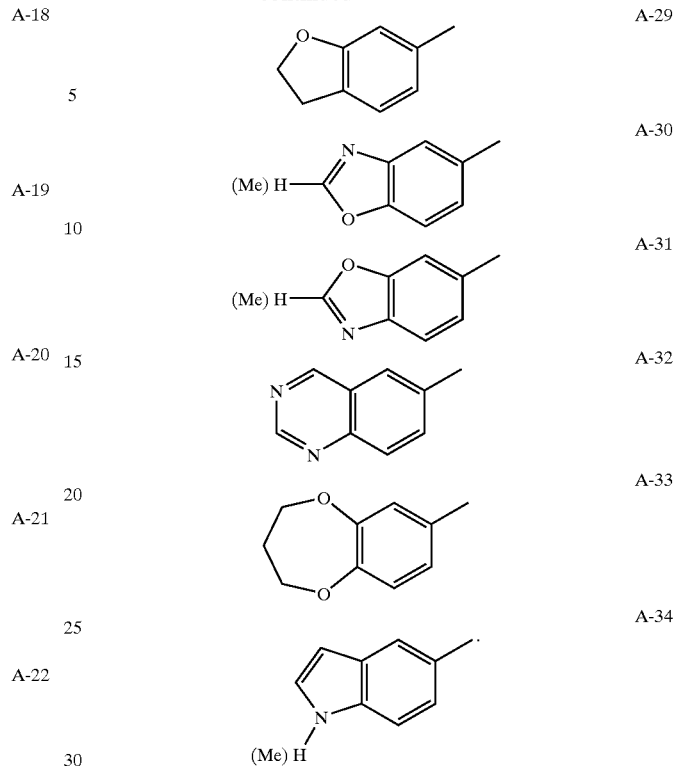

(a) m is one and n is one;
(b) Q is absent or —CH=CH—;
(c) $R^4$ and $R^5$ are each hydrogen; and
(d) Ring A is a substituted or unsubstituted pyridyl ring, substituted phenyl, or a substituted or unsubstituted ring selected from the group consisting of: T 20. The compound of claim 19 having the features (a), (b), (c), and (d).

21. The compound of claim 20 wherein the Ring A system is substituted phenyl.

22. A compound selected from the group consisting of:

VI-1: 6-Chloro-1-methyl-4-(1-quinolin-6-ylmethyl-piperidin-4-ylamino)-1H-quinazolin-2-one;

VI-2: 4-(1-Benzo[1,3]dioxol-5-ylmethyl-piperidin-4-ylamino)-6-Chloro-1-(2,2,2-trifluoro-ethyl)-1H-quinazolin-2-one;

VI-3: 6-Chloro-4-(1-naphthalen-2-ylmethyl-piperidin-4-ylamino)-1-pentyl-1H-quinazolin-2-one;

VI-4: 4-(8-Benzo[1,3]dioxol-5-ylmethyl-8-aza-bicyclo[3.2.1]oct-3-ylamino)-6-chloro-1-(2,2,2-trifluoro-ethyl)-1H-quinazolin-2-one;

VI-5: 4-(1-Benzo[1,3]dioxol-5-ylmethyl-piperidin-4-ylamino)-6-Chloro-1-(3H-imidazol-4-ylmethyl)-1H-quinazolin-2-one; and VI-6: 4-(1-Benzo[1,3]dioxol-5-ylmethyl-piperidin-4-ylamino)-6-Chloro-1-thiazol-5-ylmethyl-1H-quinazolin-2-one.

23. A pharmaceutical composition comprising a compound of claim 17 and a pharmaceutically acceptable carrier.

* * * * *